(12) United States Patent
Shao et al.

(10) Patent No.: US 8,877,975 B2
(45) Date of Patent: Nov. 4, 2014

(54) CYCLOALKYLAMINES AS MONOAMINE REUPTAKE INHIBITORS

(75) Inventors: Liming Shao, Lincoln, MA (US); Fengjiang Wang, Northborough, MA (US); Scott Christopher Malcolm, Southborough, MA (US); Michael Charles Hewitt, Somerville, MA (US); Larry R. Bush, Worcester, MA (US); Jianguo Ma, Natick, MA (US); Mark A. Varney, Laguna Niguel, CA (US); Una Campbell, Marlborough, MA (US); Sharon Rae Engel, Hudson, MA (US); Larry Wendell Hardy, Sturbridge, MA (US); Patrick Koch, Marlborough, MA (US); John E. Campbell, Cambridge, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 443 days.

(21) Appl. No.: 12/688,474

(22) Filed: Jan. 15, 2010

(65) Prior Publication Data
US 2010/0190861 A1    Jul. 29, 2010

Related U.S. Application Data

(63) Continuation of application No. 11/649,927, filed on Jan. 5, 2007, now abandoned.

(60) Provisional application No. 60/756,550, filed on Jan. 6, 2006.

(51) Int. Cl.
| | |
|---|---|
| *C07C 211/17* | (2006.01) |
| *A61K 31/137* | (2006.01) |
| *C07C 211/29* | (2006.01) |
| *C07C 211/40* | (2006.01) |
| *C07C 215/42* | (2006.01) |
| *C07C 215/44* | (2006.01) |
| *C07C 217/52* | (2006.01) |
| *C07C 217/74* | (2006.01) |
| *C07C 323/32* | (2006.01) |
| *C07D 207/06* | (2006.01) |
| *C07D 207/08* | (2006.01) |
| *C07D 211/14* | (2006.01) |
| *C07D 265/14* | (2006.01) |
| *C07D 277/28* | (2006.01) |
| *C07D 295/06* | (2006.01) |
| *C07D 307/52* | (2006.01) |
| *C07D 317/58* | (2006.01) |
| *C07D 317/72* | (2006.01) |
| *C07D 319/06* | (2006.01) |
| *C07D 333/20* | (2006.01) |
| *C07D 491/056* | (2006.01) |

(52) U.S. Cl.
CPC ............. *C07C 211/29* (2013.01); *C07C 211/17* (2013.01); *C07C 211/40* (2013.01); *C07C 215/42* (2013.01); *C07C 215/44* (2013.01); *C07C 217/52* (2013.01); *C07C 217/74* (2013.01); *C07C 323/32* (2013.01); *C07C 2101/02* (2013.01); *C07C 2101/08* (2013.01); *C07C 2101/10* (2013.01); *C07C 2101/14* (2013.01); *C07C 2101/16* (2013.01); *C07C 2102/08* (2013.01); *C07D 207/06* (2013.01); *C07D 207/08* (2013.01); *C07D 211/14* (2013.01); *C07D 265/14* (2013.01); *C07D 277/28* (2013.01); *C07D 295/06* (2013.01); *C07D 307/52* (2013.01); *C07D 317/58* (2013.01); *C07D 317/72* (2013.01); *C07D 319/06* (2013.01); *C07D 333/20* (2013.01); *C07D 491/056* (2013.01)
USPC ........... 564/442; 564/338; 564/381; 564/382; 514/650; 514/659

(58) Field of Classification Search
CPC .............................. C07C 211/17; A61K 31/137
USPC ........... 564/338, 381, 382, 442; 514/650, 659
See application file for complete search history.

(56) References Cited

U.S. PATENT DOCUMENTS

| | | | |
|---|---|---|---|
| 3,405,139 A * | 10/1968 | Haack et al. ................... | 549/440 |
| 4,105,762 A | 8/1978 | Miller et al. | |
| 4,540,690 A | 9/1985 | Szmuszkovicz | |
| 4,587,258 A | 5/1986 | Gold et al. | |

(Continued)

FOREIGN PATENT DOCUMENTS

| | | |
|---|---|---|
| BE | 616646 | 5/1962 |
| CA | 2066593 A1 | 2/1992 |

(Continued)

OTHER PUBLICATIONS

West, Anthony R., Solid State Chemistry and its Applications, Wiley, New York, 1988, pp. 358 & 365.*
Mndzhoyan, A. L "Studies of substituted acetic acids. XXXII. Amino esters of 1-(.alpha.-naphthyl)cycloalkane-1-carboxylic acids and 1-(.alpha.-naphthyl)cycloalkane-1-methylguanidines." Armyanskii Khimicheskii Zhurnal, 1976 29(2), 194-9 (Abstract Only).*
Adam, Octavian R. "Symptomatic Treatment of Huntington Disease" Neurotherapeutics: The Journal of the American Society for Experimental NeuroTherapeutics Apr. 2008, vol. 5, 181-197.*

(Continued)

*Primary Examiner* — David K O Dell
(74) *Attorney, Agent, or Firm* — Choate, Hall & Stewart LLP; Andrea L. C. Reid; Daniel A. Klein

(57) ABSTRACT

The invention relates to novel cyclohexylamine derivatives and their use in the treatment and/or prevention of central nervous system (CNS) disorders, such as depression, anxiety, schizophrenia and sleep disorder as well as methods for their synthesis. The invention also relates to pharmaceutical compositions containing the compounds of the invention, as well as methods of inhibiting reuptake of endogenous monoamines, such as dopamine, serotonin and norepinephrine from the synaptic cleft and methods of modulating one or more monoamine transporter.

23 Claims, No Drawings

(56) References Cited

U.S. PATENT DOCUMENTS

| | | | |
|---|---|---|---|
| 4,738,709 A | 4/1988 | Nielsen | |
| 4,751,231 A | 6/1988 | Halczenko et al. | |
| 4,981,870 A | 1/1991 | Koe | |
| 5,086,054 A | 2/1992 | Parish | |
| 5,373,018 A | 12/1994 | Cugola et al. | |
| 5,374,649 A | 12/1994 | Cugola et al. | |
| 5,523,278 A | 6/1996 | Wepplo | |
| 5,550,255 A | 8/1996 | Urbach et al. | |
| 5,578,627 A | 11/1996 | Takeda et al. | |
| 5,620,997 A | 4/1997 | Bolton et al. | |
| 5,668,162 A | 9/1997 | Domagala et al. | |
| 5,686,461 A | 11/1997 | Cugola et al. | |
| 5,859,042 A | 1/1999 | Lee et al. | |
| 5,962,496 A | 10/1999 | Cugola et al. | |
| 5,965,591 A | 10/1999 | Kojima et al. | |
| 6,096,771 A | 8/2000 | Kojima et al. | |
| 6,100,289 A | 8/2000 | Cugola et al. | |
| 6,174,925 B1 | 1/2001 | Bailey et al. | |
| 6,331,636 B1 | 12/2001 | Romero et al. | |
| 6,372,919 B1 | 4/2002 | Lippa et al. | |
| 6,399,601 B1 | 6/2002 | Du Bois | |
| 6,464,956 B1 | 10/2002 | Elomari | |
| 6,479,527 B1 | 11/2002 | Barker et al. | |
| 6,576,653 B2 | 6/2003 | Du Bois | |
| 6,589,949 B1 | 7/2003 | Moriwaki et al. | |
| 6,603,000 B2 | 8/2003 | Yee et al. | |
| 6,828,460 B2 | 12/2004 | Browning et al. | |
| 6,995,144 B2 | 2/2006 | Ozaki et al. | |
| 7,166,725 B2 | 1/2007 | Fang et al. | |
| 7,226,938 B2 | 6/2007 | Cai et al. | |
| 7,488,747 B2 | 2/2009 | Fang et al. | |
| 7,579,370 B2 | 8/2009 | Heffernan et al. | |
| 7,615,572 B2 | 11/2009 | Fang et al. | |
| 2002/0010198 A1 | 1/2002 | Jerussi et al. | |
| 2002/0058606 A1 | 5/2002 | Gonzalez et al. | |
| 2002/0085976 A1 | 7/2002 | Elomari | |
| 2002/0123490 A1 | 9/2002 | Howard, Jr. | |
| 2002/0183369 A1 | 12/2002 | Du Bois | |
| 2003/0087803 A1 | 5/2003 | Yatvin et al. | |
| 2003/0171440 A1 | 9/2003 | Senanayake et al. | |
| 2003/0195361 A1 | 10/2003 | Du Bois | |
| 2003/0215523 A1 | 11/2003 | Ozawa et al. | |
| 2004/0048878 A1 | 3/2004 | Cai et al. | |
| 2004/0067998 A1 | 4/2004 | Le Borgne et al. | |
| 2004/0072880 A1 | 4/2004 | Lloyd et al. | |
| 2004/0092605 A1 | 5/2004 | Jerussi et al. | |
| 2004/0106681 A1 | 6/2004 | Rao et al. | |
| 2004/0220229 A1 | 11/2004 | Bussolotti et al. | |
| 2005/0020645 A1 | 1/2005 | Ohta et al. | |
| 2005/0089935 A1 | 4/2005 | Cai et al. | |
| 2005/0143434 A1 | 6/2005 | Fang et al. | |
| 2005/0143443 A1 | 6/2005 | Fang et al. | |
| 2006/0019944 A1 | 1/2006 | Wu et al. | |
| 2006/0229286 A1 | 10/2006 | Kakigami et al. | |
| 2006/0235002 A1 | 10/2006 | Nagai et al. | |
| 2007/0100135 A1 | 5/2007 | Riggs et al. | |
| 2007/0142452 A1 | 6/2007 | Banner et al. | |
| 2007/0197588 A1 | 8/2007 | Shao et al. | |
| 2007/0203111 A1 | 8/2007 | Shao et al. | |
| 2008/0004327 A1 | 1/2008 | Heffernan et al. | |
| 2008/0004328 A1 | 1/2008 | Dorsey et al. | |
| 2008/0058395 A1 | 3/2008 | Heffernan et al. | |
| 2009/0005456 A1 | 1/2009 | Shao et al. | |
| 2009/0099248 A1 | 4/2009 | Heffernan et al. | |
| 2009/0149549 A1 | 6/2009 | Zhao et al. | |
| 2010/0016397 A1 | 1/2010 | Fang et al. | |
| 2010/0022612 A1 | 1/2010 | Dorsey et al. | |
| 2010/0029737 A1 | 2/2010 | Heffernan et al. | |
| 2010/0029741 A1 | 2/2010 | Dorsey et al. | |
| 2010/0120740 A1 | 5/2010 | Heffernan et al. | |

FOREIGN PATENT DOCUMENTS

| | | |
|---|---|---|
| CA | 2410077 A1 | 11/2001 |
| CA | 2474451 A1 | 8/2003 |
| CA | 2498152 A1 | 3/2004 |
| CA | 2498175 A1 | 3/2004 |
| CA | 2565852 A1 | 11/2005 |
| CA | 2566094 A1 | 12/2005 |
| CN | 1106386 A | 8/1995 |
| CN | 1709871 A | 12/2005 |
| CN | 1962656 A | 5/2007 |
| DE | 112485 | 3/1962 |
| DE | 1124485 A | 3/1962 |
| DE | 3431541 A1 | 3/1986 |
| EP | 0034415 | 8/1981 |
| EP | 0101786 A1 | 3/1984 |
| EP | 0346791 | 12/1989 |
| EP | 0396124 A2 | 11/1990 |
| EP | 1136071 A2 | 9/2001 |
| EP | 1219603 A2 | 7/2002 |
| EP | 1262181 A1 | 12/2002 |
| EP | 1362864 A1 | 11/2003 |
| EP | 1088824 B1 | 1/2004 |
| EP | 1391460 A1 | 2/2004 |
| EP | 1420028 A2 | 5/2004 |
| ES | 2081747 A1 | 3/1996 |
| GB | 1 530 172 | 10/1978 |
| JP | S54-059269 A | 5/1979 |
| JP | H01-016786 A | 1/1989 |
| JP | H01-172388 A | 7/1989 |
| JP | H04-077476 A | 3/1992 |
| JP | 2005060375 | 3/2005 |
| WO | WO 86/00896 A1 | 2/1986 |
| WO | WO 9319749 | 10/1993 |
| WO | WO 95/17381 A1 | 6/1995 |
| WO | WO 98/42709 A1 | 10/1998 |
| WO | WO 99/10343 A1 | 3/1999 |
| WO | WO 99/18065 A1 | 4/1999 |
| WO | WO 99/40913 A1 | 8/1999 |
| WO | WO 99/40914 A1 | 8/1999 |
| WO | WO 99/48868 A2 | 9/1999 |
| WO | WO 00/25770 A1 | 5/2000 |
| WO | WO 01/02427 A1 | 1/2001 |
| WO | WO 01/27103 A1 | 4/2001 |
| WO | WO 01/79208 A1 | 10/2001 |
| WO | WO 01/87866 | 11/2001 |
| WO | WO 02/12249 A2 | 2/2002 |
| WO | WO 02/20530 A1 | 3/2002 |
| WO | WO 0224685 | 3/2002 |
| WO | WO 02/31128 A1 | 4/2002 |
| WO | WO 03/016302 A1 | 2/2003 |
| WO | WO 03/039540 A2 | 5/2003 |
| WO | WO 03/063797 A2 | 8/2003 |
| WO | WO 03/074531 A1 | 9/2003 |
| WO | WO 03/074532 A1 | 9/2003 |
| WO | WO 03/091213 A1 | 11/2003 |
| WO | WO 03/092670 A1 | 11/2003 |
| WO | WO 2004/022537 A2 | 3/2004 |
| WO | WO 2004/031193 A1 | 4/2004 |
| WO | WO 2004/031194 A1 | 4/2004 |
| WO | WO 2004/039787 A1 | 5/2004 |
| WO | WO 2004/041780 A2 | 5/2004 |
| WO | WO 2004/089470 A2 | 10/2004 |
| WO | WO 2004/113345 A1 | 12/2004 |
| WO | WO 2005/013981 A1 | 2/2005 |
| WO | WO 2005/018637 A1 | 3/2005 |
| WO | WO 2005/020986 A1 | 3/2005 |
| WO | WO 2005/020987 A1 | 3/2005 |
| WO | WO 2005035514 | 4/2005 |
| WO | WO 2005/046575 A2 | 5/2005 |
| WO | WO 2005/066135 A2 | 7/2005 |
| WO | WO 2005/066143 A2 | 7/2005 |
| WO | WO 2005/089753 A2 | 9/2005 |
| WO | WO 2005/105096 | 11/2005 |
| WO | WO 2005108384 | 11/2005 |
| WO | WO 2005/123677 A1 | 12/2005 |
| WO | WO 2006/004040 A1 | 1/2006 |
| WO | WO 2006/001958 A2 | 2/2006 |
| WO | WO 2006/021000 A2 | 2/2006 |

(56) References Cited

FOREIGN PATENT DOCUMENTS

| | | |
|---|---|---|
| WO | WO 2006/077412 A1 | 7/2006 |
| WO | WO 2007/039773 A1 | 4/2007 |
| WO | WO 2007/068621 A1 | 6/2007 |
| WO | WO 2007/081542 A2 | 7/2007 |
| WO | WO 2007/081857 A2 | 7/2007 |
| WO | WO 2007/115185 A2 | 10/2007 |
| WO | WO 2008/005456 A2 | 1/2008 |
| WO | WO 2008/089453 A2 | 7/2008 |
| WO | WO 2008/151156 A1 | 12/2008 |
| WO | WO 2009/020814 A2 | 2/2009 |
| WO | WO 2010/017418 A1 | 2/2010 |

OTHER PUBLICATIONS

Hook V. Y.H. "Neuroproteases in Peptide Neurotransmission and Neurodegenerative Diseases Applications to Drug Discovery Research" Biodrugs 2006, 20, 105-119.*
Eric R. Marcotte J "Animal models of schizophrenia: a critical review" Psychiatry Neurosci 2001;26(5):395-410.*
Aetna Intellihealth website "Narcolepsy" "http://www.intelihealth.com/IH/ihtIH/WSIHW000/24597/24598/210412.html?d=dmtHealthAZ" online: accessed Aug. 22, 2010.*
Drew Dawson and Stuart Maxwell Amstrong "Chronobiotics—Drugs That Shift Rhythms" Pharmacology and Therapeutics 1996, 69, 15-36.*
Yvan Touitou, André Bogdan "Promoting adjustment of the sleep-wake cycle by chronobiotics" Physiology & Behavior 2007, 90, 294-300.*
Le Bars, et. al. "Animal Models of Nociception" Pharmacological Reviews 2001, 53, 597-652.*
Petit-Demouliere et. al. "Forced swimming test in mice: a review of antidepressant activity." Psychopharmacology 2005, 177, 245-255.*
Burton et al., 2003, "Two Novel Extra-Large Pore Zeolites," Chemistry: A European Journal, 9(23), 5737-48.
Schmalhofer et al., 2002, "Identification of a New Class on Inhibitors of the Voltage-Gated Potassium Channel, Kv1.3, with Immunosuppressant Properties," Biochemistry, 41(24), 7781-94.
Aboul-Enein et al., "Synthesis and antiemetic profile of N-[1-[(diethylamino)methyl]cyclohexl]amides," Scientia Pharmaceutica, 58(3):273-280 (1990). (abstract only).
Arya et al., "Synthesis of new heterocycles: Part XV. Synthesis of novel cyclic and acyclic sulfamides," Indian Journal of Chemistry, Section B: Organic Chemistry Including Medicinal Chemistry, 14B(10):766-9 (1976). (abstract only).
Bolshakov et al., "Design of antagonists for NMDA and AMPA receptors," Neuropharmacology, 49(2): 144-155 (2005).
"Borane-tetrahydrofuran Complex (BTHF)," Product Bulletin BASF, p. 1-14 (2002).
Calderon et al., "Novel 1-Phenylcycloalkanecarboxylic Acid Derivatives as Potential Anticonvulsant Agents," J. Med. Chem. 34: 3159-3164 (1991).
Chen et al., "Studies on the SAR and pharmacophore of milnacipran derivatives as monoamine transporter inhibitors," Bioorganic and Medicinal Chemistry Letters, 18:1346-1349 (2008).
Database Caplus (online), Chemical Abstracts Service, Columbus, Ohio, Uyeo, et al., "Synthesis of tetrahydrooxocrinine methane," XP002670895, retrieved from STN Database accession No. 1965:431871. (abstract only).
Database Caplus (online), Chemical Abstracts Service, Columbus, Ohio, Yashihiro et al., "Synthesis and pharmacological action of galanthamine related compounds. III. Analgesic actions. II," XP002670889, retrieved from STN Database accession No. 1979:145557. (abstract only).
Database Caplus (online), Chemical Abstracts Service, Columbus, Ohio, Wang et al., "Halogen cation induced stereoselective semipinacol-type rearrangement of alpha-quaternary beta-haloketo compounds," XP002670893, retrieved from STN Database accession No. 2003:657557. (abstract only).
Dorwald, F.A., "Side Reactions in Organic Synthesis," Wiley: VCH, Weinheim, p. IX of Preface, p. 41 (2005).

Eliel, "infelicitous Stereochemical Nomenclature," Chirality, 9:428-430 (1997).
Huffman et al., "The Synthesis of (+/−)-Hexahydropruciferine and Related Compounds," J. Org. Chem., 36(1): 111-117 (1971).
Kuo et al., "G-protein coupled receptors: SAR analyses of neurotransmitters and antagonists," Journal of Clinical Pharmacy and Therapeutics, 29:279-298 (2004).
Martin et al., "Do Structurally Similar Molecules Have Similar Biological Activity?" Journal of Medicinal Chemistry, 45:4350-4358 (2002).
Miao, "Benzamide Derivatives as Blockers of Kv1.3 Ion Channel," Bioorganic and Medicinal Chemistry Letters, 13(6): 1161-1164 (2003).
Meltzer et al., "The synthesis of bivalent 2β-carbomethoxy-3β-(3,4-dichlorophenyl)-8-heterobicyclo[3.2.1]octanes as probes for proximal binding sites on the dopamine and serotonin transporters," Bioorganic and Medicinal Chemistry, 16:1832-1840 (2008).
Sergievskaya et al., "N-Bis(chloroethyl)aminos with alicyclic and aromatic radicals in the molecules II," Zhurnal Obshchei Khimii, 28:1845-1849 (1958). (abstract only).
Shirai, Hideaki, "Reduction of 1-(m-methoxyphenyl)-4-oxocycloalkanecarbonitrites with lithium aluminum hydride," Nagoyashiritsu Daigaku Yakugakubu Kenkyu Nenpo, 17:33-37 (1969). (abstract only).
Shirai, Hideaki, "Synthesis of spiro[4-hydroxycyclohexane-1,4,2',3'-dihydro-6'-methoxy-1'-substituted-2'-methyl-1'H-isoquinoline]," Chemical and Pharmaceutical Bulletin, 20(1):41-46 (1972). (abstract only).
STN CAS—Registry File [RN 23528-18-9 (1984) RN 23528-19-0 (1984) RN 23528-20-3 (1984) RN 23528-55-4 (1984) RN 30488-71-2 (1984) RN 32153-36-9 (1984) RN 32153-37-0 (1984) RN 32153-38-1 (1984) RN 37416-50-5 (1984) RN 47323-97-7 (1984) RN 47565-69-5 (1984) 59725-72-3 (1984) RN 59725-73-4 (1984) RN 59725-80-3 (1984) RN 75180-50-6 (1984) RN 75180-51-7 (1984) RN 92322-75-3 (1984) RN 642425-45-0 (2001) RN 359715-60-9 (2001) RN 359715-61-0 (2001) RN 378247-79-1 (2001) RN 440345-09-5 (2002) RN 626603-31-4 (2003) RN 736131-37-6 (2004) RN 748757-96-2 (2004) RN 771583-23-4 (2004) RN 771583-24-5 (2004) RN 774526-63-5 (2004) RN 801207-80-7 (2004) RN 802046 (2004) RN 802896-47-5 (2004) RN 851067-30-6 (2005) RN 802894-81-1 (2004) RN 802321-69-3 (2004) RN 736869-01-5 (2004) RN 676138-32-2 (2004) RN 626603-27-8 (2003) RN 483368-74-7 (2003) RN 483368-73-6 (2003) RN 476373-61-2 (2002) RN 351343-80-1(2001) RN 324532-35-6 (2001) RN 303728-37-2 (2000) RN 214262-91-6 (1998) RN 233669-17-5 (1999) RN 233669-20-0 (1999) RN 214262-90-5 (1998) RN 124388-17-6 (1989) RN 125558-58-9 (1990) RN 143328-16-9 (1992) RN 143328-18-1 (1992) RN 143328-19-2 (1992) RN 162732-99-2 (1995) RN 189810-98-8 (1997) RN 213755-91-0 (1998) RN 100240-30-0 (1986) RN 21846-02-6 (1984) RN 23528-49-6 (1984) RN 25288-77-1 (1984) RN 36263-47-5 (1984) RN 36263-52-2 (1984) RN 37408-66-5 (1984) RN 37408-83-6 (1984) RN 37416-47-0 (1984) RN 53697-53-3 (1984) RN 53697-54-4 (1984) RN 56327-00-5 (1984) RN 56327-01-6 (1984) RN 56477-61-3 (1984) RN 56477-62-4 (1984) RN 64399-26-4 (1984) RN 64399-28-6 (1984) RN 65619-32-1 (1984) RN 65619-33-2 (1984) RN 65619-34-3 (1984) RN 71486-43-6 (1984) RN 74316-84-0 (1984) RN 83706-50-7 (1984) RN 91174-86-6 (1984) RN 91175-04-1 (1984)].
Thurkauf et al., "Synthesis and Anticonvulsant Activity of 1-Phenylcyclohexylamine Analogues," J. Med. Chem. 33: 1452-14558 (1990).
Wang et al., "Quinine/selecfluor combination induced asymmetric semipinacol rearrangement of allylic alcohols: an effective and enantioselective approach to alpha-quaternary beta-fluoro aldehydes," Chem. Commun., pp. 5580-5582 (2005).
West, Anthony, "Solid State Chemistry and its Applications," Wiley, New York, pp. 358 and 365 (1988).
Yardley et al., "2-Phenyl-2-(1-hydroxycycloalkyl)thylamine Derivatives: Synthesis and Antidepressant Activity," Journal of Medicinal Chemistry, 33:2899-2905 (1990).
Non-final office action for U.S. Appl. No. 11/649,927 dated Mar. 2, 2009.

(56) References Cited

OTHER PUBLICATIONS

Final office action for U.S. Appl. No. 11/649,927 dated Sep. 18, 2009.
Abarbri et al., "Les beta-cétonitriles groupes protecteurs de la fonction amine. Préparation d'amino-alcools", Helv. Chim. Acta 1995, 78(1), 109-121.
Alvaro et al., "Preparation and photolysis of diaryl esters of acetylenedicarboxylic acid", Tetrahedron 1992, 48(16), 3437-3444.
Ando et al., "3-(Arylacetylamino)-N-methylbenzamides: A Novel Class of Selective Anti-Helicobacter pylori Agents", J. Med. Chem. 2001, 44(25), 4468-4474.
Ashton et al., "Nonpeptide angiotensin II antagonists derived from 1H-pyrazole-5-carboxylates and 4-aryl-1H-imidazole-5-carboxylates", J. Med. Chem. 1993, 36(23), 3595-3605.
Associated Press, "FDA mulls drug to slow late-stage Alzheimer's", CNN.com, Sep. 24, 2003, URL: <http://www.cnn.com/2003/HEALTH/conditions/09/24/alzheimers.drug.ap/index.html>.
Aubert et al., "New cyclopenta[b]-pyrroles and -pyridines by reaction of 2-azido- and 2-phosphoranylideneaminocyclopent-1-ene-1-carbaldehydes with aliphatic esters", J. Chem. Soc. Perkin Trans. 1 1989(8), 1369-1373.
Azéma et al., "Efficient approach to acyloxymethyl esters of nalidixic acid and in vitro evaluation as intra-ocular prodrugs", Bioorg. Med. Chem. 2006, 14(8), 2569-2580.
Baba et al., "Structure-Based Design of a Highly Selective Catalytic Site-Directed Inhibitor of Ser/Thr Protein Phosphatase 2B (Calcineurin)", J. Am. Chem. Soc. 2003, 125(32), 9740-9749.
Babu et al., "Simple and facile oxidation of aldehydes to carboxylic acids", Org. Prep. Proced. Int. 1994, 26(1), 123-125.
Bagal et al., "Radicals from Aldehydes: A Convergent Access to Dienes and δ-Lactones", Synlett 2006(10), 1485-1490.
Balsamini et al., "(E)-3-(2-(N-phenylcarbamoyl)vinyl)pyrrole-2-carboxylic acid derivatives. A novel class of glycine site antagonists", J. Med. Chem. 1998, 41(6), 808-820.
Balsamini et al., "An improved route to cycloalka[b]pyrrole 2-carboxylates", Org. Prep. Proced. Int. 1997, 29(4), 471-473.
Bambury et al., "Trifluoromethylfurans II", J. Heterocycl. Chem. 1970, 7(2), 269-273.
Banekovich et al., "Synthesis and biological activities of novel dexibuprofen tetraacetylriboflavin conjugates", Bioorg. Med. Chem. Lett. 2007, 17(3), 683-687.
Banfi et al., "Synthesis of New Imidazole Derivatives as Potential Inhibitors of Thromboxane Synthetase", J. Heterocycl. Chem. 1990, 27, 215-219.
Bardakos et al., "Enhydrazine, 10. Einige aliphatische Enhydrazone", Chem. Ber. 1975, 108(7), 2161-2170.
Bartlett et al., "Evaluation of alternative approaches for the synthesis of macrocyclic bisindolylmaleimides", Org. Biomol. Chem. 2004, 2(19), 2874-2883.
Baumes et al., "No. 227.—Recherches sur les enehydrazines. VI.—Condensation de methylhydrazones de cetones sur les esters acyleniques: synthese de carbomethoxypyrroles", Bull. Soc. Chim. Fr. 1974(5-6), 1147-1150.
Beaumont et al., "Design of Ester Prodrugs to Enhance Oral Absorption of Poorly Permeable Compounds: Challenges to the Discovery Scientist", Curr. Drug Metab. 2003, 4(6), 461-485.
Bedford et al., "Quaternary salts of 2-[(hydroxyimino)methyl]imidazole. 2. Preparation and in vitro and in vivo evaluaton of 1-(alkoxymethyl)-2-[(hydroxyimino)methyl]-3-methylimidazolium halides for reactivation of organophosphorus-inhibited acetylcholinesterases", J. Med. Chem. 1989, 32(2), 493-503.
Benson et al., "Aliphatic β-Chlorovinyl Aldoximes", J. Org. Chem. 1965, 30(4), 1126-1129.
Bergauer et al., "Practical ex-chiral-pool methodology for the synthesis of dopaminergic tetrahydroindoles", Tetrahedron 2004, 60(5), 1197-1204.
Bialer et al., "Pharmacokinetic analysis and antiepileptic activity of tetra-methylcyclopropane analogues of valpromide", Pharm. Res. 1996, 13(2), 284-289.
Biggadike et al., "Selective plasma hydrolysis of glucocorticoid gamma-lactones and cyclic carbonates by the enzyme paraoxonase: an ideal plasma inactivation mechanism." J. Med. Chem. 2000, 43(1), 19-21.
Birkofer et al., "The Use of Silylation in Organic Syntheses", Angew. Chem. Int. Ed. 1965, 4(5), 417-429.
Black, D., "Product Class 13: 1H-Pyrroles" in "Science of Synthesis: Houben-Weyl Methods of Molecular Transformations", vol. 9; Maas, G., ed.; Thieme Medical Publishers: Stuttgart, 2001; pp. 441-552.
Blanchfield et al., "The stability of lipidic analogues of GnRH in plasma and kidney preparations: the stereoselective release of the parent peptide", Bioorg. Med. Chem. Lett. 2005, 15(6), 1609-1612.
Bobbitt et al., "Organic Nitrosonium Salts. II. Stability Studies and Oxidations of Some Indole Derivatives", Heterocycles 1990, 30(2), 1131-1140.
Bobosik et al., "Synthesis of N-Phenylsulfonyl Protected Furo[3,2-b]pyrroles", Collect. Czech. Chem. Commun. 1994, 59(2), 499-502.
Boeshagen et al., "Ueber 3-Acylimino-3H-1.2-benzodithiole", Chem. Ber. 1968, 101(7), 2472-2484.
Borza et al., "Selective NR1/2B N-Methyl-d-aspartate Receptor Antagonists among Indole-2-carboxamides and Benzimidazole-2-carboxamides" J. Med. Chem. 2007, 50(5), 901-914.
Braga et al., "Making crystals from crystals: a green route to crystal engineering and polymorphism", Chem. Commun. 2005(29), 3635-3645.
Bregant et al., "Orthogonally Protected Lanthionines: Synthesis and Use for the Solid-Phase Synthesis of an Analogue of Nisin Ring C", J. Org. Chem. 2005, 70(7), 2430-2438.
Brunner et al., "Asymmetrische Hydrierung von (Z)-α-(Acetylamino)-zimtsäure mit einem Rh/norphos-Katalysator", Angew. Chem. 1979, 91(8), 655-656.
Brunner-Guenat et al., "Esters of L-dopa: structure-hydrolysis relationships and ability to induce circling behaviour in an experimental model of hemiparkinsonism", J. Pharm. Phamiacol. 1995, 47(10), 861-869.
Bueno et al., "Dipeptides as effective prodrugs of the unnatural amino acid (+)-2-aminobicyclo[3.1.0]hexane-2,6-dicarboxylic acid (LY354740), a selective group II metabotropic glutamate receptor agonist." J. Med. Chem. 2005, 48(16), 5305-5320.
Bundgaard et al., "Esters of N,N-disubstituted 2-hydroxyacetamides as a novel highly biolabile prodrug type for carboxylic acid agents", J. Med. Chem 1987, 30(3), 451-454.
Byrn et al., "Solid-State Chemistry of Drugs", 2nd ed.; SSCI, Inc.: West Lafayette, Indiana, 1999; pp. 232-247.
Cai et al., "Synthesis of 2,4,5-Trisubstituted Oxazoles", Synthesis 2005(10), 1569-1571.
Calderon et al., "Novel 1-Phenylcycloalkanecarboxylic Acid Derivatives Are Potent and Selective .sigma.1 Ligands", J. Med. Chem. 1994, 37(15), 2285-2291.
Callis et al., "A Tandem Horner-Emmons Olefination-Conjugate Addition Approach to the Synthesis of 1,5-Disubstituted-6-azabicyclo[3.2.1]octanes Based on the AE Ring Structure of the Norditerpenoid Alkaloid Methyllycaconitine", J. Org. Chem. 1996, 61(14), 4634-4640.
Cartoon et al., "Lithiation reactions of 1-(2'-bromophenyl)pyrrole and related compounds", J. Organomet. Chem. 1981, 212(1), 1-9.
Chakraborty et al., "Synthesis and characterization of Boc-protected 4-amino- and 5-amino-pyrrole-2-carboxylic acid methyl esters", Tetrahedron Lett. 2006, 47(27), 4631-4634.
Chapman et al., "The Analytical Reduction of Porphyrins to Pyrroles", Can. J. Chem. 1971, 49(21), 3544-3564.
Chaubey et al., "Kinetics of the Oxidation of Heterocyclic Aldehydes by Quinolinium Dichromate", Bull. Chem. Soc. Jpn. 2002, 75(10), 2215-2220.
Chen et al., "4,4-Difluoro-4-bora-3a,4a-diaza-s-indacene (BODIPY) Dyes Modified for Extended Conjugation and Restricted Bond Rotations", J. Org. Chem. 2000, 65(10), 2900-2906.
Chimichi et al., "New 5-(2-ethenylsubstituted)-3(2H)-furanones with in vitro antiproliferative activity", Tetrahedron 2003, 59(28), 5215-5223.

(56) References Cited

OTHER PUBLICATIONS

Cottineau et al., "Synthesis and hypoglycemic evaluation of substituted pyrazole-4-carboxylic acids", Bioorg. Med. Chem. Lett. 2002, 12(16), 2105-2108.
Crane et al., "A Novel Enantioselective Synthetic Route to Omuralide Analogues with the Potential for Species Selectivity in Proteasome Inhibition", Org. Lett. 2001, 3(9), 1395-1397.
Cuevas-Yañez et al., "Rhodium(II) catalyzed intramolecular insertion of carbenoids derived from 2-pyrrolyl and 3-indolyl α-diazo-β-ketoesters and α-diazoketones", Tetrahedron 2004, 60(7), 1505-1511.
Cyranski et al., "Aromaticity of dihetero analogues of pentalene dianion. X-Ray and ab initio studies of eight methyl furo[3,2-b]pyrrole-5-carboxylate derivatives and five methyl furo[2,3-b]pyrrole-5-carboxylate derivatives", Tetrahedon 2001, 57(42), 8867-8873.
Damaslo, A. R., "Alzheimer's Disease and Related Dementias" in "Cecil Textbook of Medicine", 20th ed., vol. 2; W.B. Saunders Co.: Philadelphia, 1996; pp. 1992-1996.
Dandarova et al., "13C NMR spectra of some substituted furo[3,2-b]pyrroles", Magn. Reson. Chem. 1990, 28(9), 830-831.
Das et al., "Synthesis of some N-substituted carbazoles and their larvicidal studies", J. Indian Chem. Soc. 2005, 82, 158-160.
Database Beilstein, Beilstein Institute for Organic Chemistry, Frankfurt-Main, DE; Database Accession No. BRN: 10196160 Abstract; and Eur. J. Org. Chem. 2005(21), 4670-4679.
Database Beilstein, Beilstein Institute for Organic Chemistry, Frankfurt-Main, DE; Database Accession No. BRN: 1074598 Abstract; and Can. J. Chem. 1978, 56(10), 1429-1434.
Database Beilstein, Beilstein Institute for Organic Chemistry, Frankfurt-Main, DE; Database Accession No. BRN: 4185621 Abstract; and Collect. Czech. Chem. Commun. 1986, 51(1), 106-111.
Database Beilstein, Beilstein Institute for Organic Chemistry, Frankfurt-Main, DE; Database Accession No. BRN: 4429388 Abstract; and Collect. Czech. Chem. Commun. 1984, 49(1), 65-70.
Database Beilstein, Beilstein Institute for Organic Chemistry, Frankfurt-Main, DE; Database Accession No. BRN: 7812555 Abstract; and Collect. Czech. Chem. Commun. 1997, 62(10), 1612-1622.
Database CAPLUS on STN, Acc. No. 1977:83511, Koe, J. Pharmacol. Exp. Ther. 1976, 199(3), 649-661. [abstract].
De Luca et al., "A New, Simple Procedure for the Synthesis of Formyl Amides", Synlett 2004(14), 2570-2572.
Denmark et al., "Chiral fluoro ketones for catalytic asymmetric epoxidation of alkenes with oxone", J. Org. Chem. 2002, 67(10), 3479-3486.
Denmark et al., "Organocerium additions to SAMP-hydrazones: general synthesis of chiral amines", J. Am. Chem. Soc. 1987, 109(7), 2224-2225.
Dhanak et al., "Studies in the protection of pyrrole and indole derivatives", J. Chem. Soc., Perkin Trans. 1, 1986, 2181-2186.
Durrer et al., "Structure-metabolism relationships in the hydrolysis of nicotinate esters by rat liver and brain subcellular fractions", Pharm. Res. 1991, 8(7), 832-839.
Elghamry, "Synthesis of ethyl pyrrole-2-carboxylates: a regioselective cyclization of enaminones under knorr-type conditions", Synth. Commun. 2002, 32(6), 897-902.
El-Nagger et al., "Synthesis and Biological Activity of Some New Aminoacylcarbazole Derivatives. Part I", J. Heterocycl. Chem. 1982, 19, 1025-1028.
English et al., "Orally effective acid prodrugs of the beta-lactamase inhibitor sulbactam", J. Med. Chem. 1990, 33(1), 344-347.
Eras et al., "Reactivity of thienopyrroles. Synthesis of isomeric nitro and bromothienopyrroles", J. Heterocycl. Chem. 1984, 21(1), 215-217.
Estep, "An Efficient Synthesis of 4-Hydroxy-1H-indole-2-carbonitrile and Its Conversion to DPI 201-106", Synth. Commun. 1995, 25(4), 507-514.
Fagan et al., "A new approach to the core of roseophilin", Tetrahedron Lett. 1999, 40(33), 6117-6120.
Ferguson et al., "N-Acetyl-5,6-dihydrofuro[3,2-b]pyrid-2-one, C9H9NO3", Cryst. Struct. Comm. 1976, 5, 911-914.
Fischer et al., "On Benzisothiazolones: A Series with a Wide Range of Bacteriostatic and Fungistatic Activity", Arzneimittel-Forschung 1964, 14(12), 1301-1306.
Fischer et al., "Synthese einiger Pyrrole und ihre Umsetzungen", Justus Liebigs Ann. Chem. 1932, 492(1), 128-155.
Fischer et al., "Synthesen der Opso- und Hämopyrrolcarbonsäure. Neue Synthese von Koproporphyrin. II", Justus Liebigs Ann. Chem. 1928, 462(1), 240-250.
Fischer et al., "Synthesen von Koproporphyrin I und II, sowie Mesoporphyrin II, V und XII", Justus Liebigs Ann. Chem. 1928, 466(1), 147-178.
Fisera et al., "Correlation of Kinetic Data of 1,3-Dipolar Cycloadditions of C-Benzoyl-N-phenylnitrones with the Homo Energies of Furan Derivatives", Collect. Czech. Chem. Commun. 1981, 46, 1504-1512.
Fisera et al., "Cycloadditions of C-Benzoyl-N-phenylnitrone with Furocondensed Derivatives", Collect. Czech. Chem. Commun. 1981, 46, 2421-2427.
Flaugh et al., "Synthesis of porphyrins. Deoxophylloerythroetioporphyrin", J. Am. Chem. Soc. 1968, 90(24), 6877-6879.
Foucaud et al., "The [1+4] cycloaddition of isocyanides with 1-aryl-2-nitro-1-propenes. Methyl 2-nitro-3-arylpropenoates and methyl 2-nitro-2,4-pentadienoates. Synthesis of 1-hydroxyindoles and 1-hydroxypyrroles", J. Org. Chem. 1983, 48(21), 3639-3644.
Fraga-Dubreuil et al., "Grafted ionic liquid-phase-supported synthesis of small organic molecules", Tetrahedron Lett. 2001, 42(35), 6097-6100.
Franciò et al., "Asymmetric Catalysis with Chiral Phosphane/Phosphoramidite Ligands Derived from Quinoline (Quinaphos)", Angew. Chem. Int. Ed. 2000, 39(8), 1428-1430.
Frisell et al., "Flavoenzyme Catalysis. Substrate-Competitive Inhibition of D-Amino Acid Oxidase", J. Biol. Chem. 1956, 223, 75-83.
Fu et al., "Design and synthesis of novel bis(l-amino acid) ester prodrugs of 9-[2-(phosphonomethoxy)ethyl]adenine (PMEA) with improved anti-HBV activity", Bioorg. Med. Chem. Lett. 2007, 17(2), 465-470.
Fukuda et al., "Tensidols, New Potentiators of Antifungal Miconazole Activity, Produced by Aspergillus niger FKI-2342", J. Antibiot. 2006, 59(8), 480-485.
Gabbutt et al., "A Facile Synthesis of Some Benzothiopyrano[4,3-b]pyrroles", J. Chem. Res. (S) 1997(3), 102-103.
Gale et al., "Preparation and Reactions of 5-Carbethoxythieno[3,2-b]pyrrole and Some of Its Derivatives", J. Org. Chem. 1964, 29(8), 2160-2165.
Garg et al., "Development of an Enantiodivergent Strategy for the Total Synthesis of (+)- and (−)-Dragmacidin F from a Single Enantiomer of Quinic Acid", J. Am. Chem. Soc. 2005, 127(16), 5970-5978.
Gelas-Mialhe et al., "Photochemical heterocyclization of functionalized dienamines", J. Org. Chem. 1987, 52(24), 5395-5400.
Gelas-Mialhe et al., "Réactivité des N-vinylaziridines fonctionnalisées. Synthèse de dérivés des α,β-déhydro α-amino acides", Can. J. Chem. 1982, 60(22), 2830-2851.
Geraldine et al., "How an increase in the carbon chain length of the ester moiety affects the stability of a homologous series of oxprenolol esters in the presence of biological enzymes", J. Pharm. Sci. 1998, 87(7), 880-885.
Gross et al., "Direct observation of 1-azafulven-6-one and annelated derivatives", J. Chem. Soc., Chem. Commun. 1982(6), 360-361.
Grygorenko et al., "Stereoselective synthesis of 2,4-methanoproline homologues", Tetrahedron Asymmetry 2006, 17(2), 252-258.
Guan et al., "Design and synthesis of aminopropyl tetrahydroindole-based indolin-2-ones as selective and potent inhibitors of Src and Yes tyrosine kinase", Bioorg. Med. Chem. Lett. 2004, 14(1), 187-190.
Haginoya et al., "Synthesis and conformational analysis of a non-amidine factor Xa inhibitor that incorporates 5-methyl-4,5,6,7-tetrahydrothiazolo[5,4-c]pyridine as S4 binding element", J. Med. Chem. 2004, 47(21), 5167-5182.
Haj-Yehia et al., "Pharmacokinetic analysis of the structural requirements for forming "stable" analogues of valpromide", Pharm. Res. 1992, 9(8), 1058-1063.

(56) References Cited

OTHER PUBLICATIONS

Haj-Yehia et al., "Structure-pharmacokinetic relationships in a series of valpromide derivatives with antiepileptic activity", Pharm. Res. 1989, 6(8), 683-689.
Harada et al., "A Simple Preparation of Chloromethyl Esters of the Blocked Amino Acids", Synth. Commun. 1994, 24(6), 767-772.
Harrak et al.,"PtCl2-Catalyzed Cycloisomerizations of 5-En-1-yn-3-ol Systems", J. Am. Chem. Soc. 2004, 126(28), 8656-8657.
Harrison et al., "Cyclopenta[b]indoles. Part 2. Model studies towards the tremorgenic mycotoxins", J. Chem. Soc. Perkin Trans. 1 1995(9), 1131-1136.
Harwood et al., "Tandem generation and intramolecular trapping of chiral stabilised azomethine ylids with alkyne dipolarophiles", Tetrahedron Lett. 1993, 34(41), 6603-6606.
Hauptmann et al., "Beiträge zum Reaktionsverhalten von 2-Aminovinylcarbonylverbindungen", Journal für Praktische Chemie 1972, 314(2), 353-364.
Hauptmann et al., "Eine neue Synthese substituierter Thiophene und Pyrrole", Tetrahedron Lett. 1968, 9(11), 1317-1319.
Hemetsberger et al., "Synthese und Thermolyse von α-Azidoacrylestern", Monatsh. Chem. 1972, 103(1), 194-204.
Hillenweck et al., "Chlorothalonil Biotransformation by Gastrointestinal Microflora: In Vitro Comparative Approach in Rat, Dog, and Human", Pestic. Biochem. Physiol. 1997, 58(1), 34-48.
Hilton et al., "Observations on the reactivity of thiyl radicals derived from 3,6-epidithiodiketopiperazine-2,5-diones and related congeners", Bioorg. Med. Chem. Lett. 2005, 15(9), 2239-2242.
Hoffman, R. V., "Organic Chemistry: An Intermediate Text, Second Edition"; Wiley: Hoboken, 2004; pp. 124 and 138-144.
Holmes et al., "Reactions of N-Benzylthieno[3,2-b]pyrrole. I. Metalation and an Electrophilic Substitution", J. Org. Chem. 1964, 29(8), 2155-2160.
Howarth et al., "Pyrroles and related compounds. Part XXVI. Pyrrole beta-keto-esters", J. Chem. Soc. Perkin Trans. 1 1974, 490-501.
Hu et al., "Synthesis of a Porphyrin with Fused Five- and Seven-membered Exocyclic Rings from a Cross-conjugated Tetracydic Dipyrrole", Synlett 1994(11), 909-910.
Ikegami et al., "Synthesis and pharmacological activity of O-(5-isoxazolyl)-L-serine", Chem. Pharm. Bull. 2000, 48(2), 278-280.
Ilyin et al., "Synthesis of Annelated Azaheterocycles Containing a 5-Carbamoylpyrazin-3-one Fragment by a Modification of the Four-Component Ugi Reaction", Eur. J. Org. Chem. 2005(21), 4670-4679.
Ingram et al., "Investigation of enzyme activity by SERRS using poly-functionalised benzotriazole derivatives as enzyme substrates", Org. Biomol. Chem. 2006, 4(15), 2869-2873.
Inukai et al., "ortho-Disubstituted F-Benzenes. III. Preparation of (F-Benzo)heterocyclic Compounds from F-Benzoic Acid and F-Phenol, and the Reactions of Some Intermediary F-Benzoyl- and F-Phenoxy Compounds", Bull. Chem. Soc. Jpn. 1981, 54(11), 3447-3452.
Iranpoor et al., "A Rapid and Facile Conversion of Primary Amides and Aldoximes to Nitriles and Ketoximes to Amides with Triphenylphosphine and N-Chlorosuccinimide", Synth. Commun. 2002, 32(16), 2535-2541.
Isoherranen et al., "New CNS-active drugs which are second-generation valproic acid: can they lead to the development of a magic bullet?", Curr. Opin. Neurol. 2003, 16(2), 203-211.
Jacob et al., "gamma-Aminobutyric acid esters. 2. Synthesis, brain uptake, and pharmacological properties of lipid esters of gamma-aminobutyric acid", J. Med. Chem. 1985, 28(1), 106-110.
Java et al., "Chimie Organique.—Synthese de selenolo, furo et pyrrolopyrroles", C. R. Acad. Sc. Paris 1975, 281 Serie C (19), 793-795.
Jolicoeur et al., "Pyrrole protection", Tetrahedron 2006, 62(50), 11531-11563.
Katritzky et al., "Efficient Conversion of Carboxylic Acids into N-Acylbenzotriazoles", Synthesis 2003(18), 2795-2798.
Katritzky et al., "Novel Synthesis of Bicycles with Fused Pyrrole, Indole, Oxazole, and Imidazole Rings", J. Org. Chem. 2004, 69(26), 9313-9315.
Katritzky et al., "Regiospecific C-Acylation of Pyrroles and Indoles Using N-Acylbenzotriazoles", J. Org. Chem. 2003, 68(14), 5720-5723.
Katterle et al., "A Heck-Type Coupling for the Synthesis of Novel Bridged Metallochlorin-Fullerene C60 Dyads", European J. Org. Chem. 2006(2), 414-422.
Keener et al., "Synthesis of 6-substituted thieno[3,2-b]pyrroles", J. Org. Chem. 1968, 33(4), 1355-1359.
Kesel, "Synthesis of Novel Test Compounds for Antiviral Chemotherapy of Severe Acute Respiratory Syndrome (SARS)", Curr. Med. Chem. 2005, 12(18), 2095-2162.
Khanna et al., "Evaluation of glycolamide esters of indomethacin as potential cyclooxygenase-2 (COX-2) inhibitors", Bioorg. Med. Chem. 2006, 14(14), 4820-4833.
Kittredge et al., "alpha-Helical Polypeptide Films Grown From Sulfide or Thiol Linkers on Gold Surfaces", Helv. Chim. Acta 2002, 85(3), 788-798.
Kleinspehn et al., "The Synthesis of Some β,β-Dipyrrylpropionic Esters", J. Am. Chem. Soc. 1954, 76(22), 5641-5646.
Koe, "Molecular geometry of inhibitors of the uptake of catecholamines and serotonin in synaptosomal preparations of rat brain", J. Pharmacol. Exp. Ther. 1976, 199(3), 649-661.
Kralovicova et al., "Electrophilic Substitution Reactions of Furo[3,2-b]pyrrole Derivatives", Collect. Czech. Chem. Commun. 1986, 51(1), 106-111.
Krayushkin et al., "Synthesis of Photochromic 1,2-Dihetarylethene Using Regioselective Acylation of Thienopyrroles", Org. Lett. 2002, 4(22), 3879-3881.
Kren et al., "Clustered ergot alkaloids modulate cell-mediated cytotoxicity", Bioorg. Med. Chem. 2002, 10(2), 415-424.
Krutosikova et al., "Addition and Cycloaddition Reactions of Furo[3,2-b]pyrroles and Their Benzo[b] Analogues: An NMR Study of Structure of Products", Collect. Czech. Chem. Commun. 1988, 53(5), 1770-1778.
Krutosikova et al., "Effect of microwave irradiation on reaction of furo[3,2-b]pyrrole and furo[2,3-b]pyrrole-2-carbaldehydes with some active methylene compounds", ARKIVOC 2000(iii), 409-420.
Krutosikova et al., "Reactions of Ethyl 2-(4-chlorophenyl)-4H-furo[3,2-b]pyrrole-5-carboxylate", Collect. Czech. Chem. Commun. 1980, 45(III), 2949-2957.
Krutosikova et al., "Reactions of furo[3,2-b]pyrroles and their benzo[b] analogues", Chem. Papers 1988, 42(1), 89-95.
Krutosikova et al., "Reactions of Methyl 2-Formylfuro[3,2-b]pyrrole-5-carboxylates", Chem. Papers 1996, 50(2), 72-76.
Krutosikova et al., "Substituted 4-Benzylfuro[3,2-b]pyrroles", Collect. Czech. Chem. Commun. 1992, 57(5), 1487-1494.
Krutosikova et al., "Substituted Vinyl Azides in the Synthesis of Condensed Nitrogen Heterocycles", Chem. Papers 1994, 48(4), 268-273.
Krutosikova et al., "Synthesis and Reactions of 4-Oxiranylmethylfuro[3,2-b]pyrroles and Their Benzo Derivatives", Chemistry of Heterocyclic Compounds 2001, 37(12), 1511-1517.
Krutosikova et al., "Synthesis and Reactions of 8-Hydrazinofuro[2',3':4,5]pyrrolo-[1,2-d][1,2,4]triazines", Collect. Czech. Chem. Commun. 1997, 62(10), 1612-1622.
Krutosikova et al., "Synthesis and Reactions of Furo[2,3-b]pyrroles", Molecules 1997, 2(4), 69-79.
Krutosikova et al., "Synthesis and Reactions of Furocondensed Derivatives", Collect. Czech. Chem. Commun. 1984, 49(1), 65-70.
Krutosikova et al., "Synthesis and Reactions of Substituted Furo[3,2-b]pyrrole Derivatives", Collect. Czech. Chem. Commun. 1981, 46, 2564-2572.
Kukolja et al., "Orally absorbable cephalosporin antibiotics. 2. Structure-activity studies of bicyclic glycine derivatives of 7-aminodeacetoxycephalosporanic acid", J. Med. Chem. 1985, 28(12), 1896-1903.
Kumar et al., "Synthesis and biological evaluation of thiophene [3,2-b] pyrrole derivatives as potential anti-inflammatory agents", Bioorg. Med. Chem. 2004, 12(5), 1221-1230.
Lamboley et al., "Synthesis and Properties of Conformationally Constrained Analogues of Floral-Type Odorants", Helv. Chim. Acta 2004, 87(7), 1767-1793.

(56) References Cited

OTHER PUBLICATIONS

Lash et al., "Influence of carbocyclic rings on porphyrin cyclizations: synthesis of geochemically significant cycloalkanoporphyrins", Energy Fuels 1990, 4(6), 668-674.

Lash et al., "Normal and Abnormal Heme Biosynthesis. 2.1 Synthesis and Metabolism of Type-III Pentacarboxylic Porphyrinogens: Further Experimental Evidence for the Enzymic Clockwise Decarboxylation of Uroporphyrinogen-III", J. Org. Chem. 1999, 64(2), 478-487.

Lash et al., "Porphyrins with exocyclic rings. 1. Chemistry of 4,5,6,7-tetrahydro-1H-indoles: synthesis of acetoxy derivatives, dihydroindoles, and novel porphyrins with four exocyclic rings", J. Org. Chem. 1992, 57(18), 4809-4820.

Lash et al., "Porphyrins with exocyclic rings. Part 3. A reassessment on the utility of cyclopenta[b]pyrroles in the synthesis of porphyrin molecular fossils. Preparation of three type II porphyrins related to deoxophylloerythroetioporphyrin (DPEP)", Tetrahedron 1993, 49(20), 4159-4172.

Lash et al., "Recent advances in the synthesis of porphyrins with five-membered exocyclic rings", Energy Fuels 1993, 7(2), 172-178.

Law et al., "The synthesis and chemistry of azolenines. Part 2. A general synthesis of pyrrole-2-carboxylic acid derivatives by the reaction of 2H-azirines with enamines, and the crystal and molecular structure of ethyl 3-phenyl-4,5,6,7-tetrahydroindole-2-carboxylate", J. Chem. Soc. Perkin Trans. 1 1984, 111-118.

Layzer, R. B., "Section Five—Degenerative Diseases of the Nervous System" in "Cecil Textbook of Medicine", 20th ed., vol. 2; W.B. Saunders Co.: Philadelphia, 1996; pp. 2050-2057.

Lee at al., "Amphiphilic amino acid copolymers as stabilizers for the preparation of nanocrystal dispersion", Eur. J. Pharm. Sci. 2005, 24(5), 441-449.

Lee et al., "An Effective and Convenient Esterification of Cephalosporin Derivatives by Using Quarternary Ammonium Salts as Catalysts", Synth. Commun. 1998, 28(23), 4345-4354.

Lerche et al., "Umsetzungen mit Monohydrazonen von Dicarbonylverbindungen, V: Umsetzungen von Hydrazonoethylidenammonium-Salzen und Hydrazonoaldehyden mit Grignard-Verbindungen", Chem. Ber. 1978, 111(3), 1195-1209.

Li et al., "Synthesis of deoxophylloerythroetioporphyrin (DPEP) and three ring homologs by an improved b-bilene methodology", Tetrahedron Lett. 1998, 39(47), 8571-8574.

Liederer et al., "Enzymes involved in the bioconversion of ester-based prodrugs", J. Pharm. Sci. 2006, 95(6), 1177-1195.

Liederer et al., "Stability of oxymethyl-modified coumarinic acid cyclic prodrugs of diastereomeric opioid peptides in biological media from various animal species including human", J. Pharm. Sci. 2005, 94(10), 2198-2206.

Liu et al., "Facile construction of the pentacyclic framework of subincanadine B. Synthesis of 20-deethylenylated subincanadine B and 19,20-dihydrosubincanadine B", Org. Lett. 2006, 8(1), 115-118.

Liu et al., "Indole-5-phenylcarbamate derivatives as human non-pancreatic secretory phospholipase A2 inhibitor", Bioorg. Med. Chem. Lett. 2005, 15(20), 4540-4542.

Liu et al., "The synthesis of camostat intermediate", Huaxue Shiji, 2006, 28(6), 371-372.

Ma et al., "Hydrolysis of angiotensin II receptor blocker prodrug olmesartan medoxomil by human serum albumin and identification of its catalytic active sites", Drug Metab. Dispos. 2005, 33(12), 1911-1919.

Majumdar et al., "α-(1H-Imidazol-1-yl)alkyl (IMIDA) carboxylic acid esters as prodrugs of carboxylic acid containing drugs", Tetrahedron Lett. 2007, 48(26), 4609-4611.

Mal et al., "Regioselective synthesis of 1-hydroxycarbazoles via anionic [4+2] cycloaddition of furoindolones: a short synthesis of murrayafoline-A", Tetrahedron Lett. 2006, 47(7), 1071-1075.

Mamber et al., "Tubulin polymerization by paclitaxel (taxol) phosphate prodrugs after metabolic activation with alkaline phosphatase", J. Pharmacol. Exp. Ther. 1995, 274(2), 877-883.

Mandel et al., "Neuroprotective Strategies in Parkinson's Disease: An Update on Progress", CNS Drugs 2003, 17(10), 729-762.

Marrel et al., "L-Dopa esters as potential prodrugs 1. Physicochemical properties", Eur. J. Med. Chem. 1985, 20(5), 459-465.

Marrel et al., "L-Dopa esters as potential prodrugs 2. Chemical and enzymatic-hydrolysis", Eur. J. Med. Chem. 1985, 20(5), 467-470.

Martin et al., "Das Diazo-chinon von PQQ als mögliches Reagenz für die Kartierung von Chinoproteinen mittels Photoaffinitätsmarkierung", Helv. Chim. Acta 1993, 76(4), 1674-1677.

McConnaughie et al., "Novel Acridine-Triazenes as Prototype Combilexins: Synthesis, DNA Binding, and Biological Activity" J. Med. Chem. 1995, 38(18), 3488-3501.

McLaughlin, "Suzuki-Miyaura Cross-Coupling of Benzylic Phosphates with Arylboronic Acids", Org. Lett. 2005, 7(22), 4875-4878.

Medforth et al., "Nonplanar distortion modes for highly substituted porphyrins", J. Am. Chem. Soc. 1992, 114(25), 9859-9869.

Mergen et al., "Antiepileptic activity of 1,3-dihexadecanoylamino-2-valproyl-propan-2-ol, a prodrug of valproic acid endowed with a tropism for the central nervous system", J. Pharm. Pharmacol. 1991, 43(11), 815-816.

Merisor et al., "Synthesis of New Derivatives in the Izoxazole Class with Potential Antimicrobial Activity", Rev. Chim. (Bucharest, Romania) 2001, 52(4), 206-209.

Mikhaleva et al., "Expedient synthesis of 1-vinylpyrrole-2-carbaldehydes", Tetrahedron Lett. 2006, 47(22), 3693-3696.

Miki et al., "Synthesis of 3-Methoxyellipticine and Ellipticine by Friedel-Crafts Reaction of Indole-2,3-dicarboxylic Anhydride and Selective Demethylation", Heterocycles 2005, 65(11), 2693-2703.

Milkiewicz et al., "Synthesis of a novel series of tetra-substituted furan[3,2-b]pyrroles", Tetrahedron Lett. 2003, 44(22), 4257-4260.

Mishra et al., "Synthesis, characterization and pharmacological evaluation of amide prodrugs of ketorolac", Eur. J. Med. Chem. 2008, 43(11), 2464-2472.

Mokhallalati et al., "A single-pot synthesis of 1,1,2-trisubstituted 1,2-dihydronaphthalenes in high enantiomeric purity", Tetrahedron Lett. 1994, 35(25), 4267-4270.

Montero et al., "Solid-Phase Combinatorial Synthesis of Peptide-Biphenyl Hybrids as Calpain Inhibitors", Org. Lett. 2004, 6(22), 4089-4092.

Morgan et al., "Synthesis of hydrocarbon-strapped porphyrins containing quinone and phenolic groups", J. Org. Chem. 1987, 52(24), 5364-5374.

Morissette et al., "High-throughput crystallization: polymorphs, salts, co-crystals and solvates of pharmaceutical solids", Adv. Drug Deliv. Rev. 2004, 56(3), 275-300.

Mork et al., "Stereoselective enzymatic hydrolysis of various ester prodrugs of ibuprofen and flurbiprofen in human plasma", Pharm. Res. 1992, 9(4), 492-496.

Muchowski et al., "Protecting groups for the pyrrole and indole nitrogen atom. The [2-(trimethylsilyl)ethoxy]methyl moiety. Lithiation of 1-[[2-(trimethylsilyl)ethoxy]methyl]pyrrole", J. Org. Chem. 1984, 49(1), 203-205.

Murakami et al., "The Friedel-Crafts Acylation of Ethyl Pyrrole-2-carboxylate. Scope, Limitations, and Application to Synthesis of 7-Substituted Indoles", Heterocycles 1988, 27(8), 1855-1860.

Nacci et al., "Polycondensed Heterocycles. I. Synthesis of 11-Oxo-5H,11H-pyrrolo[2,1-c][1,4]benzothiazepine, Derivative of a Novel Ring System", J. Heterocycl. Chem. 1985, 22(2), 259-263.

Nacci et al., "Polycondensed Heterocycles. II. A New Preparative Route to 11-Oxo-5H,11H-pyrrolo[2,1-c][1,4]benzothiazepine", J. Heterocycl. Chem. 1986, 23(3), 769-773.

Nagarathnam et al., "Design and Synthesis of Novel α1a Adrenoceptor-Selective Dihydropyridine Antagonists for the Treatment of Benign Prostatic Hyperplasia", J. Med. Chem. 1998, 41(26), 5320-5333.

Nagel et al., "Enantioselektive Katalyse, 4. Synthese N-substituierter (R,R)-3,4-Bis(diphenylphosphino)-pyrrolidine und Anwendung ihrer Rhodiumkomplexe zur asymmetrischen Hydrierung von α-(Acylamino)acrylsäure-Derivaten", Chem. Ber. 1986, 119(11), 3326-3343.

Narasimhan et al., "A QSAR approach for the prediction of stability of benzoglycolamide ester prodrugs", Chem. Pharm. Bull. 2006, 54(8), 1067-1071.

(56) References Cited

OTHER PUBLICATIONS

Nelson et al., "Stereoselective Synthesis of a Potent Thrombin Inhibitor by a Novel P2-P3 Lactone Ring Opening", J. Org. Chem. 2004, 69(11), 3620-3627.
New et al., "The thieno[3,2-c]pyridine and furo[3,2-c]pyridine rings: new pharmacophores with potential antipsychotic activity", J. Med. Chem. 1989, 32(6), 1147-1156.
Newman-Evans et al., "The influence of intramolecular dynamics on branching ratios in thermal rearrangements", J. Org. Chem. 1990, 55(2), 695-711.
Nielsen et al., "Bioreversible quaternary N-acyloxymethyl derivatives of the tertiary amines bupivacaine and lidocaine—synthesis, aqueous solubility and stability in buffer, human plasma and simulated intestinal fluid", Eur. J. Pharm. Sci. 2005, 24(5), 433-440.
Nielsen et al., "Glycolamide esters as biolabile prodrugs of carboxylic acid agents: Synthesis, stability, bioconversion, and physicochemical properties", J. Pharm. Sci. 1988, 77(4), 285-298.
Nudelman et al., "Novel anticancer prodrugs of butyric acid. 2.", J. Med. Chem. 1992, 35(4), 687-694.
Nudelman et al., "The role of intracellularly released formaldehyde and butyric acid in the anticancer activity of acyloxyalkyl esters." J. Med. Chem. 2005, 48(4), 1042-1054.
Ogawa et al., "Preparation of oxygen-bridged aza[15]- and aza[17]annulene dicarboxylates by intramolecular azide cyclization", Tetrahedron Lett. 1988, 29(2), 219-222.
Ojida et al., "Highly Enantioselective Reformatsky Reaction of Ketones: Chelation-Assisted Enantioface Discrimination", Org. Lett. 2002, 4(18), 3051-3054.
Ouyang et al., "Steric hindrance is a key factor in the coupling reaction of (acyloxy) alkyl-α-halides with phenols to make a new promoiety for prodrugs", Tetrahedron Lett. 2002, 43(4), 577-579.
Paine et al., "Regioselectivity of pyrrole synthesis from diethyl aminomalonate and 1,3-diketones: further observations", J. Org. Chem. 1987, 52(18), 3986-3993.
Parikh et al., "The Use of Amino Acid Oxidases for the Small-scale Preparation of the Optical Isomers of Amino Acids", J. Am. Chem. Soc. 1958, 80(4), 953-958.
Paxéus et al., "Screening for non-regulated organic compounds in municipal wastewater in Göteborg, Sweden", Water Sci. Technol. 1996, 33(6), 9-15.
Pérez-Balderas et al., "Synthesis of multivalent neoglycoconjugates by 1,3 dipolar cycloaddition of nitrile oxides and alkynes and evaluation of their lectin-binding affinities", Tetrahedron 2005, 61(39), 9338-9348.
Pfeiffer et al., "Synthesen and Eigenschaften von Pyrrolindigo-Verbindungen", Liebigs Ann. Chem. 1980(4), 564-589.
Poszavacz et al., "New Synthesis of Naratriptan", Heterocycles 2006, 68(4), 713-719.
Puterova et al., "Reaction of Substituted Furan-2-carboxaldehydes and Furo[b]pyrrole Type Aldehydes with Hippuric Acid", Molecules 2004, 9(1), 11-21.
Puterova et al., "Reactions of Substituted Furan-2-carboxaldehydes and Furo[b]pyrrole Type Aldehydes with Benzothiazolium Salts", Molecules 2004, 9(4), 241-255.
Quizon-Colquitt et al., "Porphyrins with exocyclic rings. Part 4. An improved one step synthesis of cyclopenta[b]pyrroles", J. Heterocycl. Chem. 1993, 30(2), 477-482.
Rautio et al., "Synthesis and in Vitro Evaluation of Novel Morpholinyl- and Methylpiperazinylacyloxyalkyl Prodrugs of 2-(6-Methoxy-2-naphthyl)propionic Acid (Naproxen) for Topical Drug Delivery", J. Med. Chem. 2000, 43(8), 1489-1494.
Rodriguez et al., "Conformational and molecular study of the 4-(2-carboxyethyl)-1,2,3,4-tetrahydrocyclopent[b]indole", Tetrahedron 1985, 41(18), 3813-3823.
Romanova et al., "DC Polarographic and UV Spectrometric Studies of Substituted Furo[3,2-b]- and Furo[2,3-b]pyrroles", Collect. Czech. Chem. Commun. 2001, 66(11), 1615-1622.
Rosati et al., "Cephalosporins to carbapenems: 1-oxygenated carbapenems and carbapenams.", J. Med. Chem. 1990, 33(1), 291-297.

Rose et al., "Preclinical antitumor activity of water-soluble paclitaxel derivatives", Cancer Chemother. Pharmacol. 1997, 39(6), 486-492.
Salim et al., "Pharmacokinetic analysis of esteric prodrugs of valproic acid", Pharm. Res. 1990, 7(9), S222.
Sambasivarao et al., "Synthetic approach to pentaleno[2,1-b:5,4-b']diindoles", J. Org. Chem. 1990, 55(12), 3858-3866.
Sandham et al., "Synthesis and biological properties of novel glucocorticoid androstene C-17 furoate esters", Bioorg. Med. Chem. 2004, 12(19), 5213-5224.
Sandler et al., "Organic Functional Group Preparations", vol. 3; Academic Press: New York, 1972; pp. 372-381.
Satake et al., "The Reaction of Electron Excess Aromatic Heterocycle, 1,4-Dihydropyrrolo[3,2-b]pyrrole and Some Related Compounds with Chlorosulfonyl Isocyanate (CSI)", Heterocycles 1996, 43(11), 2361-2365.
Scott et al., "Preparation and Reductive Cydization of Some Carbon-Alkylated Derivatives of Ethyl 3-Nitro-2-thienylpyruvate", J. Org. Chem. 1964, 29(8), 2165-2168.
Severin et al., "Umsetzungen von Ketonen mit azavinylogen Säureamiden", Chem. Ber. 1975, 108(5), 1756-1767.
Sewald et al., "Synthesis of homochiral camphor annulated pyrrole derivatives", Tetrahedron Asymmetry 1996, 7(5), 1269-1272.
Sha et al., "Synthesis of 2,4-Dihydropyrrolo[3,4-b]pyrroles and 4,6-Dihydro-2H-dipyrrolo[3,4-b:3',4'-d]pyrroles", Heterocycles 1990, 31(4), 603-609.
Shaaya et al., "Anhydride prodrugs for nonsteroidal anti-inflammatory drugs", Pharm. Res. 2003, 20(2), 205-211.
Shek, "Chemical delivery systems and prodrugs of anticonvulsive drugs", Adv. Drug Deliv. Rev. 1994, 14(2-3), 227-241.
Shvedov et al., "Monoarylhydrazones of di- and tricarbonyl compounds in the Knorr synthesis of pyrroles", Khimiya Geterotsiklicheskikh Soedinenii 1972(3), 342-344. [translation].
Silvestri et al., "Simple, short peptide derivatives of a sulfonylindolecarboxamide (L-737,126) active in vitro against HIV-1 wild type and variants carrying non-nucleoside reverse transcriptase inhibitor resistance mutations.", J. Med. Chem. 2004, 47(15), 3892-3896.
Sivy et al., "Structure of a furo[3,2-b]pyrrole derivative", Acta Crystallogr. 1988, C44(11), 2032-2033.
Skolnick et al., "Antidepressant-like actions of DOV 21,947: a "triple" reuptake inhibitor", Eur. J. Pharmacol. 2003, 461(2-3), 99-104.
Slawik et al., "Lipophilicity of a series of 1,2-benzisothiazol-3(2H)-ones determined by reversed-phase thin-layer chromatography", J. Chromatogr. A 2002, 952(1-2), 295-299.
Sleath et al., "Synthesis of 7,9-didecarboxymethoxatin (4,5-dihydro-4,5-dioxo-1H-pyrrolo[2,3-f]quinoline-2-carboxylic acid) and comparison of its chemical properties with those of methoxatin and analogous o-quinones. Model studies directed toward the action of PQQ requiring bacterial oxidoreductases and mammalian plasma amine oxidase", J. Am. Chem. Soc. 1985, 107(11), 3328-3338.
Sleziak et al., "Furo[2,3-b]pyrrole Derivatives. Syntheses and Reactions in the Furan and Pyrrole Ring", Pol. J. Chem. 2000, 74(2), 207-217.
Sleziak et al., "Reactions of Furo[2,3-b]pyrrole and Furo[3,2-b]pyrrole-Type Aldehydes", Collect. Czech. Chem. Commun. 1999, 64(7), 1135-1146.
Smith et al., "Deacylation and deformylation of pyrroles", J. Org. Chem. 1983, 48(24), 4779-4781.
Snyder et al., "Synthesis of the Thieno [3,2-b]pyrrole System", J. Am. Chem. Soc. 1957, 79(10), 2556-2559.
Sohma et al., "Controlled Drug Release: Design and Application of New Water-soluble Prodrugs" in "Peptide Science 2001"; Aoyagi, H., Ed.; The Japanese Peptide Society, 2002; pp. 249-252.
Sorotskaya et al., "The Series of Substituted Butanolides and Butenolides. IV. 4-Arylidene(heteroarylidene)-2-butenolides", Zhurnal Organicheskoi Khimii 1989, 25(1), 175-182. [translation].
Soth et al., "Recherches en série hétérocyclique. XXIX. Sur des voies d'accès à des thiéno, sélénolo, furo et pyrrolopyrroles", Can. J. Chem. 1978, 56(10), 1429-1434.
Sparey et al., "The discovery of fused pyrrole carboxylic acids as novel, potent d-amino acid oxidase (DAO) inhibitors", Bioorg. Med. Chem. Lett. 2008, 18(11), 3386-3391.

(56) References Cited

OTHER PUBLICATIONS

STN—Registry file (RN 132857-67-1, RN 109252-80-4, RN 93144-92-4, RN 92321-04-5, RN 83957-46-4, RN 83957-32-8, RN 69740-90-5, RN 69640-94-4, RN 69640-90-0, RN 69640-89-7, RN 69640-88-6, RN 69640-87-5, RN 69640-86-4, RN 69640-85-3, RN 69640-84-2, RN 69640-83-1, RN 69640-82-0, RN 69640-80-8, RN 67313-00-2, RN 67312-99-6, RN 67312-98-5, RN 60068-34-0, RN 60068-33-9, RN 60068-32-8, RN 58379-13-8, RN 57955-60-9, RN 57955-59-6, RN 51074-73-8, RN 51074-72-7, RN 51074-71-6, RN 51074-69-2, RN 36373-65-6, RN 36373-63-4, RN 34779-69-6, RN 34779-67-4, RN 33317-36-1, RN 33317-33-8).
STN Registry File No. 67268-37-5. Registry File. Retrieved from STN Mar. 17, 2008. One page.
Stuart et al., "Cobalt-mediated Alkylation of Siloxy Furans", Heterocycles 1991, 32(5), 949-963.
Svahn et al., "Tranexamic acid derivatives with enhanced absorption", J. Med. Chem. 1986, 29(4), 448-453.
Takahashi et al., "Asymmetric α-Substituted Phenethylamines. I. Synthesis of Optically Pure 1-Aryl-N-(2'-hydroxy-1'-isopropylethyl)-2-phenylethylamines", Chem. Pharm. Bull. 1982, 30(9), 3160-3166.
Tammara et al., "Morpholinoalkyl ester prodrugs of diclofenac: synthesis, in vitro and in vivo evaluation", J. Pharm. Sci. 1994, 83(5), 644-648.
Treibs et al., "Über einige Pyrrolderivate mit angegliedertem isocyclischem Ring. Bz-Tetrahydrindole und Cyclopentenopyrrole", Justus Liebigs Ann. Chem. 1935, 517, 152-169.
Trost et al., "Palladium-Catalyzed Enantioselective C-3 Allylation of 3-Substituted-1H-Indoles Using Trialkylboranes", J. Am. Chem. Soc. 2006, 128(19), 6314-6315.
Ueda et al., "Novel water soluble phosphate prodrugs of taxol® possessing in vivo antitumor activity", Bioorg. Med. Chem. Lett. 1993, 3(8), 1761-1766.
Ueda et al., "Novel, water-soluble phosphate derivatives of 2'-ethoxy carbonylpaclitaxel as potential prodrugs of paclitaxel: Synthesis and antitumor evaluation", Bioorg. Med. Chem. Lett. 1995, 5(3), 247-252.
Urbach et al., "Eine einfache diastereoselektive Synthese von (1SR,3SR,5SR)-2-Azabicyclo [3.3.0] octan-3-carbonsäure", Tetrahedron Lett. 1985, 26(15), 1839-1842.
van Herk et al., "Pyrazole Derivatives as Partial Agonists for the Nicotinic Acid Receptor", J. Med. Chem. 2003, 46(18), 3945-3951.
Vicini et al., "Biological studies on 1,2-benzisothiazole derivatives. I. Evaluation of antibacterial, antifungal and DNA-damaging activity", Farmaco 1989, 44(5), 511-517.
Vicini et al., "Sintesi e proprieta antiflogistiche antipiretiche ed analgesiche di 5-(1,2-benzisotiazolil)tetrazoli", Farmaco Sci. 1986, 41(2), 111-118.
Vicini et al., "Sintesi e proprieta antiflogistiche antipiretiche ed analgesiche di acidi 5-benzisotiazolilalcanoici e di loro derivati funzionali", Farmaco Sci. 1984, 39(10), 817-829.
Vippagunta et al., "Crystalline solids", Adv. Drug Deliv. Rev. 2001, 48(1), 3-26.
Viswanathan et al., "Free Radical-Mediated Aryl Amination and Its Use in a Convergent [3+2] Strategy for Enantioselective Indoline α-Amino Acid Synthesis", J. Am. Chem. Soc. 2003, 125(1), 163-168.
Vitali et al., "Ricerche nella classe dei fitocidi 3-benzisotiazolacetici", Farmaco Sci. 1973, 28(1), 8-18.
Vogel et al., "Cycloalkano-2H-pyrrole als stabile Zwischenstufen bei der Umwandlung von β-Cycloalkenyl-α-azidoacrylestern in Cycloalkano-1H-pyrrole", Angew. Chem. 1993, 105(7), 1116-1117.
Vogel et al., "Cycloalkano-2H-pyrrole as a Stable Intermediate in the Conversion of beta-Cycloalkenyl-alpha-azidoacrylates to Cycloalkano-1H pyrroles", Angew. Chem. Int. Ed. Engl. 1993, 32(7), 1051-1052. [translation of Angew. Chem. 1993, 105(7), 1116-1117.]
Wang et al., "Synthesis of ethyl cyclopenteno- or cyclohexeno[b]pyrrolyl-2-carboxylates", Youji Huaxue 1997, 17(6), 524-528.
Watanabe et al., "Enantioselective addition of chirally modified allylboranes to N-(trimethylsilyl)benzaldehyde imine", Tetrahedron Asymmetry 1995, 6(7), 1531-1534.

Welch et al., "Improved Syntheses of [3,2-b]- and [2,3-b]-fused Selenolo- and Thienopyrroles, and of Furo[3,2-b]pyrrole", Heterocycl. Comm. 1999, 5(4), 305-310.
Wen et al., "Cell differentiation enhancement by hydrophilic derivatives of 4,8-Dihydrobenzo[1,2-b:5,4-b']dithiophene-4,8-diones in HL-60 leukemia cells", Bioorg. Med. Chem. Lett. 2007, 17(10), 2908-2912.
Wensbo et al., "Indole-3-Acetic Acids and Hetero Analogues by One Pot Synthesis including Heck Cyclisation", Tetrahedron 1995, 51(37), 10323-10342.
Wensbo et al., "Indole-3-pyruvic acid oxime ethers and thieno analogues by Heck cyclisation. Application to the synthesis of thia-tryptophans", Tetrahedron 1996, 52(47), 14975-14988.
Wernly-Chung et al., "Structure-reactivity relationships in the chemical hydrolysis of prodrug esters of nicotinic acid", Int. J. Pharm. 1990, 63(2), 129-134.
Wright et al., "Derivatives of 11-(1-piperazinyl)-5H-pyrrolo[2,1-c][1,4]benzodiazepine as central nervous system agents", J. Med. Chem. 1980, 23(4), 462-465.
Xue et al., "An Efficient Synthesis of Glycoprotein IIb/IIIa Inhibitor DMP728. A Novel Synthesis of N.alpha.-Methylarginine-Containing Peptide", J. Org. Chem. 1995, 60(4), 946-952.
Yarovenko et al., "Regioselective acylation of methyl 2-methyl-4H-thieno[3,2-b]pyrrole-5-carboxylate", Russ. Chem. Bull., Int. Ed., 2003, 52(2), 451-456.
Yasuhara et al., "Prodrugs of 3-(3,4-dichlorobenzyloxy)-2-amino-6-fluorobicyclo[3.1.0]hexane-2,6-dicarboxylic acid (MGS0039): A potent and orally active group II mGluR antagonist with antidepressant-like potential", Bioorg. Med. Chem. 2006, 14(12), 4193-4207.
Yevich et al., "Synthesis and biological evaluation of 1-(1,2-benzisothiazol-3-yl)- and (1,2-benzisoxazol-3-yl)piperazine derivatives as potential antipsychotic agents", J. Med. Chem. 1986, 29(3), 359-369.
Yu et al., "The regiospecific C-4 lithiation of 2-(tert-butyldimethylsilyl)-3-furoic acid", J. Chem. Soc., Perkin Trans. 1, 1991(10), 2600-2601.
Yudina et al., "Synthesis and alkylation of indolo[3,2-b]carbazoles", Tetrahedron 2003, 59(8), 1265-1275.
Zani et al., "Biological studies on 1,2-benzisothiazole derivatives. VI. Antimicrobial activity of 1,2-benzisothiazole and 1,2-benzisothiazolin-3-one derivatives and of some corresponding 1,2-benzisoxazoles", Farmaco 1996, 51(11), 707-713.
Zhang et al., "Synthesize the china 3-pyridyl ester analogs of anaddicted analgesic Epibatidine", Journal of Shangqiu Teachers College (Shangqiu Shifan Xueyuan Xuebao) 2004, 20(5), 90-94.
Zhang et al., "Total synthesis of the porphyrin mineral abelsonite and related petroporphyrins with five-membered exocyclic rings", Tetrahedron Lett. 2003, 44(39), 7253-7256.
Zinoune et al., "Aminoalkylation of Aldehydes with Glyoxal N,N-Dimethlmonohydrazone Yields Stable 4-Substituted Pyrrolin-3-ones", Heterocycles 1989, 28(2), 1077-1084.
Zong et al., "A new and efficient synthetic route toward 3,4-alkylenedioxypyrrole (XDOP) derivatives via Mitsunobu chemistry", Tetrahedron Lett. 2006, 47(21), 3521-3523.
Eliel, Ernest L., "Infelicitous Stereochemical Nomenclature," Chirality, 9:428-430 (1997).
Arya, et al., "Synthesis of New Heterocycles: Part XV. Synthesis of Novel Cyclic and Acyclic Sulfamides," Indian Journal of Chemistry, Section B: Organic Chemistry Including Medicinal Chemistry, 14B(10):766-769 (1976) Abstract only.
Aboul-Enein, et al., "Synthesis and Antiemetic Profile of N-[1-[(diethylamino)methyl]cyclohexyl]amides," Scientia Pharmaceutica, 58(3):273-80 (1990) Abstract only.
Hori, Mikio, "Syntheses of Analgesics. XIV. Aminocyclohexane Derivatives. 8." Yakugaku Zasshi, 78:11-14 (1958) Abstract only (ISSN: 0031-6903).
Shirai, Hideaki, "Reduction of 1-(m-methoxyphenyl)-4-oxocycloalkanecarbonitriles with Lithium Aluminum Hydride," Nagoya-shiritsu Daigaku Yakugakubu Kenkyu Nenpo, 17:33-7 (1969) Abstract only.

(56) References Cited

OTHER PUBLICATIONS

Shirai, Hideaki, Synthesis of spiro[4-hydroxycyclohexane-1,4,2',3'-dihydro-6'-methoxy-1'-substituted-2'methyl-1'H-isoquinoline], *Chemical & Pharmaceutical Bulletin*, 20(1):41-46 (1972) Abstract only.

Miao, et al., "Benzamide Derivatives as Blockers of Kv1.3 Ion Channel," *Bioorganic & Medicinal Chemistry Letters*, 13(6):1161-1164 (2003).

Dorwald, F. Saragosa, "Side Reactions in Organic Synthesis," *Wiley: VCH, Weinheim*, p. IX of Preface, p. 41 (2005).

"Borane-tetrahydrofuran Complex (BTHF)," *Product Bulletin BASF*, pp. 1-14 (2002).

Yardley, et al., "2-Phenyl-2-(1-hydroxycycloalkyl)ethylamine Derivatives: Synthesis and Antidepressant Activity," *Journal of Medicinal Chemistry*, 33:2899-2905 (1990).

Meltzer, et al., "The Synthesis of Bivalent 2β-carbonnethoxy-3β-(3,4-dichlorophenyl)-8-heterobicyclo[3.2.1]octanes as Probes for Proximal Binding Sites on the Dopamine and Serotonin Transporters," *Bioorganic and Medicinal Chemistry*, 16:1832-1841 (2008).

Kuo, et al., "G-protein Coupled Receptors: SAR Analyses of Neurotransmitters and Antagonists," *Journal of Clinical Pharmacy and Therapeutics*, 29:279-298 (2004).

Chen, et al., "Studies on the SAR and Pharmacophore of Milnacipran Derivatives as Monoamine Transporter Inhibitors," *Bioorganic & Medicinal Chemistry Letters*, 18:1346-1349 (2008).

Martin, et al., "Do Structurally Similar Molecules Have Similar Biological Activity?" *Journal of Medicinal Chemistry*, 45:4350-4358 (2002).

West, Anthony R., "Solid State Chemistry and its Applications," Wiley, New York, pp. 358 and 365 (1988).

\* cited by examiner

CYCLOALKYLAMINES AS MONOAMINE REUPTAKE INHIBITORS

CROSS REFERENCE TO RELATED APPLICATIONS

This application is a continuation of U.S. patent application Ser. No. 11/649,927, filed Jan. 5, 2007, which claims priority under 35 U.S.C. 119(e) from U.S. Provisional Patent Application No. 60/756,550, filed Jan. 6, 2006, the disclosures of all of which are hereby incorporated by reference in their entirety for all purposes.

FIELD OF THE INVENTION

The invention relates to compounds and compositions for the treatment of central nervous system (CNS) disorders.

BACKGROUND OF THE INVENTION

Psychiatric disorders are pathological conditions of the brain characterized by identifiable symptoms that result in abnormalities in cognition, emotion, mood, or affect. These disorders may vary in severity of symptoms, duration, and functional impairment. Psychiatric disorders afflict millions of people worldwide resulting in tremendous human suffering and economic burden due to lost productivity and dependent care.

Over the past several decades, the use of pharmacological agents to treat psychiatric disorders has greatly increased, largely due to research advances in both neuroscience and molecular biology. In addition, chemists have become increasingly sophisticated at creating chemical compounds that are more effective therapeutic agents with fewer side effects, targeted to correct the biochemical alterations that accompany mental disorders.

Yet, despite the many advances that have occurred, many psychiatric diseases remain untreated or inadequately treated with current pharmaceutical agents. In addition, many of the current agents interact with molecular targets not involved with the psychiatric disease. This indiscriminate binding can result in side effects that can greatly influence the overall outcome of therapy. In some cases the side effects are so severe that discontinuation of therapy is required.

Depression is an affective disorder, the pathogenesis of which cannot be explained by any single cause or theory. It is characterized by a persistently low mood or diminished interests in one's surroundings, accompanied by at least one of the following symptoms: reduced energy and motivation, difficulty concentrating, altered sleep and appetite, and at times, suicidal ideation (American Psychiatric Association: *Diagnostic and Statistical Manual of Mental Disorders*, ed. 4. Washington, American Psychiatric Association, 1994). Major depression is associated with high rates of morbidity and mortality, with suicide rates of 10-25% (Kaplan H I, Sadock B J (eds): *Synopsis of Psychiatry*. Baltimore, Williams & Wilkins, 1998, p. 866). The compounds of the invention may also be used to reduce fatigue commonly associated with depression (see, for example, "Bupropion augmentation in the treatment of chronic fatigue syndrome with coexistent major depression episode" Schonfeldt-Lecuona et al., *Pharmacopsychiatry* 39(4):152-4, 2006; "Dysthymia: clinical picture, extent of overlap with chronic fatigue syndrome, neuropharmacological considerations, and new therapeutic vistas" Brunello et al., *J. Affect. Disord.* 52(1-3):275-90, 1999; "Chronic fatigue syndrome and seasonal affective disorder: comorbidity, diagnostic overlap, and implications for treatment" Terman et al., *Am. J. Med.* 105(3A):115S-124S, 1998.).

Depression is believed to result from dysfunction in the noradrenergic or serotonergic systems, more specifically, from a deficiency of certain neurotransmitters (NTs) at functionally important adrenergic or serotonergic receptors.

Neurotransmitters produce their effects as a consequence of interactions with specific receptors. Neurotransmitters, including norepinephrine (NE) and/or serotonin (5-hydroxytryptamine, or 5-HT), are synthesized in brain neurons and stored in vesicles. Upon a nerve impulse, NTs are released into the synaptic cleft, where they interact with various postsynaptic receptors. Regional deficiencies in the synaptic levels of 5-HT and/or NE are believed to be involved in the etiology of depression, wakefulness, and attention.

Norepinephrine is involved in regulating arousal, dreaming, and moods. Norepinephrine can also contribute to the regulation of blood pressure, by constricting blood vessels and increasing heart rate.

Serotonin (5-HT) is implicated in the etiology or treatment of various disorders. The most widely studied effects of 5-HT are those on the CNS. The functions of 5-HT are numerous and include control of appetite, sleep, memory and learning, temperature regulation, mood, behavior (including sexual and hallucinogenic behavior), cardiovascular function, smooth muscle contraction, and endocrine regulation. Peripherally, 5-HT appears to play a major role in platelet homeostasis and motility of the GI tract. The actions of 5-HT are terminated by three major mechanisms: diffusion; metabolism; and reuptake. The major mechanism by which the action of 5-HT is terminated is by reuptake through presynaptic membranes. After 5-HT acts on its various postsynaptic receptors, it is removed from the synaptic cleft back into the nerve terminal through an uptake mechanism involving a specific membrane transporter in a manner similar to that of other biogenic amines. Agents that selectively inhibit this uptake increase the concentration of 5-HT at the postsynaptic receptors and have been found to be useful in treating various psychiatric disorders, particularly depression.

Approaches to the treatment of depression over the years have involved the use of agents that increase the levels of NE and 5-HT, either by inhibiting their metabolism (e.g., monoamine oxidase inhibitors) or reuptake (e.g., tricyclic antidepressants or selective serotonin reuptake inhibitors (SSRIs)).

There are more than twenty approved antidepressant drugs available in the United States. The classical tricyclic antidepressants (TCAs) currently available block primarily the uptake of NE and also, to varying degrees, the uptake of 5-HT, depending on whether they are secondary or tertiary amines. Tertiary amines such as imipramine and amitriptyline are more selective inhibitors of the uptake of 5-HT than of catecholamines, compared with secondary amines such as desipramine.

Selective serotonin reuptake inhibitors have been investigated as potential antidepressants. Fluoxetine (PROZAC®), sertraline (ZOLOFT®), and paroxetine (PAXIL®) are three examples of SSRIs currently on the U.S. market. These agents do not appear to possess greater efficacy than the TCAs, nor do they generally possess a faster onset of action; however, they do have the advantage of causing less side-effects. Of these three SSRIs, paroxetine is the most potent inhibitor of 5-HT uptake, fluoxetine the least. Sertaline is the most selective for 5-HT versus NE uptake, fluoxetine the least selective. Fluoxetine and sertraline produce active metabolites, while paroxetine is metabolized to inactive metabolites. The SSRIs, in general, affect only the uptake of serotonin and display little or no affinity for various receptor systems including muscarinic, adrenergic, dopamine, and histamine receptors.

In addition to treating depression, several other potential therapeutic applications for SSRIs have been investigated. They include treatment of Alzheimer's disease, aggressive behavior, premenstrual syndrome, diabetic neuropathy, chronic pain, fibromyalgia, and alcohol abuse. For example, fluoxetine is approved for the treatment of obsessive-compulsive disorder (OCD). Of particular significance is the observation that 5-HT reduces food consumption by increasing meal-induced satiety and reducing hunger, without producing the behavioral effects of abuse liability associated with amphetamine-like drugs. Thus, there is interest in the use of SSRIs in the treatment of obesity.

Venlafaxine (EFFEXOR®) is a dual-reuptake antidepressant that differs from the classical TCAs and the SSRIs chemically and pharmacologically in that it acts as a potent inhibitor of both 5-HT and NE uptake. Neither venlafaxine nor its major metabolite have a significant affinity for adrenergic alpha-1 receptors. Venlafaxine possesses an efficacy equivalent to that of the TCAs, and a benign side effect profile similar to those of the SSRIs.

Dopamine is hypothesized to play a major role in psychosis and certain neurodegenerative diseases, such as Parkinson's disease, where a deficiency in dopaminergic neurons is believed to be the underlying pathology. Dopamine affects brain processes that control movement, emotional response, and ability to experience pleasure and pain. Regulation of DA plays a crucial role in our mental and physical health. Certain drugs increase DA concentrations by preventing DA reuptake, leaving more DA in the synapse. An example is methylphenidate (RITALIN®), used therapeutically to treat childhood hyperkinesias and symptoms of schizophrenia. Dopamine abnormalities are believed to underlie some of the core attentional abnormalities seen in acute schizophrenics.

A therapeutic lag is associated with the use of these drugs. Patients must take a drug for at least three (3) weeks before achieving clinically meaningful symptom relief. Furthermore, a significant number of patients do not respond to current therapies at all. For example, it is currently estimated that up to thirty percent (30%) of clinically diagnosed cases of depression are resistant to all forms of drug therapy.

SUMMARY OF THE INVENTION

The present invention relates to novel cycloalkylamines and salts thereof. It further relates to novel pharmaceutical compositions, and their use in the treatment of CNS disorders such as depression (e.g., major depressive disorder, bipolar disorder), fibromyalgia, pain (e.g., neuropathic pain), sleep apnea, attention deficit disorder (ADD), attention deficit hyperactivity disorder (ADHD), restless leg syndrome, schizophrenia, anxiety, obsessive compulsive disorder, post-traumatic stress disorder, seasonal affective disorder (SAD), premenstrual dysphoria as well as neurodegenerative disease (e.g., Parkinson's disease, Alzheimer's disease).

Hence, in a first aspect the invention provides a compound having a structure according to Formula (I):

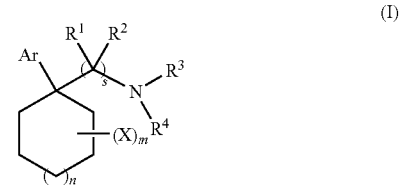

In Formula (I), n is an integer from 0 to 2; s is an integer from 1 to 3. The integer m is selected from 0 to 12. When n is 0, m is preferably not greater than 8; when n is 1, m is preferably not greater than 10. Ar is a member selected from the group consisting of substituted or unsubstituted aryl, substituted or unsubstituted heteroaryl and a fused ring system.

Each X is an independently selected alkyl group substituent. In an exemplary embodiment, each X is a member independently selected from the group consisting of H, halogen, CN, $CF_3$, $OR^5$, $SR^5$, acyl, $C(O)OR^5$, $C(O)NR^6R^7$, $S(O)_2R^5$, $S(O)_2NR^6R^7$, $NR^6R^7$, $NR^6S(O)_2R^5$, $NR^6C(O)R^5$, substituted or unsubstituted alkyl, substituted or unsubstituted heteroalkyl, substituted or unsubstituted aryl, substituted or unsubstituted heteroaryl and substituted or unsubstituted heterocycloalkyl, wherein each $R^5$, $R^6$ and $R^7$ is a member independently selected from the group consisting of H, acyl, substituted or unsubstituted alkyl, substituted or unsubstituted heteroalkyl, substituted or unsubstituted aryl and substituted or unsubstituted heteroaryl, wherein two of $R^5$, $R^6$ and $R^7$, together with the atoms to which they are attached, are optionally joined to form a 3- to 7-membered ring.

Each $R^1$ and $R^2$ is an independently selected alkyl group substituent. In an exemplary embodiment, each $R^1$ and $R^2$ is a member independently selected from the group consisting of H, halogen, CN, $CF_3$, $OR^8$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^8$ is a member selected from the group consisting of H, substituted or unsubstituted alkyl, substituted or unsubstituted heteroalkyl, substituted or unsubstituted aryl, substituted or unsubstituted heteroaryl and substituted or unsubstituted heterocycloalkyl.

$R^3$ and $R^4$ are members independently selected from the group consisting of H, $OR^9$, acyl, $C(O)OR^9$, $S(O)_2R^9$, =N=N, substituted or unsubstituted alkyl, substituted or unsubstituted heteroalkyl, substituted or unsubstituted aryl, substituted or unsubstituted heteroaryl and substituted or unsubstituted heterocycloalkyl. When one member of $R^3$ and $R^4$ is =N=N, the other member is preferably not present. $R^9$ is a member selected from the group consisting of H, substituted or unsubstituted alkyl, substituted or unsubstituted heteroalkyl, substituted or unsubstituted aryl, substituted or unsubstituted heteroaryl and substituted or unsubstituted heterocycloalkyl.

At least two of $R^1$, $R^2$, $R^3$, $R^4$ and any of the substituents X, together with the atoms to which they are attached, are optionally joined to form a 3- to 7-membered ring.

Any pharmaceutically acceptable salt, solvate, enantiomer, diastereomer, racemic mixture, enantiomerically enriched mixture, and enantiomerically pure form of the above described compounds falls within the scope of the invention.

In a second aspect, the invention provides a pharmaceutical composition including a compound of the invention or a pharmaceutically acceptable salt or solvate thereof, and a pharmaceutically acceptable carrier.

In a third aspect, the invention provides a method of inhibiting binding of a monoamine transporter ligand to a monoamine transporter, such as serotonin transporter, dopamine transporter and norepinephrine transporter. The method includes contacting the monoamine transporter and a compound of the invention. In an exemplary embodiment the monoamine transporter ligand is a monoamine, such as serotonin, dopamine and norepinephrine.

In a fourth aspect, the invention provides a method of inhibiting the activity of at least one monoamine transporter, such as serotonin transporter, dopamine transporter and norepinephrine transporter. The method includes contacting the monoamine transporter and a compound of the invention.

In another aspect, the invention provides a method of inhibiting uptake of at least one monoamine, such as serotonin, dopamine and norepinephrine, by a cell. The method includes contacting the cell with a compound of the invention. In an exemplary embodiment, the cell is a brain cell, such as a neuronal cell or a glial cell.

In yet another aspect, the invention provides a method of treating depression by inhibiting the activity at least one monoamine transporter. The method includes administering to a mammalian subject a compound of the invention. In a preferred embodiment, the compound of the invention inhibits the activity of at least two different monoamine transporters. In another preferred embodiment, the mammalian subject is a human.

In a further aspect, the invention provides a method of treating a central nervous system disorder. The method includes administering to a subject in need thereof a therapeutically effective amount of a compound of the invention or a pharmaceutically acceptable salt or solvate thereof In a preferred embodiment, the subject is a human.

DETAILED DESCRIPTION OF THE INVENTION

I. Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO₂R', —CONR'R", —OC(O)NR'R", —NR"C(O)R', —NR'—C(O)NR"R"', —NR"C(O)₂R', —NR—C(NR'R"R"')=NR"", —NR—C(NR'R")=NR"', —S(O)R', —S(O)₂R', —S(O)₂NR'R", —NRSO₂R', —CN and —NO₂ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO₂R', —CONR'R", —OC(O)NR'R", —NR"C(O)R', —NR'—C(O)NR"R"', —NR"C(O)₂R', —NR—C(NR'R"R"')=NR"", —NR—C(NR'R")=NR"', —S(O)R', —S(O)₂R', —S(O)₂NR'R", —NRSO₂R', —CN and —NO₂, —R', —N₃, —CH(Ph)₂, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently -NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH₂)$_r$-D-, wherein A and D are independently —CRR'—, —O—, —NR—, —S—, —S(O)—, —S(O)₂—, —S(O)₂NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X"—(CR"R"')$_d$—, where s and d are independently integers of from 0 to 3, and X" is —O—, —NR'—, —S—, —S(O)—, —S(O)₂—, or —S(O)₂NR'—. The substituents R, R', R" and R"' are preferably independently selected from hydrogen or substituted or unsubstituted ($C_1$-$C_6$)alkyl.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S), silicon (Si) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups.

The phrase "therapeutically effective amount" as used herein means that amount of a compound, or composition comprising a compound of the present invention which is effective for producing some desired therapeutic effect (e.g., by inhibiting uptake of a monoamine from the synaptic cleft of a mammal, thereby modulating the biological consequences of that pathway in the treated organism) at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in human beings and animals without excessive toxicity, irritation, allergic response, or other problem or complication, commensurate with a reasonable benefit/risk ratio.

The phrase "pharmaceutically acceptable carrier" as used herein means any pharmaceutically acceptable material, which may be liquid or solid. Exemplary carriers include vehicles, diluents, additives, liquid and solid fillers, excipients, solvents, solvent encapsulating materials. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, sulfamate, bisulfate, phosphate, nitrate, acetate, valerate, oleate, palmitate, stearate, laurate, benzoate, lactate, tosylate, citrate, maleate, ascorbate, palmitate, fumarate, succinate, tartrate, napthylate, mesylate, hydroxymaleate, phenylacetate, glutamate, glucoheptonate, salicyclate, sulfanilate, 2-acetoxybenzoate, methanesulfonate, ethane disulfonate, oxalate, isothionate, lactobionate, and laurylsulphonate salts and the like. See, for example, Berge et al. (1977) "Pharmaceutical Salts", *J. Pharm. Sci.* 66:1-19.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention. "Compound or a pharmaceutically acceptable salt or solvate of a compound" intends the inclusive meaning of "or", in that a material that is both a salt and a solvate is encompassed.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge out-lines and dotted or broken lines denote enantiomerically pure compounds of indeterminate absolute configuration.

The terms "enantiomeric excess" and "diastereomeric excess" are used interchangeably herein. Compounds with a single stereocenter are referred to as being present in "enantiomeric excess," those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "monoamine transporter ligand" refers to any compound, which binds to a monoamine transporter. Ligands include endogenous monoamines, which are the natural ligands for a given monoamine transporter as well as drug molecules and other compounds, such as synthetic molecules known to bind to a particular monoamine transporter. In one example, the ligand includes a radioisotope, such as tritium or is otherwise (e.g., fluorescently) labeled. It is within the abilities of a skilled person to select an appropriate ligand for a given monoamine transporter. For example, known ligands for the dopamine transporter include dopamine and WIN35428, known ligands for the serotonin transporter include 5-hydroxytryptamine (serotonin) and citalopram, and ligands for the norepinephrine transporter include norepinephrine and nisoxetine.

The term "central nervous system disorder" refers to any abnormal condition of the central nervous system of a mammal. Central nervous system disorder includes neurodegenerative diseases such Alzheimer's disease and Parkinson's disease, neuropsychiatric diseases (e.g. schizophrenia), anxieties, sleep disorders, depression, dementias, movement disorders, psychoses, alcoholism, post-traumatic stress disorder and the like. "Central nervous system disorder" also includes any condition associated with the disorder, such as loss of memory and/or loss of cognition. For instance, a method of treating a neurodegenerative disease would also include treating or preventing loss of neuronal function characteristic of such disease. "Central nervous system disorder" also includes any disease or condition that is implicated, at least in part, in monoamine (e.g., norepinephrine) signaling pathways (e.g., cardiovascular disease).

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

The term "depression" includes all forms of depression, which include major depressive disorder (MDD), bipolar disorder, seasonal affective disorder (SAD) and dysthymia. "Major depressive disorder" is used herein interchangeably with "unipolar depression" and "major depression. "Depression" also includes any condition commonly associated with depression, such as all forms of fatigue (e.g., chronic fatigue syndrom) and cognitive deficits.

II. Introduction

One strategy to develop effective therapies is the use of broad spectrum antidepressants that simultaneously inhibit the reuptake of more than one biogenic amine, such as serotonin (5-HT), norepinephrine (NE) and dopamnine (DA). The rationale for this approach is based upon clinical and preclinical evidence showing that deficiencies in dopaminergic function can be correlated with anhedonia, which is a core symptom of depression. Baldessarini, R. J., "Drugs and the Treatment of Psychiatric Disorders: Depression and Mania, in Goodman and Gilman's The Pharmacological Basis of Therapeutics 431-459 ($9^{th}$ ed 1996) Hardman et al. eds.

An advantage of the compounds and compositions of the present invention is their ability to increase synaptic availability of at least two neurotransmitters (e.g, NE, 5-HT and DA) by inhibiting their (re)uptake from the synaptic cleft. Skolnick and coworkers report on a body of preclinical evidence suggesting that the therapeutic profile of an antidepressant concurrently increasing the synaptic availability of DA, NE and 5-HT will differ from a compound inhibiting only NE and/or 5-HT. Skolnick, P. et al., "Antidepressant-like actions of DOV-21,947: a "triple" reuptake inhibitor," *Eur. J. Pharm.* 2003, 461, 103.

For example, Skolnick and coworkers have reported that a compound, DOV 21,947 ((+)-1-(3,4-dichlorophenyl)-3-azabicyclo[3.1.0]hexane), inhibits the reuptake of serotonin, norepinephrine, and dopamine in human embryonic kidney (HEK293) cells expressing the corresponding human recombinant transporters ($IC_{50}$ values of 12, 23 and 96 nM, respectively). Skolnick, P. et al., "Antidepressant-like actions of DOV-21,947: a "triple" reuptake inhibitor," *Eur. J. Pharm.* 2003, 461, 99. In addition, DOV 21,947 reduces the duration of immobility in the forced swim test (in rats) and also produces a dose-dependent reduction in immobility in the tail suspension test. Additional evidence can be found in preclinical data for new triple reuptake inhibitors such as DOV 21,947 in, e.g., U.S. Pat. No. 6,372,919, wherein DOV 21,947 was disclosed as having a significantly greater affinity for the norepinephrine and serotonin uptake sites than the racemic compound, (±)-1-(3,4-dichlorophenyl)-3-azabicyclo[3.1.0] hexane.

Taken together, the preclinical data for compounds such as DOV 21,947 indicate that dual or triple reuptake inhibitors may hold potential as novel treatments for depression in the clinic.

III. Compositions

A. Cycloalkyl Amines

In a first aspect, the invention provides a compound having a structure according to Formula (I):

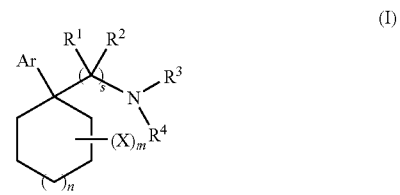

(I)

In Formula (I), n is an integer from 0 to 2. Hence, in one embodiment, the invention provides cyclopentyl-, cyclohexyl- and cycloheptylamines. The integer s is selected from 0 to 3, preferably from 1 to 2. In a particularly preferred embodiment, s is 1. The integer m is selected from 0 to 12. When n is 0, m is preferably not greater than 8; when n is 1, m is preferably not greater than 10. Ar is a member selected from the group consisting of substituted or unsubstituted aryl, substituted or unsubstituted heteroaryl and a fused ring system.

Each X is a member independently selected from an alkyl group substituent. In an exemplary embodiment, each X is a member independently selected from the group consisting of H, halogen, CN, $CF_3$, $OR^5$, $SR^5$, acyl, $C(O)OR^5$, $C(O)NR^6R^7$, $S(O)_2R^5$, $S(O)_2NR^6R^7$, $NR^6R^7$, $NR^6S(O)_2R^5$, $NR^6C(O)R^5$, substituted or unsubstituted alkyl, substituted or unsubstituted heteroalkyl, substituted or unsubstituted aryl, substituted or unsubstituted heteroaryl and substituted or unsubstituted heterocycloalkyl. Each $R^5$, $R^6$ and $R^7$ is a member independently selected from the group consisting of H, acyl, substituted or unsubstituted alkyl, substituted or unsubstituted heteroalkyl, substituted or unsubstituted aryl and substituted or unsubstituted heteroaryl, wherein two of $R^5$, $R^6$ and $R^7$, together with the atoms to which they are attached, are optionally joined to form a 3- to 7-membered ring.

Each $R^1$ and $R^2$ is an independently selected alkyl group substituent. In an exemplary embodiment, each $R^1$ and $R^2$ is a member independently selected from the group consisting of H, halogen, CN, $CF_3$, $OR^8$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^8$ is a member selected from the group consisting of H, substituted or unsubstituted alkyl, substituted or unsubstituted heteroalkyl, substituted or unsubstituted aryl, substituted or unsubstituted heteroaryl and substituted or unsubstituted heterocycloalkyl.

In one embodiment, $R^3$ and $R^4$ are members independently selected from the group consisting of H, $OR^9$, acyl, $C(O)OR^9$, $S(O)_2R^9$, =N=N, substituted or unsubstituted alkyl, substituted or unsubstituted heteroalkyl, substituted or unsubstituted aryl, substituted or unsubstituted heteroaryl and substituted or unsubstituted heterocycloalkyl. When one member of $R^3$ and $R^4$ is =N=N, the other member is preferably not present. $R^9$ is a member selected from the group consisting of H, substituted or unsubstituted alkyl, substituted or unsubstituted heteroalkyl, substituted or unsubstituted aryl, substituted or unsubstituted heteroaryl and substituted or unsubstituted heterocycloalkyl.

At least two of $R^1$, $R^2$, $R^3$, $R^4$ and any substituent X, together with the atoms to which they are attached, are optionally joined to form a 3- to 7-membered ring. In an exemplary embodiment, two substituents X, together with the atoms to which they are attached, are optionally joined to form a 3- to 7-membered ring. In another exemplary embodiment, $R^3$ and $R^4$ are joined to form a ring, such as a morpholine, N-methyl-piperazine and the like. In another exemplary embodiment, $R^1$ and $R^3$ are joined to form a ring, such as a pyrrolidine ring. In yet another exemplary embodiment, at least one of $R^1$, $R^2$, $R^3$ and $R^4$ is optionally joined with the Ar group or a substituent on the Ar group to form a 5- to 7-membered ring. An exemplary structure, in which Ar—s substituted phenyl and $R^3$ is joined with Ar to form a 6-membered ring is provided below:

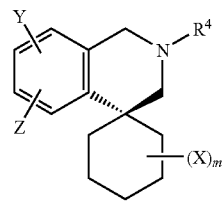

wherein Y and Z are as defined below.

In an especially preferred embodiment, the integer s in Formula (I) is 1. Exemplary compounds according to this embodiment have a Formula, which is a member selected from Formula (II) and Formula (III):

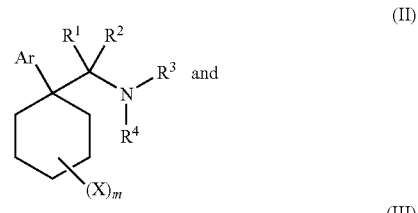

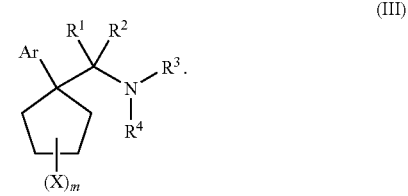

In an exemplary embodiment, the cycloalkyl ring is mono- or disubstituted at either the 2-, 3-, or 4-position. Exemplary compounds according to this embodiment have a Formula, which is a member selected from the group consisting of:

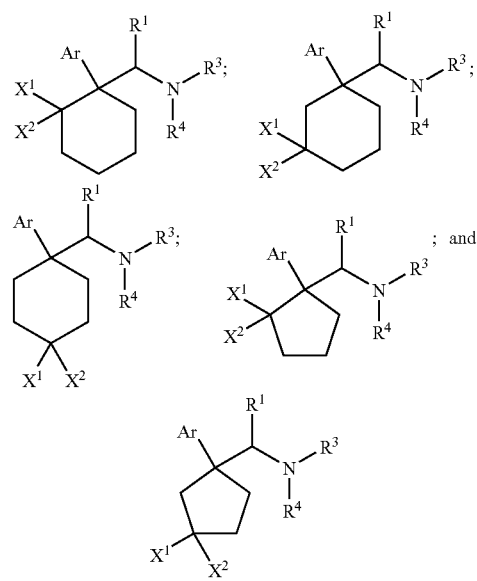

wherein $X^1$ and $X^2$ are alkyl group substituents. In an exemplary embodiment, $X^1$ and $X^2$ are each defined as the substituent X, above. In another exemplary embodiment, $X^1$ and $X^2$ are members independently selected from the group consisting of H, $OR^5$, $SR^5$, halogen, CN, $CF_3$, $S(O)_2R^5$, $NR^6R^7$, NR$^6$S(O)$_2$R$^5$, NR$^6$C(O)R$^5$, acyl, substituted or unsubstituted C$_1$-C$_4$ alkyl and substituted or unsubstituted C$_1$-C$_4$ heteroalkyl, wherein at least two of R$^1$, R$^3$, R$^4$, X$^1$ and X$^2$, together with the atoms to which they are attached, are optionally joined to form a 3- to 7-membered ring.

In a preferred embodiment, X$^1$ and X$^2$ are members independently selected from H, methyl, ethyl, propyl, OR$^5$ (e.g., OH, OMe, OEt, OPh), CH$_2$OR$^5$ (e.g., CH$_2$OH), halogen substituted alkyl (e.g., CF$_3$, CH$_2$F), halogen (e.g., F or Cl) and CN. In another preferred embodiment, R$^1$ is a member selected from H and substituted or unsubstituted C$_1$-C$_4$ alkyl. In yet another preferred embodiment, R$^3$ and R$^4$ are members independently selected from H, substituted or unsubstituted alkyl and substituted or unsubstituted heteroalkyl, such as substituted or unsubstituted C$_1$-C$_4$ alkyl or substituted or unsubstituted C$_1$-C$_4$ heteroalkyl. In one example, R$^3$ and R$^4$, together with the nitrogen atom to which they are attached, are joined to form a 3- to 7-membered ring, such as a morpholine, piperidine, pyrrolidine or N-alkyl-piperazine moiety.

In another embodiment, the compound of the invention includes a cyclobutyl ring. An exemplary structure is provided below in Formula (IV):

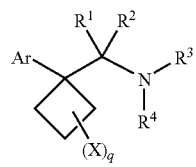

(IV)

wherein the integer q is selected from 0 to 6.

Aryl Group Substituent (Ar)

In one embodiment, Ar is a member selected from substituted or unsubstituted aryl, substituted or unsubstituted heteroaryl and a fused ring system. Preferably, Ar is a member selected from substituted or unsubstituted phenyl and substituted or unsubstituted naphthyl, including 1-naphthyl and 2-naphthyl analogs. Hence, in one embodiment, Ar is a member selected from:

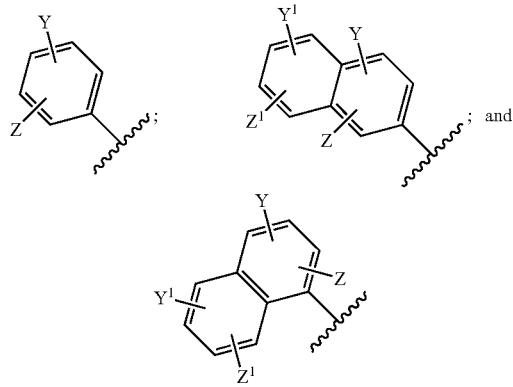

wherein Y, Z, Y$^1$ and Z$^1$ are members independently selected from aryl group substituents. In an exemplary embodiment, Y, Z, Y$^1$ and Z$^1$ are members independently selected from H, halogen, CF$_3$, CN, OR$^{11}$, SR$^{11}$, NR$^{12}$R$^{13}$, NR$^{12}$S(O)$_2$R$^{11}$, NR$^{12}$C(O)R$^{11}$, S(O)$_2$R$^{11}$, acyl, C(O)OR$^{11}$, C(O)NR$^{12}$R$^{13}$, S(O)$_2$NR$^{12}$R$^{13}$, substituted or unsubstituted alkyl, substituted or unsubstituted heteroalkyl, substituted or unsubstituted aryl, substituted or unsubstituted heteroaryl and substituted or unsubstituted heterocycloalkyl. Each R$^{11}$, R$^{12}$ and R$^{13}$ is a member independently selected from the group consisting of H, acyl, substituted or unsubstituted alkyl, substituted or unsubstituted heteroalkyl, substituted or unsubstituted aryl, substituted or unsubstituted heteroaryl, substituted or unsubstituted heterocycloalkyl, wherein two of R$^{11}$, R$^{12}$ and R$^{13}$, together with the atoms to which they are attached, are optionally joined to form a 3- to 7-membered ring.

Two of Y, Z, Y$^1$ and Z$^1$, together with the atoms to which they are attached, are optionally joined to form a 5- to 7-membered ring, such as a dioxolyl ring. In another exemplary embodiment, Y, Z, Y$^1$ and Z$^1$ are members independently selected from the group consisting of H, halogen, CN, halogen substituted C$_1$-C$_4$ alkyl (e.g., CF$_3$) and C$_1$-C$_4$ alkoxy (e.g., OMe, OEt, OCF$_3$).

In yet another exemplary embodiment, Ar is a 3,4-disubstituted phenyl moiety and has the structure:

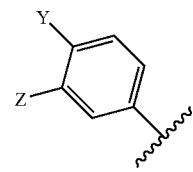

In a preferred embodiment, Y and Z, in the structure above, are members independently selected from H, halogen, CN, CF$_3$ and OR$^{16}$ (e.g., OMe, OEt, OCF$_3$). In a particular preferred embodiment, Y and Z are both halogen. In an exemplary embodiment, Ar in any of the structures above is 3,4-dichlorophenyl.

Exemplary compounds according to the above described embodiments are provided below:

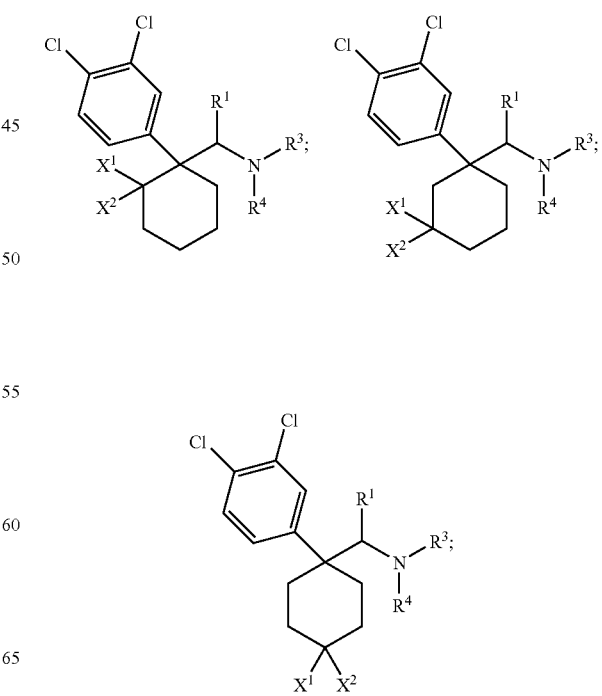

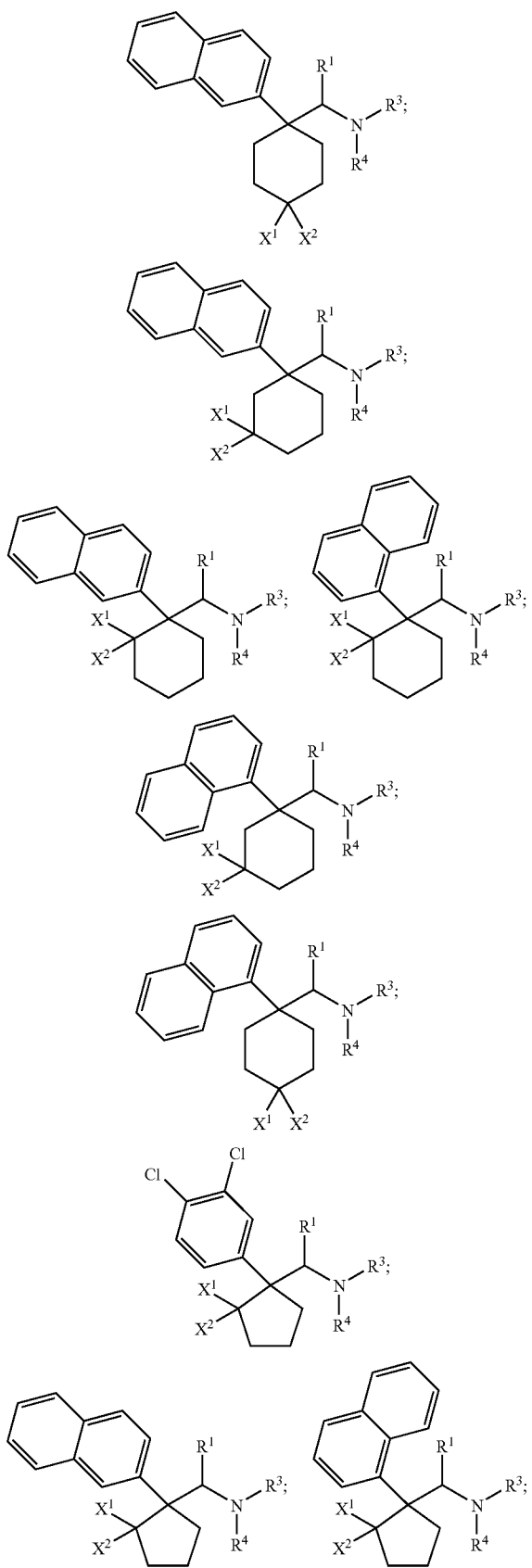

In an exemplary embodiment, in the structures above, $R^1$, $R^3$ and $R^4$ are independently selected from H and $C_1$ to $C_4$ alkyl (e.g., methyl) and $X^1$ and $X^2$ are independently selected from H, OH, OMe, methyl, ethyl, $CH_2OH$, halogen (e.g., Cl and F), CN and $CF_3$.

The compounds of the invention include an amine moiety (e.g., a primary, secondary or tertiary amino group) and as such can be converted into a salt form by contacting the compound (e.g., the free base) with an acid. In an exemplary embodiment, the salt form is generated to convert an otherwise oily or viscous compound into a solid substance for easier handling. In another exemplary embodiment, converting the free base of a compound of the invention into a corresponding salt increases solubility of the compound in aqueous media, which can effect biological characteristics, such as bioavailability, pharmacokinetics and pharmacodynamics. Hence, any salt forms, such as pharmaceutically acceptable salts, including salts of inorganic acids (e.g., hydrochloride salts) or organic acids, of the compounds of the invention are within the scope of the current invention. Also within the scope of the invention are any prodrugs of the compounds of the invention. For example, $R^3$ and $R^4$ can be any group, which is cleavable in vivo to result in an amine, such as a primary or secondary amine.

In another embodiment, the invention provides synthetic precursors for the cyclolkylamines of the invention. For example, a large subset of the currently provided amines can be synthesized via the corresponding nitrile (e.g., by reduction) or the corresponding aldehyde (e.g., by reductive amination). Thus, the invention provides compounds having a structure selected from the following Formulae:

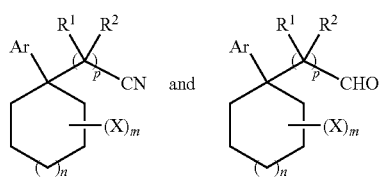

wherein p is an integer selected from 0 to 2. Ar, $R^1$, $R^2$, X and the integers m and n are as defined above. In a preferred embodiment p is 0.

In another embodiment, the invention provides cycloalkylamines, wherein the cycloalkyl ring includes one or more double bonds. Exemplary compounds are shown below:

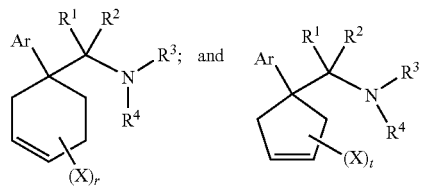

wherein the integer r is selected from 0 to 8 and t is selected from 0 to 6.

B. Compositions Including Stereoisomers

The compound of the invention can include one or more stereocenter and may exist in particular geometric or stereoisomeric forms. Compounds can be chiral, racemic or be present in a composition including one or more stereoisomer. The current invention encompasses any enantiomer, diastereomer, racemic mixtures, enantiomerically enriched mixtures, and diastereomerically enriched mixture as well as any enantiomerically or diastereomerically (essentially) pure forms of the compounds of the invention. The invention contemplates cis- and trans-isomers, (−)- and (+)-enantiomers, (D)-isomers, (L)-isomers, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts may be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

As used herein, the term "enantiomerically enriched" or "diastereomerically enriched" refers to a compound having an enantiomeric excess (ee) or a diastereomeric excess (de) greater than about 50%, preferably greater than about 70% and more preferably greater than about 90%. In general, higher than about 90% enantiomeric or diastereomeric purity is particularly preferred, e.g., those compositions with greater than about 95%, greater than about 97% and greater than about 99% ee or de.

The terms "enantiomeric excess" and "diastereomeric excess" are used interchangeably herein. Compounds with a single stereocenter are referred to as being present in "enantiomeric excess", those with at least two stereocenters are referred to as being present in "diastereomeric excess".

For example, the term "enantiomeric excess" is well known in the art and is defined as:

$$ee_a = \left(\frac{conc.\ of\ a - conc.\ of\ b}{conc.\ of\ a + conc.\ of\ b}\right) \times 100$$

The term "enantiomeric excess" is related to the older term "optical purity" in that both are measures of the same phenomenon. The value of ee will be a number from 0 to 100, zero being racemic and 100 being enantiomerically pure. A compound which in the past might have been called 98% optically pure is now more precisely characterized by 96% ee. A 90% ee reflects the presence of 95% of one enantiomer and 5% of the other(s) in the material in question.

Hence, in one embodiment, the invention provides a composition including a first stereoisomer and at least one additional stereoisomer of a compound of the invention. The first stereoisomer may be present in a diastereomeric or enantiomeric excess of at least about 80%, preferably at least about 90% and more preferably at least about 95%. In a particularly preferred embodiment, the first stereoisomer is present in a diastereomeric or enantiomeric excess of at least about 96%, at least about 97%, at least about 98%, at least about 99% or at least about 99.5%. Enantiomeric or diastereomeric excess may be determined relative to exactly one other stereoisomer, or may be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

C. Synthesis of the Compounds

1. General

Compounds of the invention may be synthesized as a racemic mixture, a mixture of cis and trans isomers, or a mixture of two or more diastereomers. Stereoisomers may be separated at an appropriate synthetic stage, for example, by chiral column chromatography, such as HPLC to give enantiomerically/diastereomerically enriched or enantiomerically or diastereomerically pure forms of the respective stereoisomers. Cis and trans assignments may be made on the basis of NMR coupling patterns optionally in conjunction with literature values. Absolute configurations can be determined by synthesis from chiral precursor of known configuration, or by X-ray crystallographic determination using crystallized materials.

Numbering of the positions within the cycloalkyl ring structure is based on the following Scheme:

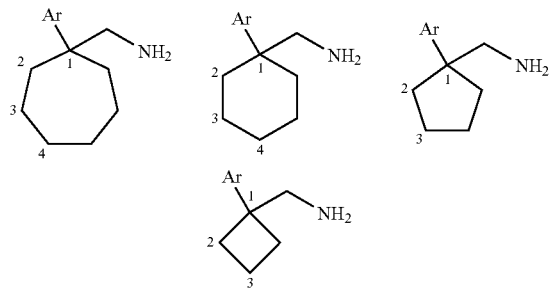

Cis- and trans-configurations are defined according to the relative configuration of the amine-bearing side chain and the substituent on the cyclalkyl ring. When more than one substituent is present, the higher order (IUPAC) substituent is used for the determination of cis- and trans-configuration. Examples are outlined below:

(a) 2-(aminomethyl)-2-(3,4-dichlorophenyl)cyclohexanol

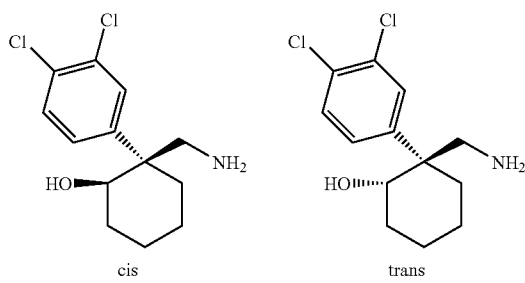 [SMILES: NC[C@@]1(c2ccc(Cl)c(Cl)c2)CCCC[C@H]1O ; NC[C@@]1(c2ccc(Cl)c(Cl)c2)CCCC[C@@H]1O]

(b) 3-(aminomethyl)-3-(3,4-dichlorophenyl)-1-methylcyclohexanol

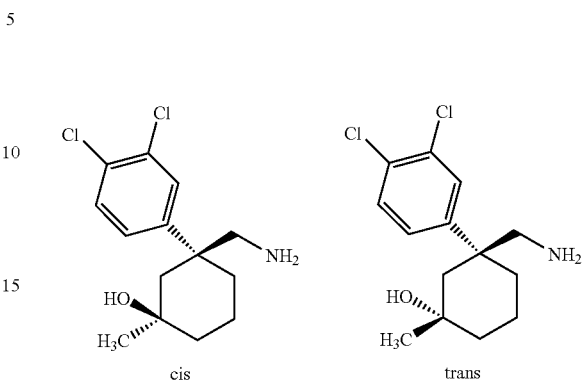

Compounds of the invention may be synthesized according to Schemes 1 to 23, below. It is within the abilities of a person skilled in the art to select appropriate alternative reagents replacing the exemplary reagents shown in Schemes 1-23 in order to synthesize a desired compound of the invention. It is also within the abilities of a skilled artisan to omit or add synthetic steps when necessary. As a non-limiting example, Ar in Schemes 1 to 23 is selected from substituted or unsubstituted phenyl. In an exemplary embodiment, Ar is 3,4-dichlorophenyl.

2. General Synthesis of Cycloalkylamines

In one embodiment, the compounds of the invention are synthesized from the corresponding nitrile C as shown in Scheme 1, below.

Scheme 1: Exemplary Synthesis of Cycloalkylamines from Nitriles

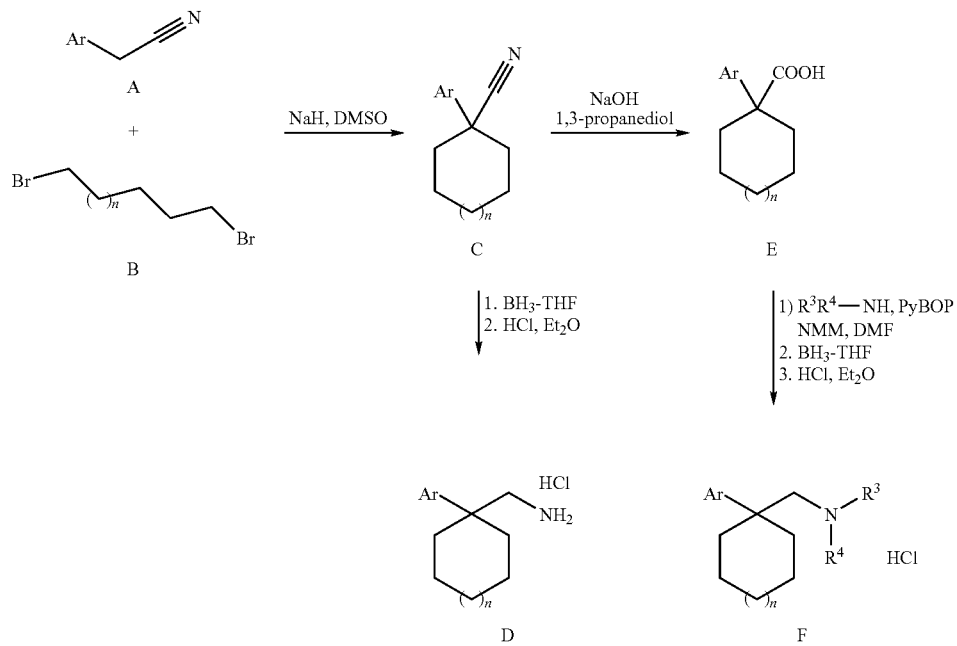

Synthesis of the nitrile C and the carboxylic acid intermediate E can, for example, be accomplished as described by Calderon et al., *J. Med. Chem.* 1994, 37, 2285, which is incorporated herein by reference. In addition, the reduction of the nitrile C to the corresponding primary amine D can be accomplished by borane reduction, for example, as described by Nagarathnam et al., *J. Med. Chem.* 1998, 41, 5320, which is also incorporated herein by reference.

Referring to Scheme 1, alkylation of the acetonitrile A with dibromoalkane B (e.g., with NaH in DMSO) gives the nitrile C, which is subsequently converted to acid E (e.g., NaOH, 1,3-propanediol). The dibromoalkane can optionally be substituted to afford a substituted cycloalkane analog of the invention. The integer n may be selected from 0 to 2, resulting in cyclopentyl, cyclohexyl and cycloheptyl intermediates, respectively. Alternatively, substituted or unsubstituted 1,3-dibromopropane may be used to prepare a cyclobutyl analog of the invention.

Coupling of acid E with either a primary amine ($R^4$=H) or a secondary amine is performed using peptide coupling reagents known in the art resulting in the corresponding amide (not shown). In an exemplary embodiment the amide is formed using EDCI and HOBt in DMF as the coupling reagents. In another exemplary embodiment, the amide is formed using PyBOP in DMF as the coupling reagent. Exemplary coupling procedures are described in General Procedures G to G3.

Referring to Scheme 1, the amide is then reduced using a reducing agent, such as borane. Exemplary borane reagents include $BH_3$.THF and borane.dimethylsulfide complexes. The resulting amine may be converted to the corresponding salt form. For example, treatment of the amine with HCl in $Et_2O$ affords the HCl salt, which may be recrystallized to give the amine F as a solid.

Alternatively, the nitrile C can be reduced to the primary amine D using a reducing agent, such as borane (e.g., $BH_3$.THF). The amine may be converted to the corresponding salt form. For example, treatment of the amine with HCl in $Et_2O$ affords the HCl salt, which may be recrystallized to give a pure solid. The primary amine may be converted to a secondary or tertiary amine by alkylation of the amino group as described below.

Alternatively, the carboxylic acid intermediate E can be activated by formation of an acid chloride, which may then be reacted with a primary or secondary amine to give the amide, as outlined for an exemplary cyclopentylamine in Scheme 2, below.

Scheme 2: Synthesis of Cycloalkylamines via the Acid Chloride

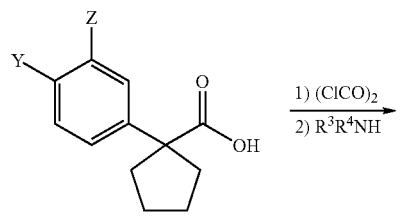

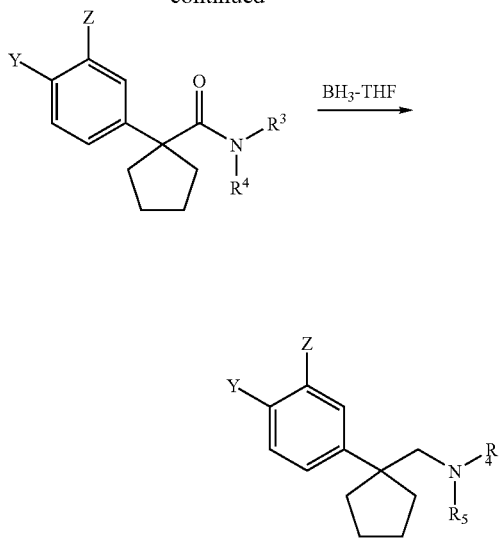

In another approach, the nitrile C can be converted to the corresponding aldehyde G using a reducing agent, such as DIBAL (Scheme 3). The aldehyde can then be converted to an amine, for example, through reductive amination. This synthetic route is particularly useful for the preparation of secondary amines of the invention ($R^4$=H), as the amination of the aldehyde with a secondary amine to form a tertiary amine may be sluggish.

Scheme 3: Reduction of Nitriles to Aldehydes and Synthesis of Secondary Amines

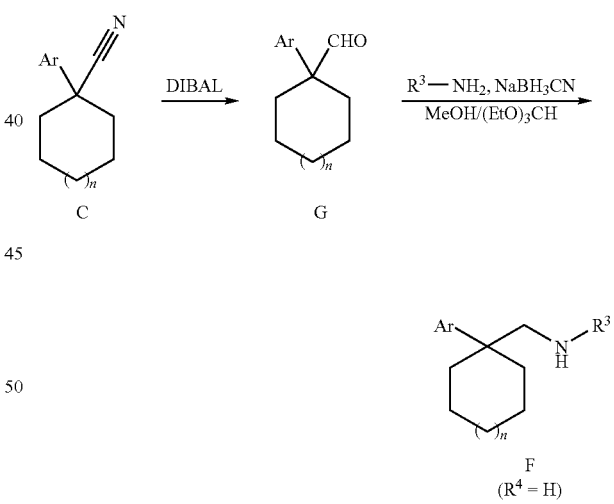

3. Synthesis of Substituted Cyclopentyl Amines

Substituted cyclopentyl amines (n=0) can be synthesized according to the route outlined in Scheme 4, below. The nitrile H may be synthesized from dibromobutene and an appropriate aryl acetonitrile and can be converted to the racemic cis and trans hydroxylamines I and J via reduction of the nitrile and hydroboration of the alkene with $BH_3/H_2O_2$, NaOH. Alternatively, reduction of H to the aldehyde K, followed by reductive amination affords the ene-amine L. The double bond of L may be used to introduce a substituent (X) into the 5-membered ring structure.

Scheme 4: Synthesis of Substituted Cyclopentyl Amines

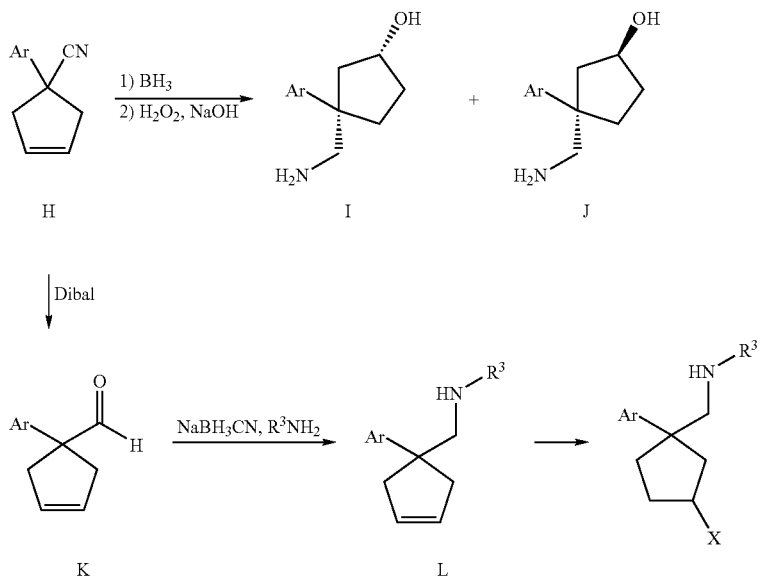

4. Synthesis of Secondary and Tertiary Amines

The synthesis of secondary amines from primary amines can, for example, be accomplished using the method described by De Luca et al., *Synlett* 2004, 2570, which is incorporated herein by reference. The method is outlined in Scheme 5, below. The primary amine is converted to the N-formylated intermediate M, which may be reduced to the corresponding methyl amine. Typically, N-formylation followed by borane reduction led to clean mono-methylated products.

Scheme 5: Exemplary Synthesis of Secondary Amines

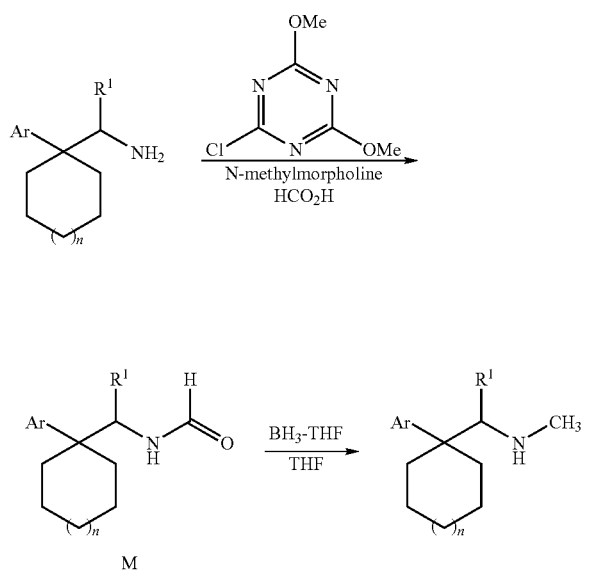

M

Dialkylamine analogs of the invention can be synthesized according to Scheme 6 below. In this method, a secondary amine is reacted with formaldehyde and concentrated formic acid to form a methylated tertiary amine.

Scheme 6: Exemplary Synthesis of Tertiary Amines from Secondary Amines

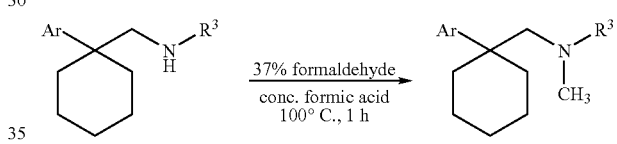

In an exemplary embodiment, reaction of a methyl amine analog ($R^3$=Me) with a 1:1 mixture of concentrated formic acid and 37% aqueous formaldehyde at 100° C. for 1h, typically gives the dimethyl amine in good yield.

Another method useful for the synthesis of N,N-dimethyl and N-methyl amines is shown in Scheme 7, below. Treatment of a primary amine with diisopropylethylamine (DIEA) and methyl iodide (e.g., in $CH_2Cl_2$) leads to the formation of both the N-methyl amine and the N,N-dimethyl amine, which can be separated chromatographically. Selectivity for either the mono- or dimethylated product can be controlled by altering the ratio of methyl iodide to the amine as well as the reaction time. For example, mono-methylated analogs may be obtained selectively by keeping the concentration of methyl iodide low and reaction times short.

Scheme 7: Synthesis of N-methyl and N,N-dimethyl amines

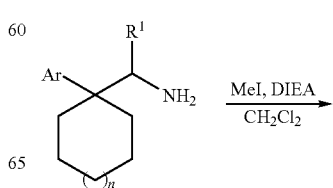

-continued

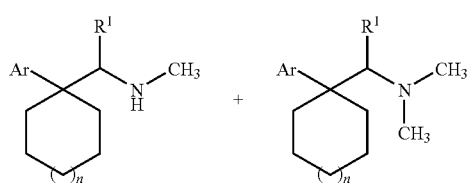

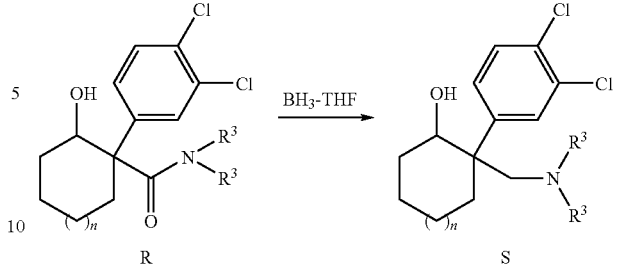

5. Synthesis of 2-Substituted Cycloalkylamines

In an exemplary embodiment, cycloalkylamines of the invention are substituted at the 2-position. Such compounds may be synthesized according to Scheme 8, below.

Scheme 8: Synthesis of 2-Substituted Cycloalkylamines

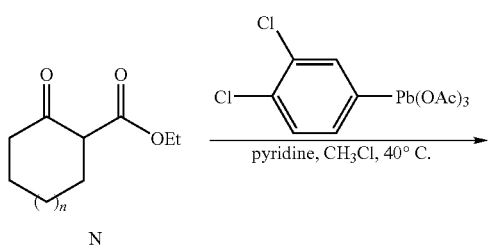

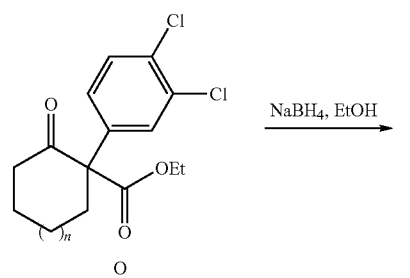

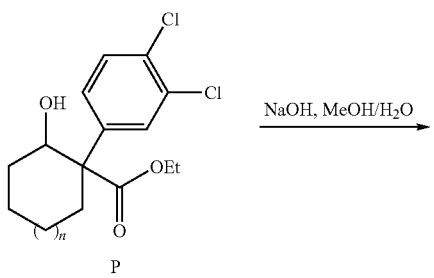

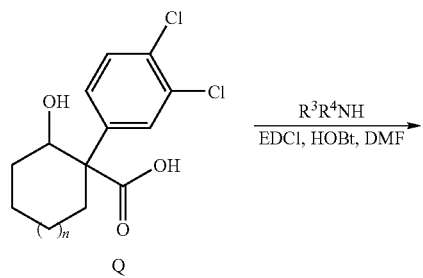

The method, outlined above for an exemplary 3,4-diphenyl cyclohexylamine of the invention, is applicable to the synthesis of 2-substituted cycloalkylamines. Reaction of ethyl 2-oxocyclohexanecarboxylate N with an aryl-lead triacetate (e.g., 3,4-dichlorophenyllead triacetate) affords the ethyl 1-aryl-2-oxocyclohexanecarboxylate O. NaBH$_4$ mediated reduction of the keto-ester yields the alcohol P, which is subsequently saponified to afford the acid Q as a mixture of diastereomers. Amide coupling and reduction of the resulting amide group affords the amine S. Chiral HPLC can be used to separate enantiomers/diastereomers. The hydroxyl group of S may be functionalized (e.g., alkylation) or replaced by another substituent (X), such as a halogen atom (e.g., Cl or F) to yield compound T. Alternatively the hydroxyl group may be converted to a leaving group, which can subsequently be replaced with a selected nucleophile.

Corresponding dialkylamines of S or another hydroxyamine can be prepared from the corresponding primary amine or mono-alkylated analog (R$^4$=H) when using an appropriate base, such as DIEA. For example, synthesis of the N,N-dimethyl amino-alcohols is prepared via alkylation of the N-methyl amines with methyl iodide and DIEA in acetone, as shown in Scheme 9, below.

Scheme 9: Synthesis of N,N-Dimethyl Aminoalcohols

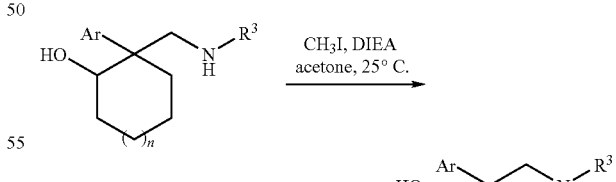

In another exemplary embodiment, the invention provides compounds, which include a substituted alkyl-substituent within in the cycloalkyl ring structure. For example, hydroxymethyl analogs may be synthesized according to Scheme 10 below. The hydroxyl group may optionally be replaced with another substituent, such as a halogen atom.

Scheme 10: Synthesis of 2-Hydroxymethyl Analogs

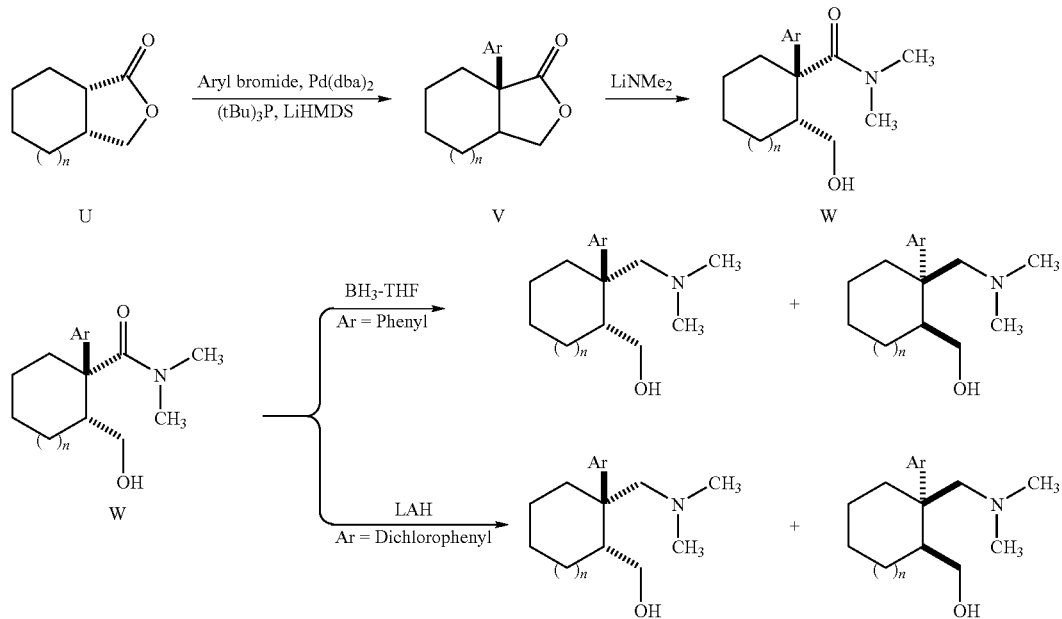

Referring to Scheme 10, the cycloalkyl lactone U is converted to the aryl derivative V. The lactone is then reacted with a lithium salt of a selected amine (e.g., dimethylamine) to give the amido-alcohol W, which is subsequently reduced to the amine. For certain amides W (e.g., dichlorophenyl analogs) it may be preferable to use LAH as the reducing agent instead of borane.

6. Synthesis of 3-Substituted Cycloalkylamines

In another exemplary embodiment, the compounds of the invention are substituted at the 3-position of the cycloalkyl ring. Exemplary synthetic approaches for the preparation of such compounds are outlined below. Referring to Scheme 11, treatment of ketone X with an aryl Grignard reagent, followed by acidic hydrolysis and Michael addition of the cyanide (e.g., following the procedure described by Callis et al., *J. Org. Chem.* 1996, 61, 4634) gives the cyano-ketone Y. Addition of an alkyl lithium reagent to the carbonyl group affords the alcohol Z. In one example, this addion is stereoselective and racemic cis Z is formed selectively. The cyano group of the alcohol Z can be reduced with a reducing agent, such as borane, and the resulting amine can be N-BOC protected to give the racemic alcohol AA. Chiral chromatography followed by removal of the BOC group (e.g., by TFA) gives the enantiomeric cis amino-alcohols BB and CC. The amines can then be converted to the corresponding alkyl amines (e.g., N-Me and NMe₂ derivatives) as described herein, above.

Scheme 11: Exemplary Synthesis of 3-substituted Cycloalkylamines

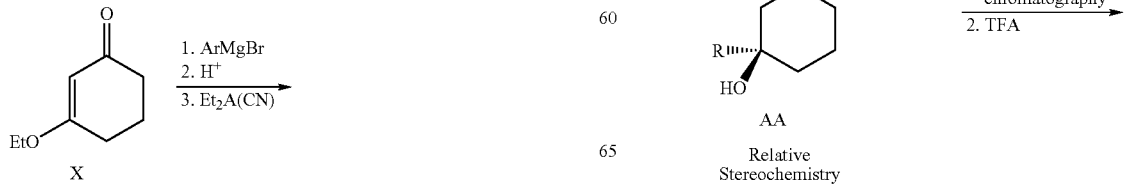

-continued

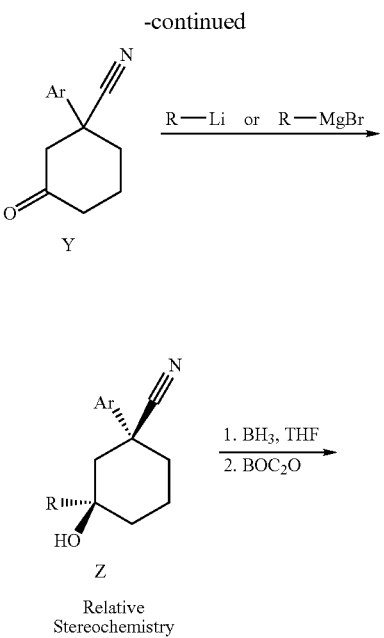

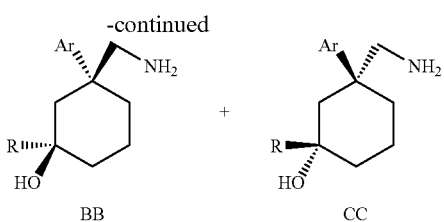

Alternatively, the ketone Y can be treated with sodium borohydride to afford DD as a mixture of cis- and trans-diastereomers (Scheme 12). In an exemplary embodiment, in which Ar is 3,4-dichlorophenyl, the cis-diastereomer of DD was formed primarily. Reduction of the nitrile and BOC protection of the resulting amino group affords the amine EE. The stereoisomers may be separated by chiral chromatography to give two pairs of enantiomers derived from cis EE and trans EE.

Scheme 12: Exemplary Synthesis of 3-OH-Substituted Cyclohexylamines

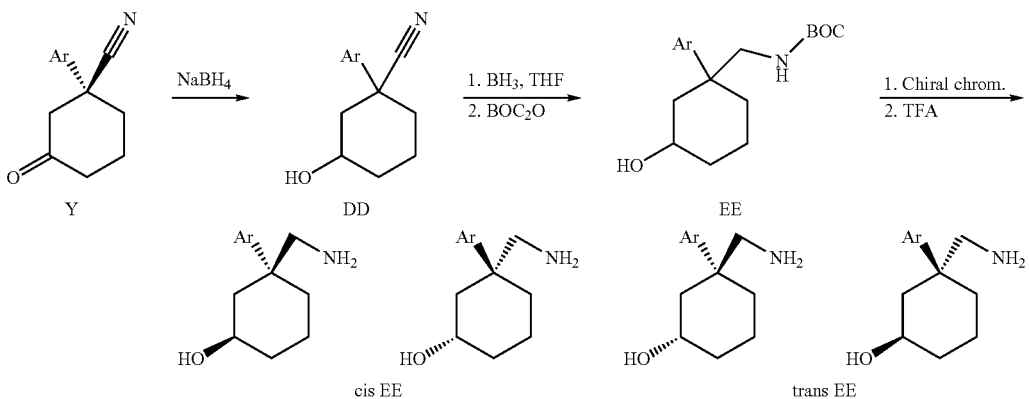

In addition, the hydroxyl group of any of the above analogs (e.g., compound DD) can be functionalized or replaced to generate further 3-substituted cyclohexyl amine analogs. For example, alkyation of the hydroxyl group of DD with methyl iodide gave the methoxy nitrile FF as described in Scheme 13, below. Stereoisomers of FF may be isolated through chiral chromatography. The nitrile is further processed to generate an amine. For example, the nitrile group is reduced (e.g., borane reduction) to afford the corresponding amine, which may then be converted to the corresponding alkylamine (e.g., methylamine or dimethylamine) as described above.

Scheme 13: Exemplary Synthesis of 3-Alkoxy-Cyclohexylamines

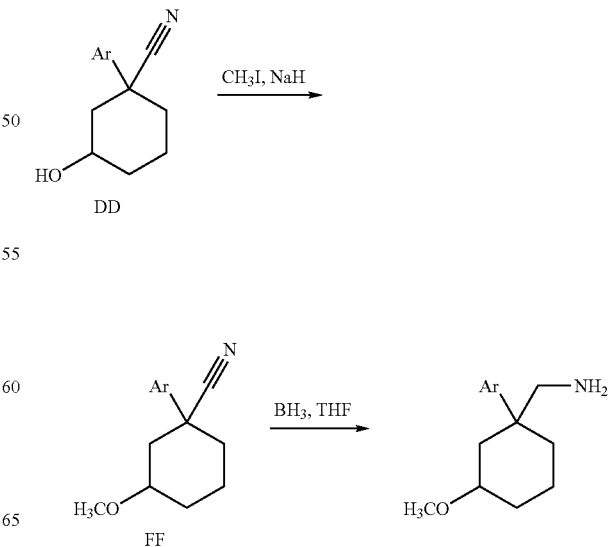

In another exemplary embodiment, 3,3-difunctionalized cycloalkylamine derivatives are synthesized from the ketonitrile Y according to the procedure outlined in Scheme 14, below. For example, the 3,3-difluoro-cyclohexylamine GG is synthesized by treatment of the ketonitrile Y with diethylaminosulfur trifluoride (DAST), followed by reduction of the nitrile group. Treatment of GG with methyl iodide and Hunig's base leads to a separable mixture of the corresponding N-methyl amine HH and N,N-dimethyl amine II. The enantiomers of both HH and II can be resolved by chiral chromatography.

Scheme 14: Exemplary Preparation of 3,3-Difluoro Chiral Amines

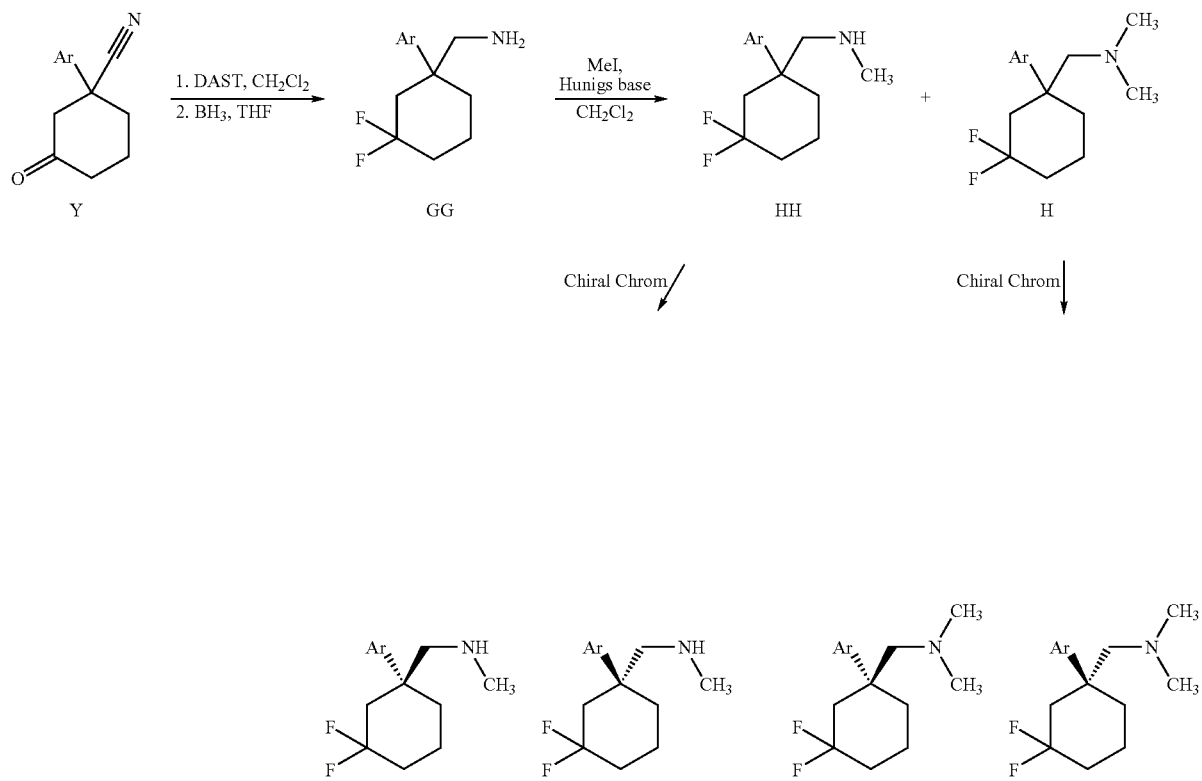

7. Synthesis of 4-Substituted Cycloalkylamines

The invention further provides cycloalkylamines, in which the 4-position of the cycloalkyl ring is derivatized. An exemplary method for the synthesis of 4-substituted cycloalkyl amines was adapted from a procedure described in WO 03/063797, which is incorporated herein by reference in its entirety for all purposes. The method is outlined in Scheme 15, below.

Scheme 15: Exemplary Sythesis of 4-OH-Cycloalkylamines

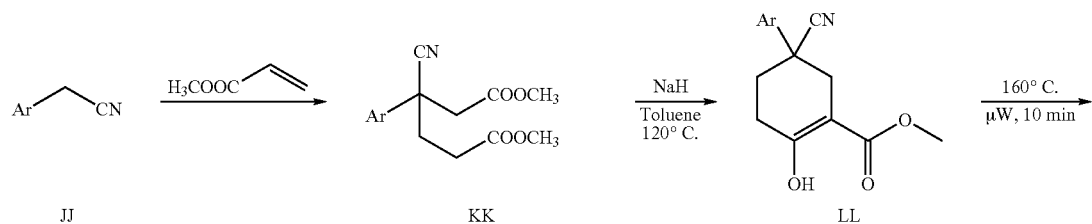

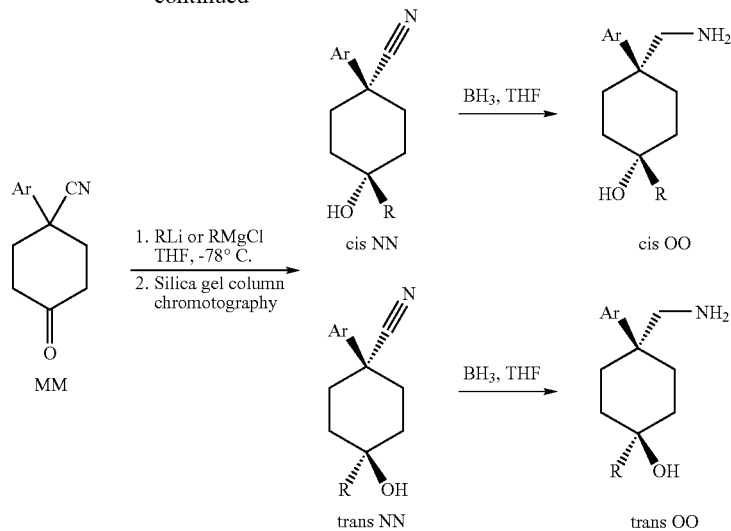

Referring to Scheme 15, above, the acetonitrile JJ is condensed with methyl acrylate to give the di-ester KK, which is cyclized via Dieckmann condensation to give the cyclic hydroxy ester LL. Conversion of LL to the key intermediate MM can, for example, be affected by heating the compound in the microwave to about 160° C. Addition of an alkyl nucleophile (such as MeLi or EtLi) gives a mixture of the hydroxynitriles cis NN and trans NN, which may be separated by silica gel column chromatography. In an exemplary embodiment, in which Ar=3,4-dichlorophenyl and in which propylmagnesium chloride is used as the nucleophile, only the cis analog NN was obtained. Reduction of the nitrile group (e.g., borane) affords the corresponding amines cis OO and trans OO. Subsequent alkylation of the amines as described herein give corresponding alkyl amines, such as methyl- and dimethyl amines.

Alternatively, the intermediate nitrile alcohol NN can be reacted with an alkyl lithium reagent (such as MeLi/NaBH$_4$) to add an $R^1$ group (e.g., a methyl group) before further processing as shown in Scheme 16, below, to afford the racemic amine PP. The enantiomers of PP can be separated by chiral chromatography.

Scheme 16: Exemplary Synthesis of Chiral 4-Substituted Cycloalkylamines

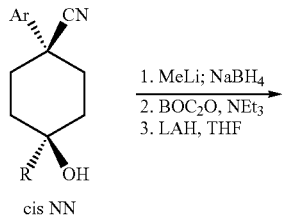

cis NN

-continued

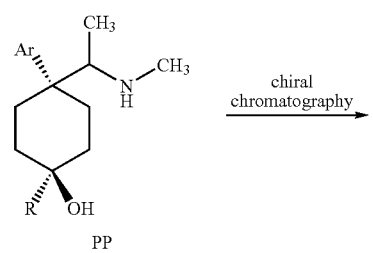

PP

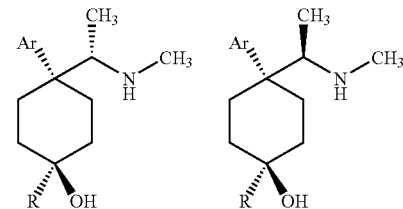

In another exemplary embodiment, the ketonitrile MM is converted to chiral 4-hydroxy cyclohexylamines as shown in Scheme 17, below. Reduction of the carbonyl group (e.g., NaBH$_4$), followed by reduction of the nitrile group (e.g., borane) affords the primary amine QQ, which typically has cis configuration. Alternatively, the keto group of the ketonitrile MM is reduced (e.g., NaBH$_4$) and the stereocenter carrying the resulting hydroxyl group is inverted under Mitsonobu conditions to afford the hydroxynitrile RR, which is further processed to the corresponding primary amine SS or to the respective alkyl amine as described herein, above.

Scheme 17: Exemplary Synthesis of Chiral 4-OH-Cycloalkylamines

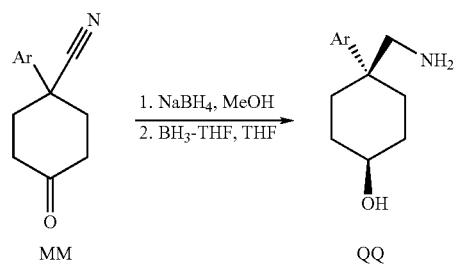

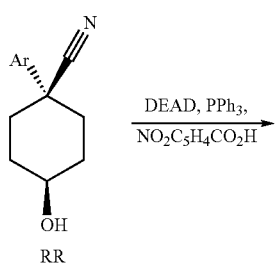

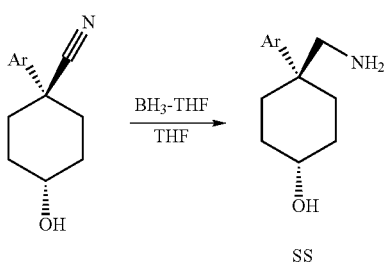

In an exemplary embodiment, the hydroxyl group of the intermediate hydroxynitrile RR is replaced or functionalized before further processing to the amine. For example, synthesis of O-alkylated or O-arylated species is accomplished through alkylation of the hydroxynitrile as shown in Scheme 18, below. Alkylation with methyl iodide followed by borane reduction of the nitrile provides the primary amine TT. A Mitsonobu protocol utilizing an alcohol, such as phenol, followed by borane reduction can be used to convert RR to the trans-analog UU, with inverted stereochemistry at the 4-position.

Scheme 18: Exemplary of 4-Alkoxy-Cyclohexylamines

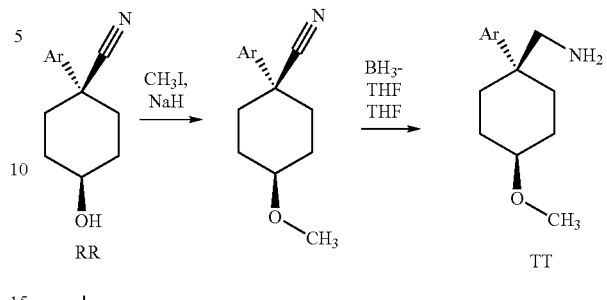

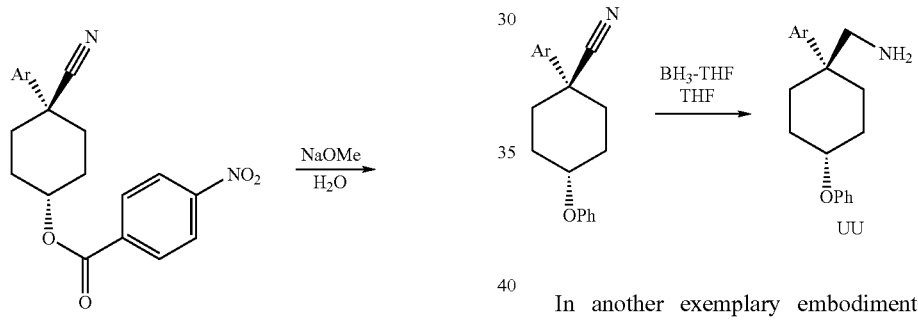

In another exemplary embodiment, the intermediate hydroxyl nitrile RR can be monofluorinated, for example, with morpholino sulfurtrifluoride or DAST to give the 4-fluoro species VV, which may be obtained along with the elimination product WW (Scheme 19), which can be separated chromatographically. Both, the 4-fluoro nitrile VV and the alkene WW can be converted to the corresponding primary amines or alkyl amine species as described herein, above. The double bond can optionally be used to introduce a substituent in to the cycloalkyl ring (e.g, by hydroboration).

Scheme 19: Synthesis of 4-Fluoro-Cyclohexylamines and 3,4-Unsaturated Cyclohexylamines

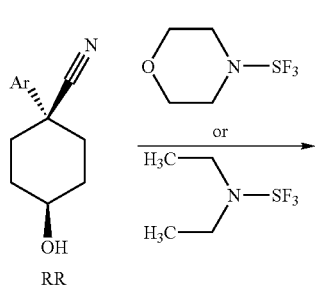

-continued

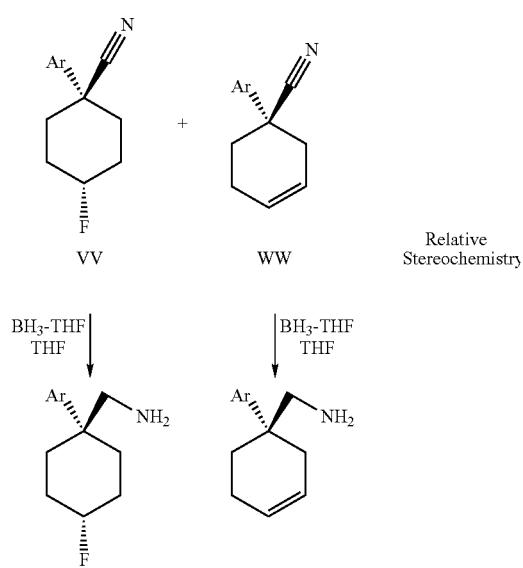

1:1

VV     WW     Relative Stereochemistry

In yet another exemplary embodiment, the ketonitrile MM is converted to a 4,4-disubstituted cycloalkylamine. For example, synthesis of the 4,4-difluoro amine XX could be affected via the action of morpholino sulfurtrifluoride or diethylamino trifluoride (DAST), followed by reduction of the nitrile group (e.g., by borane) as outlined in Scheme 19, below. The resulting primary amine may be converted to the corresponding alkyl amines as described herein.

Scheme 20: Exemplary Synthesis of 4,4-Disbustituted Cycloalkylamines

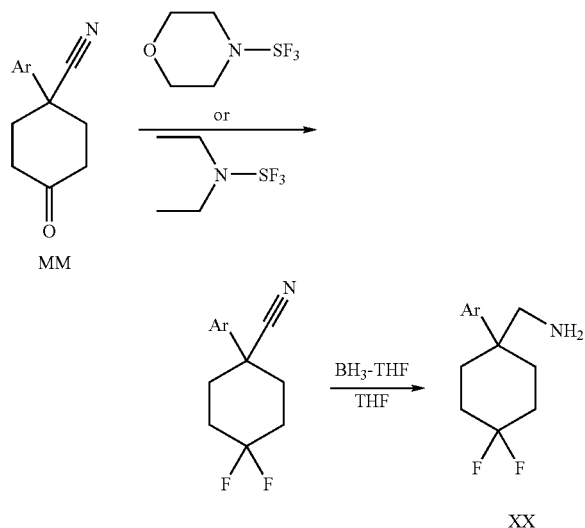

The 4-position of the present cycloalkylamines can also be derivatized via the formation of an intermediate epoxide, as shown in Scheme 21, below. For example, epoxidation of the ketonitrile MM using trimethylsulfonium iodide/KO$^t$Bu affords diastereomeric epoxides, which may be separated by column chromatography. The epoxide ring can be opened in a regioselective reaction with an appropriate nucleophile, such as TBAF/HF to give the corresponding hydroxyl derivative and subsequent reduction of the nitrile group affords the primary amine, such as the fluoromethyl analog YY. The primary amine is optionally converted to corresponding alkylamine species as described herein.

Scheme 21: Exemplary Synthesis of Fluoromethyl-Substituted Cyclohexylamines

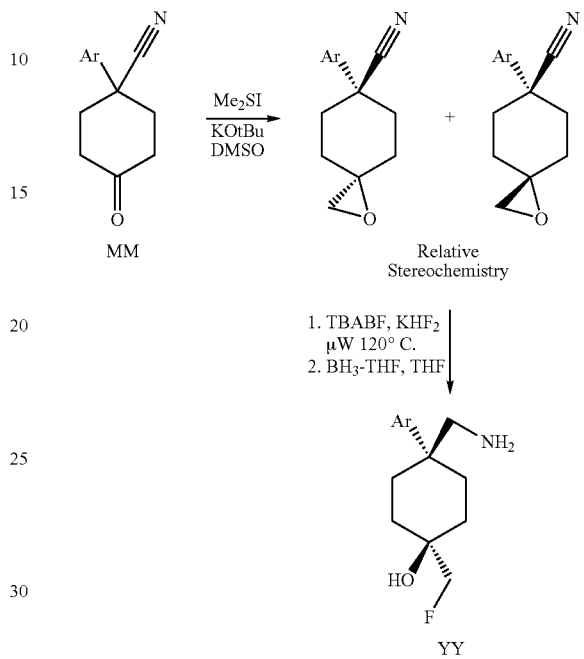

In another embodiment, the invention provides cycloalkylamines with an additional amino group substituent in the cycloalkyl ring structure. In one example, the amine substituent is located at the 4-position of the cycloalkyl ring. For instance, the ketonitrile MM can be converted to a 4-aminocyclohexylamine using the exemplary synthetic conversions outlined in Scheme 22, below. Protection of the keto group of MM (e.g., through formation of a dioxolane), reduction of the nitrile group (e.g., with borane), alkylation of the primary amine (e.g., methylation with methyl iodide) and deprotection of the ketone functionality affords the analog ZZ. Reductive amination of the keto group (e.g., using methyl amine and sodium cyanoborohydride) affords a mixture of diastereomers, which may be separated by preparative HPLC to give the corresponding analogs cis- and trans AAA.

Scheme 22: Synthesis of 4-Amino Cycloalkylamines via Reductive Amination

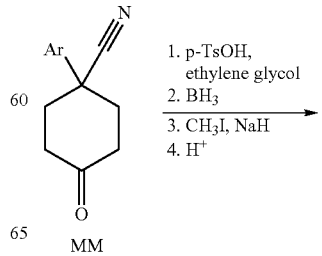

1. p-TsOH, ethylene glycol
2. BH$_3$
3. CH$_3$I, NaH
4. H$^+$

41

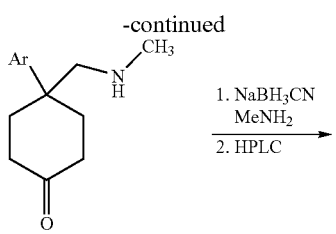

ZZ

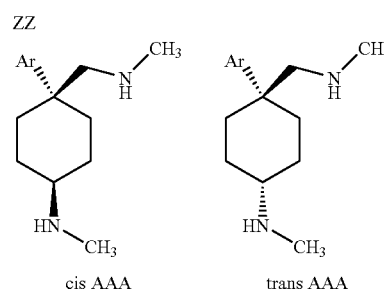

cis AAA     trans AAA

8. Introduction of $R^1$ and/or $R^2$

The invention further provides cycloalkylamines, in which the amine-bearing side chain is substituted with substituents $R^1$ and $R^2$. In an exemplary embodiment, $R^1$ is a short alkyl group, such as $C_1$- to $C_4$-alkyl. Introduction of a $R^1$ group can, for example, be accomplished using the synthetic procedure outlined in Scheme 23, below.

Scheme 23: Synthesis of Chiral Cycloalkylamines Including an $R^1$ Group

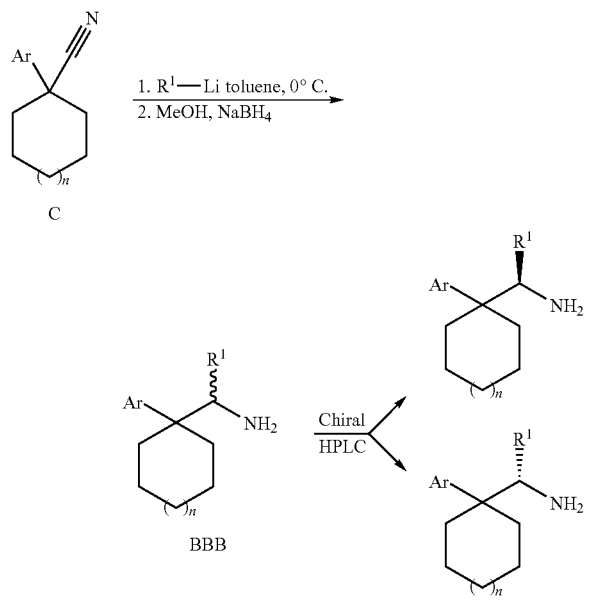

For example, addition of an alkyl lithium reagent to the aryl nitrile C, followed by reduction of the resulting imine affords the racemic primary amines BBB. The corresponding enantiomeric primary amines may be obtained by chiral HPLC chromatography.

9. Synthesis of Cycloalkylamines, in Which $R^1$ and $R^3$ are Joined in a Ring

The invention further provides cycloalkylamines, in which the amine nitrogen is part of a ring. In an exemplary embodiment, $R^1$ and $R^3$, together with the atoms to which they are attached, are joined to form a 3- to 7-membered ring, such as

42 a substituted or unsubstituted pyrrolidine or piperidine ring. An exemplary synthetic method for the preparation of pyrrolidine analogs according to this embodiment is outlined in Scheme 24, below.

Scheme 24: Synthesis of Cycloalkyl-Pyrrolidine Analogs of the Invention

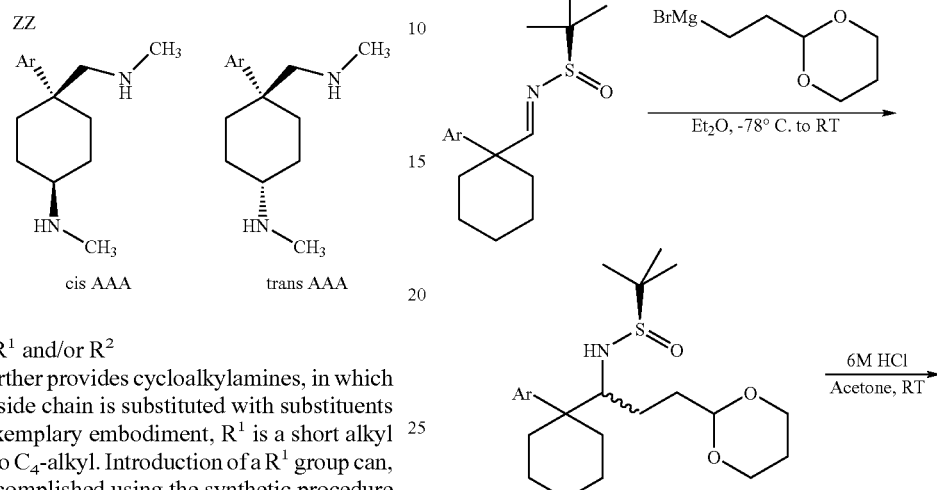

For example, addition of an acetal Grignard reagent to an aryl (e.g. 3,4-dichlorophenyl or 2-naphthyl) (R)-sulfinamine leads to the corresponding sulfinamide CCC as mixtures of diastereomers. Subsequent hydrolysis (e.g., 6M HCl in acetone) can be used to remove both, the sulfinamine auxiliary and ketal side chain. Intramolecular reductive amination (e.g., using polymer bound sodium cyanoborohydride) affords the racemic pyrollidine DDD.

D. Pharmaceutical Compositions

In a second aspect, the invention provides a pharmaceutical composition including a compound of the invention (e.g., a compound of Formulae (I) to (IV)) or a pharmaceutically acceptable salt or solvate thereof, and at least one pharmaceutically acceptable carrier.

As described in detail below, the pharmaceutical compositions of the present invention may be specially formulated for administration in solid or liquid form, including those adapted for oral administration, e.g., tablets, drenches (aqueous or non-aqueous solutions or suspensions), parenteral administration (including intravenous and intramuscular), or epidural injection as, for example, a sterile solution or suspension, or sustained release formulation. The pharmaceutical compositions of the present invention may also be specifically formulated for administration transdermally.

The pharmaceutical compositions of the invention may be administered orally, parenterally, subcutaneously, transdermally, nasally, or by anal suppository. The pharmaceutical compositions of the invention may also be administered using controlled delivery devices.

Formulations of the present invention include those suitable for oral and parenteral administration, particularly intramuscular, intravenous and subcutaneous administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect, without being toxic to the patient. Generally, out of one hundred percent, this amount will range from about 1 percent to about ninety-nine percent of active ingredient.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, caplets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound of the present invention as an active ingredient. A compound of the present invention may also be administered as a bolus, electuary or paste.

In solid dosage forms of the invention for oral administration (capsules, tablets, caplets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue. Pharmaceutical compositions or unit dosage forms of the present invention in the form of prolonged-action tablets may comprise compressed tablets formulated to release the drug substance in a manner to provide medication over a period of time. There are a number of tablet types that include delayed-action tablets in which the release of the drug substance is prevented for an interval of time after administration or until certain physiological conditions exist. Repeat action tablets may be formed that periodically release a complete dose of the drug substance to the gastrointestinal fluids. Also, extended release tablets that continuously release increments of the contained drug substance to the gastrointestinal fluids may be formed.

Compounds of the invention can be also administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compounds of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Compounds of the present invention may also be formulated as transdermal, topical, and mucosal dosage forms, which forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

When the compounds of the present invention are administered as pharmaceuticals, to humans and animals, they can be given per se or as a pharmaceutical composition containing, for example, 0.1 to 99.5% of active ingredient in combination with a pharmaceutically acceptable carrier.

The preparations of the present invention may be given orally and parenterally. They are of course given in forms suitable for each administration route. For example, they are administered in tablets or capsule form, by injection, and by intravenous administration. In one embodiment, oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.005 mg per kilogram to about 5 mg per kilogram of body weight per day.

The terms "treatment" or "treating" is intended to encompass therapy, preventing (prophylaxis), preventing relapse, and amelioration of acute symptoms. Note that "treating" refers to either or both of the amelioration of symptoms and the resolution of the underlying condition. In many of the conditions of the invention, the administration of a compound or composition of the invention may act not directly on the disease state, but rather on some pernicious symptom, and the improvement of that symptom leads to a general and desirable amelioration of the disease state The patient receiving this treatment is any animal in need, including primates, in particular humans, and other mammals such as equines, cattle, swine and sheep, as well as poultry and pets in general.

The compounds and pharmaceutical compositions of the invention can be administered in conjunction with other pharmaceutical agents, for instance antimicrobial agents, such as penicillins, cephalosporins, aminoglycosides and glycopeptides. Conjunctive therapy thus includes sequential, simultaneous and separate administration of the active compound in a way that the therapeutic effects of the first administered agent have not entirely disappeared when the subsequent agent is administered.

IV. Methods

A. Binding To Monoamine Transporter

In another aspect the invention provides a method of binding a compound of the invention to a monoamine transporter. The method includes contacting the monoamine transporter and a compound of the invention.

In yet another aspect, the invention provides a method of inhibiting binding of a monoamine transporter ligand to a monoamine transporter (such as serotonin transporter, dopamine transporter and norepinephrine transporter). The method includes contacting the monoamine transporter and a compound of the invention. In an exemplary embodiment the monoamine transporter ligand is an endogenous monoamine, such as serotonin, dopamine or norepinephrine. In another exemplary embodiment, the ligand is a drug molecule or another small molecule known to have binding affinity to a monoamine transporter. In another exemplary embodiment, the monoamine transporter ligand is a radioactively labeled compound, known to bind to the monoamine transporter.

In an exemplary embodiment, inhibition of ligand binding is shown using an ex vivo binding assay, such as those described herein, below in Example 7. In an exemplary embodiment, the compound of the invention inhibits mean binding by between about 1% and about 100%, preferably by between about 10% and about 100%, more preferably by between about 20% and about 90% when compared to vehicle. Inhibition of mean binding is preferably dose dependent.

B. Inhibition of Monoamine Transporter Activity

In yet another aspect, the invention provides a method of modulating (e.g. inhibiting, augmenting) the activity of at least one monoamine transporter, such as serotonin transporter, dopamine transporter and norepinephrine transporter. The method includes contacting the monoamine transporter and a compound of the invention. In an exemplary embodiment, the monoamine transporter is contacted with a compound of the invention by administering to a subject a therapeutically effective amount of the compound of the invention, e.g., a compound according to Formulae (I) to (V), or a pharmaceutically acceptable salt or solvate therof. In a preferred embodiment, the subject is a human. In another exemplary embodiment, the monoamine transporter is dopamine transporter (DAT), serotonin transporter (SERT) or norepinephrine transporter (NET). In another exemplary embodiment, the compound of the invention inhibits the activity of at least two different monoamine transporters. Inhibition of monoamine transporter activity may be measured using assays known in the art. Exemplary assay formats include in vitro functional uptake assays (Example 6). In an exemplary embodiment, the functional uptake assay utilizes an appropriate cell-line expressing a desired monoamine transporter. In another exemplary embodiment, the functional uptake assay utilizes synaptosomes isolated from brain tissue of an appropriate organism. Alternatively, inhibition of monoamine transporter activity may be assessed using receptor binding experiments known in the art, e.g., utilizing appropriate membrane preparations. Another assay involves treatment of a test subject (e.g., a rat) with a compound of the invention as well as a reference compound, followed by isolation of brain tissue and ex vivo analysis of receptor occupancy, as described herein.

C. Inhibition of Monoamine Uptake

In yet another aspect, the invention provides a method of inhibiting uptake of at least one monoamine (e.g., dopamine, serotonin, norepinephrine) by a cell. The method includes contacting the cell with a compound of the invention. In an exemplary embodiment, the cell is a brain cell, such as a neuron or a glial cell. In one example, inhibition of monoamine uptake occurs in vivo. In an organism, neuronal uptake (also termed reuptake) of a monoamine such as dopamine or serotonin occurs, for example, from the synaptic cleft. Thus, in one embodiment, the neuronal cell is in contact with a synaptic cleft of a mammal. In another exemplary embodiment, inhibition of monoamine uptake occurs in vitro. In those methods the cell, may be a brain cell, such as a neuronal cell or a cell-type, which expresses a recombinant monoamine transporter.

In one embodiment, the compound inhibits uptake of at least two different monoamines. This can, for example, be shown by performing various in vitro functional uptake assays utilizing a cell-type, which simultaneously expresses multiple different monoamine transporters (such as isolated synaptosomes), or may be shown by using two different cell types, each expressing a different monoamine transporter, such as a recombinant dopamine transporter, together with an appropriate, labelled monoamine (Example 6). Inhibition of monoamine uptake is demonstrated when the inhibitor (e.g., a compound of the invention) has an $IC_{50}$ of between about 0.1 nM and about 10 µM, preferably between about 1nM and about 1 µM, more preferably between about 1 nM and about 500 nM, and even more preferably between about 1 nM and about 100 nM in a functional monoamine uptake assay, such as those described herein below.

D. Treatment of CNS Disorders

In another aspect, the invention provides a method of treating depression by inhibiting the activity at least one monoamine transporter. The method includes administering to a mammalian subject a compound of the invention. In an exemplary embodiment, the mammalian subject is a human. In another exemplary embodiment, the compound of the invention inhibits the activity of at least two different monoamine transporters. For example, the compound of the invention inhibits the activity of at least two of serotonin transporter, dopamine transporter and norepinephrine transporter. Inhibition of monoamine transporter activity may be shown by functional monoamine uptake assays as described herein below (Example 6). Demonstration of anti-depressant activity of a compound of the invention may be shown by utilizing an appropriate animal model of depression, such as the Rat Forced Swim Test, the Mouse Tail Suspension Test and Rat Locomotor Activity Analyses (Example 8). The Rat Forced Swim Test is also suitable for the analysis of compounds having activities against more than one monoamine transporter (mixed monoamine transporter activity). For example, an increase in swimming activity is indicative of serotonin reuptake inhibition, while an increase in climbing activity is indicative of norepinephrine reuptake inhibition. In a preferred embodiment, the compounds of the invention are active in at least one animal model, which can be used to measure anti-depressant-like activities, for instance those assessing immobility. In an exemplary embodiment, the compounds of the invention are active when they inhibit mean immobility by between about 5% and about 90%, preferably between about 10% and about 70% and more preferably between about 10% and about 50% in at least one animal model, when compared to vehicle.

In yet another aspect, the invention provides a method of effecting an anti-depressant-like effect. The method includes administering to a mammalian subject in need thereof a therapeutically effective amount of a compound or composition of the invention, e.g., a compound according to Formulae (I) to (IV), or a pharmaceutically acceptable salt or solvate thereof. Anti-depressant-like effectes may be measured using an animal model of disease, such as those described herein.

In a further aspect, the invention provides a method of treating a central nervous system disorder. The method includes administering to a subject in need thereof a therapeutically effective amount of a composition or compound of the invention, e.g., a compound according to Formulae (I) to (IV), or a pharmaceutically acceptable salt or solvate thereof. In a preferred embodiment, the subject is a human.

In another exemplary embodiment, the central nervous system disorder is a member selected from the group consisting of depression (e.g., major depressive disorder, bipolar disorder, unipolar disorder, dysthymia and seasonal affective disorder), cognitive deficits, fibromyalgia, pain (e.g., neuropathic pain), sleep related disorders (e.g., sleep apnea, insomnia, narcolepsy, cataplexy) including those sleep disorders, which are produced by psychiatric conditions, chronic fatigue syndrom, attention deficit disorder (ADD), attention deficit hyperactivity disorder (ADHD), restless leg syndrome, schizophrenia, anxieties (e.g. general anxiety disorder, social anxiety disorder, panic disorder), obsessive compulsive disorder, posttraumatic stress disorder, seasonal affective disorder (SAD), premenstrual dysphoria, postmenopausal vasomotor symptoms (e.g., hot flashes, night sweats), and neurodegenerative disease (e.g., Parkinson's disease, Alzheimer's disease and amyotrophic lateral sclerosis), manic conditions, dysthymic disorder, and cyclothymic disorder. In a preferred embodiment, the CNS disorder is depression, such as major depressive disorder. In an exemplary embodiment, the compounds of the invention are useful to treat two conditions/disorders, which are comorbid, such as cognitive defict and depression.

Central nervous system disorder includes cerebral function disorders, including without limitation, senile dementia, Alzheimer's type dementia, cognition, memory loss, amnesia/amnestic syndrome, epilepsy, disturbances of consciousness, coma, lowering of attention, speech disorders, Lennox syndrome, autism, and hyperkinetic syndrome.

Neuropathic pain includes without limitation post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated using the methods of the invention include obesity; migraine or migraine headache; urinary incontinence, including without limitation involuntary voiding of urine, dribbling or leakage of urine, stress urinary incontinence (SUI), urge incontinence, urinary exertional incontinence, reflex incontinence, passive incontinence, and overflow incontinence; as well as sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

EXAMPLES

1. General Procedures

In the examples, below, the following general experimental procedures were used unless otherwise noted: All commercial reagents were used without further purification. Anhydrous reactions were performed in flame-dried glassware under $N_2$. NMR spectra were recorded on a Varian 400 MHz spectrometer in deuterochloroform or methanol-d$^4$ with trimethylsilane (TMS) as an internal reference. Silica gel column chromatography was performed using an ISCO Combiflash system with detection at 254 nm or using ISCO normal phase silica gel cartridges.

Analytical HPLC

Analytical HPLC was performed on a Hewlett Packard Series 1100 pump connected to an Agilent Zorbax RX-C18 5 μm, 4.6×250 mm column, with detection on a Hewlett Packard Series 1100 UV/Vis detector monitoring at 214 and 254 nm. Typical flow rate=1 ml/min. Three different HPLC columns and various elution protocols were used. For example, (1) Agilent Zorbax RX-C18 5 μm, 4.6×250 mm column running a linear gradient. Solvent A=$H_2O$ w/0.05% TFA, Solvent B=MeCN w/0.05% TFA. Time 0 min=5% Solvent B, time 4 min=40% Solvent B, time 8 min=100% Solvent B, 12 min=5% Solvent B, 20 min=5% Solvent B; (2) Phenomenex 3μ C18 column running a 3 minute gradient of 5→100% B (acetonitrile/0.1% formic acid) and solvent A (water/0.1% formic acid); (3) Phenomenex 5μ C18 column running a 5 minute gradient of 5→100% B where solvent B (acetonitrile/0.1% formic acid) and solvent A (water/0.1% formic acid).

Reverse Phase HPLC Purification

Reverse phase HPLC purification was performed on a Gilson system using a Phenomenex 5μ C18 (50×21.2 mm) column. The standard separation method was: 10 minute gradient of 10→100% B (acetonitrile/0.1% formic acid) in solvent A (water/0.1% formic acid). Crude samples were typically dissolved in MeOH. Fractions were concentrated by Genovac (centrifugation at low pressure).

GC-MS

Gas chromatography was performed on a Hewlett Packard 6890 Series GC System with an HP1 column (30 meters, 0.15μ film thickness) coupled to a Hewlett Packard 5973 Series Mass Selective Detector. The following linear temperature gradient was used: 100° C. for 5 minutes, then 20° C./min to 320° C. Hold @320° C. for 10 minutes.

LCMS

LCMS was performed on an Agilent 1100 Series system connected to a Micromass Platform LC. The following column and gradient was used: Column: Luna C 18(2), 3 um particle size 30×2.0 mm column dimension. Flow rate=0.5 mL/min, Solvent A=0.1 M $NH_4Ac$ in 95% $H_2O$, 5% MeOH, pH 6.0, Solvent B=Solvent B: 0.1 M $NH_4Ac$ in MeOH. Linear gradient with 6 entries: Time 0 min=100% Solvent A, time 10 min=100% Solvent B, time 12 min=100% Solvent B, 12 min 10 sec=100% Solvent A, time 14 min=100% Solvent A, time 14 min 20 sec=100% Solvent A.

Microwave (μW) Recrystallization

The crude salt (e.g., HCl salt) was loaded into a microwave vessel with a stir bar. The recrystallization solvent was added and the vessel was heated at the target temperature for a given time. The vessel was cooled to 50° C. in the reactor, was then removed and allowed to slowly cool to RT. N,N-dimethyl amines were typically recrystallized in EtOAc or EtOAc:$CH_3CN$ (2:1). N-Me or primary amines were typically recrystallized in $CH_3CN$.

Formylation-Reduction 1 (General Procedure A)

The amine free base was dissolved in $CH_2Cl_2$ at approximately 0.4 M and concentrated formic acid (1.0 eq relative to the amine), 1-chloro-3,5-dimethoxytriazine (1.1 eq), DMAP (0.03 eq) and N-methylmorpholine (1.1 eq) were added in this order. The solution was heated in the μW (60° C., 10 min.) and cooled to RT. The reaction was monitored by HPLC. When the starting material was consumed, the crude reaction mixture was diluted with $CH_2Cl_2$ (15 mL) and washed with aqueous HCl (twice), saturated aqueous $K_2CO_3$ and brine. The crude product was dried ($Na_2SO_4$), filtered and concentrated. The crude N-formyl amide was dissolved in anhydrous THF at approximately 0.2 M and borane-THF (e.g., 1.0 M in THF, 3 eq) was added dropwise. The clear solution was heated via μW (150° C., 30 min, FHT), cooled to RT and quenched with 6M HCl (e.g., 10 mL). The solution was washed twice with $Et_2O$ (e.g., 20 mL). The aqueous phase was adjusted to pH 12 with 3M NaOH and was then washed three times with EtOAc (e.g., 20 mL). The combined organic layers were dried ($Na_2SO_4$), filtered and concentrated.

Formylation-Reduction 2 (General Procedure B)

To acetic anhydride (1 eq relative to the amine) under nitrogen at 0° C. was added formic acid (3 eq) dropwise over 3 min. After stirring the reaction mixture for 1 h, a 0.1 M solution of the amine (1 eq) in THF was added dropwise over 5 min. The mixture was allowed to slowly warm, stirring at room temperature for 3 d. The volatiles were removed in vacuo and the residue was purified over silica gel. To a solution of the formamide (1 eq) in THF (10 mL) under nitrogen was added $BH_3.S(CH_3)_2$ (2 M in THF, 2 eq) dropwise over 5 min. The mixture was stirred at room temperature for 20 hours. MeOH, and 2 N aqueous HCl were added and the mixture was washed with diethyl ether (50 mL). The pH was adjusted to 14 by addition of 2 N NaOH and the mixture was extracted with diethyl ether (50 mL). The combined organic phases were dried (sodium sulfate), filtered, and concentrated. The crude N-methyl amine was purified by either Gilson RP-HPLC or by transformation to the HCl salt and recrystallization in the indicated solvent.

HCl Salt Formation

The crude amine was dissolved in $Et_2O$ (e.g., 3 mL) and HCl (e.g., 3-5 mL, 2.0 M in $Et_2O$). The solution was stirred for 1 h and evaporated twice from $CH_2Cl_2$ (e.g., 20 mL). The crude HCl salt was recrystallized in the indicated solvent, filtered and dried in vacuo.

Eschweiler-Clarke N,N-Dimethylation (General Procedure C)

The amine free base (up to 100 mg) was suspended in 37% aqueous formaldehyde (3 mL) and concentrated formic acid (3 mL) was added. The yellowish solution was heated at 100° C. for 1 h and cooled to RT. The clear solution was poured into saturated aqueous $K_2CO_3$ (20 mL) and washed with EtOAc (3×20 mL). The organic washes were combined, washed with brine (1×10 mL), dried ($Na_2SO_4$), filtered and concentrated. The crude amine was dissolved in $Et_2O$ (3 mL) and HCl (3-5 mL, 2.0 M in $Et_2O$) was added. The solution was stirred for 1 h and concentrated with $CH_2Cl_2$ (2×20 mL). The crude HCl salt was recrystallized in the indicated solvent, filtered and dried in vacuo. Alternatively, the dimethylamine could be purified on the reverse-phase HPLC system if recrystallization was not unsuccessful.

Methylation Via Reductive Amination with Formaldehyde and NaB(CN)H₃ (General Procedure D)

To a stirred solution of the amine (approximately 0.05 M, 1 eq), 37% formaldehyde (10 eq), and acetic acid (1 drop) in CH₂Cl₂ at room temperature was added NaBH(OAc)₃ (4 eq). The reaction mixture was stirred for 3 days. Saturated NaHCO₃ solution was then added and the mixture was extracted with EtOAc. The combined organic layers were dried (sodium sulfate), filtered, and concentrated. The crude amine was purified by either Gilson RP-HPLC or by transformation to the HCl salt and recrystallization.

Borane Reduction of Amide or Nitrile (General Procedure E)

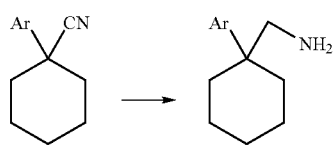

To a solution of the nitrile in anhydrous THF (final concentration: about 0.1M to about 0.2 M) was added dropwise borane-THF (e.g., 1.0M in THF, 3 eq). The reaction mixture was heated in the microwave (maximum temperature: 150° C., about 1 min to about 40 min), cooled to room temperature and then quenched with 6N HCl. The solution was washed with EtOAc. The aqueous phase was adjusted to pH 12 with 3N NaOH and extracted three times with EtOAc. The combined organic layers were dried (Na₂SO₄), filtered and concentrated.

The crude amine was purified by column chromatography and/or isolated as the HCl salt after precipitation from ether (e.g., Et₂O) and HCl (e.g., 2.0 M in Et₂O). The crude HCl salt was optionally recrystallized from the indicated solvent.

Reduction of Nitrile with LiAlH₄ (General Procedure E1)

To a 0.05 M solution of the nitrile (1 eq) in diethyl ether was added LiAlH₄ (5 eq). The reaction mixture was heated at reflux for 30 min before NaOH solution was slowly added to quench the reaction. The product was extracted with diethyl ether. The combined extracts were dried (Na₂SO₄), filtered and concentrated. The residue was dissolved in MeOH and purified by reverse phase HPLC.

JianguoMa Alkylation (General Procedure F)

The primary amine free base or HCl salt was dissolved/suspended in anhydrous CH₂Cl₂ (volume to make amine concentration=0.1 M) and neat anhydrous diisopropylethylamine (3 eq) and methyl iodide (1-5 equiv. depending on desired outcome) was added. The clear solution was stirred at RT for 1-5 h and monitored by HPLC. Longer reaction times favor the formation of the N,N-dimethyl amines; shorter reaction times favor formation of the N-methyl amines. The reaction was checked by HPLC and quenched with MeOH (5 mL) when the desired ratio of N-methyl:N,N-dimethyl amines was reached. The reaction was concentrated under reduced pressure and loaded directly onto a Biotage samplet. Purification by silica gel column chromatography used hexane/0.1% DEA as the non-polar phase and ethyl acetate as the polar phase. The following gradient was employed: equilibration with hexane/0.1% DEA, 3 column volumes (CV), linear 0-50% ethyl acetate over 7 CV, hold at 50% ethyl acetate for 5.5 CV. Fractions were checked by HPLC and LCMS. Product fractions eluted around fractions 7-15. Positive fractions were concentrated and converted into HCl salts.

Amide Coupling (General Procedure G)

A solution of the respective carboxylic acid (approximately 0.1M, 1 eq), the respective amine (1-2 eq), N-methylmorpholine (1-2 eq) and PyBOP (1-2 eq) in anhydrous DMF was stirred at RT overnight (The reaction mixture may optionally include DMAP). The reaction mixture was poured into H₂O (e.g., 20 mL) and washed three times with Et₂O (e.g., 3×20 mL). The combined organic layers were dried (Na₂SO₄), filtered and concentrated. The crude product was purified by either silica gel column chromatography, reverse phase HPLC or by transformation to the HCl salt and recrystallization.

Alkyl Lithium Addition to Nitrile (General Procedure I)

To a solution of arylcyclohexanecarbonitrile (approximately 0.16 M, e.g., 12.8 g, 49.0 mmol) in anhydrous toluene at 0° C. was added dropwise a solution of methyllithium (1.6 M, 1.5 eq) over 10 min. The ice bath was removed and the reaction mixture stirred for 30 min. Methanol (65 eq) and sodium borohydride (6 eq) were added portionwise. The mixture was stirred for 45 min and was then carefully quenched with 6 N HCl. The mixture was washed with ethyl acetate. The pH of the aqueous layer was adjusted to 14 by addition of 6 N NaOH and was then extracted with ethyl acetate. The combined organic layers were dried (Na₂SO₄), filtered and concentrated to give the crude racemic primary amine. The crude amine was purified by either Gilson RP-HPLC or by transformation to the HCl salt and recrystallization.

Cycloalkyl Nitrile Synthesis (General Procedure J)

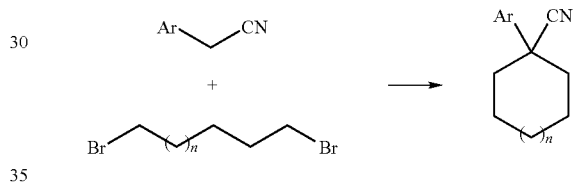

To a 0.1 M suspension of sodium hydride (2.5 eq) in anhydrous DMSO was added a 0.4 M solution of aryl acetonitrile (1 eq) in anhydrous DMSO dropwise over 35 min. The mixture was stirred for 30 min and was then added to a 0.24 M solution of 1,5-dibromopentane (1.5 eq) in anhydrous DMSO dropwise over 20 min. The mixture was stirred overnight at room temperature, poured into water and extracted with chloroform or CH₂Cl₂. The organic layers were combined, washed with water, dried (Na₂SO₄), filtered and concentrated. The resulting residue was chromatographed on silica gel to give the arylcyclohexanecarbonitrile.

Alkylation of Alcohol (General Procedure Y)

To a 0.2 M solution of the alcohol (1 eq) in THF was added NaH (60% in mineral oil, 1.5 eq). The reaction mixture was stirred for 20 min before alkyl halide (2 eq) was added. The reaction mixture was stirred for 4 h and was then quenched with saturated NH₄Cl solution. The product was extracted with diethyl ether. The combined organic layers were dried (Na₂SO₄), filtered and concentrated. The residue was purified by silica gel column chromatography (e.g., ethyl acetate/hexane) to give O-alkylated product.

Lithio-Amine Addition to Lactone (General Procedure AA)

To a cold solution of alkylamine (5 eq) at −78° C. was added n-Buli (3eq) and the reaction mixture was stirred for five minutes. A 0.3 M solution of the aryl lactone (1 eq) in anhydrous THF was then added. The mixture was stirred at the low temperature for one hour and at ambient temperature for an additional hour. The reaction was then quenched with saturated ammonium chloride and extracted with MTBE. The combined organic layers were evaporated and the crude oil purified on silica gel to give the amide.

Example 1

Synthesis of Cycloalkyl Amines

1.1. Synthesis of Cycloalkyl Nitriles

The following exemplary cycloalkylcarbonitriles were prepared from the respective aryl nitriles according to General Procedure J:

1-(biphenyl-4-yl)cyclohexanecarbonitrile

HPLC $R_t$=11.29 min; GC-MS, SCOUT program 13.85 min, $M^+$ 261.

1-(thiophen-2-yl)cyclohexanecarbonitrile

HPLC $R_t$=10.24 min; GC-MS, SCOUT program 8.42 min, $M^+$ 191.

1-(naphthalen-1-yl)cyclohexanecarbonitrile

HPLC $R_t$=10.82 min; GC-MS 12.6 min, $M^+$ 235.

1-(4-(trifluoromethoxy)phenyl)cyclohexanecarbonitrile

HPLC $R_t$=10.76 min; GC-MS 8.59 min, $M^+$ 269.

1.2. Synthesis of Primary Amines from Cycloalkyl Nitriles

The primary amines summarized in Table 1, below, were prepared from the corresponding nitriles according to the indicated General Procedures. Enantiomeric mixtures of selected primary amines were separated by chiral chromatography using the indicated chromatographic methods to give the fast moving enantiomer (E1) and the slow moving enantiomer (E2), respectively.

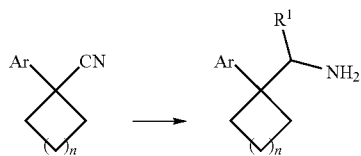

TABLE 1

Summary of Exemplary Primary Amines

| Ar | n | $R^1$ | General Procedure |
|---|---|---|---|

(1-(3,4-dichlorophenyl)cyclobutyl)methanamine (1)

| | | | |
|---|---|---|---|
| 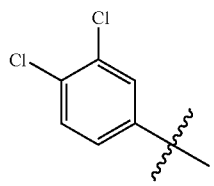 [SMILES: *c1ccc(Cl)c(Cl)c1] | 1 | H | E |

HPLC $R_t$ = 8.16 min; $^1$H NMR (400 mHz, MeOH-d$^4$) 7.48 (d, J = 8.31 Hz, 1H), 7.37 (m, 1H), 7.14-7.10 (m, 1H), 3.23 (m, 2H), 2.44-2.34 (m, 2H), 2.29-2.20 (m, 2H), 2.14-2.05 (m, 1H), 1.93-1.86 (m, 1H); LC-MS 6.91 min, (M + 1)$^+$ 230 @ 7.27 min.

TABLE 1-continued

Summary of Exemplary Primary Amines

| Ar | n | $R^1$ | General Procedure |
|---|---|---|---|

(±) 1-(1-(3,4-dichlorophenyl)cyclohexyl)ethanamine (2)

| | | | |
|---|---|---|---|
| 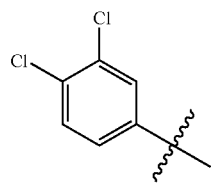 [SMILES: *c1ccc(Cl)c(Cl)c1] | 3 | CH$_3$ | I |

Chiral HPLC (AD column; 98:2:0.1 hexanes:isopropanol:diethylamine, 280 nm) to give 2 E1 ($R_t$ = 8 min) and 2 E2 ($R_t$ = 10 min).
HPLC $R_t$ = 8.77 min; $^1$H NMR (400 mHz, CD$_3$OD) 7.52 (d, J = 8.8 Hz, 1H), 7.48 (d, J = 2.2 Hz, 1H), 7.26 (dd, J = 2.2, 8.8 Hz, 1H), 3.21 (1H, under solvent peak), 2.35 (broad d, 13.2 Hz, 1H), 2.24 (broad d, 13.9 Hz, 1H), 1.57-1.46 (m, 5H), 1.24-1.11 (m, 3H), 1.04 (d, J= 6.6 Hz, 3H); LC-MS 8.13 min, (M + 1)$^+$ 272 @ 8.37 min (±) 1-(1-(3,4-dichlorophenyl)cyclohexyl)-3-methylbutan-1-amine (3)

| | | | |
|---|---|---|---|
| 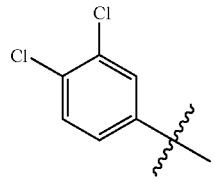 [SMILES: *c1ccc(Cl)c(Cl)c1] | 3 | iso-butyl | I |

HPLC $R_t$ = 9.49 min; $^1$H NMR (400 MHz, MeOH-d$^4$) 7.4-7.38 (m, 2H), 7.17-7.15 (m, 1H), 2.58-2.55 (m, 1H), 2.27-2.18 (m, 2H), 1.64-1.44 (m, 5H), 1.27-1.11 (m, 7H), 0.83 (d, J = 6.96, 3H), 0.78 (d, J = 6.96 Hz, 3H), 0.69-0.62 (m, 1H); LC-MS 9.81 min, (M + 1)$^+$ 314 @ 9.95 min.

(1-(3,4-dichlorophenyl)cycloheptyl)methanamine (4)

| | | | |
|---|---|---|---|
| 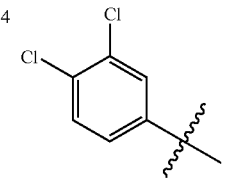 [SMILES: *c1ccc(Cl)c(Cl)c1] | 4 | H | E |

HPLC $R_t$ = 8.96 min; $^1$H NMR (400 MHz, CDCl$_3$) 7.51-7.48 (m, 2H), 7.29 (dd, J = 2.2, 8.4 Hz, 1H), 3.0 (s, 2H), 2.12-2.07 (m, 2H), 1.79-1.73 (m, 2H), 1.66-1.38 (m, 7H); LC-MS 8.61 min, (M + 1)$^+$ 272 @ 8.81 min (±) 1-(1-(4-methoxyphenyl)cyclohexyl)ethanamine (5)

| | | | |
|---|---|---|---|
| 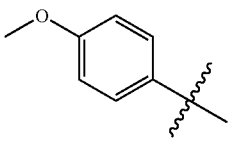 [SMILES: *c1ccc(OC)cc1] | 3 | CH$_3$ | I |

HPLC $R_t$ = 8.07 min; LC-MS 5.57 min, (M + 1)$^+$ 234 @ 5.98 min.

(±) 1-(1-(thiophen-2-yl)cyclohexyl)ethanamine (6)

| | | | |
|---|---|---|---|
| 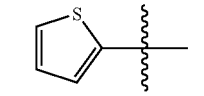 | 3 | CH$_3$ | I |

HPLC $R_t$ = 7.81 min; LC-MS 4.90 min, (M + 1)$^+$ 210 @ 5.78 min.

TABLE 1-continued

Summary of Exemplary Primary Amines

| Ar | n | R¹ | General Procedure |
|---|---|---|---|

(±) 1-(1-(biphenyl-4-yl)cyclohexyl)ethanamine (7)

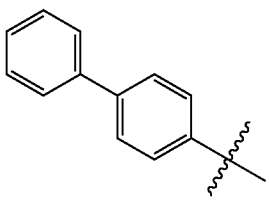 [SMILES: *c1ccc(-c2ccccc2)cc1]

| | 3 | CH₃ | I |

HPLC R$_t$ = 9.07 min; LC-MS 7.47 min, (M + 1)⁺ 280 @ 7.94 min.

(1-(biphenyl-4-yl)cyclohexyl)methanamine (8)

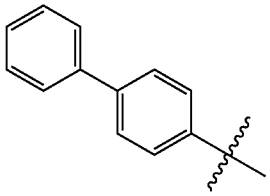

| | 3 | H | E |

HPLC R$_t$ = 8.96 min; ¹H NMR (400 MHz, CD₃OD) 7.64 (d, J = 8.43 Hz, 2H), 7.57 (d, J = 7.70 Hz, 2H), 7.47 (d, J = 8.06 Hz, 2H), 7.39-7.36 (m, 2H), 7.27 (t, J = 7.33 Hz, 1H), 3.01 (s, 2H), 2.26-2.24 (m, 2H), 1.64-1.52 (m, 5H), 1.39-1.38 (m, 3H); LC-MS 7.48 min, (M + 1)⁺ 266 @ 7.86 min.

(1-(thiophen-2-yl)cyclohexyl)methanamine (9)

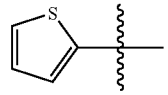

| | 3 | H | E |

HPLC R$_t$ = 7.62 min; ¹H NMR (400 MHz, CD₃OD) 7.36 (dd, J = 1.1, 4.76 Hz, 1H), 7.02-6.98 (m, 2H), 2.98 (s, 2H), 2.13-2.01 (m, 2H), 1.98-1.35 (m, 8H); LC-MS 4.55 min, (M + 1)⁺ 196 @ 5.12 min.

(1-(4-(methylthio)phenyl)cyclohexyl)methanamine (10)

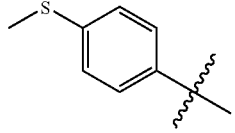 [SMILES: *c1ccc(SC)cc1]

| | 3 | H | E |

HPLC R$_t$ = 8.30 min; ¹H NMR (400 MHz, CD₃OD) 7.33-7.26 (m, 4H), 2.96 (s, 2H), 2.42 (d, J = 1.47 Hz, 3H), 2.19-2.16 (m, 2H), 1.60-1.49 (m, 5H), 1.39-1.31 (m, 3H); LC-MS 6.07 min, (M + 1)⁺ 236 @ 6.45 min.

(±) 1-(1-(4-chlorophenyl)cyclohexyl)ethanamine (11)

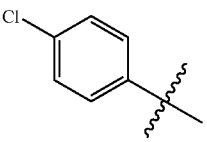 [SMILES: *c1ccc(Cl)cc1]

| | 3 | CH₃ | I |

HPLC R$_t$ = 8.38 min; LC-MS 6.13 min, (M + 1)⁺ 238 @ 5.84 min.

(1-(naphthalen-1-yl)cyclohexyl)methanamine (12)

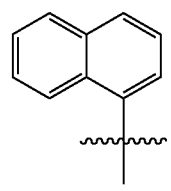 [SMILES: *c1cccc2ccccc12]

| | 3 | H | E |

HPLC R$_t$ = 8.49 min. ¹H NMR (400 MHz, CD₃OD) 8.39 (d, J = 8.43 Hz, 1H), 7.90 (d, J = 7.70 Hz, 1H), 7.82 (d, J = 8.06 Hz, 1H), 7.58 (d, J = 7.33 Hz, 1H), 7.51-7.42 (m, 3H), 3.64 (bs, 2H), 2.56-2.51 (m, 2H), 1.98-1.94 (m, 2H), 1.62-1.50 (m, 6H); LC-MS 7.40 min, (M + 1)⁺ 240 @ 7.62 min.

(±) 1-(1-(naphthalen-2-yl)cyclohexyl)ethanamine (13)

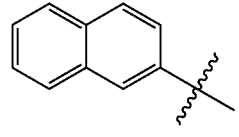

| | 3 | CH₃ | I |

SFC w/AD column and 33% MeOH/0.1% DEA, 25° C. column temp., 10 ml/min total flow, 280 nm to give the fast moving enantiomer 13 E1 (R$_t$ = 3.8 min) and the slow moving enantiomer 13 E2 (R$_t$ = 5 min).
13 E1
LC-MS (M + 1)⁺ 254 @ 8.31 min
13 E2
LC-MS (M + 1)⁺ 254 @ 8.33 min (±) 1-(1-(4-chlorophenyl)cyclohexyl)-2-methylpropan-1-amine (14)

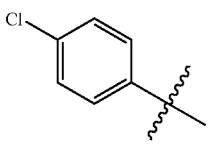 [SMILES: *c1ccc(Cl)cc1]

| | 3 | iso-propyl | I |

HPLC R$_t$ = 8.89 min; LC-MS 8.67 min, (M + 1)⁺ 266 @ 8.85 min.

(1-(4-(trifluoromethoxy)phenyl)cyclohexyl)methanamine (15)

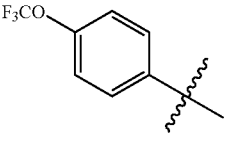 [SMILES: *c1ccc(OC(F)(F)F)cc1]

| | 3 | H | E |

HPLC R$_t$ = 8.63 min; ¹H NMR (400 MHz, CD₃OD) 7.50 (d, J = 9.16 Hz, 2H), 7.28 (d, J = 8.80 Hz, 2H), 3.02 (s, 2H), 2.19 (d, J = 12.8 Hz, 2H), 1.67-1.31 (m, 8H); LC-MS 7.93 min, (M + 1)⁺ 274 @ 8.18 min.

1-(1-(naphthalen-1-yl)cyclohexyl)ethanamine (16)

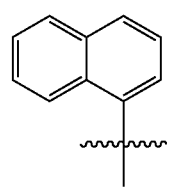 [SMILES: *c1cccc2ccccc12]

| | 3 | CH₃ | I |

SFC w/AS column and 30% MeOH/0.1% DEA, 280 nm.
16 E1: HPLC R$_t$ = 2.23 min; LC-MS 7.56 min, (M + 1)⁺ 254 @ 7.78 min
16 E2: LC-MS 7.59 min, (M + 1)⁺ 254 @ 7.9 min.

TABLE 1-continued

Summary of Exemplary Primary Amines

| Ar | n | R¹ | General Procedure |
|---|---|---|---|

1-(1-(3,4-dichlorophenyl)cyclohexyl)propan-1-amine (17)

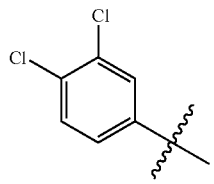 [SMILES: *c1ccc(Cl)c(Cl)c1]

| | 3 | CH₂CH₃ | I |

SFC w/AS column and 20% MeOH/0.1% DEA, 280 nm.
17 E1: HPLC R$_t$ = 1.58 min; ¹H NMR(400 MHz, CDCl₃) 7.50 (d, J = 1.47 Hz, 1H), 7.44 (d, J = 8.43 Hz, 1H), 7.29-7.27 (m, 1H), 3.01-2.97 (m, 1H), 2.44 (d, J = 13.2 Hz, 1H), 2.21 (d, J = 13.2 Hz, 1H), 1.98-1.92 (m, 1H), 1.79-1.25 (m, 8H), 1.09-1.03 (m, 4H); LC-MS 8.89 min, (M + 1)⁺ 286 @ 9.01 min.
17 E2: LC-MS 8.89 min, (M + 1)⁺ 288 @ 8.91 min.

(±) 1-(1-(4-chlorophenyl)cyclohexyl)propan-1-amine (18)

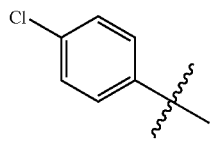 [SMILES: *c1ccc(Cl)cc1]

| | 3 | CH₂CH₃ | I |

HPLC R$_t$ = 8.68 min; LC-MS 7.91 min, (M + 1)⁺ 252 @ 8.04 min.

1-(1-(4-(trifluoromethoxy)phenyl)cyclohexyl)ethanamine (19)

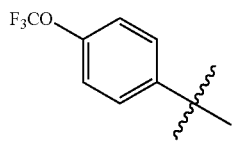 [SMILES: *c1ccc(OC(F)(F)F)cc1]

| | 3 | CH₃ | I |

Chiral HPLC with AD column and 100% MeOH/0.1% DEA, 280 nm
19 E1: HPLC R$_t$ = 1.52 min; LC-MS (15 minute method) 8.18 min, (M + 1)⁺ 288 @ 8.35 min.
19 E2: LC-MS (15 minute method) 8.24 min, (M + 1)⁺ 288 @ 8.27 min.

1-(1-(4-(furan-3-yl)phenyl)cyclohexyl)ethanamine (20)

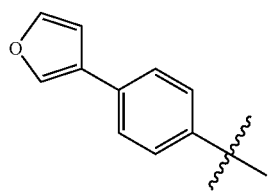 [SMILES: *c1ccc(-c2ccoc2)cc1]

| | 3 | CH₃ | I |

SFC w/AD column and 35% MeOH/10% IPA/0.1% DEA, 25° C. column temp., 10 ml/min total flow, 280 nm to give the fast moving enantiomer E1 and the slow moving enantiomer E2.
20 E1: ¹H NMR (400 MHz, CDCl₃) 7.73 (s, 1H), 7.48-7.46 (m, 3H), 7.32 (d, J = 8.43 Hz, 2H), 6.70 (d, J = 0.7 Hz, 1H), 2.77-2.72 (m, 1H), 2.37 (d, J = 13.2 Hz, 1H), 2.30 (d, J = 13.2 Hz, 1H), 1.58-1.42 (m, 5H), 1.32-1.22 (m, 3H), 0.87 (d, J = 6.60 Hz, 3H); LC-MS 7.94 min, (M + 1)⁺ 270 @ 8.06 min
20 E2: LC-MS 7.97 min, (M + 1)⁺ 270 @ 8.12 min 1-(1-(4-chlorophenyl)cyclohexyl)-3-methylbutan-1-amine (21)

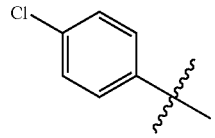 [SMILES: *c1ccc(Cl)cc1]

| | 3 | iso-butyl | I |

SFC w/AS column and 15% IPA/0.1% DEA, 25° C. column temp., 10 ml/min total flow, 280 nm to give the fast moving enantiomer E1 and the slow moving enantiomer E2.
21 E1: HPLC R$_t$ = 9.26 min; ¹H NMR (400 MHz, CDCl₃); 7.31-7.23 (m, 4H), 2.57-2.54 (m, 1H), 2.32-2.23 (m, 2H), 1.65-1.43 (m, 6H), 1.24-1.13 (m, 4H), 0.93-0.78 (m, 7H), 0.70-0.63 (m, 1H); LC-MS 9.01 min, (M + 1)⁺ 280 @ 9.19 min
21 E2: LC-MS 9.01 min, (M + 1)⁺ 280 @ 9.19 min 1-(1-(4-(furan-2-yl)phenyl)cyclohexyl)ethanamine (22)

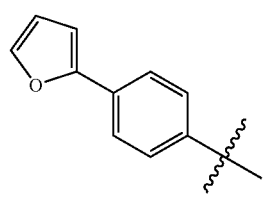 [SMILES: *c1ccc(-c2ccco2)cc1]

| | 3 | CH₃ | I |

SFC w/OD column and 12% MeOH/0.1% DEA, 40° C. column temp., 10 ml/min total flow, 280 nm to give the fast moving enantiomer E1 and the slow moving enantiomer E2.
22 E1: HPLC R$_t$ = 8.76 min; ¹H NMR (400 MHz, CDCl₃) 7.66 (d, J = 8.54 Hz, 2H), 7.45 (d, J = 1.71 Hz, 1H), 7.34 (d, J = 8.54 Hz, 2H), 6.63 (d, J = 3.42 Hz, 1H), 6.45 (dd, J = 1.71, 3.42 Hz, 1H), 2.83 (bs, 1H), 2.39 (d, J = 12.7 Hz, 1H), 2.30 (d, J = 11.7 Hz, 1H), 1.56-1.45 (m, 5H), 1.26 (bs, 3H), 0.90 (d, J = 6.35 Hz, 3H); LC-MS 8.09 min (M + 1)⁺ 270 @ 8.24 min.
22 E2: LC-MS 8.09 min (M + 1)⁺ 280 @ 8.24 min.

(1-(3',5'-difluorobiphenyl-4-yl)cyclohexyl)methanamine (23)

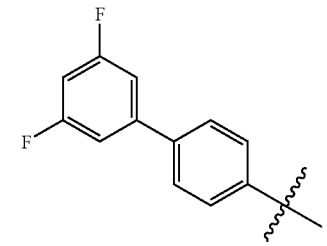 [SMILES: *c1ccc(-c2cc(F)cc(F)c2)cc1]

| | 3 | H | E |

HPLC R$_t$ = 9.24 min; ¹H NMR (400 mHz, CD₃OD) 7.68-7.64 (m, 2H), 7.51 (dd, J = 1.95, 8.96 Hz, 2H), 7.26-7.19 (m, 2H), 6.90-6.84 (m, 1H), 3.03 (s, 2H), 2.28-2.24 (m, 2H), 1.67-1.36 (m, 8H).

(±) 1-(1-(4-(thiazol-2-yl)phenyl)cyclohexyl)ethanamine (24)

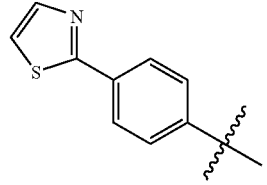 [SMILES: *c1ccc(-c2nccs2)cc1]

| | 3 | CH₃ | I |

TABLE 1-continued

Summary of Exemplary Primary Amines

| Ar | n | R¹ | General Procedure |
|---|---|---|---|

HPLC $R_t$ = 1.50 min; LC-MS (15 minute method) 7.51 min, (M + 1)⁺ 287 @ 7.72 min; ¹H NMR (400 MHz, CDCl₃) 7.95 (d, J = 8.43 Hz, 2H), 7.85 (d, J = 3.30 Hz, 1H), 7.44 (d, J = 8.43 Hz, 2H), 7.32 (d, J = 3.30 Hz, 1H), 3.13 (d, J = 6.23 Hz, 1H), 2.50 (d, J = 11.36 Hz, 1H), 2.33 (d, J = 12.10 Hz, 1H), 1.60-1.57 (m, 2H), 1.33-1.20 (m, 6H), 0.97-0.83 (m, 3H).

(±) 1-(1-(3,4-dichlorophenyl)cyclohexyl)pentan-1-amine (25)

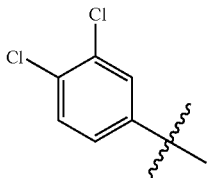 [SMILES: *c1ccc(Cl)c(Cl)c1]

| | 3 | n-butyl | I |

HPLC $R_t$ = 1.68 min; LC-MS (15 minute method) 9.92 min, (M + 1)⁺ 316 @ 10.04 min; ¹H NMR (400 MHz, CDCl₃) 7.47-7.42 (m, 2H), 7.26-7.23 (m, 1H), 2.95 (d, J = 9.16 Hz, 1H), 2.38 (d, J = 12.10 Hz, 1H), 2.23 (d, J = 12.83 Hz, 1H), 1.77-1.56 (m, 5H), 1.45 (s, 3H), 1.28-1.14 (m, 6H), 0.78 (t, J₁ = 13.56 Hz, J₂ = 6.60 Hz, 3H).

(±) 1-(1-(3,4-dichlorophenyl)cyclohexyl)heptan-1-amine (26)

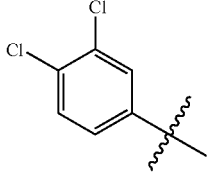 [SMILES: *c1ccc(Cl)c(Cl)c1]

| | 3 | n-hexyl | I |

HPLC $R_t$ = 1.78 min; LC-MS (15 minute method) 10.73 min, (M + 1)⁺ 344 @ 10.8 min; ¹H NMR (400 MHz, CDCl₃) 7.46-7.41 (m, 2H), 7.26-7.21 (m, 1H), 2.91 (d, J = 9.17 Hz, 1H), 2.36 (d, J = 12.46 Hz, 1H), 2.23 (d, J = 13.20 Hz, 1H), 1.73-1.44 (m, 7H), 1.28-1.14 (m, 11H), 0.82 (t, J₁ = 14.30 Hz, J₂ = 6.96 Hz, 3H).

The following compounds were synthesized from the respective cyclohexyl nitrile according to General Procedure E, and were optionally converted to the respective HCl salt form:

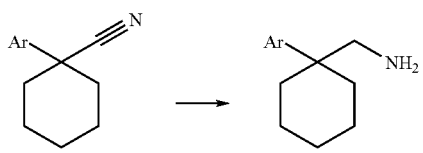

(1-(3,4-dichlorophenyl)cyclohexyl)-methanamine hydrochloride (27)

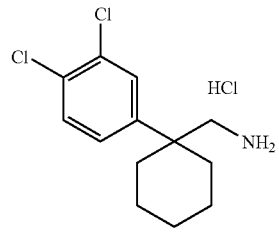 [SMILES: NCC1(c2ccc(Cl)c(Cl)c2)CCCCC1 ; Cl]

The title compound was synthesized from 1-(3,4-dichlorophenyl)-cyclohexanecarbonitrile (920 mg, 3.62 mmol). The crude HCl salt was recrystallized from 1:5 CH₃CN/IPA (10 mL) to give pure [1-(3,4-Dichloro-phenyl)-cyclohexyl]-methylamine hydrochloride as an off-white solid. HPLC $R_t$=8.66 min; ¹H NMR (400 mHz, MeOH-d⁴) 7.55-7.51 (m, 2H), 7.35-7.31 (dd, J=2.44, 8.55 Hz, 1H), 3.01 (s, 2H), 2.17-2.12 (m, 2H), 1.65-1.28 (m, 8H); LCMS 8.52 min, (M+1)⁺ 258@8.78 min.

(1-(3-chlorophenyl)cyclohexyl)methanamine hydrochloride (28)

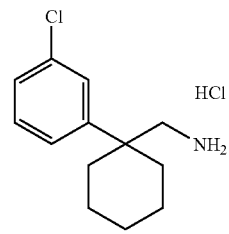 [SMILES: NCC1(c2cccc(Cl)c2)CCCCC1 ; Cl]

The title compound was synthesized from 1-(3-chlorophenyl)-cyclohexanecarbonitrile (320 mg, 1.46 mmol). The crude HCl salt was recrystallized from CH₃CN (7.5 mL) to give pure (1-(3-chlorophenyl)cyclohexyl)-methanamine hydrochloride as off-white needles/hay. HPLC $R_t$=8.18 min; ¹H NMR (400 mHz, MeOH-d⁴) 7.41-7.26 (m, 4H), 3.0 (s, 2H), 2.18-2.15 (m, 2H), 1.64-1.30 (m, 8H); LC-MS 7.72 min, (M+1)⁺ 224@8.0 min.

(1-(4-chlorophenyl)cyclohexyl)methanamine hydrochloride (29)

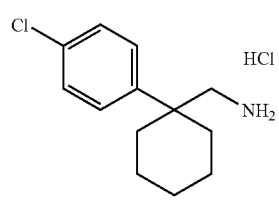 [SMILES: NCC1(c2ccc(Cl)cc2)CCCCC1 ; Cl]

The title compound was synthesized from 1-(4-chlorophenyl)-cyclohexanecarbonitrile. The crude HCl salt was recrystallized from CH₃CN (3 mL) to give pure (1-(4-chlorophenyl)cyclohexyl)methanamine hydrochloride as off-white needles/hay. HPLC $R_t$=8.22 min; $^1$H NMR (400 mHz, MeOH-d$^4$) 7.38 (s, 4H), 2.97 (s, 2H), 2.19-2.14 (m, 2H), 1.63-1.30 (m, 8H); LC-MS 7.83 min, (M+1)$^+$ 224 at 8.1 min.

(1-(3,4-difluorophenyl)cyclohexyl)methanamine hydrochloride (30)

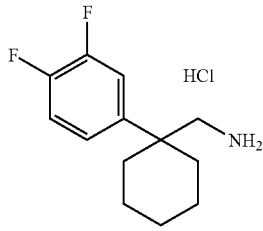 [SMILES: NCC1(c2ccc(F)c(F)c2)CCCCC1 ; Cl]

The title compound was synthesized from 1-(3,4-difluorophenyl)-cyclohexanecarbonitrile. The crude HCl salt was recrystallized from CH$_3$CN (6 mL) to give pure (1-(3,4-difluorophenyl)cyclohexyl)methanamine hydrochloride (38 mg, 17%) as off-white needles/hay HPLC $R_t$=8.06 min; $^1$H NMR (400 mHz, MeOH-d$^4$) 7.34-7.20 (m, 3H), 2.99 (m, 2H), 2.15-2.12 (m, 2H), 1.64-1.31 (m, 8H); LC-MS 7.01 min, (M+1)$^+$ 226@7.16 min.

(1-phenylcyclohexyl)methaneamine hydrochloride (31)

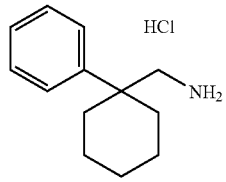 [SMILES: NCC1(c2ccccc2)CCCCC1 ; Cl]

The title compound was synthesized from 1-phenylcyclohexane-carbonitrile. The crude HCl salt was recrystallized from CH$_3$CN to give pure (1-phenylcyclohexyl)methaneamine hydrochloride as off-white needles. HPLC $R_t$=7.59 min; $^1$H NMR (400 mHz, MeOH-d$^4$) 7.40-7.36 (m, 4H), 7.27-7.25 (m, 1H), 2.98 (s, 2H), 2.22-2.20 (m, 2H), 1.62-1.32 (m, 8H); LC-MS 6.16 min, (M+1)$^+$ 190@6.36 min.

(1-(3-chloro-4-fluorophenyl)cyclohexyl)-methanamine (32)

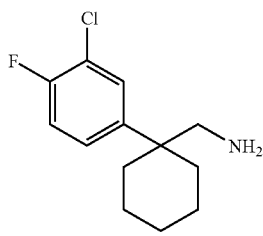 [SMILES: NCC1(c2ccc(F)c(Cl)c2)CCCCC1]

The title compound was prepared from 1-(3-chloro-4-fluorophenyl)cyclohexanecarbonitrile. A solution of the crude product in MTBE was basicified at 0° C. with KOH, extracted with MTBE and evaporated. The residue was diluted in DCM, filtered through an aminopropyl column and evaporated to give the primary amine (64.1 mg, 25%) as an oil. LCMS $R_t$=7.62 min, m/z=242 (M+1). $^1$H NMR (CDCl$_3$, δ) 7.34 (dd, J=2.4, 7.1 Hz, 1H), 7.19 (ddd, J=2.4, 4.6, 8.7 Hz, 1H), 7.11 (t, J=8.7 Hz, 1H), 2.68 (s, 2H), 2.1 (m, 2H), 1.6-1.2 (m, 8H), 0.79 (bs, 2H). $^{13}$C NMR (CDCl$_3$, δ, mult): 157.4(0), 154.9(0), 142.2(0), 129.5(0), 127.0(0), 126.9(1), 120.8(1), 120.6(1), 116.3(1), 116.1(1), 54.5(2), 43.3(0), 33.7(2), 26.5(2), 22.0 (2).

(1-(naphthalen-2-yl)cyclohexyl)methanamine (33)

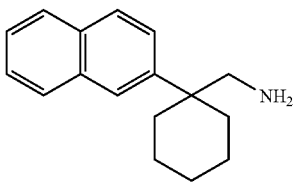 [SMILES: NCC1(c2ccc3ccccc3c2)CCCCC1]

The title compound was synthesized in 37% yield from 1-(naphthalen-2-yl)cyclohexane-carbonitrile. HPLC $R_t$ (5-100-8)=8.44 min. LCMS $R_t$=8.22 min, m/z=240 (M+1). $^1$H NMR (CDCl$_3$, δ): 7.9-7.2 (m, 7H), 2.78 (s, 2H), 2.3 (m, 2H), 1.7-1.3 (m, 8H), 0.9 (bs, 2H). $^{13}$C NMR (CDCl$_3$, δ, mult): 133.4(0), 131.7(0), 128.0(1), 127.8(1), 127.3(1), 126.4 (1), 125.8(1), 125.4(1), 125.2(1), 54.6(2), 43.7(0), 33.8(2), 26.7(2), 22.2(2).

(1-(4-(trifluoromethyl)phenyl)-cyclohexyl)methanamine (34)

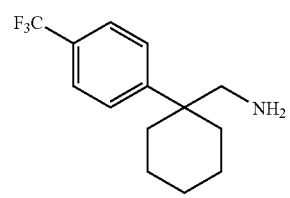 [SMILES: NCC1(c2ccc(C(F)(F)F)cc2)CCCCC1]

The title compound was prepared from 1-(4-(trifluoromethyl)phenyl)-cyclohexanecarbonitrile (127 mg, 0.50 mmol). The crude product was purified by silica gel column chromatography (MeOH/CH$_2$Cl$_2$, MeOH from 0% to 10%) to give (1-(4-(trifluoromethyl)phenyl)cyclohexyl)methanamine (62 mg, 48%) as a clear oil. $^1$H NMR (CDCl$_3$): δ 1.26-1.52 (m 4H), 1.54-1.61 (m, 2H), 1.66-1.73 (m, 2H), 2.13-2.18 (m, 2H), 2.28 (s, 3H), 2.63 (s, 2H), 7.49 (d, J=8.0 Hz, 2H), 7.59 (d, J=8.0 Hz, 2H). $^{13}$C NMR (CDCl$_3$) δ 22.3, 26.7, 34.8, 42.9, 54.4, 125.5, 125.6, 127.9, 129.9, 149.1. ESI MS m/z 258.

(1-(benzo[d][1,3]dioxol-5-yl)cyclohexyl)methanamine (35)

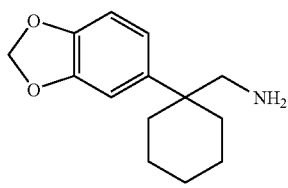 [SMILES: NCC1(c2ccc3c(c2)OCO3)CCCCC1]

The title compound was prepared from 1-(benzo[d][1,3]dioxol-5-yl)cyclohexanecarbonitrile (115 mg, 0.50 mmol). The crude product was purified by chromatography (SiO$_2$, MeOH/CH$_2$Cl$_2$, MeOH from 0% to 10%) to give (±) (1-(benzo[d][1,3]dioxol-5-yl)cyclohexyl)methanamine (58 mg, 50%) as a clear oil. $^1$H NMR (CDCl$_3$) 1.34-1.39 (m, 3H), 1.46-1.54 (m, 7H), 2.01-2.06 (m, 2H), 2.64 (s, 2H), 5.93 (s, 2H), 6.78 (s, 2H), 6.84 (s, 1H). $^{13}$C NMR (CDCl$_3$) 22.3, 26.9, 34.3, 43.5, 54.9, 101.1, 107.9, 108.2, 120.6, 138.7, 145.6, 148.2. ESI MS m/z 234.

(1-(3-(trifluoromethyl)phenyl)-cyclohexyl)methanamine (36)

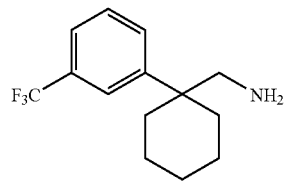 [SMILES: NCC1(c2cccc(C(F)(F)F)c2)CCCCC1]

The title compound was prepared from 1-(3-(trifluoromethyl)phenyl)-cyclohexanecarbonitrile (127 mg, 0.50 mmol). The crude product was purified by chromatography (SiO$_2$, MeOH/CH$_2$Cl$_2$, MeOH from 0% to 10%) to give (±) (1-(3-(trifluoromethyl)phenyl)-cyclohexyl)methanamine (26 mg, 20%) as a clear oil. $^1$H NMR (CDCl$_3$): 1.26-1.41 (m, 5H), 1.50-1.63 (m, 5H), 2.12-2.16 (m, 2H), 2.73 (s, 2H), 7.47-7.49 (m, 2H), 7.52-7.55 (m, 1H), 7.58 (s, 1H). $^{13}$C NMR (CDCl$_3$) 22.3, 26.7, 33.8, 43.9, 54.6, 122.9, 124.1, 124.2, 129.1, 130.8, 130.9, 146.3. ESI MS m/z 257.

(1-(3-fluorophenyl)cyclohexyl)methanamine (37)

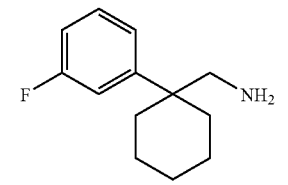 [SMILES: NCC1(c2cccc(F)c2)CCCCC1]

The title compound was prepared from 1-(3-fluorophenyl)cyclohexanecarbonitrile (102 mg, 0.50 mmol). The crude product was purified by chromatography (SiO$_2$, MeOH/CH$_2$Cl$_2$, MeOH from 0% to 10%) to give (±) (1-(3-fluorophenyl)cyclohexyl)methanamine (32 mg, 31%) as a clear oil. $^1$H NMR (CDCl$_3$): 1.26-1.39 (m, 5H), 1.51-1.58 (m, 5H), 2.07-2.10 (m, 2H), 2.69 (s, 2H), 6.88-6.93 (m, 1H), 7.04 (d, J=8.0 Hz, 1H), 7.11 (d, J=8.0 Hz, 1H), 7.27-7.34 (m, 1H). $^{13}$C NMR (CDCl$_3$) 22.3, 26.8, 33.8, 43.9, 54.8, 112.7, 113.0, 114.5, 114.7, 123.0, 123.1, 129.9, 130.0, 162.3, 164.7. ESI MS m/z 208.

(1-(2,4-dichlorophenyl)cyclohexyl)methanamine (38)

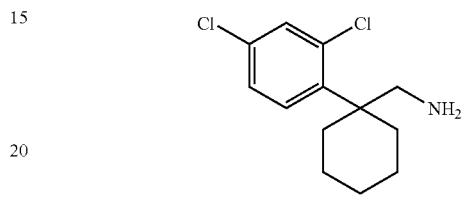

$^1$H NMR (400 MHz, CD$_3$Cl) δ 7.35 (d, J=2.4 Hz, 1 H), 7.32 (d, J=8.4 Hz, 1 H), 7.19 (dd, J=2.4, 8.4 Hz, 1 H), 3.08 (s, 2 H), 2.25 (m, 2 H), 1.45 (m, 2 H), 1.31 (m, 2 H), 1.28-1.18 (m, 4 H); $^{13}$C NMR (100 MHz, CD$_3$Cl) δ 139.91, 134.39, 133.70, 132.89, 132.23 48.61, 45.83, 33.70, 26.77, 26.66, 22.56; ESI MS m/z 258.1.

(1-(6-fluoronaphthalen-2-yl)cyclohexyl)methanamine (39)

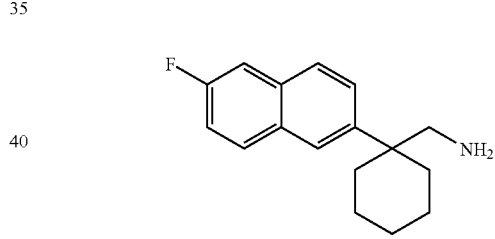

The title compound was synthesized according to Scheme 25, below.

Scheme 25:

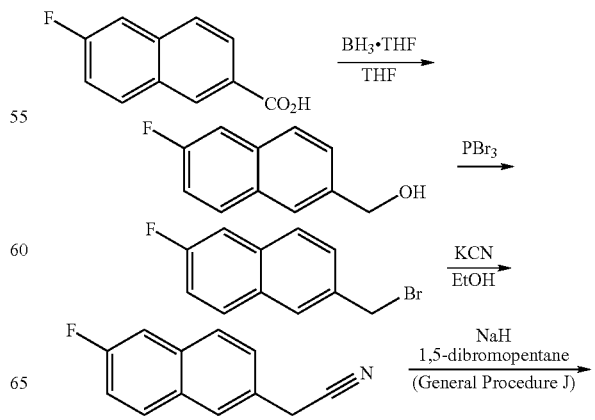

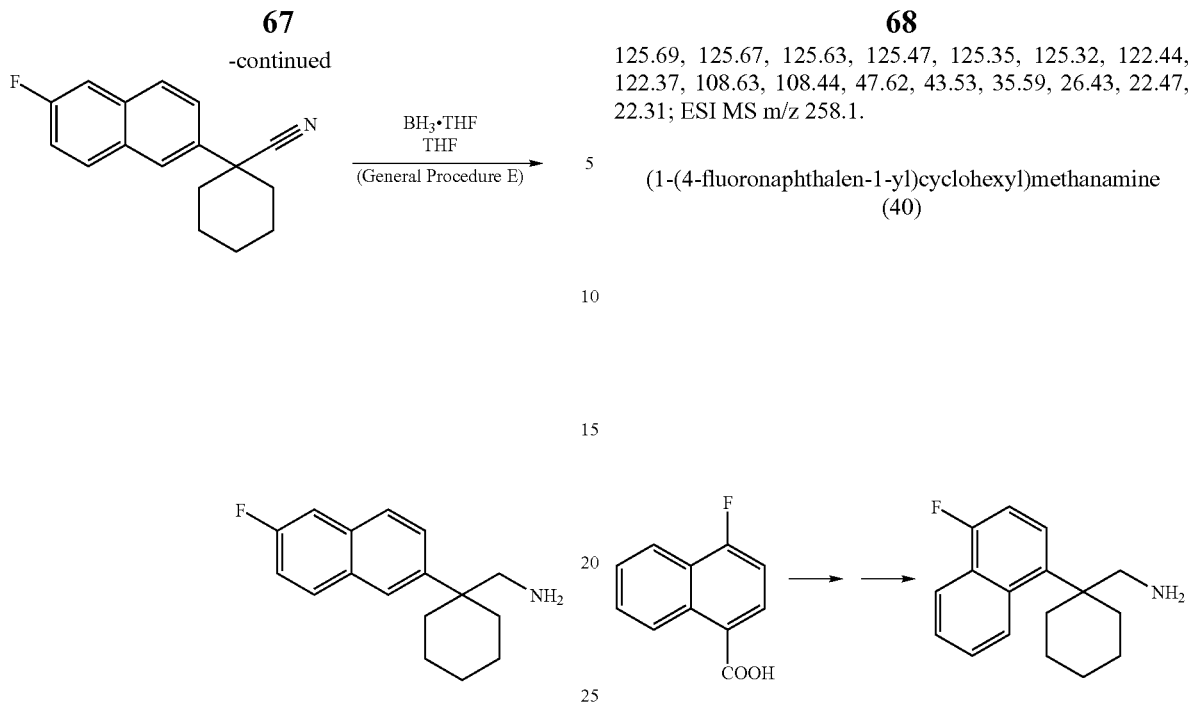

To a solution of 6-fluoro-naphthalene-2-carboxylic acid (3.0 g, 15.8 mmol) was added BH$_3$.THF (31.6 mL, 31.6 mmol). The reaction mixture was stirred overnight before being concentrated. To the residue was added diethyl ether (100 mL) and NaOH solution (10 mL). The organic layer was separated, dried and concentrated. The resultant residue was purified by silica gel column chromatography (ethyl acetate/hexane 1:7) to afford (6-fluoro-naphthalen-2-yl)-methanol (2.28 g, 82%).

To a solution of (6-fluoro-naphthalen-2-yl)-methanol (2.0 g, 11.3 mmol) in CH$_2$Cl$_2$ (30 mL) was added PBr$_3$ (1.0 M in CH$_2$Cl$_2$, 22.6 mmol). The reaction mixture was stirred for 3 h at room temperature before being quenched by NH$_4$Cl (30 mL). The organic layer was separated, dried and concentrated. The resultant residue was purified by silica gel column chromatography (ethyl acetate/hexane=1:10) to afford 2-bromomethyl-6-fluoro-naphthalene (2.23 g, 74%).

To a mixture of 2-bromomethyl-6-fluoro-naphthalene (1.5 g, 5.9 mmoL) in CH$_3$CN (30 mL) was added KCN (1.16 g, 17.8 mmoL). The reaction mixture was heated at reflux for 6 h before being concentrated. To the residue was added diethyl ether (100 mL) and H$_2$O (15 mL). The organic layer was separated, dried and concentrated. The resultant residue was purified by silica gel column chromatography (ethyl acetate/hexane=1:10) to afford the (6-fluoro-naphthalen-2-yl)-acetonitrile (0.88 g, 70%).

The title compound was synthesized from (6-fluoro-naphthalen-2-yl)-acetonitrile (1.0 g, 5.48 mmoL) according to General Procedure J to form the intermediate nitrile (0.98 g, 71%), which was purified by silica gel column chromatography (ethyl acetate/hexane 1:7), followed by General Procedure E.

The crude product was dissolved in MeOH (4 mL) and subjected to reverse phase column chromatography (CH$_3$CN/H$_2$O/0.1% formic acid=5% to 100%) to give the title compound (0.53 g, 75%). $^1$H NMR (400 MHz, CD$_3$Cl) δ 8.29 (m, 1 H), 8.18 (m, 1 H), 7.83 (m, 1 H), 7.50 (dd, J=3.6, 6.8 Hz, 1 H), 7.41 (dd, J=6.0 Hz, 8.8 Hz, 1 H0, 7.06 (dd, J=8.8, 8.8 Hz, 1 H), 3.37 (s, 2 H), 2.34 (m, 2 H), 1.89 (m, 2 H), 1.58 (m, 2 H), 1.45 (m, 2 H); $^{13}$C NMR (100 MHz, CD$_3$Cl) δ 168.08, 159.85, 157.34, 132.96, 132.93, 128.58, 128.50, 126.04, 125.69, 125.67, 125.63, 125.47, 125.35, 125.32, 122.44, 122.37, 108.63, 108.44, 47.62, 43.53, 35.59, 26.43, 22.47, 22.31; ESI MS m/z 258.1.

(1-(4-fluoronaphthalen-1-yl)cyclohexyl)methanamine (40)

The title compound was synthesized from 4-fluoro-naphthalene-1-carboxylic acid (2.0 g, 10.3 mmol) according to the synthetic procedures described above for the synthesis of 39 (Scheme 25). The crude product was dissolved in MeOH (4 mL) and subjected to reverse phase column chromatography (CH$_3$CN/H$_2$O/0.1% formic acid=5% to 100%) to give 40 (0.51 g). $^1$H NMR (400 MHz, CD$_3$OD) δ 8.48(d, J=8.4 Hz, 1 H), 8.20 (d, J=8.4 Hz, 1 H), 7.6 (m, 3 H), 7.21 (dd, J=8.4, 8.4 Hz, 1 H), 3.67 (s, 2 H), 2.52 (m, 2 H), 2.04 (m, 2 H), 1.68 (m, 2 H), 1.50 (m, 4 H); $^{13}$C NMR (100 MHz, CD$_3$OD), δ 160.04, 157.54, 133.03, 132.99, 131.91, 160.04, 157.54, 133.03, 132.99, 131.01, 128.74, 128.64, 126.64, 125.67, 125.65, 125.51, 125.24, 125.22, 121.80, 121.73, 108.33, 108.14, 47.00, 42.50, 35.12, 26.03, 21.89; ESI MS m/z 258.2.

1.3. Synthesis of Secondary and Tertiary Amines

Compounds in Table 2, below, were synthesized from the indicated primary amine according to the indicated General Procedure and were optionally converted to the corresponding HCl salt form.

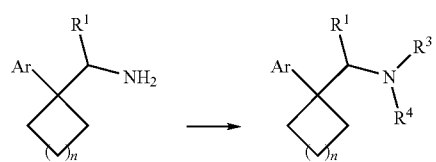

TABLE 2

Summary of Exemplary Secondary and Tertiary Amines

| Ar | n | R¹ | R³ | R⁴ | General Procedure | Prepared From |
|---|---|---|---|---|---|---|
| 1-(1-(3,4-dichlorophenyl)cyclobutyl)-N,N-dimethylmethanamine (41) | | | | | | |
| 3,4-dichlorophenyl | 1 | H | CH₃ | CH₃ | C | 1 |

HPLC R$_t$ = 8.42 min; ¹H NMR (400 mHz, MeOH-d⁴) 7.58-7.53(m, 2H), 7.34-7.31(m, 1H), 3.63(s, 2H), 2.65(s, 6H), 2.49-2.29(m, 4H), 2.07-1.87(m, 2H); LC-MS 8.12 min, (M + 1)⁺ 258 @ 8.1 min 1-(1-(3,4-dichlorophenyl)cyclobutyl)-N-methylmethanamine (42)

| Ar | n | R¹ | R³ | R⁴ | General Procedure | Prepared From |
|---|---|---|---|---|---|---|
| 3,4-dichlorophenyl | 1 | H | H | CH₃ | A | 1 |

HPLC R$_t$ = 8.37 min; ¹H NMR (400 mHz, MeOH-d⁴) 7.57(d, J = 8.43 Hz, 1H), 7.44(d, J = 1.83 Hz, 1H), 7.20(dd, J = 2.2, 8.43 Hz, 1H), 3.45(s, 2H), 2.65(s, 3H), 2.47-2.43(m, 2H), 2.37-2.31(m, 2H), 2.22-2.15(1H), 1.98-1.92(m, 1H); LC-MS 7.1 min, (M + 1)⁺ 244 @ 7.28 min.

(±) 1-(1-(3,4-dichlorophenyl)cyclohexyl)-N,N-dimethylethanamine (43)

| Ar | n | R¹ | R³ | R⁴ | General Procedure | Prepared From |
|---|---|---|---|---|---|---|
| 3,4-dichlorophenyl | 3 | CH₃ | CH₃ | CH₃ | C | 2 |

HPLC R$_t$ = 8.93 min; ¹H NMR (400 mHz, CDCl₃) 7.43(d, J = 1.83 Hz, 1H), 7.35(d, J = 8.8 Hz, 1H), 7.22-7.19(m, 1H), 2.54(d, J = 12.8 Hz, 1H), 2.44-2.40 (m, 1H), 2.09-2.05(d, J = 13.9 Hz, 1H), 1.95(s, 6H), 1.56-1.48(m, 5H), 1.25-1.11(m, 3H), 0.76(d, J = 6.97 Hz, 3H); LC-MS 10.2 min, (M + 1)⁺ 300 @ 10.26 min.

1-(1-(3,4-dichlorophenyl)cyclohexyl)-N-methylethanamine (44 E1)

| Ar | n | R¹ | R³ | R⁴ | General Procedure | Prepared From |
|---|---|---|---|---|---|---|
| 3,4-dichlorophenyl | 3 | CH₃ | CH₃ | CH₃ | D | 2 E1 |

HPLC R₁ = 9.02 min; ¹H NMR (400 MHz, CD₃OD) 7.68(d, J = 2.2 Hz, 1H), 7.64-7.62(m, 1H), 7.45(dd, J = 2.2, 8.43 Hz, 1H), 3.56-3.52(m, 1H), 2.88(s, 3H), 2.71(d, J = 12.8 Hz, 1H), 2.36(d, J = 13.2 Hz, 1H), 2.19(s, 3H), 1.70-1.60 (m, 5H), 1.38-1.25(m, 5H), 1.18-1.12(m, 1H); LC-MS 9.55 min, (M + 1)⁺ 300 @ 9.84 min.

1-(1-(3,4-dichlorophenyl)cyclohexyl)-N-methylethanamine (44 E2)

| Ar | n | R¹ | R³ | R⁴ | General Procedure | Prepared From |
|---|---|---|---|---|---|---|
| 3,4-dichlorophenyl | 3 | CH₃ | CH₃ | CH₃ | D | 2 E2 |

TABLE 2-continued

Summary of Exemplary Secondary and Tertiary Amines

| Ar | n | R¹ | R³ | R⁴ | General Procedure | Prepared From |
|----|---|----|----|----|-------------------|---------------|

LC-MS 9.47 min, (M + 1)⁺ 300 @ 9.64 min.
(±) 1-(1-(3,4-dichlorophenyl)cyclohexyl)-N,3-dimethylbutan-1-amine (45)

| 3,4-dichlorophenyl | 3 | iso-butyl | H | CH₃ | A | 3 |

HPLC R$_t$ = 9.57 min; ¹H NMR (400 MHz, CD₃OD) 7.59(d, J = 2.20 Hz, 1H), 7.54(d, J = 8.80 Hz, 1H), 7.35(dd, J = 2.20, 8.43 Hz, 1H), 3.01-2.98(m, 1H), 2.66(s, 3H), 2.39(m, 1H), 2.30(m, 1H), 1.97-1.46(m, 7H), 1.31-1.22(m, 3H), 1.12-1.06(m, 2H), 0.84(d, J = 6.60 Hz, 3H), 0.70(d, J = 6.60 Hz, 3H); LC-MS 8.93 min, (M + 1)⁺ 328 @ 9.18 min.
(±) 1-(1-(3,4-dichlorophenyl)cyclohexyl)-N,N,3-trimethylbutan-1-amine (46)

| 3,4-dichlorophenyl | 3 | iso-butyl | CH₃ | CH₃ | C | 3 |

R$_t$ = 9.72 min; ¹H NMR (400 MHz, CD₃OD) 8.05(bs, 1H), 7.48-7.46(m, 1H), 7.40(d, J = 8.43 Hz, 1H), 7.23(dd, J = 1.83-8.43 Hz, 1H), 2.62(dd, J = 3.67, 9.16 Hz, 1H), 2.59-2.56(m, 1H), 2.30(s, 6H), 2.19-2.16(m, 1H), 1.61-1.11(m, 12H), 0.88-0.85(m, 6H); LC-MS 11.32 min, (M + 1)⁺ 342 @ 11.7 min.
(±) 1-(1-(4-methoxyphenyl)cyclohexyl)-N-methylethanamine (47)

| 4-methoxyphenyl | 3 | CH₃ | H | CH₃ | A | 5 |

HPLC R$_t$ = 8.22 min; ¹H NMR (400 MHz, CD₃OD) 7.30-7.26(m, 2H), 6.97-6.94(m, 2H), 3.76(s, 3H), 3.09-3.04(m, 1H), 2.57(s, 3H), 2.50-2.47(m, 2H), 2.31-2.28(m, 2H), 1.59-1.45(m, 5H), 1.29-1.22(m, 3H), 1.09(d, J = 6.60 Hz, 3H); LC-MS 5.57 min, (M + 1)⁺ 248 @ 6.07 min
1-(1-(3,4-dichlorophenyl)cyclohexyl)-N-methylethanamine (48 E1)

| 3,4-dichlorophenyl | 3 | CH₃ | H | CH₃ | A | 2 E1 |

HPLC R$_t$ = 8.94 min; ¹H NMR (400 MHz, CD₃OD) 7.61-7.58(m, 2H), 7.36(dd, J = 2.2, 8.43 Hz, 1H), 3.20-3.16(m, 1H), 2.65(s, 3H), 2.51(d, J = 12.5 Hz, 1H), 2.34(d, J = 10.6 Hz, 1H), 1.69-1.55(m, 5H), 1.35-1.12(m, 6H); LC-MS 7.08 min, (M + 1)⁺ 286 @ 7.46 min. [α]$_D$ = −2.68 (c = 0.41, MeOH).
1-(1-(3,4-dichlorophenyl)cyclohexyl)-N-methylethanamine (48 E2)

| 3,4-dichlorophenyl | 3 | CH₃ | H | CH₃ | A | 2 E2 |

TABLE 2-continued

Summary of Exemplary Secondary and Tertiary Amines

| Ar | n | R$^1$ | R$^3$ | R$^4$ | General Procedure | Prepared From |
|---|---|---|---|---|---|---|

LC-MS 7.03 min, (M + 1)$^+$ 286 @ 7.58 min.
1-(1-(biphenyl-4-yl)cyclohexyl)-N-methylmethanamine (49)

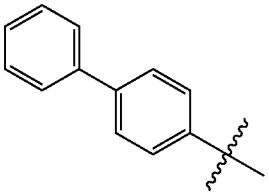 [SMILES: *c1ccc(-c2ccccc2)cc1]

| | 3 | H | H | CH$_3$ | A | 8 |

HPLC R$_t$ = 9.06 min; $^1$H NMR (400 MHz, CD$_3$OD) 7.66(d, J = 8.06 Hz, 2H), 7.59(d, J = 8.43 Hz, 2H), 7.50(d, J = 8.06 Hz, 2H), 7.40(d, J = 7.70 Hz, 2H), 7.31-7.29(m, 1H), 3.14(s, 2H), 2.54(s, 3H), 2.29-2.27(m, 2H), 1.69-1.52(m, 5H), 1.43-1.37(m, 3H); LC-MS 7.05 min, (M + 1)$^+$ 280 @ 7.52 min.
(±) 1-(1-(4-chlorophenyl)cyclohexyl)-N-methylethanamine (50)

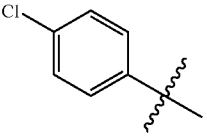

| | 3 | CH$_3$ | H | CH$_3$ | A | 11 |

HPLC R$_t$ = 8.59 min; $^1$H NMR (400 MHz, CD$_3$OD) 7.43-7.34(m, 4H), 3.14-3.08(m, 1H), 2.59(d, J = 0.73 Hz, 3H), 2.52-2.48(d, J = 12.2 Hz, 1H), 2.33-2.29(d, J = 13.4 Hz, 1H), 1.59-1.47(m, 5H), 1.31-1.13(m, 3H), 1.09(d, J = 6.84 Hz, 3H); LC-MS 7.10 min, (M + 1)$^+$ 252 @ 7.32 min.
(±) N-methyl-1-(1-(thiophen-2-yl)cyclohexyl)ethanamine (51)

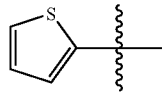 [SMILES: *c1cccs1]

| | 3 | CH$_3$ | H | CH$_3$ | A | 6 |

HPLC R$_t$ = 7.92 min; $^1$H NMR (400 MHz, CD$_3$OD) 7.42-7.40(m, 1H), 7.07-7.04(m, 1H), 7.01-6.99(m, 1H), 3.17-3.10(m, 1H), 2.61(s, 3H), 2.42-2.38(m, 1H); 2.14-2.10(m, 1H), 1.64-1.26(m, 8H), 1.19(d, J = 6.59 Hz, 3H); LC-MS 5.80 min, (M + 1)$^+$ 224 @ 6.19 min.
N,N-dimethyl-1-(1-(4-(methylthio)phenyl)cyclohexyl)methanamine (52)

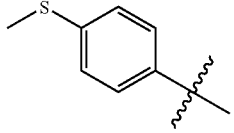 [SMILES: *c1ccc(SC)cc1]

| | 3 | H | CH$_3$ | CH$_3$ | C | 10 |

HPLC R$_t$ = 8.54 min; $^1$H NMR (400 MHz, CD$_3$OD) 7.39(d, J = 8.07 Hz, 2H), 7.30-7.28(m, 2H), 3.34(s, 2H), 2.52(s, 6H), 2.43(s, 3H), 2.26-2.23(d, J = 11.7 Hz, 2H), 1.66-1.52(m, 5H), 1.38-1.37(m, 3H); LC-MS 6.97 min, (M + 1)$^+$ 264 @ 7.16 min.
N,N-dimethyl-1-(1-(naphthalen-1-yl)cyclohexyl)methanamine (53)

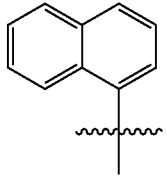

| | 3 | H | CH$_3$ | CH$_3$ | F | 12 |

HPLC R$_t$ = 8.96 min; $^1$H NMR (400 Mhz, CD$_3$OD) 8.00-7.86(m, 4H), 7.65(dd, J = 2.2, 8.8 Hz, 1H), 7.54-7.51(m, 2H), 3.52(s, 2H), 2.54(s, 6H), 2.46-2.44(d, J = 8.43 Hz, 2H), 1.84-1.50(m, 9H); LC-MS 8.28 min, (M + 1)$^+$ 268 @ 8.39 min.

TABLE 2-continued

Summary of Exemplary Secondary and Tertiary Amines

| Ar | n | R¹ | R³ | R⁴ | General Procedure | Prepared From |
|---|---|---|---|---|---|---|
| (±) 1-(1-(4-chlorophenyl)cyclohexyl)-N,2-dimethylpropan-1-amine (54) | | | | | | |
| 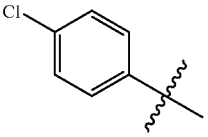 [SMILES: *c1ccc(Cl)cc1] | 3 | iso-propyl | H | CH₃ | F | 14 |

HPLC $R_t$ = 9.09 min; ¹H NMR (400 MHz, CD₃OD) 7.40(s, 4H), 2.99(s, 1H), 2.67(s, 3H), 2.45-2.38(m, 2H), 2.17-2.14(m, 1H), 1.61-1.53(m, 5H), 1.31-1.16 (m, 3H), 0.98(d, J = 7.33 Hz, 3H), 0.65(d, J = 6.97 Hz, 3H); LC-MS 9.26 min, (M + 1)⁺ 280 @ 9.29 min.

(±) N,N-dimethyl-1-(1-(naphthalen-2-yl)cyclohexyl)ethanamine (55)

| | | | | | | |
|---|---|---|---|---|---|---|
| 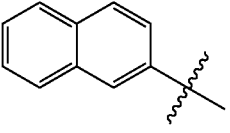 | 3 | CH₃ | CH₃ | CH₃ | F | 13 |

HPLC $R_t$ = 9.04 min; ¹H NMR (400 MHz, CDCl₃) 7.82-7.76(m, 4H), 7.58-7.56 (m, 1H), 7.45-7.39(m, 2H), 2.78(d, J = 12.5 Hz, 1H), 2.53-2.48(m, 1H), 2.30 (d, J = 13.6 Hz, 1H), 1.94-1.18(m, 8H), 0.76(d, J = 6.96 Hz, 3H); LC-MS 8.04 min, (M + 1)⁺ 282 @ 8.16 min.

N,N-dimethyl-1-(1-(naphthalen-2-yl)cyclohexyl)ethanamine (56 E1)

| | | | | | | |
|---|---|---|---|---|---|---|
| 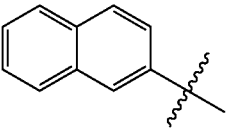 | 3 | CH₃ | CH₃ | CH₃ | F | 13 E1 |

HPLC $R_t$ = 9.12 min; ¹H NMR (400 MHz, CD₃OD) 8.03(d, J = 1.1 Hz, 1H), 7.99(d, J = 8.80 Hz, 1H), 7.96-7.93(m, 1H), 7.90-7.88(m, 1H), 7.65(dd, J = 1.83, 8.80 Hz, 1H), 7.56-7.51(m, 2H), 3.59(q, J = 6.97, 13.9 Hz, 1H), 2.95-2.92 (m, 1H), 2.87(s, 3H), 2.59-2.56(m, 1H), 2.0(s, 3H), 1.76-1.19(m, 11H); LC-MS 7.37 min, (M + 1)⁺ 282 @ 7.60 min.

N,N-dimethyl-1-(1-(naphthalen-2-yl)cyclohexyl)ethanamine (56 E2)

| | | | | | | |
|---|---|---|---|---|---|---|
| 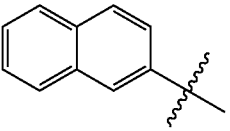 [SMILES: *c1ccc2ccccc2c1] | 3 | CH₃ | CH₃ | CH₃ | F | 13 E2 |

LC-MS 8.42 min, (M + 1)⁺ 282 @ 8.57 min.

N-methyl-1-(1-(naphthalen-1-yl)cyclohexyl)methanamine (57)

| | | | | | | |
|---|---|---|---|---|---|---|
| 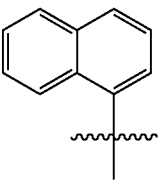 [SMILES: *c1cccc2ccccc12] | 3 | H | H | CH₃ | A | 12 |

HPLC $R_t$ = 8.65 min; ¹H NMR (400 MHz, CD₃OD) 8.67(d, J = 8.8 Hz, 1H), 7.98(d, J = 1.47 Hz, 1H), 7.96(d, J = 1.83 Hz, 1H), 7.89(d, J = 8.43 Hz, 1H), 7.67-7.50(m, 3H), 3.80(bs, 2H), 2.63-2.58(s, 2H), 2.55(s, 3H), 2.05-2.01(bs, 2H), 1.69(bs, 2H), 1.55(bs, 3H); LC-MS 7.36 min, (M + 1)⁺ 254 @ 7.50 min.

N-methyl-1-(1-(naphthalen-2-yl)cyclohexyl)ethanamine (58 E1)

| | | | | | | |
|---|---|---|---|---|---|---|
| 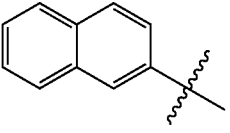 [SMILES: *c1ccc2ccccc2c1] | 3 | CH₃ | H | CH₃ | A | 13 E1 |

TABLE 2-continued

Summary of Exemplary Secondary and Tertiary Amines

| Ar | n | R¹ | R³ | R⁴ | General Procedure | Prepared From |
|---|---|---|---|---|---|---|

HPLC R$_t$ = 8.93 min; ¹H NMR (400 MHz, CD$_3$OD) 7.98-7.87(m, 4H), 7.60-7.57(m, 1H), 7.55-7.50(m, 2H), 3.30(1H, hidden), 2.76-2.72(m, 1H), 2.64(s, 3H), 2.59-2.55(m, 1H), 1.69-1.60(m, 6H), 1.41-1.30(m, 3H), 1.21(d, J = 6.96 Hz, 3H); LC-MS 7.92 min, (M + 1)⁺ 268 @ 8.06 min.
N-methyl-1-(1-(naphthalen-2-yl)cyclohexyl)ethanamine (58 E2)

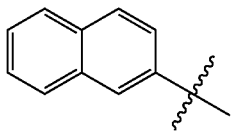

| | 3 | CH$_3$ | H | CH$_3$ | A | 13 E2 |

LC-MS 7.88 min, (M + 1)⁺ 268 @ 8.00 min.
N-methyl-1-(1-(naphthalen-1-yl)cyclohexyl)ethanamine (59 E1)

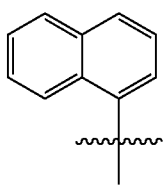 [SMILES: *c1cccc2ccccc12]

| | 3 | CH$_3$ | H | CH$_3$ | A | 16 E1 |

HPLC R$_t$ = 1.56 min; LC-MS (5 minute method) 2.75 min, (M + 1)⁺ 268 @ 2.84 min.; ¹H NMR (300 MHz, CD$_3$OD) 8.43(s, 1H), 8.33(d, J = 8.80 Hz, 1H), 7.85(t, 1H), 7.78(d, J = 8.07 Hz, 1H), 7.56(d, J = 7.70 Hz, 1H), 7.45-7.38(m, 2H), 4.05 (m, 1H), 2.52(bs, 5H), 1.82-1.78(m, 2H), 1.75-1.48(m, 4H), 1.32-1.06(m, 5H).
N-methyl-1-(1-(naphthalen-1-yl)cyclohexyl)ethanamine (59 E2)

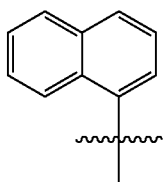 [SMILES: *c1cccc2ccccc12]

| | 3 | CH$_3$ | H | CH$_3$ | A | 16 E2 |

LC-MS (15 minute method) 7.19 min, (M + 1)⁺ 268 @ 7.52 min.
N,N-dimethyl-1-(1-(naphthalen-1-yl)cyclohexyl)ethanamine (60 E1)

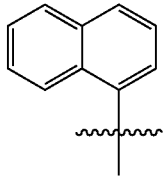

| | 3 | CH$_3$ | CH$_3$ | CH$_3$ | F | 16 E1 |

HPLC R$_t$ = 1.85 min; LC-MS (5 minute method) 2.63 min, (M + 1)⁺ 282 @ 2.74 min.
N,N-dimethyl-1-(1-(naphthalen-1-yl)cyclohexyl)ethanamine (60 E2)

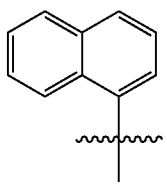 [SMILES: *c1cccc2ccccc12]

| | 3 | CH$_3$ | CH$_3$ | CH$_3$ | F | 16 E2 |

LC-MS (15 minute method) 8.08 min, (M + 1)⁺ 282 @ 8.14 min.

TABLE 2-continued

Summary of Exemplary Secondary and Tertiary Amines

| Ar | n | R[1] | R[3] | R[4] | General Procedure | Prepared From |
|---|---|---|---|---|---|---|
| 1-(1-(3,4-dichlorophenyl)cyclohexyl)-N,N-dimethylpropan-1-amine (61 E1) | | | | | | |
| 3,4-dichlorophenyl | 3 | ethyl | CH$_3$ | CH$_3$ | F | 17 |

HPLC R$_t$ = 1.61 min; LC-MS (15 minute method) 11.91 min, (M + 1)$^+$ 316 @ 12.08 min; $^1$H NMR (300 mHz, CD$_3$OD) 8.40(s, 1H), 7.43-7.37(m, 2H), 7.26-7.22(m, 1H), 2.62(d, J = 12.46, 1H), 2.46-2.42(m, 1H), 2.33(s, 6H), 2.17(d, J = 2.57, 1H), 1.63-1.46(m, 6H), 1.31-1.18(m, 3H), 1.13-1.04(m, 1H), 0.89(t, 3H).

1-(1-(3,4-dichlorophenyl)cyclohexyl)-N,N-dimethylpropan-1-amine (61 E2)

| Ar | n | R[1] | R[3] | R[4] | General Procedure | Prepared From |
|---|---|---|---|---|---|---|
| 3,4-dichlorophenyl | 3 | ethyl | CH$_3$ | CH$_3$ | F | 17 E2 |

LC-MS (15 minute method) 11.90 min, (M + 1)$^+$ 316 @ 12.04 min.

1-(1-(3,4-dichlorophenyl)cyclohexyl)-N-methylpropan-1-amine (62 E1)

| Ar | n | R[1] | R[3] | R[4] | General Procedure | Prepared From |
|---|---|---|---|---|---|---|
| 3,4-dichlorophenyl | 3 | ethyl | H | CH$_3$ | A | 17 E1 |

HPLC R$_t$ = 1.61 min; LC-MS (15 minute method) 9.09 min, (M + 1)$^+$ 302 @ 9.21 min; $^1$H NMR (400 mHz, CDCl$_3$) 7.47-7.42(m, 2H), 7.25(d, J = 7.70 Hz, 1H), 2.54(s, 3H), 2.42-2.40(m, 1H), 2.33(d, J = 13.20, 1H), 2.20(d, J = 12.83, 1H), 1.76(t, J = 11.73, 1H), 1.68-1.57(m, 5H), 1.36-1.14(m, 4H), 0.89(t, J = 7.33 Hz, 4H).

1-(1-(3,4-dichlorophenyl)cyclohexyl)-N-methylpropan-1-amine (62 E2)

| Ar | n | R[1] | R[3] | R[4] | General Procedure | Prepared From |
|---|---|---|---|---|---|---|
| 3,4-dichlorophenyl | 3 | ethyl | H | CH$_3$ | A | 17 E2 |

LC-MS (15 minute method) 9.31 min, (M + 1)$^+$ 302 @ 9.36 min.

N,N-dimethyl-1-(1-(4-(trifluoromethoxy)phenyl)cyclohexyl)ethanamine (63 E1)

| Ar | n | R[1] | R[3] | R[4] | General Procedure | Prepared From |
|---|---|---|---|---|---|---|
| 4-(trifluoromethoxy)phenyl | 3 | CH$_3$ | CH$_3$ | CH$_3$ | F | 19 E1 |

HPLC R$_t$ = 1.58 min; LC-MS (15 minute method) 9.68 min, (M + 1)$^+$ 316 @ 9.90 min. $^1$H NMR (400 MHz, CDCl$_3$) 7.64(d, J = 8.80 Hz, 2H), 7.39(d, J = 8.43 Hz, 2H), 4.85(s, 3H), 3.59-3.53(m, 1H), 3.34-3.30(m, 3H), 2.78(d, J = 12.5 Hz, 1H), 2.40(d, J = 13.2 Hz, 1H), 1.73-1.59(m, 5H), 1.40-1.34(m, 2H), 1.27-1.25(m, 3H), 1.16-1.15(m, 1H).

TABLE 2-continued

Summary of Exemplary Secondary and Tertiary Amines

| Ar | n | R$^1$ | R$^3$ | R$^4$ | General Procedure | Prepared From |
|---|---|---|---|---|---|---|
| N,N-dimethyl-1-(1-(4-(trifluoromethoxy)phenyl)cyclohexyl)ethanamine (63 E2) | | | | | | |
| 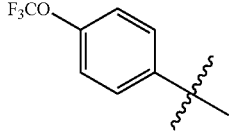 [SMILES: *c1ccc(OC(F)(F)F)cc1] | 3 | CH$_3$ | CH$_3$ | CH$_3$ | F | 19 E2 |
| LC-MS (15 minute method) 9.69 min, (M + 1)$^+$ 316 @ 9.88 min. | | | | | | |
| N-methyl-1-(1-(4-(trifluoromethoxy)phenyl)cyclohexyl)ethanamine (64 E1) | | | | | | |
| 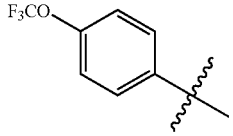 [SMILES: *c1ccc(OC(F)(F)F)cc1] | 3 | CH$_3$ | H | CH$_3$ | A | 19 E1 |
| HPLC R$_t$ = 1.52 min; LC-MS (15 minute method) 7.82 min, (M + 1)$^+$ 302 @ 7.94 min.; $^1$H NMR (400 MHz, CD$_3$OD) 7.54(d, J = 8.80 Hz, 2H), 7.37(d, J = 8.43 Hz, 2H), 3.19-3.14(m, 1H), 2.64(s, 3H), 2.57(d, J = 11.73 Hz, 1H), 2.39(d, J = 12.83 Hz, 1H), 1.69-1.57(m, 5H), 1.37-1.22(m, 3H), 1.14-1.13(d, J = 6.6 Hz, 3H). | | | | | | |
| N-methyl-1-(1-(4-(trifluoromethoxy)phenyl)cyclohexyl)ethanamine (64 E2) | | | | | | |
| 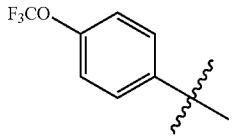 [SMILES: *c1ccc(OC(F)(F)F)cc1] | 3 | CH$_3$ | H | CH$_3$ | A | 19 E2 |
| LC-MS (15 minute method) 7.91 min, (M + 1)$^+$ 302 @ 8.20 min. | | | | | | |

The following compounds were synthesized from the corresponding primary amine according to General Procedure F. The crude product was purified by silica gel column chromatography to give the respective mono- and di-methylated products.

1-(1-(2,4-dichlorophenyl)cyclohexyl)-N-methyl-methanamine (65)

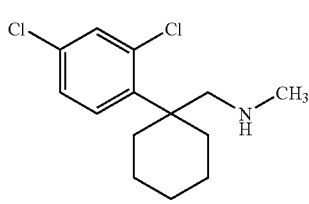 [SMILES: CNCC1(c2ccc(Cl)cc2Cl)CCCCC1]

The title compound was synthesized from 38. $^1$H NMR (400 MHz, CD$_3$Cl) δ 7.35 (d, J=8.4 Hz, 1 H), 7.34 (d, J=2.4 Hz, 1 H), 7.19 (dd, J=8.4, 2.4 Hz, 1 H), 3.00 (s, 2 H), 2.31 (s, 3 H), 2.31-2.28 (m, 2 H), 1.83 (m, 2 H), 1.56 (m, 2 H), 1.48-1.29 (m, 4 H); $^{13}$C NMR (400 MHz, CD$_3$Cl) δ 140.61, 134.31, 132.63, 132.53, 132.08, 126.99, 58.24, 44.40, 37.68, 34.44, 26.67, 22.58; ESI MS m/z 272.07.

1-(1-(2,4-dichlorophenyl)cyclohexyl)-N,N-dimethyl-methanamine (66)

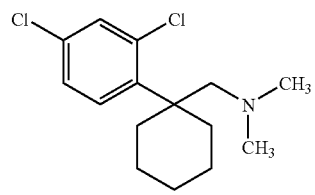 [SMILES: CN(C)CC1(c2ccc(Cl)cc2Cl)CCCCC1]

The title compound was synthesized from 38. $^1$H NMR (400 MHz, CD$_3$Cl) δ 7.42 (d, J=8.8 Hz, 1 H), 7.32 (d, J=2.0 Hz, 1 H), 7.20 (dd, J=8.8, 2.0 Hz, 1 H), 3.04 (s, 2 H), 2.40 (m, 2 H), 2.18 (s, 6 H), 1.80 (m, 2 H), 1.54 (m, 2 H), 1.48-1.32 (m, 4 H); $^{13}$C NMR (100 MHz, CD$_3$Cl) δ 139.8, 134.27, 133.03, 132.99, 132.07, 127.29, 65.40, 47.26, 44.12, 34.37, 26.37, 22.34; ESI MS m/z 286.1.

1-(1-(6-fluoronaphthalen-2-yl)cyclohexyl)-N-methylmethanamine (67)

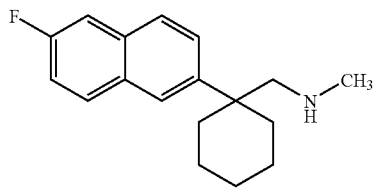 [SMILES: CNCC1(c2ccc3cc(F)ccc3c2)CCCCC1]

The title compound was synthesized from 39. $^1$H NMR (400 MHz, CD$_3$Cl) δ 8.55 (m, 1 H), 8.19 (m, 1 H), 7.56-7.40 (m, 2 H), 7.30 (m, 1 H), 3.22 (s, 2 H), 2.32 (m, 1 H), 2.25 (s, 3 H), 2.26 (m, 1 H), 1.62 (m, 1 H), 1.54-1.35 (m, 5 H); $^{13}$C NMR (400 MHz, CD$_3$Cl) 167.08, 159.65, 156.34, 132.86, 132.83, 127.56, 127.49, 126.06, 125.92, 125.85, 125.83, 125.72, 125.32, 125.29, 122.11, 122.03, 108.64, 108.45, 60.17, 44.42, 37.61, 36.73, 35.90, 26.89, 26.82, 22.68, 22.73; ESI MS m/z 272.1.

1-(1-(6-fluoronaphthalen-2-yl)cyclohexyl)-N,N-dimethylmethanamine (68)

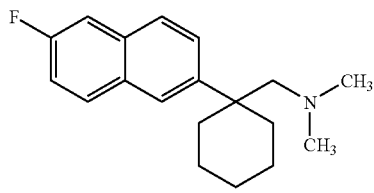 [SMILES: CN(C)CC1(c2ccc3cc(F)ccc3c2)CCCCC1]

The title compound was synthesized from 39. $^1$H NMR (400 MHz, CD$_3$Cl) δ 8.47 (m, 1 H), 8.17 (m, 1 H), 7.50-7.44 (m, 2 H), 7.08 (dd, J=10.0, 8.4 Hz, 1 H), 2.95 (m, 2 H), 2.39 (m, 2 H), 2.14 (m, 2 H), 1.97 (s, 6 H), 1.59 (m, 2 H), 1.44 (m, 2 H); $^{13}$C NMR (100 MHz, CD$_3$Cl) 167.07, 158.95, 158.31, 133.87, 132.73, 127.32, 127.23, 126.74, 126.72, 125.32, 125.00, 124.99, 121.96, 121.90, 108.61, 108.41, 68.39, 48.40, 45.03, 37.61, 36.62, 26.91, 22.74; ESI MS m/z 286.3.

1-(1-(4-fluoronaphthalen-1-yl)cyclohexyl)-N-methylmethanamine (69)

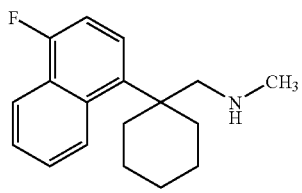 [SMILES: CNCC1(c2ccc(F)c3ccccc23)CCCCC1]

The title compound was synthesized from 40. $^1$H NMR (400 MHz, CD$_3$OD) δ 8.5 (m, 1 H) 8.19 (m, 1 H), 7.5 (m, 3H), 7.10 (dd, J=8.4, 9.0 Hz, 1 H), 3.22 (s, 2 H), 2.31 (m, 2 H), 2.25 (s, 3 H), 2.04 (m, 2 H), 1.61 (m, 2 H), 1.44 (m, 4 H); $^{13}$C NMR (100 MHz, CD$_3$OD) δ 159.26, 156.78, 136.59, 133.32, 133.29, 159.26, 156.78, 136.59, 133.32, 133.29, 127.56, 127.48, 125.85, 125.85, 125.31, 125.29, 122.11, 122.03, 108.64, 108.46, 60.13, 44.41, 37.59, 36.72, 29.94, 26.89, 26.82, 22.72; ESI MS m/z 272.2.

1-(1-(4-fluoronaphthalen-1-yl)cyclohexyl)-N,N-dimethylmethanamine (70)

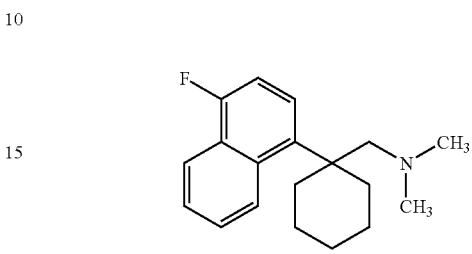

The title compound was synthesized from 40. $^1$H NMR (400 MHz, CD$_3$OD) δ 8.44 (m, 1 H), 8.18 (m, 1 H), 7.50 (m, 3 H), 7.09 (dd, J=8.8, 8.8 Hz, 1 H), 2.95 (s, 2 H), 2.38 (m, 2 H), 2.20 (m, 2 H), 1.96 (s, 6 H), 1.60 (m, 4 H), 1.44 (m, 2 H); $^{13}$C NMR (100 MHz, CD$_3$OD), δ 159.06, 156.57, 133.53, 127.22, 126.76, 126.73, 125.32, 125.00, 124.99, 121.96, 121.89, 108.00, 108.43, 68.40, 48.42, 45.03, 36.63, 29.94, 26.92, 22.74; ESI MS m/z 286.2.

1-(1-(3,4-dichlorophenyl)cyclohex-3-enyl)-N,N-dimethylmethanamine (72)

The title compound was synthesized according to Scheme 26, below.

Scheme 26:

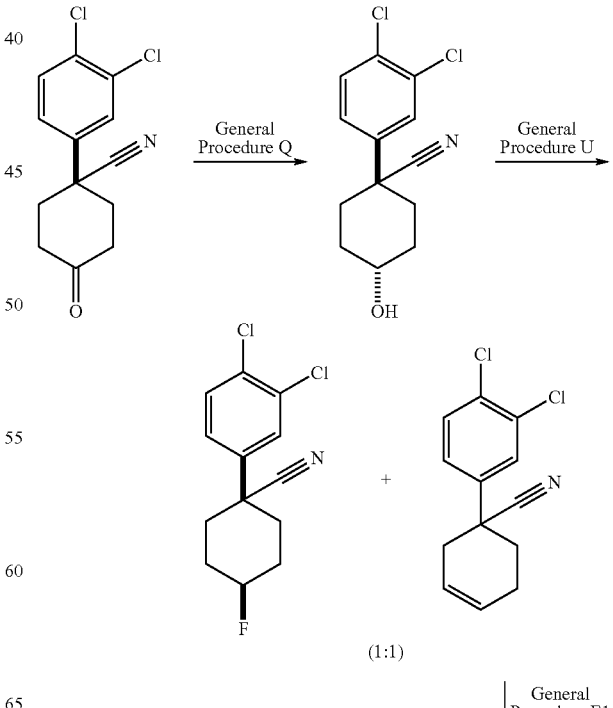

-continued

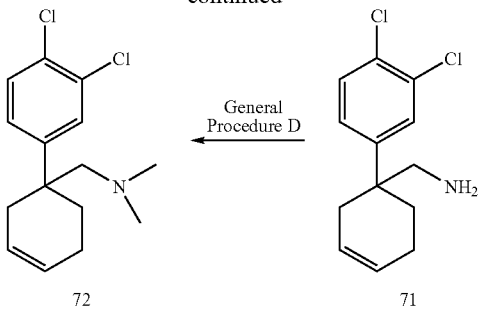

(a) The primary amine 71 was synthesized from 1-(3,4-dichlorophenyl)-4-oxocyclohexanecarbonitrile according to General Procedures Q, U, and E1. $^1$H NMR (400 MHz, CDCl$_3$) δ 7.45 (d, J=8.4 Hz, 1 H), 7.39(s, 1 H), 7.17 (d, J=8.4 Hz, 1 H), 5.75 (m, 1 H), 5.64 (m, 1 H), 3.16 (d, J=12.8 Hz, 1 H), 3.03 (d, J=12.8 Hz, 1 H), 2.5 (d, J=16.8 Hz, 1 H), 2.23 (d, J=16.8 Hz, 1 H), 2.06 (m, 1 H), 1.95 (m, 1 H), 1.84 (m, 1 H), 1.74 (m, 1 H); $^{13}$C NMR (100 MHz, CDCl$_3$) δ 140.55, 133.33, 131.96, 131.33, 129.30, 127.53, 126.59, 123.44, 50.25, 39.35, 32.24, 30.58, 22.03; ESI MS m/z 256.1.

The title compound was synthesized from 71 according to General Procedure D. $^1$H NMR (400 MHz, CDCl$_3$) δ 8.35 (broad, 1 H), 7.41(s, 1 H), 7.40 (d, J=8.4 Hz, 1 H), 7.20 (d, J=8.4 Hz, 1 H), 5.75 (m, 1 H), 5.62 (m, 1 H), 3.02 (s, 2 H), 2.64 (d, J=15.6 Hz, 1 H), 2.45 (d, J=18.8 Hz, 1 H), 2.36 (s, 6 H), 1.98 (m, 1 H), 1.88 (m, 2 H), 1.58 (m, 1 H); $^{13}$C NMR (100 MHz, CDCl$_3$), δ 144.16, 138.66, 132.99, 131.14, 130.70, 129.04, 127.36, 126.53, 124.13, 69.27, 47.54, 46.45, 40.38, 33.04, 32.93, 21.99; ESI MS m/z 284.0.

N-((1-(3,4-dichlorophenyl)cyclohexyl)methyl)-N-ethylethanamine (hydrochloride) (73)

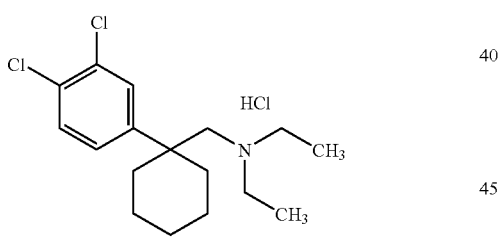

(a) Synthesis of 1-(3,4-dichlorophenyl)-N,N-diethyl-cyclohexane-carboxamide

The amide was synthesized from 1-(3,4-dichlorophenyl)-cyclohexanecarboxylic acid (232 mg, 0.85 mmol) and diethyl amine using General Procedure G and was isolated in 13% yield as a white solid. HPLC R$_t$=12.0 min; $^1$H NMR (400 mHz, CDCl$_3$) 7.38-7.26 (m, 2H), 7.08 (dd, J=2.2, 8.4 Hz, 1H), 3.29 (bs, 2H), 2.84 (bs, 2H), 2.26 (d, J=12.1 Hz, 2H), 1.73-1.54 (m, 7H), 1.29-1.24 (m, 2H), 1.08 (bs, 3H), 0.82 (bs, 3H); $^{13}$C NMR (100 mHz, CDCl$_3$) 172.9, 147.2, 133.0, 130.8, 130.4, 127.5, 125.2, 51.2, 42.0, 40.9, 37.3, 26.0, 23.7, 13.4, 12.4; GC-MS (SCOUT) 13.2 min, M$^+$ 327.

(b) Synthesis of N-((1-(3,4-dichlorophenyl)cyclohexyl)methyl)-N-ethylethanamine (hydrochloride)

The title compound was synthesized from 1-(3,4-dichlorophenyl)-N,N-diethylcyclohexanecarboxamide (19 mg, 0.058 mmol) using General Procedure E followed by HCL salt formation. The crude HCl salt was recrystallized from EtOAc (1.5 mL) to give pure [1-(3,4-Dichloro-phenyl)-cyclohexylmethyl]-diethyl-amine hydrochloride as an off-white solid. HPLC R$_t$=9.07 min; $^1$H NMR (MeOH-d$^4$) 7.65 (d, J=2.20 Hz, 1H), 7.55 (d, J=8.55 Hz, 1H), 7.43 (dd, J=2.2, 8.55 Hz, 1H), 3.24 (s, 2H), 2.90-2.83 (m, 4H), 2.30-2.25 (m, 2H), 1.68-1.53 (m, 5H), 1.35-1.24 (m, 3H), 1.10 (at, 6H); LCMS 10.8 min, (M+1)$^+$ 314@11.0 min.

1-(1-(3,4-dichlorophenyl)cyclohexyl)-N,N-dimethyl-methanamine (hydrochloride) (74)

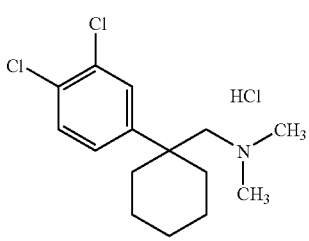 [SMILES: CN(C)CC1(c2ccc(Cl)c(Cl)c2)CCCCC1 ; Cl]

(a) Synthesis of 1-(3,4-dichlorophenyl)-N,N-dimethylcyclohexane carboxamide

The amide was synthesized from 1-(3,4-dichlorophenyl)-cyclohexanecarboxylic acid (182 mg, 0.67 mmol) and dimethyl amine using General Procedure G and isolated in 36% yield as a white solid. HPLC R$_t$=11.27 min; $^1$H NMR (400 mHz, CDCl$_3$) 7.36-7.34 (m, 2H), 7.06 (dd, J=2.2, 8.4 Hz, 1H), 2.71 (bs, 6H), 2.29 (d, J=12.1 Hz, 2H), 1.68-1.53 (m, 7H), 1.25-1.21 (m, 2H); $^{13}$C NMR (100 mHz, CDCl$_3$) 173.9, 146.9, 133.0, 130.9, 130.4, 127.4, 125.2, 51.0, 38.1, 36.7, 25.9, 23.6; GC-MS (SCOUT) 12.8 min, M$^+$ 299.

(b) Synthesis of 1-(1-(3,4-dichlorophenyl)cyclohexyl)-N,N-dimethylmethanamine (hydrochloride)

The title compound was synthesized from 1-(3,4-dichlorophenyl)-N,N-dimethylcyclohexanecarboxamide (71 mg, 0.24 mmol) using General Procedure E followed by HCl salt formation. The crude HCl salt was recrystallized from CH$_3$CN (3 mL) to afford the product as an off-white solid. HPLC R$_t$=8.70 min; $^1$H NMR (400 mHz, MeOH-d$^4$) 7.72 (d, J=2.44 Hz, 1H), 7.63 (d, J=8.55 Hz, 1H), 7.49 (dd, J=2.44, 8.55 Hz, 1 H), 3.47 (bs, 2H), 3.32 (s, 6H), 2.28-2.24 (bs, 2H), 1.81-1.39 (m, 8H); LCMS 9.79 min, (M+1)⁺ 286@10.0 min.

Synthesis of 1-(1-(3,4-dichlorophenyl)cyclohexyl)-N-methylmethanamine (hydrochloride) (75)

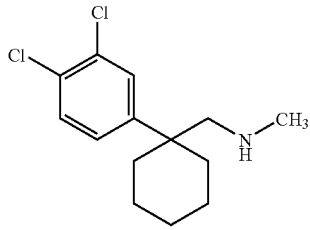 [SMILES: CNCC1(c2ccc(Cl)c(Cl)c2)CCCCC1]

(a) Synthesis of 1-(3,4-dichlorophenyl)-N-methylcyclohexane-carboxamide

The amide was synthesized from 1-(3,4-dichlorophenyl)-cyclohexanecarboxylic acid (218 mg, 0.80 mmol) and methyl amine using General Procedure G and was isolated in 35% yield as a white solid. HPLC $R_t$=10.3 min; ¹H NMR (400 mHz, CDCl₃) 7.47 (d, J=2.20 Hz, 1H), 7.41 (d, J=8.55 Hz, 1H), 7.24 (dd, J=2.44, 8.55 Hz, 1H), 2.71 (d, J=4.88 Hz, 3H), 2.29-2.21 (m, 2H), 1.93-1.85 (m, 2H), 1.61-1.38 (m, 6H); GC-MS (SCOUT) 12.87 min, M⁺ 285.

(b) Synthesis of 1-(1-(3,4-dichlorophenyl)cyclohexyl)-N-methylmethanamine (hydrochloride)

The title compound was synthesized from 1-(3,4-dichlorophenyl)-N-methylcyclohexanecarboxamide (80 mg, 0.28 mmol) using General Procedure E followed by HCL salt formation. The crude HCl salt was recrystallized from CH₃CN (3 mL) to give pure 1-(1-(3,4-dichlorophenyl)cyclohexyl)-N-methylmethanamine hydrochloride as an off-white solid. HPLC $R_t$=8.67 min; ¹H NMR (400 mHz, CDCl₃) 7.57-7.54 (m, 2H), 7.34 (dd, J=2.2, 8.43 Hz, 1H), 3.12 (s, 2H), 2.54 (s, 3H), 2.16-2.13 (m, 2H), 1.68-1.50 (m, 5H), 1.41-1.30 (m, 3H); LCMS 8.26 min, (M+1)⁺ 272@8.50 min.

N-((1-(3,4-dichlorophenyl)cyclohexyl)methyl)-N-methylethanamine (hydrochloride) (76)

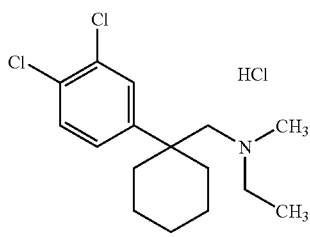 [SMILES: CCN(C)CC1(c2ccc(Cl)c(Cl)c2)CCCCC1 ; Cl]

(a) 1-(3,4-dichlorophenyl)-N-ethyl-N-methyl-cyclohexane-carboxamide

The amide was synthesized from 1-(3,4-dichlorophenyl)-cyclohexanecarboxylic acid (390 mg, 1.43 mmol) and ethylmethylamine using General Procedure G and was isolated in 30% yield as a white solid. HPLC $R_t$=11.66 min; ¹H NMR (400 mHz, CDCl₃) 7.40-7.30 (m, 2H), 7.10 (dd, J=2.2, 8.4 Hz, 1H), 3.31 (bs, 2H), 2.59 (bs, 3H), 2.30 (d, J=12.5 Hz, 2H), 1.76-1.55 (m, 7H), 1.32-1.25 (m, 2H), 1.00 (bs, 3H); ¹³C NMR (100 mHz, CDCl₃) 147.0, 132.9, 130.8, 130.3, 127.5, 125.2, 51.0, 44.5, 36.8, 25.9, 23.5; GC-MS (SCOUT) 13.01 min, M⁺ 313.

(b) N-((1-(3,4-dichlorophenyl)cyclohexyl)methyl)-N-methylethanamine

The title compound was synthesized from 1-(3,4-dichlorophenyl)-N-ethyl-N-methylcyclohexanecarboxamide (130 mg, 0.414 mmol) using General Procedure E followed by HCl salt formation. The crude HCl salt was recrystallized from CH₃CN (3 mL) to give pure N-((1-(3,4-dichlorophenyl)cyclohexyl)methyl)-N-methylethanamine as white crystals. HPLC $R_t$=9.00 min; ¹H NMR (400 mHz, MeOH-d⁴) 7.65 (d, J=2.2 Hz, 1H), 7.56 (d, J=8.43 Hz, 1H), 7.42 (dd, J=2.2, 8.43 Hz, 1H), 3.43-3.40 (m, 1H), 2.96-2.94 (m, 2H), 2.48 (s, 3H), 2.24 (m, 2H), 1.66-1.53 (m, 5H), 1.41-1.31 (m, 3H), 1.14 (t, 3H); LC-MS 10.07 min, (M+1)⁺ 300@10.3 min.

N-((1-(3,4-dichlorophenyl)cyclohexyl)-methyl)ethanamine hydrochloride (77)

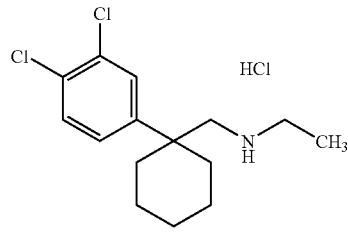 [SMILES: CCNCC1(c2ccc(Cl)c(Cl)c2)CCCCC1 ; Cl]

(a) 1-(3,4-dichlorophenyl)-N-ethylcyclohexane-carboxamide

The amide was synthesized from 1-(3,4-dichlorophenyl)-cyclohexanecarboxylic acid (280 mg, 1.03 mmol) and ethylamine using General Procedure G and was isolated in 28% yield as a white solid. HPLC $R_t$=10.61 min; ¹H NMR (400 mHz, CDCl₃) 7.44 (d, J=2.2 Hz, 1H), 7.37 (d, J=8.43 Hz, 1H), 7.21 (dd, J=2.2, 8.4 Hz, 1H), 5.4 (bs, 1H), 3.21-3.14 (m, 2H), 2.25-2.20 (m, 2H), 1.86-1.79 (m, 2H), 1.58-1.52 (m, 5H), 1.35-1.32 (m, 1H), 1.00 (at, 3H); ¹³C NMR (100 mHz, CDCl₃) 174.3, 144.8, 132.8, 130.9, 130.7, 128.7, 126.2, 50.5, 34.8, 34.7, 25.7, 23.0, 14.8; GC-MS (SCOUT) 12.9 min, M⁺ 299.

(b) N-((1-(3,4-dichlorophenyl)cyclohexyl)-methyl)ethanamine (hydrochloride)

The title compound was synthesized from 1-(3,4-dichlorophenyl)-N-ethylcyclohexanecarboxamide (86 mg, 0.286 mmol) using General Procedure E followed by HCl salt formation. The crude HCl salt was recrystallized from CH₃CN (4.5 mL) to give pure (±) N-((1-(3,4-dichlorophenyl)cyclohexyl)-methyl)ethanamine hydrochloride as colorless crystals. HPLC $R_t$=8.90 min; ¹H NMR (400 mHz, McOH-d⁴) 7.57 (d, J=2.2 Hz, 1H), 7.54 (d, J=8.43 Hz, 1H), 7.34 (dd, J=2.2, 8.43 Hz, 1H), 3.11 (s, 3H), 2.94-2.88 (q, 2H), 2.18-

2.15 (m, 2H), 1.68-1.58 (m, 5H), 1.51-1.30 (m, 3H), 1.17 (t, 3H); LC-MS 8.45 min, (M+1)⁺286 @ 8.7 min.

N-((1-(3,4-dichlorophenyl)cyclohexyl)methyl)-cyclopropanamine hydrochloride (78)

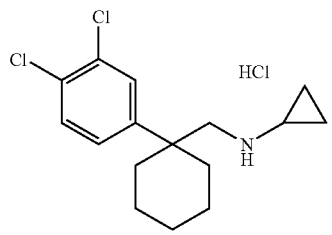 [SMILES: Clc1ccc(C2(CNC3CC3)CCCCC2)cc1Cl ; Cl]

(a) Synthesis of 1-(3,4-dichlorophenyl)-N-cyclopropylcyclo-hexanecarboxamide

The tile compound was synthesized from 1-(3,4-dichlorophenyl)-cyclohexanecarboxylic acid (372 mg, 1.37 mmol) and cyclopropylamine using General Procedure G and was isolated in 25% yield as a white solid. HPLC $R_t$=10.6 min; ¹H NMR (400 mHz, CDCl₃) 7.45 (d, J=2.2 Hz, 1H), 7.39 (d, J=8.43 Hz, 1H), 7.23-7.21 (m, 1H), 5.49 (bs, 1H), 2.62-2.59 (m, 1H), 2.25-2.20 (m, 2H), 1.84-1.78 (m, 2H), 1.59-1.55 (m, 5H), 1.38-1.33 (m, 1H), 0.73-0.68 (m, 2H), 0.37-0.33 (m, 2H); ¹³C NMR (100 mHz, CDCl₃) 176.0, 144.8, 133.0, 131.0, 130.8, 128.6, 126.2, 50.4, 34.9, 25.7, 23.1, 6.91; GC-MS (SCOUT) 13.5 min, M⁺ 311.

(b) Synthesis of N-((1-(3,4-dichlorophenyl)cyclohexyl)methyl)-cyclopropanamine hydrochloride The title compound was synthesized from 1-(3,4-dichlorophenyl)-N-cyclopropylcyclohexane carboxamide (108 mg, 0.35 mmol) using General Procedure E followed by HCl formation. The crude HCl salt was recrystallized from 3:1 EtOAc:CH₃CN (4 mL) and 1:1 EtOAc:CH₃CN (3 mL) to give pure N-((1-(3,4-dichlorophenyl)cyclohexyl)-methyl)cyclopropanamine hydrochloride as white crystals. HPLC $R_t$=9.02 min; ¹H NMR (400 mHz, MeOH-d⁴) 7.57-7.52 (m, 2H), 7.35 (dd, J=1.83, 8.43 Hz, 1H), 3.29 (s, 2H), 2.56-2.54 (m, 1H), 2.16-2.13 (m, 2H), 1.67-1.30 (m, 8H), 0.78-0.74 (m, 4H); LC-MS 10.6 min, (M+1)⁺ 298 @ 10.8 min.

Synthesis of (1-(3-chlorophenyl)cyclohexyl)-N-methylmethanamine hydrochloride (79)

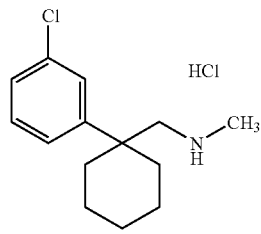 [SMILES: CNCC1(c2cccc(Cl)c2)CCCCC1 ; Cl]

General Procedure H: A solution of 1-(3-chlorophenyl) cyclohexane-carbaldehyde (119 mg, 0.53 mmol), methyl amine (291 µL, 0.58 mmol, 2.0 M in THF) and sodium cyanoborohydride (100 mg, 1.59 mmol) in 1:1 MeOH:Triethylorthoformate (4 mL) was shaken at RT overnight. The solution was poured into saturated aqueous K₂CO₃ and washed with EtOAc (2×20 mL). The combined organic washes were dried (Na₂SO₄), filtered and concentrated. The crude material was dissolved in Et₂O and HCl (1.5 mL, 2.0 M in Et₂O) was added. The reaction was concentrated and the HCl salt was recrystallized from CH₃CN (4.5 mL) to give pure (1-(3-chlorophenyl)cyclohexyl)-N-methylmethanamine hydrochloride as colorless crystals HPLC $R_t$=8.25 min; ¹H NMR (400 mHz, MeOH-d⁴) 7.43-7.28 (m, 4H) 3.12 (s, 2H), 2.54 (s, 3H), 2.19-2.16 (m, 2H), 1.67-1.30 (m, 8H); LC-MS 7.29 min, (M+1)⁻ 238 @ 7.50 min.

N-methyl(1-phenylcyclohexyl)methanamine (hydrochloride) (80)

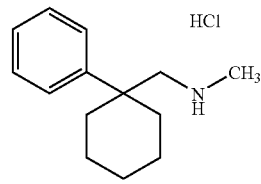

The title compound was synthesized from 1-phenylcyclohexane-carbaldehyde (126 mg, 0.67 mmol) and methyl amine (370 µL, 0.73 mmol, 2.0 M in THF) according to General Procedure H, followed by HCl salt formation. The HCl salt was recrystallized from CH₃CN to give pure N-methyl(1-phenylcyclohexyl)methanamine hydrochloride (8 mg, 6%) as colorless crystals. HPLC $R_t$=7.76 min; ¹H NMR (400 mHz, MeOH-d⁴) 7.43-7.38 (m, 4H), 7.28-7.25 (m, 1H), 3.11 (s, 2H), 2.50 (s, 3H), 2.25-2.22 (m, 2H), 1.67-1.23 (m, 8H); LC-MS 6.37 min, (M+1)⁺ 204 @ 6.62 min.

(1-(3,4-difluorophenyl)cyclohexyl)-N-methylmethanamine hydrochloride (81)

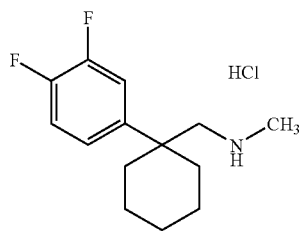 [SMILES: CNCC1(c2ccc(F)c(F)c2)CCCCC1 ; Cl]

The title compound was synthesized from 1-(3,4-difluorophenyl)-cyclohexanecarbaldehyde (131 mg, 0.58 mmol) and methyl amine (320 µL, 0.64 mmol, 2.0 M in THF) according to General Procedure H, followed by HCl salt formation. The HCl salt was recrystallized from CH₃CN to give pure (1-(3,4-difluorophenyl)cyclohexyl)-N-methylmethanamine hydrochloride as colorless crystals. HPLC $R_t$=8.15 min; ¹H NMR (400 mHz, MeOH-d⁴) 7.36-7.21 (m, 3H), 3.11 (s, 2H), 2.55 (d, J=3.67 Hz, 3H), 2.15-2.12 (m, 2H), 1.67-1.31 (m, 8H); LC-MS 7.04 min, (M+1)⁺ 240 @ 7.19 min.

(1-(3-chlorophenyl)cyclohexyl)-N,N-dimethylmethanamine hydrochloride (82)

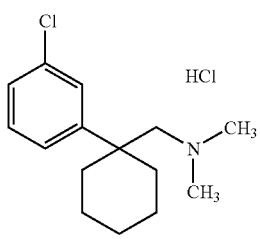 [SMILES: CN(C)CC1(c2cccc(Cl)c2)CCCCC1 ; Cl]

The title compound was synthesized from 1-(3-chlorophenyl)-N,N-dimethylcyclohexanecarboxamide (191 mg, 0.72 mmol) using General Procedure E, followed by HCl salt formation. The crude HCl salt was recrystallized from 2:1 CH$_3$CN:EtOAc (4.5 mL) to give pure (1-(3-chlorophenyl)cyclohexyl)-N,N-dimethylmethanamine hydrochloride as an off-white solid (21 mg, 12%). HPLC R$_f$=8.41 min; $^1$H NMR (400 mHz, MeOH-d$^4$) 7.51-7.30 (m, 4H), 3.26-3.24 (m, 2H), 2.54 (s, 6H), 2.24-2.20 (m, 2H), 1.72-1.33 (m, 8h); LC-MS 8.16 min, (M+1)⁻ 252 @ 8.27 min.

(1-(3,4-difluorophenyl)cyclohexyl)-N,N-dimethylmethanamine hydrochloride (83)

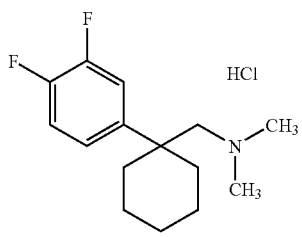 [SMILES: CN(C)CC1(c2ccc(F)c(F)c2)CCCCC1 ; Cl]

The title compound was synthesized from 1-(3,4-difluorophenyl)-N,N-dimethylcyclohexanecarboxamide (195 mg, 0.73 mmol) using General Procedure E (the amide was prepared from the corresponding carboxylic acid according to General Procedure G), followed by HCl salt formation. The crude HCl salt was recrystallized from 1:1 CH$_3$CN:EtOAc (3.0 mL) to give pure (1-(3,4-difluorophenyl)cyclohexyl)-N,N-dimethylmethanamine hydrochloride as an off-white solid (16 mg, 8%). HPLC R$_f$=8.24 min; $^1$H NMR (400 mHz, MeOH-d$^4$) 7.51-7.46 (m, 1H), 7.37-7.34 (m, 2H), 3.31-3.30 (m, 2H), 2.62 (s, 6H), 2.26-2.23 (m, 2H), 1.78-1.38 (m, 8H); LC-MS 7.69 min, (M+1)⁺ 254 @ 791 min.

(1-(4-chlorophenyl)cyclohexyl)-N-methylmethanamine hydrochloride (84)

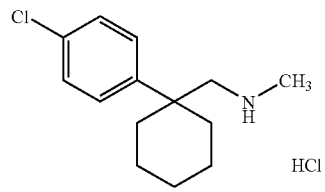 [SMILES: CNCC1(c2ccc(Cl)cc2)CCCCC1 ; Cl]

The title compound was synthesized from 1-(4-chlorophenyl)-N-methylcyclohexanecarboxamide (278 mg, 1.11 mmol) using General Procedure E, followed by HCl salt formation to give pure (1-(4-chlorophenyl)cyclohexyl)-N-methylmethanamine hydrochloride as an off-white solid (185 mg, 70%). HPLC R$_f$=8.38 min; $^1$H NMR (400 mHz, MeOH-d$^4$) 7.39 (s, 4H), 3.10 (s, 2H), 2.52 (s, 3H), 2.19-2.16 (m, 2H), 1.65-1.49 (m, 6H), 1.37-1.30 (m, 4H); LC-MS 7.49 min, (M+1)⁺0 238 @ 7.63 min.

(1-(4-chlorophenyl)cyclohexyl)-N,N-dimethylmethanamine (85)

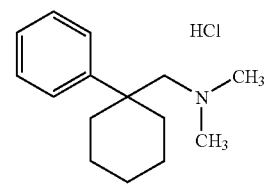 [SMILES: CN(C)CC1(c2ccccc2)CCCCC1 ; Cl]

The title compound was prepared from 1-(4-chlorophenyl)-N,N-dimethylcyclohexanecarboxamide (241 mg, 0.91 mmol) according to General Procedure E. The crude product was purified by preparative TLC with 10% MeOH/CH$_2$Cl$_2$ (R$_f$=0.74) to give (1-(4-chlorophenyl)cyclohexyl)-N,N-dimethylmethanamine free base (11 mg, 5%) as a clear oil. HPLC R$_f$=8.55 min; $^1$H NMR (400 mHz, MeOH-d$^4$) 7.30 (q, 4H), 2.30 (s, 2H), 2.09-2.06 (m, 2H), 1.97 (s, 6H), 1.60-1.25 (m, 10H); LC-MS 8.09 min, (M+1)⁺252 @ 8.15 min.

N,N-dimethyl(1-phenylcyclohexyl)methanamine hydrochloride (86)

The title compound was synthesized from N,N-dimethyl-1-phenylcyclohexanecarboxamide (200 mg, 0.87 mmol) using General Procedure E, followed by HCl salt formation. The crude HCl salt was recrystallized from 2:1 EtOAc:

CH₃CN to give N,N-dimethyl(1-phenylcyclohexyl)methanamine hydrochloride as an analytically pure off-white solid (8 mg, 4%). HPLC R$_t$=8.55 min; ¹H NMR (400 mHz, MeOH-d⁴) 7.30 (q, 4H), 2.30 (s, 2H), 2.09-2.06 (m, 2H), 1.97 (s, 6H), 1.60-1.25 (m, 10H); LC-MS 8.09 min, (M+1)⁺ 252 @ 8.15 min. HPLC R$_t$=8.03 min; ¹H NMR (400 mHz, MeOH-d⁴) 7.48-7.39 (m, 4H), 7.29-7.28 (m, 1H), 3.34 (d, J=2.57 Hz, 2H), 2.46 (d, J=3.30 Hz, 6H), 2.29-2.26 (m, 2H), 1.67-1.39 (m, 8H); LC-MS 6.62 min, (M+1)⁺ 218 @ 6.80 min.

(1-(3,4-dichlorophenyl)cyclopentyl)methanamine (87)

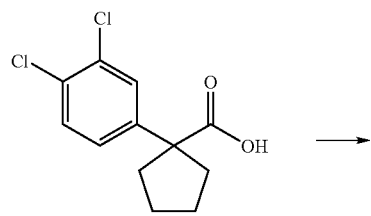

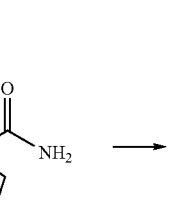

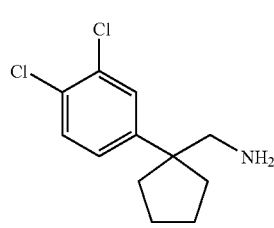

General Procedure G1—Amidation with Oxalyl Chloride: To a solution of 1-(3,4-dichlorophenyl)cyclopentanecarboxylic acid (200 mg, 0.7718 mmol) in DCM (1 mL) and DMF (1 mL) was added oxalyl chloride (1.54 mL, 1M in DCM) dropwise. After five minutes, the volatiles were removed in vacuo and the residual oil was dissolved in 2M ammonia (in ethanol). After five minutes, the solvent was again removed, and the residual oil was partitioned between MTBE and aqueous potassium bicarbonate. After drying (sodium sulfate), the solvent was removed to give the crude amide.

The title compound was synthesized from the above amide using General Procedure E. The crude product was purified by reverse-phase preparative HPLC to give the primary amine (20 mg, 11% yield) as a pale-yellow oil. LCMS R$_t$=7.92 min, m/z=244 (M+1). ¹H NMR (CDCl₃, δ): 7.35 (m, 2H), 7.11 (dd, J=2.2, 8.4Hz, 1H), 2.72 (s, 2H), 2.0-1.6 (m, 8H), 1.1 (s, 2H).

¹³C NMR (CDCl₃, δ, mult): 147.9(0), 132.1(0), 129.9(0), 129.7(1), 129.3(1), 126.7(1), 51.7(2), 35.2(2), 23.4(2).

(1-(3,4-dichlorophenyl)cyclopentyl)-N-methyl-methanamine (88)

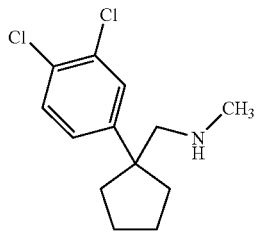 [SMILES: CNCC1(c2ccc(Cl)c(Cl)c2)CCCC1]

The title compound was synthesized from 1-(3,4-dichlorophenyl)-cyclopentanecarboxylic acid and methyl amine using General Procedure G1, followed by General Procedure E in 49% yield. LCMS R$_t$=11.16 min, m/z=258 (M+1). ¹H NMR (CDCl₃, δ): 7.4 (m, 2H), 7.17 (dd, J=2.2, 8.4 Hz, 1H), 2.65 (s, 2H), 2.34 (s, 3H), 2.1-1.6 (m, 8H). ¹³C NMR (CDCl₃, δ, mult): 148.3(0), 132.1(0), 129.9(1), 129.7(0), 129.1(1), 126.5(1), 62.1(2), 51.6(0), 37.3(3), 36.2(2), 23.5(2).

(1-(3,4-dichlorophenyl)cyclopentyl)-N,N-dimethyl-methanamine (89)

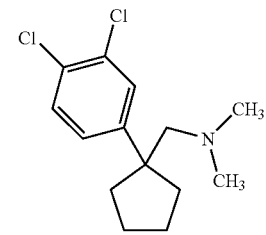 [SMILES: CN(C)CC1(c2ccc(Cl)c(Cl)c2)CCCC1]

The title compound was synthesized from 1-(3,4-dichlorophenyl)-cyclopentanecarboxylic acid and dimethyl amine using General Procedure G1, followed by General Procedure E in 87% yield. LCMS R$_t$=8.69 min, m/z=272 (M+1). ¹H NMR (CDCl₃, δ): 7.40 (d, J=2.2 Hz, 1H), 7.30 (d, J=8.4 Hz, 1H), 7.10 (dd, J=2.1, 8.4 Hz, 1H), 2.43 (s, 2H), 20.1 (s, 6H), 2.0-1.6 (m, 8H). ¹³C NMR (CDCl₃, δ, mult): 149.2(0), 129.5(0), 129.2(1), 126.7(1), 131.6(1), 69.3(2), 52.1(0), 48.0(3), 36.0(2), 23.2(2), 1-(1-(4-fluorophenyl)cyclohexyl)-N-methylmethanamine (90)

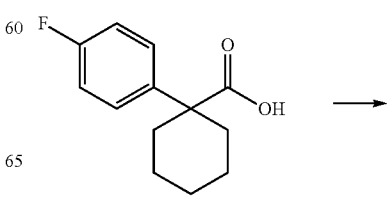

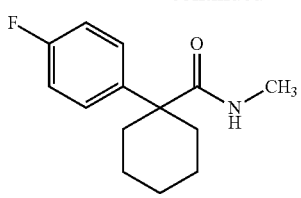

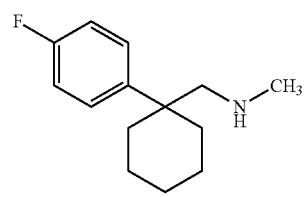

(a) Synthesis of 1-(4-fluorophenyl)-N-methylcyclohexanecarboxamide

The title compound was synthesized from 1-(4-fluorophenyl)cyclohexane-carboxylic acid (222 mg, 1 mmol) and methylamine (1 mL, 1M in THF, 1 eq) according to General Procedure G. The crude product was purified by silica gel column chromatography to give the amide (202.6 mg, 86%) as a white solid.

(b) Synthesis of 1-(1-(4-fluorophenyl)cyclohexyl)-N-methylmethanamine

The title compound was synthesized from the above amide (100 mg, 0.43 mmol) according to General Procedure E to give 1-(1-(4-fluorophenyl)cyclohexyl)-N-methylmethanamine (61.6 mg, 66%) as a clear oil. LCMS $R_t$=6.62 min, m/z=222 (M+1). $^1$H NMR (CDCl$_3$, δ): 7.30 (dd, J=5.4, 8.9 Hz, 2H), 6.97 (t, J=8.8 Hz, 2H), 2.58 (s, 2H), 2.57 (s, 3H), 2.1 (m, 2H), 1.7-1.3 (m, 8H). $^{13}$C NMR (CDCl$_3$, δ, mult): 162.1(0), 159.7(0), 141.0(0), 128.5(1), 128.4(1), 115.1(1), 114.9(1), 64.6(2), 41.8(0), 37.3(3), 34.7(2), 26.6(2), 22.1(2).

(1-(4-fluorophenyl)cyclohexyl)methaneamine (91)

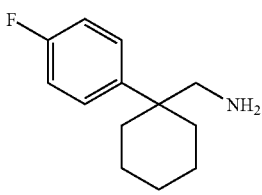 [SMILES: NCC1(c2ccc(F)cc2)CCCCC1]

The title compound was synthesized from 1-(4-fluorophenyl)-cyclohexane-carboxylic acid and ammonia using General Procedure G, followed by General Procedure E in 99% yield as a clear oil. LCMS $R_t$=6.76 min, m/z=208 (M+1). $^1$H NMR (CDCl$_3$, δ): 7.24 (ddd, J=3.2, 5.4, 12.2 Hz, 2H), 7.00 (t, J=8.8 Hz, 2H), 2.67 (s, 2H), 2.1 (m, 2H), 1.6-1.2 (m, 8H), 0.79(bs, 2H). $^{13}$C NMR (CDCl$_3$, δ, mult): 162.1(0), 159.7(0), 140.3(0), 128.7(1), 128.6(1), 115.1(1), 114.9(1), 54.8(2), 43.2(0), 33.8(2), 26.6(2), 22.1(2).

(1-(4-fluorophenyl)cyclohexyl)-N,N-dimethylmethanamine (92)

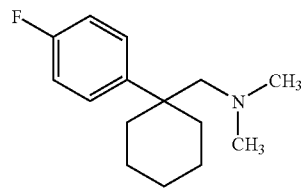 [SMILES: CN(C)CC1(c2ccc(F)cc2)CCCCC1]

The title compound was synthesized from 1-(4-fluorophenyl)cyclohexane-carboxylic acid and dimethyl amine using General Procedure G, followed by General Procedure E in 9% yield as a solid. LCMS $R_t$=7.22 min, m/z=236 (M+1). $^1$H NMR (CDCl$_3$, δ): 7.32 (dd, J=5.5, 8.9 Hz, 2H), 6.99 (t, J=8.8 Hz, 2H), 2.30 (s, 2H), 2.1 (m, 2H), 1.97, (s, 6H), 1.7-1.3 (m, 8H). $^{13}$C NMR (CDCl$_3$, δ, mult): 162.0(0), 159.6(0), 141.7(0), 128.8(1), 128.7(1), 114.7(1), 114.5(1), 72.9(2), 56.5(0), 48.4(3), 34.3(2), 26.6(2), 22.1(2).

N-methyl(1-(naphthalen-2-yl)cyclohexyl)-methanamine (93)

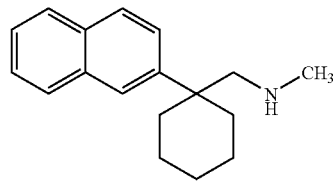 [SMILES: CNCC1(c2ccc3ccccc3c2)CCCCC1]

The title compound was synthesized from 1-(naphthalen-2-yl)cyclohexane-carboxylic acid and methyl amine using General Procedure G, followed by General Procedure E in 74% yield as a clear oil. LCMS $R_t$=7.66 min, m/z=254 (M+1). $^1$H NMR (CDCl$_3$, δ): 7.82 (m, 4H), 7.54 (dd, J=1.8, 8.7 Hz, 1H), 7.45 (m, 2H), 2.69 (s, 2H), 2.3 (m, 2H), 2.25 (m, 3H), 1.8-1.3 (m, 8H). $^{13}$C NMR (CDCl$_3$, δ, mult): 142.7(0), 133.4(0), 131.7(0), 128.0(1), 127.9(1), 127.2(1), 126.1(1), 125.7(1), 125.4(1), 125.0(1), 64.4(2), 42.4(0), 37.3(3), 34.7(2), 26.7(2), 22.3(2).

N,N-dimethyl(1-(naphthalen-2-yl)-cyclohexyl)methanamine (94)

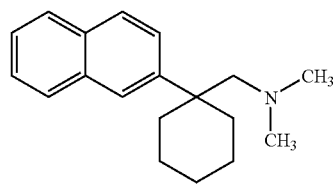 [SMILES: CN(C)CC1(c2ccc3ccccc3c2)CCCCC1]

The title compound was synthesized from 1-(naphthalen-2-yl)cyclohexane-carboxylic acid and dimethyl amine using General Procedure G, followed by General Procedure E and was obtained in 11% yield as a clear oil. LCMS $R_t$=6.47 min, m/z=268 (M+1). $^1$H NMR (CDCl$_3$, δ): 7.80 (m, 4H), 7.55 (dd, J=1.7, 8.6 Hz, 1H), 7.45 (m, 2H), 2.2 (m, 2H), 1.97 (s, 6H), 1.8-1.3 (m, 8H). $^{13}$C NMR (CDCl$_3$, δ, mult): 133.4, 131.6, 127.9, 127.4, 127.2, 126.2, 126.1, 125.8, 125.5, 125.1, 72.6, 56.6, 48.4, 34.3, 26.6, 22.3.

(1-(4-chloro-3-fluorophenyl)cyclohexyl)-N-methyl-methanamine (95)

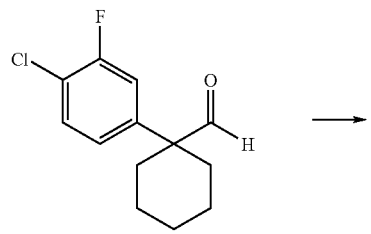

General Procedure H1—Reductive Amination: To a solution of 1-(4-chloro-3-fluorophenyl)cyclohexanecarbaldehyde (100 mg, 0.4154 mmol) in methylamine (2.1 mL, 2M in THF, 10 eq) was added acetic acid (104 ul, 5% of volume), and methanol was added until the solution became clear. The solution was stirred for two hours. To the solution was added sodium borohydride (40 mg, 3 eq) and stirring was continued for 30 minutes. The reaction was quenched with aqueous potassium carbonate and extracted with MTBE. The organic phase was separated and the solvent removed in vacuo. The residue was redissolved in MTBE and extracted with 3M HCl. The aqueous phase was separated, chilled in ice, and basicified with KOH. The aqueous phase was then extracted with MTBE and the solvent removed in vacuo. The residue was diluted in DCM, filtered through aminopropyl cartridge. The solvent was again removed to give the secondary amine (75.1 mg, 71%) as a clear oil. LCMS $R_t$=7.39 min, m/z=256 (M+1). $^1$H NMR (CDCl$_3$, δ): 7.34 (t, J=8.2 Hz, 1H), 7.15 (dd, J=2.2, 11.4 Hz, 1H), 7.09 (dd, J=1.9, 8.4 Hz, 1H), 2.58 (s, 2H), 2.28 (s, 3H), 2.0 (m, 2H), 1.7-1.3 (m, 8H). $^{13}$C NMR (CDCl$_3$, δ, mult): 159.4(0), 156.9(0), 147.2(0), 147.1(0), 130.2(1), 123.5(1), 123.5(1), 118.0(0), 117.8(0), 115.6(1), 115.4(1), 64.2(2), 42.3(0), 37.3(3), 34.5(2), 26.4(2), 22.1(2).

(1-(3-chloro-4-fluorophenyl)cyclohexyl)-N-methyl-methanamine (96)

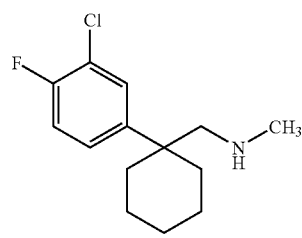 [SMILES: CNCC1(c2ccc(F)c(Cl)c2)CCCCC1]

The title compound was synthesized from 1-(3-chloro-4-fluorophenyl)-cyclohexanecarbaldehyde and methyl amine using General Procedure H1 and was obtained in 55% yield. LCMS $R_t$=7.73 min, m/z=256 (M+1). $^1$H NMR (CDCl$_3$, δ): 7.37 (dd, J=2.4, 7.1 Hz, 1H), 7.22 (ddd, J=2.4, 4.6, 8.7 Hz, 1H), 7.09 (t, J=8.7 Hz, 1H), 2.58 (s, 2H), 2.29 (s, 3H), 2.0 (m, 2H), 1.7-1.2 (m, 8H). $^{13}$C NMR (CDCl$_3$, δ, mult): 157.4(0), 154.9(0), 142.9(0), 129.2(1), 126.8(1), 126.7(1), 120.8(0), 120.6(0), 116.3(1), 116.1(1), 64.2(2), 42.1(0), 37.3(3), 34.6(2), 26.4(2), 22.1(2).

(1-(3-chloro-4-fluorophenyl)cyclohexyl)-N,N-dimethylmethanamine (97)

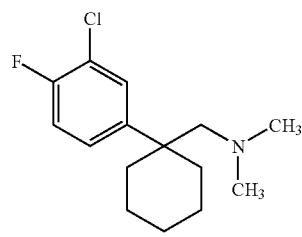 [SMILES: CN(C)CC1(c2ccc(F)c(Cl)c2)CCCCC1]

The title compound was synthesized from 1-(3-chloro-4-fluorophenyl)cyclohexanecarbaldehyde and dimethyl amine using General Procedure H1 and was obtained in 88% yield as an oily solid. The title compound was also synthesized from 1-(1-(3-chloro-4-fluorophenyl)-cyclohexyl)-N-methyl-methanamine according to General Procedure C.

LCMS $R_t$=8.81 min, m/z=270 (M+1). $^1$NMR (CDCl$_3$, δ): 7.38 (dd, J=2.4, 7.2 Hz, 1H), 7.22 (ddd, J=2.4, 4.6, 8.7 Hz, 1H), 7.07 (t, J=8.8 Hz, 1H), 2.29 (s, 2H), 2.0 (m, 2H), 1.99 (s, 6H), 1.7-1.2 (m, 8H). $^{13}$C NMR (CDCl$_3$, δ, mult): 157.2(0), 143.4(0), 129.6(1), 127.1(1), 127.1(1), 120.3(0), 120.1(0), 115.9(1), 115.7(1), 72.5(2), 48.4(3), 43.0(0), 34.1(2), 26.4(2), 22.0(2).

(1-(4-chloro-3-fluorophenyl)cyclohexyl)-methanamine (98)

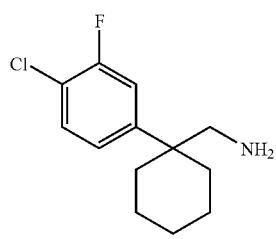 [SMILES: NCC1(c2ccc(Cl)c(F)c2)CCCCC1]

The title compound was synthesized from 1-(4-chloro-3-fluorophenyl)-cyclohexanecarbonitrile using General Procedure E and was obtained in 19% yield as a clear oil. HPLC $R_t$=8.28 min. LCMS $R_t$=8.13 min, m/z=242 (M+1). HCl salt – $^1$H NMR (DMSO-d6, δ): 7.35 (t, J=8.1 Hz, 1H), 7.17 (d, J=11.3 Hz, 1H), 7.10 (d, J=8.4 Hz, 1H), 2.82 (s, 2H), 2.1 (m, 2H), 1.7-1.1 (m, 8H). $^{13}$C NMR (DMSO-d6, δ, mult): 159.2(0), 156.7(0), 143.1(0), 143.0(0), 130.6(1), 124.1(1), 124.1(1), 118.5(0), 118.3(0), 116.2(1), 116.0(1), 50.2(2), 40.6(0), 33.3(2), 25.5(2), 21.4(2).

(1-(4-chloro-3-fluorophenyl)cyclohexyl)-N,N-dimethylmethanamine (99)

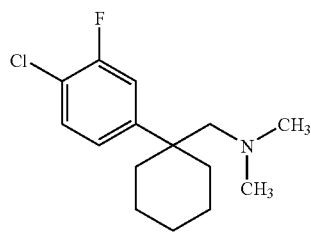 [SMILES: CN(C)CC1(c2ccc(Cl)c(F)c2)CCCCC1]

The title compound was synthesized from 1-(4-chloro-3-fluorophenyl)cyclohexanecarbaldehyde and dimethyl amine using General Procedure H1 and was obtained in 97% yield. LCMS $R_t$=9.07 min, m/z=270 (M+1). $^1$H NMR (CDCl$_3$, δ): 7.31 (t, J=8.2 Hz, 1H), 7.17 (dd, J=2.1, 11.7 Hz, 1H), 7.09 (dd, J=1.8, 8.5 Hz, 1H), 2.30 (s, 2H), 2.0 (m, 2H), 1.99 (s, 3H), 1.7-1.3 (m, 8H). $^{13}$C NMR (CDCl$_3$, δ, mult): 159.2(0), 156.7 (0), 147.8(0), 129.7(1), 123.9(1), 123.8(1), 117.5(0), 117.3(0), 115.9(1), 115.7(1), 72.5(2), 48.4(3), 43.3(0), 34.1(2), 26.4(2), 22.1(2).

N-methyl-1-(1-(4-(trifluoromethyl)phenyl)-cyclohexyl)methanamine (100)

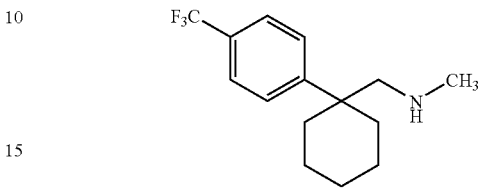

(a) Preparation of 1-(4-(trifluoromethyl)phenyl)cyclohexanecarbonitrile

The title compound was synthesized from 2-(4-(trifluoromethyl)phenyl)-acetonitrile (4.11 g, 22.2 mmol) and 1,5-dibromopentane (3.324 ml, 24.4 mmol) according to General Procedure J and was obtained as a clear oil (4.98 g, 89%). $^1$H NMR (CDCl$_3$) δ 1.23-1.39 (m, 1H), 1.76-1.92 (m, 7H), 2.17 (d, J=11.2 Hz, 2H), 7.63 (s, 4H). $^{13}$C NMR (CDCl13) δ 23.7, 25.0, 37.4, 44.7, 122.2, 126.0, 126.7, 130.2, 145.6, GC-MS m/z 253.

(b) Preparation of 1-(4-(trifluoromethyl)phenyl)cyclohexanecarbaldehyde

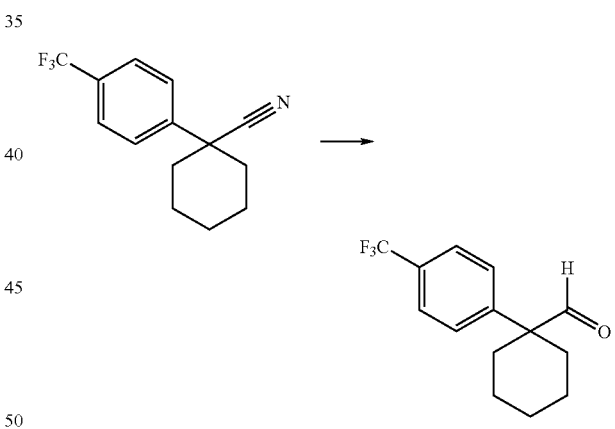

General Procedure M: To a solution of 1-(4-(trifluoromethyl)phenyl)-cyclohexanecarbonitrile (4.80 g, 18.95 mmol) in toluene (60 ml) at –70° C. was dropwise added 1 M DIBAL in hexane (38 ml, 38 mmol) over 30 min. The mixture was stirred at –70° C. for 30 min and for another 4 h at room temperature, whereupon ethyl formate (3 ml) was added. The mixture was stirred at room temperature for 1 hour and was then poured into saturated NH$_4$Cl solution (70 ml). After 30 min, 2 M aqueous H$_2$SO$_4$ (100 ml) was added and the product was extracted with hexanes (3 ×100 ml). The combined organic phases were dried over MgSO$_4$ and evaporated in vacuo. The residue was purified by silica gel column chromatography (EtOAc/hexanes, EtOAc from 0% to 25%) to give 1-(4-(trifluoromethyl)phenyl)-cyclohexanecarbaldehy (3.0 g, 65%) as clear oil. $^1$H NMR (CDCl$_3$): δ 1.29-1.37 (m, 1H), 1.46-1.55 (m, 2H), 1.59-1.69 (m, 3H), 1.83-1.90 (m, 2H), 2.29-2.34 (m, 2H), 7.45 (d, J=8.4 Hz, 2H), 7.62 (d, J=8.4 Hz, 2H), 9.40 (s, 1H). $^{13}$C NMR (CDCl$_3$) δ 22.9, 25.6, 31.5, 54.7, 125.9, 126.0, 127.8, 129.5, 144.2, 202.0.

(c) Preparation of N-methyl(1-(4-(trifluoromethyl)phenyl)cyclohexyl)-methanamine General Procedure H2 - Reductive Amination: A mixture of 1-(4-(trifluoromethyl)phenyl)cyclohexanecarbaldehyde (256 mg, 1.0 mmol) and methylamine (2.0 M in THF, 3 ml, 6.0 mmol) in 1,2-dichloroethane was stirred at room temperature for 30 min and was then treated with sodium triacetoxyborohydride (297 mg, 1.4 mmol). The reaction mixture was stirred at room temperature overnight and was then quenched with aqueous saturated NaHCO$_3$ solution (10 ml). The product was extracted with EtOAc (3 ×10 ml). The combined organic layers were dried over MgSO$_4$ and evaporated in vacuo. The residue was purified by silica gel column chromatography (MeOH/CH$_2$Cl$_2$, MeOH from 0% to 20%) to give N-methyl-1-(1-(4-(trifluoromethyl)phenyl)cyclohexyl)methanamine (178 mg, 66%). $^1$H NMR (CDCl$_3$): δ 1.26-1.52 (m 4H), 1.54-1.61 (m, 2H), 1.66-1.73 (m, 2H), 2.13-2.18 (m, 2H), 2.28 (s, 3H), 2.63 (s, 2H), 7.49 (d, J=8.0 Hz, 2H), 7.59 (d, J=8.0 Hz, 2H). $^{13}$C NMR (CDCl3) δ 22.3, 26.7, 34.7, 37.5, 42.9, 64.5, 125.4, 125.9, 127.6, 128.3, 150.2.ESI MS m/z 271.

N,N-dimethyl-1-(1-(4-(trifluoromethyl)phenyl)-cyclohexyl)methanamine (101)

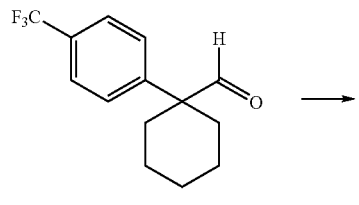

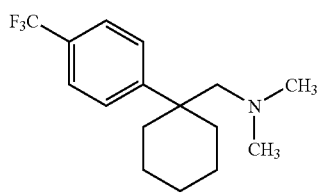 [SMILES: CNCC1(c2ccc(C(F)(F)F)cc2)CCCCC1]

The title compound was prepared from 1-(4-(trifluoromethyl)phenyl)cyclohexane-carbaldehyde (128 mg, 0.50 mmol) and dimethylamine (2.0 M in THF, 0.5 ml, 1.0 mmol) according to General Procedure H2.The crude product was purified by silica gel column chromatography (MeOH/CH$_2$Cl$_2$, MeOH from 0% to 15%) to give N,N-dimethyl-1-(1-(4-(trifluoromethyl)phenyl)-cyclohexyl)methanamine (47 mg, 33%). $^1$H NMR (CDCl$_3$): δ 1.29-1.38 (m 3H), 1.48-1.57 (m, 3H), 1.62-1.68 (m, 2H), 1.97 (s, 6H), 2.13-2.18 (m, 2H), 2.35 (s, 2H), 7.49 (d, J=8.4 Hz, 2H), 7.55 (d, J=8.4 Hz, 2H).

$^{13}$C NMR (CDCl$_3$) δ 22.4, 26.7, 34.4, 37.5, 43.9, 48.6, 72.8, 123.3, 125.0, 125.1, 126.0, 127.6, 127.9, 128.3, 150.8.ESI MS m/z 286.

1-(1-(benzo[d][1,3]dioxol-5-yl)cyclohexyl)-N,N-dimethylmethanamine (102)

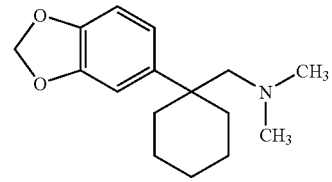 [SMILES: CN(C)CC1(c2ccc3c(c2)OCO3)CCCCC1]

(a) Synthesis of 1-(benzo[d][1,3]dioxol-5-yl)cyclohexanecarbonitrile

The title compound was prepared according to General Procedure J to give 1-(benzo[d][1,3]dioxol-5-yl)cyclohexanecarbonitrile (2.90 g, 57%) as a white solid. $^1$H NMR (CDCl$_3$): δ 1.24-1.35 (m, 1H), 1.74-1.88 (m, 7H), 2.16 (d, J=11.2 Hz, 2H), 6.79 (d, J=8.0 Hz, 1H), 6.95-6.99 (m, 2H). $^{13}$C NMR (CDCl$_3$) δ 23.7, 25.0, 37.5, 44.6, 122.5, 122.6, 124.9, 125.0, 129.5, 129.7, 142.8.

(b) Preparation of 1-(benzo[d][1,3]dioxol-5-yl)cyclohexanecarbaldehyde

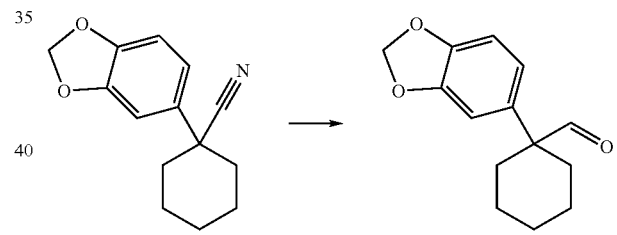

The title compound was prepared from the above nitrile according to General Procedure M. The crude product was purified by silica gel column chromatography (EtOAc/hexanes, EtOAc from 0% to 25%) to give 1-(benzo[d][1,3]dioxol-5-yl)cyclohexanecarbaldehyde (1.65 g, 56%) as a white solid. $^1$H NMR (CDCl$_3$): δ 1.25-1.34 (m, 1H), 1.41-1.50 (m, 2H), 1.57-1.70 (m, 3H), 1.73-1.80 (m, 2H), 2.23-2.30 (m, 2H), 5.94 (s, 2H), 6.75-6.82 (m, 3H), 9.30 (s, 1H). $^{13}$C NMR (CDCl$_3$) δ 23.0, 25.8, 31.7, 54.1, 101.4, 107.8, 108.7, 120.8, 133.7, 146.9, 148.5, 202.1.

(c) 1-(1-(benzo[d][1,3]dioxol-5-yl)cyclohexyl)-N,N-dimethylmethanamine

The title compound was prepared from the above 1-(benzo[d][1,3]dioxol-5-yl)cyclohexanecarbaldehyde (232 mg, 1.0 mmol) and dimethylamine (2.0 M in THF, 1.0 ml, 2.0 mmol) according to General Procedure H2.The crude product was purified by silica gel column chromatography (MeOH/CH$_2$Cl$_2$, MeOH from 0% to 15%) to give 1-(1-(benzo[d][1,3]dioxol-5-yl)cyclohexyl)-N,N-dimethylmethanamine (47 mg, 33%) as clear oil. $^1$H NMR (CDCl$_3$): δ 1.31-1.41 (m 3H), 1.42-1.53 (m, 3H), 1.56-1.63 (m, 2H), 2.01 (s, 6H), 2.03-2.08

(m, 2H), 2.30 (s, 2H), 5.91 (s, 2H), 6.75 (d, J=8.0 Hz, 1H), 6.82 (dd, J=8.0 Hz, 1.6 Hz, 1H), 6.87 (d, J=1.6 Hz, 1H). $^{13}$C NMR (CDCl$_3$) δ 22.4, 26.8, 34.7, 37.5, 43.2, 48.2, 73.0, 100.9, 108.0, 108.2, 120.5, 140.3, 145.3, 147.8.ESI MS m/z 262.

1-(1-(benzo[d][1,3]dioxol-5-yl)cyclohexyl)-N-methylmethanamine (103)

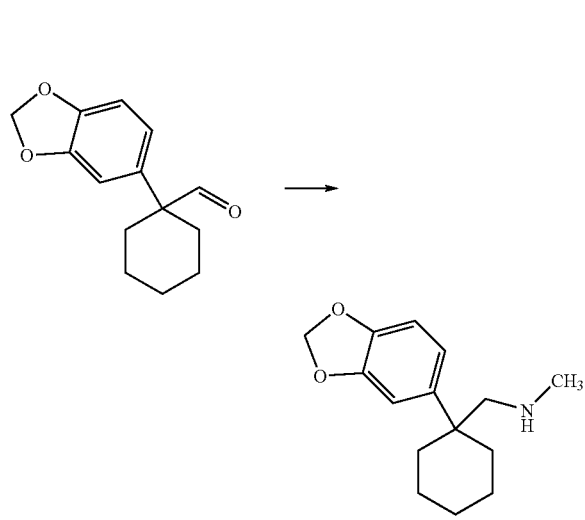

The title compound was prepared from 1-(benzo[d][1,3]dioxol-5-yl)cyclohexanecarbaldehyde (232 mg, 1.0 mmol) and methylamine (2.0 M in THF, 3 ml, 6.0 mmol) according to General Procedure H2.The crude product was purified by silica gel column chromatography (SiO$_2$, MeOH/CH$_2$Cl$_2$, MeOH from 0% to 20%) to give 1-(1-(benzo[d][1,3]dioxol-5-yl)cyclohexyl)-N-methylmethanamine (218 mg, 88%). $^1$H NMR (CDCl$_3$): δ 1.26-1.52 (m 4H), 1.54-1.61 (m, 2H), 1.66-1.73 (m, 2H), 2.03-2.12 (m, 2H), 2.28 (s, 3H), 2.60 (s, 2H), 5.90 (s, 2H), 6.75-6.86 (m, 2H), 6.90 (s, 1H). $^{13}$C NMR (CDCl$_3$) δ 22.3, 26.7, 35.2, 37.4, 42.3, 64.8, 101.0, 107.6, 108.2, 120.3, 139.4, 145.6, 148.1.ESI MS m/z 248.

N-methyl-1-(1-(3-(trifluoromethyl)phenyl)-cyclohexyl)methanamine (104)

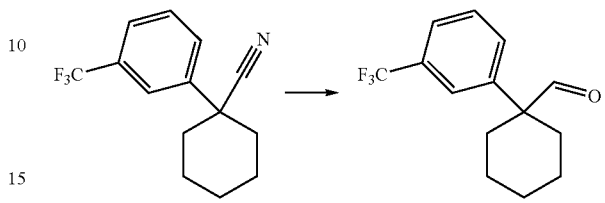

(a) Preparation of 1-(3-(trifluoromethyl)phenyl)cyclohexanecarbonitrile

The title compound was prepared from 2-(3-(trifluoromethyl)phenyl)acetonitrile (3.463 ml, 22.2 mmol) and 1,5-dibromopentane (3.324 ml, 24.4 mmol) according to General Procedure J to yield 1-(3-(trifluoromethyl)phenyl)cyclohexane-carbonitrile (5.40 g, 90%) as a clear oil. $^1$H NMR (CDCl$_3$) δ 1.26-1.39 (m, 1H), 1.76-1.88 (m, 7H), 2.17 (d, J=11.2 Hz, 2H), 7.51-7.60 (m, 3H), 7.73 (s, 1H). $^{13}$C NMR (CDCl3) δ 23.7, 25.0, 37.5, 44.6, 122.5, 125.0, 125.1, 126.0, 129.5, 130.0, 142.8,GC-MS m/z 253.

(b) Preparation of 1-(3-(trifluoromethyl)phenyl)cyclohexanecarbaldehyde

The title compound was prepared from the above 1-(3-(trifluoromethyl)phenyl)cyclohexane-carbonitrile (5.60 g, 22.1 mmol) according to General Procedure M. The crude product was purified by silica gel column chromatography (EtOAc/hexanes, EtOAc from 0% to 25%) to give 1-(3-(trifluoromethyl)phenyl)-cyclohexanecarbaldehyde (3.85 g, 68%) as a clear oil. $^1$H NMR (CDCl$_3$): δ 1.25-1.34 (m, 1H), 1.45-1.53 (m, 2H), 1.59-1.67 (m, 3H), 1.80-1.87 (m, 2H), 2.31-2.35 (m, 2H), 7.45-7.53 (m, 3H), 7.58 (s, 1H), 9.38 (s, 1H). $^{13}$C NMR (CDCl$_3$) δ 22.8, 25.6, 31.5, 54.6, 123.9, 124.0, 124.3, 129.5, 130.9, 141.3, 148.5, 202.0.

(c) Synthesis of N-methyl-1-(1-(3-(trifluoromethyl)phenyl)-cyclohexyl)methanamine The title compound was prepared from 1-(3-(trifluoromethyl)phenyl)cyclohexane-carbaldehyde (116 mg, 0.5 mmol) and methylamine (2.0 M in THF, 2.5 ml, 5.0 mmol) according to General Procedure H2.The crude product was purified by silica gel column chromatography (MeOH/CH$_2$Cl$_2$, MeOH from 0% to 15%) to give N-methyl-1-(1-(3-(trifluoromethyl)phenyl)cyclohexyl)methanamine (50 mg, 45%). $^1$H NMR (CDCl$_3$): δ 1.28-1.52 (m 4H), 1.54-1.60 (m, 2H), 1.69-1.76 (m, 2H), 2.12-2.18 (m, 2H), 2.29 (s, 3H), 2.66 (s, 2H), 7.45-7.48 (m, 2H), 7.56-7.59 (m, 1H), 7.61 (s, 1H). $^{13}$C NMR (CDCl$_3$) δ 22.3, 26.7, 34.6, 37.4, 42.6, 64.2, 123.0, 123.9, 127.9, 129.1, 130.8, 131.1, 146.7.ESI MS m/z 271.

N,N-dimethyl-1-(1-(3-(trifluoromethyl)-phenyl)cyclohexyl)-methanamine (105)

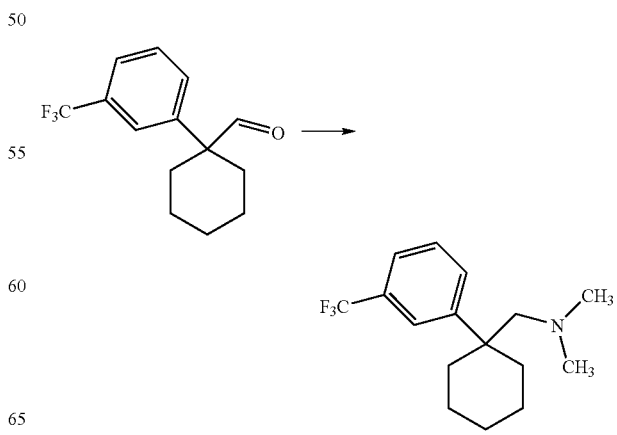

The title compound was prepared from 1-(3-(trifluoromethyl)phenyl)cyclohexane-carbaldehyde (128 mg, 0.50 mmol) and dimethylamine (2.0 M in THF, 2.5 ml, 5.0 mmol) according to General Procedure H2.The crude product was purified by silica gel column chromatography (MeOH/CH$_2$Cl$_2$, MeOH from 0% to 15%) to give N,N-dimethyl-1-(1-(3-(trifluoromethyl)phenyl)cyclohexyl)methanamine (74 mg, 52%) as a clear oil. $^1$H NMR (CDCl$_3$): δ 1.29-1.38 (m 3H), 1.48-1.57 (m, 3H), 1.63-1.70 (m, 2H), 1.97 (s, 6H), 2.11-2.15 (m, 2H), 2.34 (s, 2H), 7.41-7.43 (m, 2H), 7.56-7.59 (m, 1H), 7.63 (s, 1H). $^{13}$C NMR (CDCl$_3$) δ 22.4, 26.7, 34.3, 43.9, 48.6, 72.7, 122.4, 124.3, 128.6, 126.0, 131.1, 147.6, 150.8.ESI MS m/z 286.

1-(1-(3-fluorophenyl)cyclohexyl)-N-methylmethanamine (106)

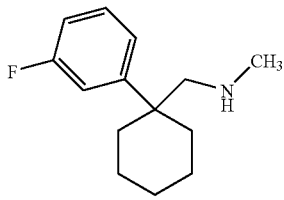 [SMILES: CNCC1(c2cccc(F)c2)CCCCC1]

(a) Preparation of 1-(3-fluorophenyl)cyclohexanecarbonitrile

The title compound was prepared from 2-(3-fluorophenyl)acetonitrile (2.58 ml, 22.2 mmol) and 1,5-dibromopentane (3.324 ml, 24.4 mmol) according to General Procedure J to yield 1-(3-fluorophenyl)cyclohexanecarbonitrile (4.43 g, 97%) as a clear oil. $^1$H NMR (CDCl$_3$) δ 1.26-1.39 (m, 1H), 1.76-1.88 (m, 7H), 2.17 (d, J=11.2 Hz, 2H), 6.93-6.98 (m, 1H), 7.04 (d, J=8.0 Hz, 1H), 7.09 (d, J=8.0 Hz, 1H), 7.30-7.35 (m, 1H). $^{13}$C NMR (CDCl3) δ 23.7, 25.0, 37.5, 44.6, 122.5, 125.0, 125.1, 126.0, 129.5, 130.0, 142.8.

(b) Preparation of 1-(3-fluorophenyl)cyclohexanecarbaldehyde

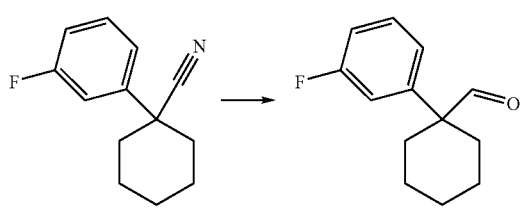 [SMILES: N#CC1(c2cccc(F)c2)CCCCC1 ; O=CC1(c2cccc(F)c2)CCCCC1]

The title compound was prepared from 1-(3-fluorophenyl)cyclohexanecarbonitrile (3.52 g, 17.32 mmol) according to General Procedure M. The crude product was purified by silica gel column chromatography (EtOAc/hexanes, EtOAc from 0% to 25%) to give 1-(3-fluorophenyl)cyclohexanecarbaldehyde (2.01 g, 56%) as a clear oil. $^1$H NMR (CDCl$_3$): δ 1.29-1.37 (m, 1H), 1.44-1.53 (m, 2H), 1.58-1.67 (m, 3H), 1.79-1.85 (m, 2H), 2.26-2.31 (m, 2H), 6.93-6.98 (m, 1H), 7.04 (d, J=8.0 Hz, 1H), 7.09 (d, J=8.0 Hz, 1H), 7.30-7.35 (m, 1H), 9.36 (s, 1H). $^{13}$C NMR (CDCl$_3$) δ 22.9, 25.7, 31.5, 54.5, 114.4, 123.0, 130.5, 142.8, 162.2, 164.7, 202.0.

(c) Synthesis of 1-(1-(3-fluorophenyl)cyclohexyl)-N-methylmethanamine

The title compound was prepared from the above 1-(3-fluorophenyl)cyclohexane-carbaldehyde (103 mg, 0.5 mmol) and methylamine (2.0 M in THF, 2.5 ml, 5.0 mmol) according to General Procedure H2.The crude product was purified by silica gel column chromatography (MeOH/CH$_2$Cl$_2$, MeOH from 0% to 15%) to give 1-(1-(3-fluorophenyl)cyclohexyl)-N-methylmethanamine (50 mg, 45%). $^1$H NMR (CDCl$_3$): 1.28-1.52 (m 4H), 1.54-1.60 (m, 2H), 1.69-1.76 (m, 2H), 2.12-2.18 (m, 2H), 2.28 (s, 3H), 2.61 (s, 2H), 7.45-7.48 (m, 2H), 6.87-6.92 (m, 1H), 7.08 (d, J=8.0 Hz, 1H), 7.16 (d, J=8.0 Hz, 1H), 7.27-7.32 (m, 1H). $^{13}$C NMR (CDCl$_3$) 22.4, 26.8, 34.9, 37.5, 42.6, 64.6, 112.7, 112.9, 114.2, 114.4, 122.8, 129.9, 130.0, 162.2, 164.7.ESI MS m/z 222.

1-(1-(3-fluorophenyl)cyclohexyl)-N,N-dimethylmethanamine (107)

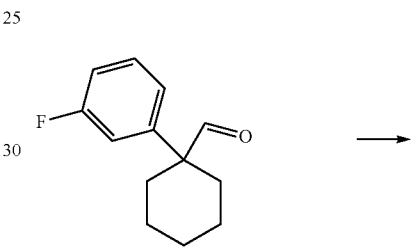

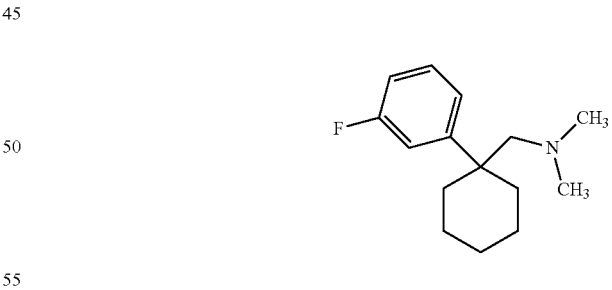

The title compound was prepared from 1-(3-fluorophenyl)cyclohexane-carbaldehyde (103 mg, 0.50 mmol) and dimethylamine (2.0 M in THF, 2.5 ml, 5.0 mmol) according to General Procedure H2.The crude product was purified by column chromatography (SiO$_2$, MeOH/CH$_2$Cl$_2$, MeOH from 0% to 15%) to give 1-(1-(3-fluorophenyl)cyclohexyl)-N,N-dimethylmethanamine (46 mg, 39%) as a clear oil. $^1$H NMR (CDCl$_3$): δ 1.32-1.38 (m 3H), 1.49-1.56 (m, 3H), 1.59-1.66 (m, 2H), 1.99 (s, 6H), 2.05-2.09 (m, 2H), 2.33 (s, 2H), 6.83-6.88 (m, 1H), 7.08 (d, J=8.0 Hz, 1H), 7.14 (d, J=8.0 Hz, 1H), 7.23-7.29 (m, 1H). $^{13}$C NMR (CDCl$_3$) δ 22.4, 26.8, 34.4, 43.6, 48.6, 72.9, 112.2, 112.4, 114.6, 114.8, 123.2, 129.4, 129.5, 162.0, 164.5.ESI MS m/z 236.

(±) 1-(1-(3,4-dichlorophenyl)cyclohexyl)-N-methyl-ethanamine (108)

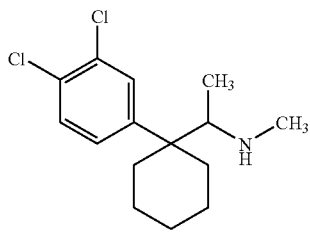 [SMILES: CNC(C)C1(c2ccc(Cl)c(Cl)c2)CCCCC1]

(a) Synthesis of 1-(1-(3,4-dichlorophenyl)cyclohexyl)ethanol

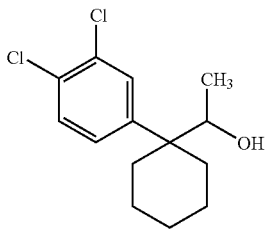 [SMILES: CC(O)C1(c2ccc(Cl)c(Cl)c2)CCCCC1]

To a solution of 1-(3,4-dichlorophenyl)cyclohexanecarbaldehyde (440 mg, 1.71 mmol) in anhydrous THF (17 mL) at 0° C. was added slowly methyl lithium (1.6 M in Et$_2$O, 3.21 mL, 5.14 mmol). The solution was allowed to warm to RT and was stirred for 16 h. It was then quenched with MeOH (5 mL). The crude reaction mixture was poured into 2M HCl (15 mL) and washed with EtOAc (3×20 mL). The combined organic layers were dried (Na$_2$SO$_4$), filtered and concentrated to give 1-(1-(3,4-dichlorophenyl)cyclohexyl)ethanol. HPLC R$_t$=11.28 min; $^1$H NMR (400 mHz, CDCl$_3$) 7.44-7.41 (m, 2H), 7.20 (dd, J=2.2, 8.4 Hz, 1H), 3.63-3.58 (m, 1H), 2.39-2.35 (m, 1H), 2.14-2.10 (m, 1H), 1.67-1.48 (m, 5H), 1.31-1.16 (m, 3H), 0.92 (d, J=6.6 Hz, 3H).

(b) Synthesis of 1-(1-(3,4-dichlorophenyl)cyclohexyl)ethanone

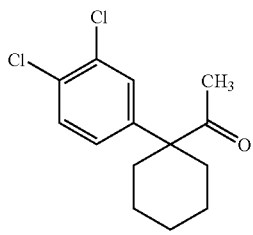

To a solution of crude 1-(1-(3,4-dichlorophenyl)cyclohexyl)ethanol (494 mg, 1.81 mmol) in CH$_2$Cl$_2$ (18 mL) was added Dess-Martin periodinane (997 mg, 2.35 mmol). The resulting suspension was stirred at RT for 2 h and was then concentrated. The crude ketone was purified by silica gel column chromatography with an EtOAc/hexane gradient (product R$_f$=0.6 in 10% EtOAc/hexanes) to give 1-(1-(3,4-dichlorophenyl)cyclohexyl)ethanone (312 mg, 67%) as an orange oil. HPLC R$_t$=11.61 min; $^1$H NMR (400 mHz, CDCl$_3$) 7.42-7.40 (m, 2H), 7.15 (dd, J=2.2, 8.4 Hz, 1H), 2.32-2.29 (m, 2H), 1.92 (s, 3H), 1.80-1.74 (m, 2H), 1.65-1.43 (m, 5H), 1.35-1.30 (m, 1H); $^{13}$C NMR (100 mHz, CDCl$_3$) 209.5, 143.3, 133.2, 131.3, 130.9, 128.9, 126.3, 56.2, 33.7, 25.8 (2 overlapping peaks), 23.2.

(c) Synthesis of (±)1-(1-(3,4-dichlorophenyl)cyclohexyl)-N-methylethanamine hydrochloride A mixture of 1-(1-(3,4-dichlorophenyl)cyclohexyl)ethanone (247 mg, 0.91 mmol) and methyl amine (455 µL, 2.0 M in THF, 0.91 mmol) was stirred at RT for 2 min. Titanium (IV) isoproxide (336 µL, 1.14 mmol) was then added. The viscous green/yellow solution was stirred at RT for 3 h. NaBH$_3$CN solution (640 µL, 1.0 M in MeOH, 0.64 mmol) was added and the cloudy solution was stirred at RT for 16 h. The solution was quenched with saturated NaCl solution (3 mL), filtered, and washed with MeOH (50 mL). 6M HCl (20 mL) was added and the aqueous phase was washed with Et$_2$O (2×20 mL). The pH of the aqueous phase was adjusted to pH=12 with 3M NaOH and washed with EtOAc (3×30 mL). The combined organic phases were dried (Na$_2$SO$_4$), filtered and concentrated. To a solution of the crude amine in Et$_2$O (3 mL) was added HCl (3 mL, 2.0 M in Et$_2$O). The crude HCl salt was recrystallized from CH$_3$CN (6 mL) at 110° c to give 1-(1-(3,4-dichlorophenyl)cyclohexyl)-N-methylethanamine (8 mg) as white crystals. HPLC R$_t$=8.90 min; $^1$H NMR (400 mHz, CD$_3$OD) 7.57-7.53 (m, 2H), 7.33-7.31 (m, 1H), 3.15-3.13 (m, 2H), 2.61 (s, 3H), 2.45 (broad d, J=11.73 Hz, 1H), 2.30 (broad d, J=12.46, 1H), 1.59-1.51 (m, 5H), 1.31-1.08 (m, 6H); LC-MS 7.87 min, (M+1) 286 @ 8.10 min.

Synthesis of 1-(1-(3,4-dichlorophenyl)cyclohexyl)propan-1-one (a) 1-(1-(3,4-dichlorophenyl)cyclohexyl)propan-1-ol

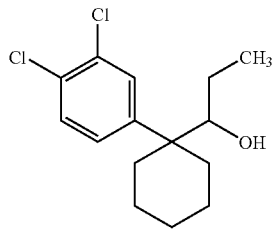 [SMILES: CCC(O)C1(c2ccc(Cl)c(Cl)c2)CCCCC1]

1-(3,4-dichlorophenyl)cyclohexanecarbaldehyde (519 mg, 2.01 mmol) was dissolved in anhydrous THF (17 mL) and cooled to 0° C. Ethyl magnesium chloride (2.0 M in THF, 3.03 mL, 6.06 mmol) was added slowly. The solution was allowed to warm to RT and stir for 16 h, then quenched with MeOH (5 mL). The crude reaction mixture was poured into 2M HCl (15 mL) and washed with EtOAc (3×20 mL). The combined organic washes were dried (Na$_2$SO$_4$), filtered and concentrated to give the secondary alcohol (443 mg, 77% for 2 steps) as a white solid. HPLC R$_t$=11.65 min; $^1$H NMR (400 mHz, CDCl$_3$) 7.43-7.41 (m, 2H), 7.19 (dd, J=2.2, 8.4 Hz, 1H), 3.27-3.23 (m, 1H), 2.37-2.33 (m, 1H), 2.17-2.14 (m, 1H), 1.57-1.46 (m, 6H), 1.29-1.17 (m, 4H), 0.90-0.77 (m, 4H); $^{13}$C NMR (125 mHz, CDCl$_3$) 143.0, 132.4, 130.9, 130.1, 130.0, 128.3, 81.7, 47.1, 32.6 (doublet), 26.7, 24.4, 22.2, 11.4.

(b) 1-(1-(3,4-dichlorophenyl)cyclohexyl)propan-1-one

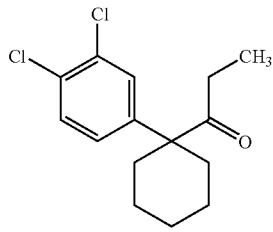 [SMILES: CCC(=O)C1(c2ccc(Cl)c(Cl)c2)CCCCC1]

The crude ethyl alcohol product (577 mg, 2.01 mmol) was dissolved in CH$_2$Cl$_2$ (20 mL) and Dess-Martin Periodinane (1.1 g, 2.61 mmol) was added. The white opaque suspension was stirred at RT for 2 h, then concentrated. The crude ketone was purified by silica gel column chromatography with an EtOAc/hexane gradient (R$_f$=0.6 in 10% EtOAc/hexanes) to give the desired ethyl ketone (443 mg, 77%) as a white solid. HPLC R$_t$=12.0 min; $^1$H NMR (400 mHz, CDCl$_3$) 7.44-7.38 (m, 2H), 7.11 (dd, J=2.6, 8.4 Hz, 1H), 2.32-2.20 (m, 4H), 1.80-1.74 (m, 2H), 1.68-1.42 (m, 5H), 1.34-1.26 (m, 2H), 0.90 (t, 3H); $^{13}$C NMR (125 mHz, CDCl$_3$) 212.1, 143.6, 133.1, 130.9, 130.8, 128.8, 126.3, 56.0, 33.7, 30.7, 25.8, 23.3, 8.49. This compound can be used to synthesize compounds of the invention with R$^1$=ethyl, e.g., through reductive amination. Exemplary compounds include:

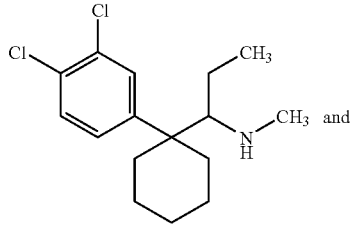

1.4. Synthesis of 3,4-dichlorophenyl cyclohexylamines with Cyclic Amine Substituents from Corresponding Carboxylic Acids

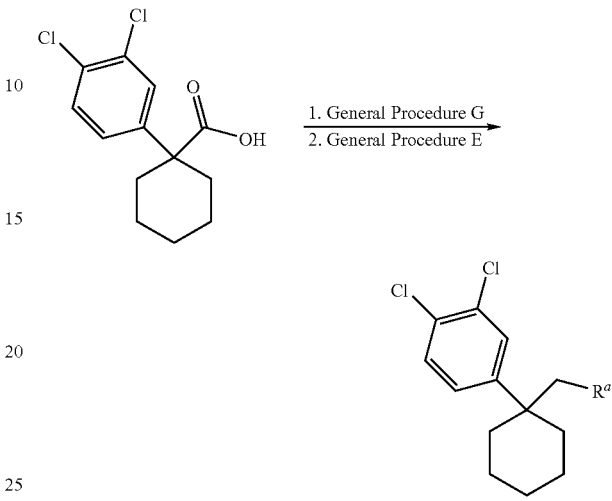

Compounds in Table 3, below, were synthesized from the corresponding carboxylic acids via the amide intermediate according to General Procedure G and General Procedure E.

TABLE 3

Summary of Exemplary Cyclic Amines 1-((1-(3,4-dichlorophenyl)cyclohexyl)methyl)piperidine (109)

R$^a$ = [piperidine]

HPLC R$_t$ = 9.20 min; $^1$H NMR (400 MHz, MeOH-d$^4$) 7.65(s, 1H), 7.50(d, J = 8.8 Hz, 1H), 7.43-7.41(m, 1H), 3.22(t, J = 1.47 Hz, 1H), 3.05-2.99(m, 2H), 2.73-2.67(m, 2H), 2.22-2.18(m, 2H), 1.71-1.126(m, 14H); LC-MS 11.79 min, (M + 1)$^+$ 326 @ 11.91 min.

4-((1-(3,4-dichlorophenyl)cyclohexyl)methyl)morpholine (110)

R$^a$ = [morpholine]

HPLC R$_t$ = 8.82 min; $^1$H NMR (400 MHz, MeOH-d$^4$) 7.66(d, J = 1.83 Hz, 1H), 7.54(d, J = 8.43 Hz, 1H), 7.43(dd, J = 2.2, 8.43 Hz, 1H), 3.81-3.70(m, 4H), 3.46 (s, 2H), 3.25-3.24(m, 2H), 3.07-3.04(m, 2H), 2.93-2.88(m, 2H), 2.24-2.20(m, 2H), 1.78-1.70(m, 2H), 1.61-1.31(m, 6H); LC-MS 11.09 min, (M + 1)$^+$ 328 @11.28 min.

TABLE 3-continued

Summary of Exemplary Cyclic Amines 1-((1-(3,4-dichlorophenyl)cyclohexyl)methyl)pyrrolidine (111)

R$^a$ = [pyrrolidine structure]

HPLC R$_t$ = 9.12 min; $^1$H NMR (400 MHz, CDCl$_3$) 7.43(d, J = 2.20 Hz, 1H), 7.35 (d, J = 8.43 Hz, 1H), 7.22-7.20(m, 1H), 2.52(s, 2H), 2.23(s, 3H), 2.05-2.02(m, 2H), 1.65-1.48(m, 10H), 1.38-1.25(m, 3H); LC-MS 9.31 min, (M + 1)$^+$ 312 @ 9.39 min.

1-((1-(3,4-dichlorophenyl)cyclohexyl)methyl)-4-methylpiperazine (112)

R$^a$ = [4-methylpiperazine structure]

Prepared from Amide Intermediate 298
HPLC R$_t$ = 9.47 min; $^1$H NMR (400 MHz, MeOH-d$^4$) 7.64(s, 1H), 7.49(d, J = 8.43 Hz, 1H), 7.42(d, J = 8.79 Hz, 1H), 3.46(bs, 4H), 3.10(bs, 3H), 2.83(s, 3H), 2.26-2.22(m, 2H), 1.73-1.67(m, 2H), 1.57-1.28(m, 7H); LC-MS 10.36 min, (M + 1)$^+$ 341 @ 10.51 min.

(±) 1-((1-(3,4-dichlorophenyl)cyclohexyl)methylamino)-2,3-dihydro-1H-inden-2-ol (113)

R$^a$ = relative stereochemistry [indanol structure]

HPLC R$_t$ = 9.44 min; $^1$H NMR (400 MHz, CDCl$_3$) 7.49(d, J = 2.2 Hz, 1H), 7.42(d, J = 8.43 Hz, 1H), 7.26-7.13(m, 4H), 6.91(d, J = 6.97 Hz, 1H), 4.35-4.32(m, 1H), 3.90(d, J = 5.13 Hz, 1H), 3.02-2.88(m, 3H), 2.79 (d, J = 11.7 Hz, 1H), 2.19-2.16(m, 1H), 2.07-2.04(m, 1H), 1.74-1.26(m, 9H); LC-MS 10.84 min, (M + 1)$^+$ 390 @ 10.99 min.

(±) 1-((1-(3,4-dichlorophenyl)cyclohexyl)methyl)-3-methylpiperidine (114)

R$^a$ = [3-methylpiperidine structure]

HPLC R$_t$ = 9.46 min; $^1$H NMR (400 MHz, CD$_3$OD) 7.69(dd, J = 1.83, 14.66 Hz, 1H), 7.54(d, J = 8.43 Hz, 1H), 7.49-7.44(m, 1H), 3.51-3.41(m, 1H), 3.26-3.25 (d, J = 1.47 Hz, 1H), 3.06-2.90(m, 3H), 2.73-2.58(m, 1H), 2.43-2.37(m, 1H), 2.25(bs, 2H), 1.96-1.29(m, 11H), 1.08-0.96(m, 1H), 0.78 (m, 3H); LC-MS 11.95 min, (M + 1)$^+$ 340 @ 12.18 min.

(±) 1-((1-(3,4-dichlorophenyl)cyclohexyl)methyl)-2-methylpyrrolidine (115)

R$^a$ = [2-methylpyrrolidine structure]

HPLC R$_t$ = 9.25 min; $^1$H NMR (400 MHz, CD$_3$OD) 7.64(s, 1H), 7.55(dd, J = 3.67, 8.43 Hz, 1H), 7.42(d, J = 7.33 Hz, 1H), 3.52(d, J = 13.6 Hz, 1H), 3.25(s, 2H), 3.00-2.98(m, 1H), 2.69-2.65(m, 1H), 2.37-2.34(m, 1H), 2.11(bs, 2H), 1.91-1.23(m, 14H); LC-MS 10.1 min, (M + 1)$^+$ 326 @ 10.1 min.

(±) 2-((1-(3,4-dichlorophenyl)cyclohexyl)methylamino)cyclopentanol (116)

R$^a$ = relative stereochemistry [cyclopentanol structure]

HPLC R$_t$ = 8.86 min; $^1$H NMR (400 MHz, CD$_3$OD) 7.58(d, J = 2.57 Hz, 1H), 7.53(d, J = 8.43 Hz, 1H), 7.39-7.36(m, 1H), 4.03-3.98(m, 1H), 3.40 (d, J = 13.2 Hz, 1H), 3.17-3.10(m, 2H), 2.17-2.04(m, 3H), 1.95-1.89(m, 1H), 1.71-1.32(m, 12H); LC-MS 9.31 min, (M + 1)$^+$ 342 @ 9.42 min.

(±) 2-((1-(3,4-dichlorophenyl)cyclohexyl)methylamino)cyclohexanol (117)

R$^a$ = relative stereochemistry [cyclohexanol structure]

HPLC R$_t$ = 9.1 min; $^1$H NMR (400 MHz, CD$_3$OD) 7.60(d, J = 2.20 Hz, 1H), 7.60-7.52(m, 1H), 7.41-7.37(m, 1H), 3.48-3.43(m, 1H), 3.15-3.11(m, 1H), 2.75-2.69 (m, 1H), 2.21-2.11(m, 2H), 1.98-1.15(m, 16H); LC-MS 9.50 min, (M + 1)$^+$ 356 @ 9.6 min.

Example 2

Synthesis of 2-Substituted Cycloalkylamines 2.1. Synthesis of 2-Hydroxy-Substituted Cycloalkylamines The below described compound of the invention were synthesized from the corresponding bromomethyl analogs according to General Procedures O and P (outlined below).

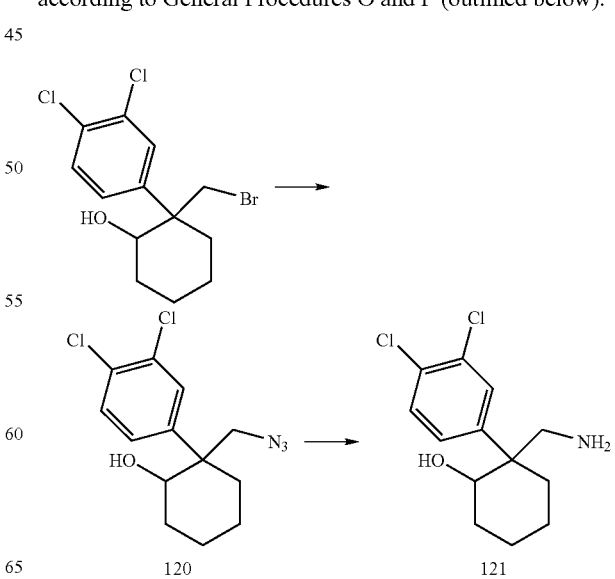

120                                 121 cis-2-(aminomethyl)-2-(3,4-dichlorophenyl)cyclohexanol (cis 121)

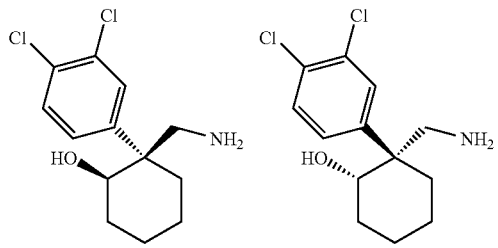 [SMILES: NC[C@@]1(c2ccc(Cl)c(Cl)c2)CCCC[C@H]1O ; NC[C@]1(c2ccc(Cl)c(Cl)c2)CCCC[C@@H]1O]

cis 121 E1
cis 121 E2

(a) Preparation of racemic (cis)-2-(azidomethyl)-2-(3,4-dichlorophenyl)-cyclohexanol General Procedure O: A mixture of (cis)-2-(bromomethyl)-2-(3,4-dichlorophenyl)cyclohexanol (148 mg, 0.438 mmol) and sodium azide (85 mg, 1.314 mmol), in DMF (2 ml) was stirred at 70° C. for 48 hours. The reaction mixture was filtered and evaporated in vacuo. The residue was partitioned between water (5 ml) and EtOAc (10 ml). The organic layer was separated, washed with water (2×5 ml), dried over $Na_2SO_4$, and evaporated to give (cis)-2-(azidomethyl)-2-(3,4-dichlorophenyl)cyclohexanol (110 mg, 84%) as a clear oil.

The enantiomers of (cis)-2-(azidomethyl)-2-(3,4-dichlorophenyl)cyclohexanol were separated using preparative HPLC (ChiralPak OJ column; hexanes:IPA=90:10; 8 ml/min; λ=280 nm) to give cis 120 E1 (retention time=10.5 min) and cis 120 E2 (retention time=13.7 min). The absolute configurations of the chiral centers were not determined. $^1$H NMR ($CDCl_3$) δ 0.96-1.03 (m, 1H), 1.43-1.54 (m, 3H), 1.67-1.75 (m, 4H), 2.00 (brs, 1H), 2.08-2.14 (m, 1H), 3.43 (d, J=12.0 Hz, 1H), 3.65 (d, J=12.0 Hz, 1H), 4.04 (t, J=6.0 Hz, 1H), 7.42 (d, J=8.4 Hz, 1H), 7.47 (dd, J=8.4, 2.4 Hz, 1H), 7.75 (s, 1H). $^{13}$C NMR ($CDCl_3$) δ 21.4, 22.8, 30.2, 30.4, 47.4, 59.8, 74.0, 127.9, 130.6, 130.8, 131.2, 132.9, 142.7.

(b) Synthesis of cis-2-(aminomethyl)-2-(3,4-dichlorophenyl)cyclohexanols

General Procedure P: To a solution of cis 120 E1 (37 mg, 0.124 mmol) in EtOAc (2 ml) was added Pd/C (10%, 20 mg). A hydrogen balloon was attached and the reaction mixture was stirred at room temperature for 30 min. The mixture was filtered and evaporated. The residue was purified by silica gel column chromatography (MeOH/$CH_2Cl_2$, MeOH from 0% to 15%) to give the primary amine cis 121 E1 (24 mg, 69%) as clear oil.

Cis 121 E2 was syntheized from cis 120 E2 (31 mg, 0.124 mmol) according to General Procedure P to give the primary amine (21 mg, 72%) as a clear oil.

$^1$H NMR ($CDCl_3$) δ 0.96-1.03 (m, 1H), 1.23-1.44 (m, 3H), 1.65-1.69 (m, 1H), 1.78-1.83 (m, 2H), 1.98-2.02 (m, 1H), 2.91 (d, J=13.6 Hz, 1H), 3.07 (d, J=13.6 Hz, 1H), 4.03 (dd, J=10.0 Hz, 3.2 Hz, 1H), 7.40 (d, J=8.4 Hz, 1H), 7.71 (dd, J=12.0, 2.4 Hz, 1H), 7.96 (s, 1H). $^{13}$C NMR ($CD_3Cl$): δ 21.4, 24.6, 30.2, 35.2, 46.9, 56.3, 81.1, 129.3, 130.3, 130.4, 131.7, 132.6, 142.7.ESI MS m/z 274.

trans-2-(aminomethyl)-2-(3,4-dichlorophenyl)cyclohexanol (trans 121)

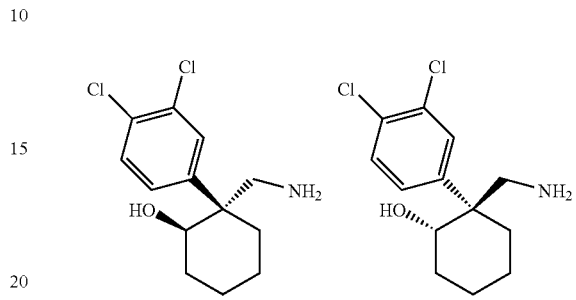

trans 121 E1
trans 121 E2

(a) Preparation of racemic (trans)-2-(Azidomethyl)-2-(3,4-dichlorophenyl)cyclohexanol The title compound was prepared from trans-2-(bromomethyl)-2-(3,4-dichlorophenyl)cyclohexanol (103 mg, 0.305 mmol) and sodium azide (59 mg, 1.314 mmol) according to General Procedure O to give the azide (70 mg, 76%) as a clear oil. The enantiomers were separated as described to give trans 120 E1 (retention time=11.7 min) and trans 120 E2 (retention time=14.2 min). $^1$H NMR ($CDCl_3$) δ 1.38-1.46 (m, 2H), 1.51-1.56 (m, 1H), 1.62-1.66 (m, 2H), 1.71-1.76 (m, 1H), 1.80-1.93 (m, 3H), 3.43 (d, J=12.4 Hz, 1H), 3.81 (d, J=12.4 Hz, 1H), 4.24 (t, J=4.0 Hz, 1H), 7.25-7.28 (m, 1H), 7.44 (d, J=8.4 Hz, 1H), 7.51 (d, J=1.6 Hz, 1H). $^{13}$C NMR ($CDCl_3$) δ 21.3, 21.6, 29.7, 29.8, 46.8, 57.6, 71.3, 126.7, 129.4, 130.4, 130.6, 132.9, 146.5.

(b) Synthesis of trans-2-(aminomethyl)-2-(3,4-dichlorophenyl)cyclohexanol

Trans 121 E1 and trans 121 E2 were prepared from trans 120 E1 and trans 120 E2, respectively, according to General Procedure P. The crude products were purified by chromatography ($SiO_2$, MeOH/$CH_2Cl_2$, MeOH from 0% to 15%) to give the primary amines (about 15 mg each, 65%) as clear oils.

$^1$H NMR ($CDCl_3$) δ 1.28-1.50 (m, 4H), 1.64-1.86 (m, 3H), 1.98-2.02 (m, 1H), 3.02 (d, J=12.4 Hz, 1H), 3.38 (d, J=12.4 Hz, 1H), 4.20 (dd, J=10.0 Hz, 3.2 Hz, 1H), 7.40-7.47 (m, 2H), 7.69 (d, J=1.6 Hz, 1H). $^{13}$C NMR ($CDCl_3$) δ 21.5, 22.3, 29.9, 30.4, 44.8, 57.1, 71.5, 126.9, 129.6, 131.1, 131.4, 133.3, 142.9.ESI MS m/z 274.

2.2.Synthesis of 2-Methoxy-Cycloalkylamines

The following compounds were synthesized according to the Scheme, below.

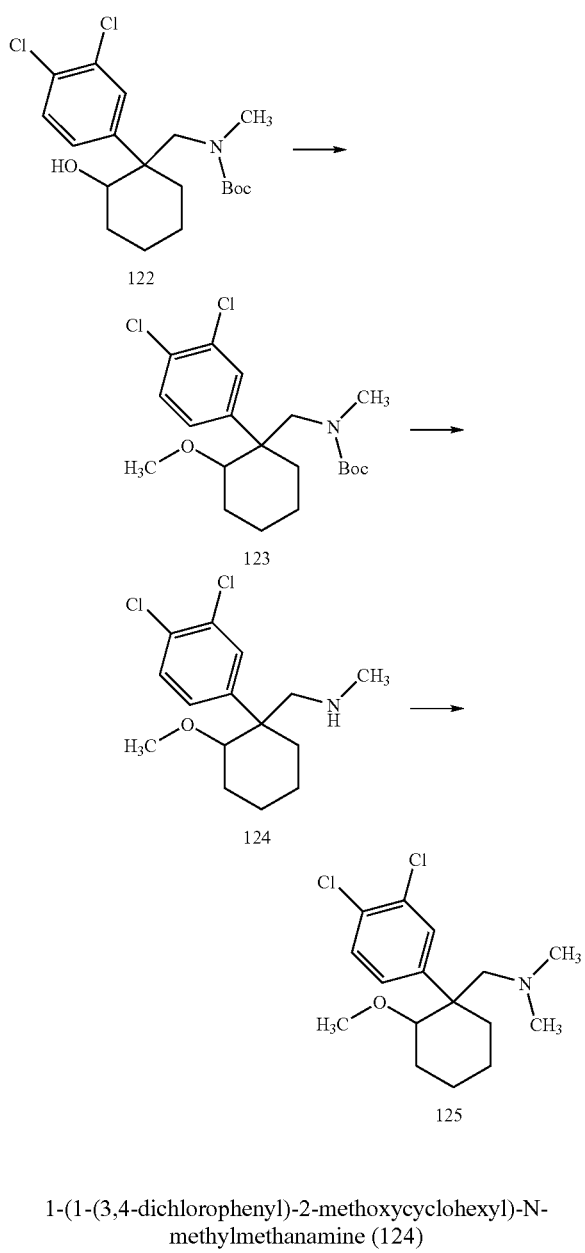

1-(1-(3,4-dichlorophenyl)-2-methoxycyclohexyl)-N-methylmethanamine (124)

A. Synthesis of cis-1-(1-(3,4-dichlorophenyl)-2-methoxycyclohexyl)-N-methylmethanamine (cis 124)

A solution of (±) cis 122 [Boc-protected (±) cis-2-(3,4-dichlorophenyl)-2-((methylamino)methyl)cyclohexanol] (0.88 g, 2.27 mmol) and NaH (100 mg, 2.50 mmol) in THF (30 ml) was stirred at room temperature for 30 min. To the mixture was added CH$_3$I (1.41 ml, 22.7 mmol) and the reaction mixture was stirred at room temperature for 24 hours. It was diluted with water (20 ml) and extracted with CH$_2$Cl$_2$ (3×30 ml). The organic layer was washed with water (2×30 ml) and brine (30 ml), dried over Na$_2$SO$_4$, and evaporated in vacuo. The residue was purified by silica gel column chromatography (MeOH/CH$_2$Cl$_2$, MeOH from 0% to 5%) to give (±) cis 123.

To a solution of (±) cis 123 in CH$_2$Cl$_2$ (5 ml) was added dropwise TFA (5 ml) at 0° C. The mixture was stirred at 0° C. for 2 hours and the solvent was removed in vacuo. The residue was dissolved in CH$_2$Cl$_2$ (10 ml), washed with saturated K$_2$CO$_3$ solution (5 ml), dried over Na$_2$SO$_4$, and evaporated in vacuo. The residue was purified by silica gel column chromatography (MeOH/CH$_2$Cl$_2$, MeOH from 0% to 15%) to give (±) cis 124 (0.225 g, 33%) as clear oil. $^1$H NMR (CDCl$_3$) δ 1.38-1.43 (m, 1H), 1.47-1.54 (m, 2H), 1.62-1.66 (m, 1H), 1.74-1.87 (m, 3H), 2.01-2.04 (m, 1H), 2.29 (s, 3H), 2.71 (d, J=14 Hz, 1H), 2.76 (d, J=14 Hz, 1H), 3.25 (s, 3H), 3.52 (dd, J=8.8, 3.2 HZ, 1H), 7.29-7.38 (m, 2H), 7.59 (s, 1H). $^{13}$C NMR (CDCl$_3$) δ 21.9, 23.7, 25.0, 31.6, 48.7, 49.1, 56.7, 68.1, 83.3, 128.4, 129.5, 129.7, 131.1, 131.8, 145.8. ESI MS m/z 302.

B. Synthesis of trans-1-(1-(3,4-dichlorophenyl)-2-methoxycyclohexyl)-N-methylmethanamine (trans 124)

The title compound was prepared from (±) trans 122 (0.91 g, 2.34 mmol) according to the procedure described above for the corresponding cis-isomer to give (±) trans 124 (0.219 g, 30%) as clear oil.

The enantiomers of (±) trans 124 were separated using preparative HPLC (ChiralPak OD column; hexanes:IPA:DEA=95:5:0.1; 8 ml/min; λ=280 nm) to give trans 124 E1 (retention time=10 min) and trans 124 E2 (retention time=18 min). The absolute configurations of the chiral centers were not determined. $^1$H NMR (CDCl$_3$) δ 1.24-1.42 (m, 2H), 1.60-1.77 (m, 2H), 1.85-1.92 (m, 2H), 2.33 (s, 3H), 2.70 (d, J=13.6 Hz, 1H), 2.93 (d, J=13.6 Hz, 1H), 3.33 (s, 3H), 3.64 (dd, J=7.6, 2.4 Hz, 1H), 7.25 (d, J=8.4 Hz, 1H), 7.39 (d, J=8.4 Hz, 1H), 7.47 (s, 1H). $^{13}$C NMR (CDCl$_3$) δ 21.6, 21.8, 24.9, 30.6, 37.4, 46.8, 57.2, 58.5, 81.5, 127.2, 129.7, 130.2, 130.4, 132.7, 145.1. ESI MS m/z 302.

1-(1-(3,4-dichlorophenyl)-2-methoxycyclohexyl)-N,N-dimethylmethanamine (125)

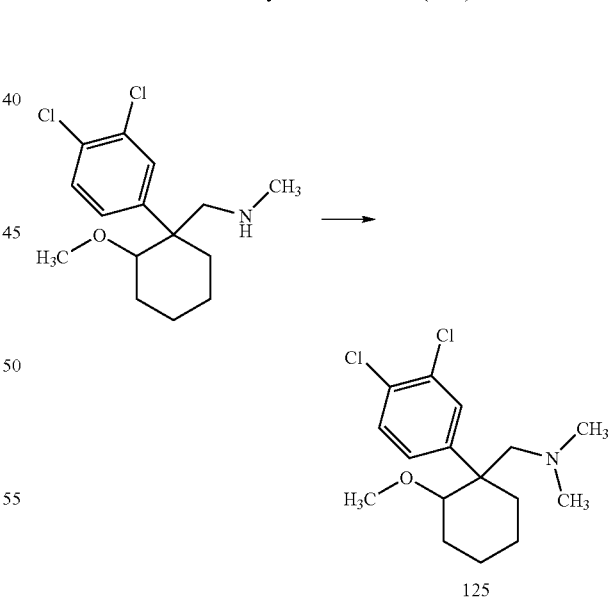

The following compounds were prepared from the respective monomethyl amine according to General Procedure F. The crude products were purified by silica gel column chromatography (dichloromethane/methanol, 0-5% MeOH) to give the desired dimethyl amine.

(±) cis 125 was prepared from (±) cis 124 (54 mg, 83%, clear oil). $^1$H NMR (CDCl$_3$) δ 1.35-1.42 (m, 2H), 1.47-1.54

(m, 2H), 1.62-1.66 (m, 1H), 1.74-1.87 (m, 2H), 2.01-2.04 (m, 1H), 2.12 (s, 6H), 2.31 (d, J=14 Hz, 1H), 2.65 (d, J=14 Hz, 1H), 3.31 (s, 3H), 3.52 (dd, J=8.8, 3.2 HZ, 1H), 7.32 (d, J=8.8 Hz, 1H), 7.42 (dd, J=8.8, 2.4 Hz, 1H), 7.70 (s, 1H), $^{13}$C NMR (CDCl$_3$) δ 21.9, 23.7, 25.0, 31.6, 48.7, 49.1, 56.7, 68.1, 83.3, 128.4, 129.5, 129.7, 131.1, 131.8, 145.8.ESI MS m/z 316.

Trans 125 E1 and trans 125 E2 were prepared from trans 124 E1 and trans 124 E2,respectively. 1H NMR (CDCl3) δ 1.24-1.39 (m, 3H), 1.42-1.60 (m, 2H), 1.77-1.88 (m, 2H), 1.91 (s, 6H), 2.25 (d, J=13.6 Hz, 1H), 2.71 (d, J=13.6 Hz, 1H), 3.36 (s, 3H), 3.76 (s, 1H), 7.25 (d, J=8.4 Hz, 1H), 7.36 (d, J=8.4 Hz, 1H), 7.49 (s, 1H). 13C NMR (CDCl3) δ 20.9, 21.5, 23.7, 28.8, 48.3, 56.5, 67.6, 79.4, 127.6, 129.8, 130.2, 130.4, 132.2, 145.6.ESI MS m/z 316.

2.3.Synthesis of 2-Aminomethyl-2-aryl-cyclohexanol Analogs via Carboxylic Acids

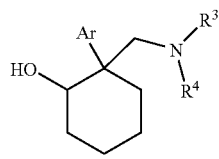

2.3.1.Preparation of Arylhydroxyacids (130a-130i)

The preparation of Arylhydroxyacids is outlined in Scheme 27,below. Commercial arylboronic acids 126 were converted to the aryllead intermediates 127 using lead acetate and mercuric acetate. Compounds 127 were used in situ to α-arylate 2-ethylcyclohexanonecarboxylate to provide ketoesters 128 as racemic mixtures in 32-71% overall yield. Reduction of racemic ketones 128 with sodium borohydride produced four isomeric hydroxyester products, 129 (±) cis and 129 (±) trans in 29% to quantitative yields. The pair of cis isomers were separated from the pair of trans isomers to give the enantiomeric mixtures 129 (±) cis and 129 (±) trans using a Biotage chromatography system (Sorbent Technologies, 800 g, 40-75 μm SiO$_2$, heptane/ether). Each of 129 (±) cis and 129 (±) trans were saponified with sodium hydroxide in methanol/water to provide the hydroxyacids 130 (±) cis and 130 (±) trans, respectively, in 55% to quantitative yield after extraction.

Scheme 27: Preparation of Arylhydroxyacids (130)

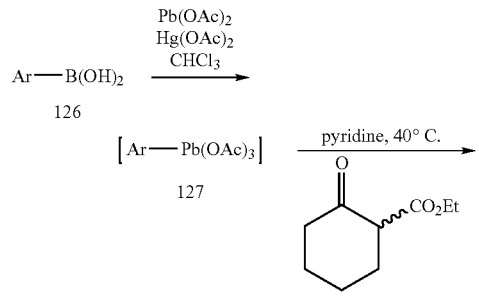

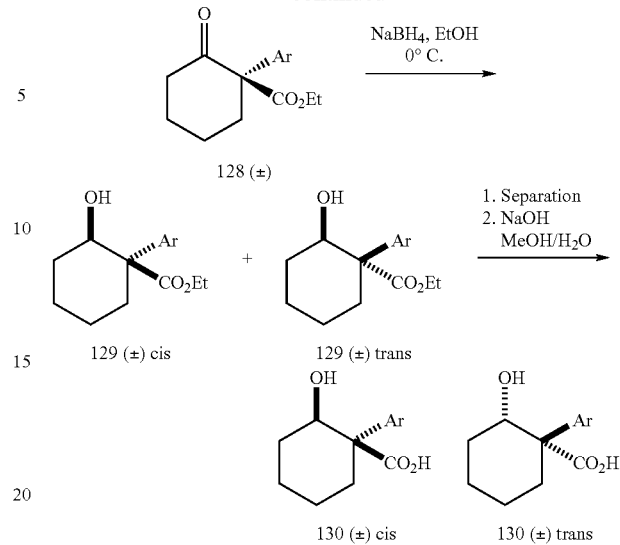

2.3.2.General Procedure N: Synthesis of Aryl-Plumbanetriyl Triacetate

A mixture of chloroform (e.g., 200 mL), lead (IV) acetate (e.g., 58.1 g, 131 mmol, 1 eq), and mercuric acetate (2.09 g, 6.55 mmol, 0.05 eq) was warmed to 40° C. The respective arylboronic acid (e.g., 131 mmol) was added in portions over 15 minutes. The mixture was stirred at 40° C. for one hour, then cooled to room temperature and stirred overnight. This crude mixture was used immediately in the next reaction step.

The following compounds were prepared from the corresponding boronic acids 126 following the procedure outlined in General Procedure N, above:
(127a) (3,4-Dichlorophenyl)plumbanetriyl triacetate
(127b) (3,4-Methylenedioxy)plumbanetriyl triacetate
(127c) (4-Chlorophenyl)plumbanetriyl triacetate
(127d) (3-Chlorophenyl)plumbanetriyl triacetate
(127e) (4-Methoxyphenyl)plumbanetriyl triacetate
(127f) (4-Chloro-3-fluorophenyl)plumbanetriyl triacetate
(127g) (4-Trifluoromethylphenyl)plumbanetriyl triacetate
(127h) (4-Trifluoromethoxyphenyl)plumbanetriyl triacetate
(127i) Naphthalen-2-ylplumbanetriyl triacetate

2.3.3 General Procedure Q: Synthesis of Esters (128a-128i)

To the crude reaction mixture of the respective lead intermediate arylplumbanetriyl triacetate 2 was slowly added pyridine (e.g., 31.8 mL, 393 mmol) and ethyl-2-oxocyclohexanecarboxylate (e.g., 22.3 g, 131 mmol). The reaction mixture was heated to 40° C. and stired for 72 hours and was then diluted with chloroform (e.g., 200 mL) and poured into water (e.g., 300 mL). The phases were separated and the organic layer was washed with 2 N H$_2$SO$_4$ (2×200 mL), dried over MgSO$_4$, filtered, and concentrated. The residue was purified by silica gel flash chromatography using the indicated solvent systems to give the alph-keto esters 3.

The following compounds were prepared from the corresponding intermediate 127 following the procedure outlined in General Procedure Q, above:
(128a) (±) Ethyl-1-(3,4-Dichlorophenyl)-2-oxocyclohexanecarboxylate (hexane/ethyl acetate, 100:0 to 90:10, 46%, white solid)

(128b) (±) Ethyl-1-(3,4-methylenedioxy)-2-oxocyclohexane-carboxylate (hexane/ethyl acetate, 9:1, 45%, white solid)

(128c) (±) Ethyl-1-(4-Chlorophenyl)-2-oxocyclohexanecarboxylate (hexane/diethyl ether, 96.6 g, 68%, light yellow oil)

(128d) (±) Ethyl-1-(3-chlorophenyl)-2-oxocyclohexane-carboxylate (hexane/diethyl ether, 130 g, 71%, white solid)

(128e) (±) Ethyl-1-(4-methoxyphenyl)-2-oxocyclohexane-carboxylate (hexane/ethyl acetate, 100:0 to 90:10, 87.0 g, 63%, yellow semi-solid)

(128f) (±) Ethyl-144-Chloro-3 -fluorophenyl)-2-oxocyclohexane-carboxylate (hexane/ethyl acetate, 100:0 to 95:5, 67.4 g, 52%, white solid).

(128g) (±) Ethyl-1-(4-Trifluoromethylphenyl)-2-oxocyclohexanecarboxylate (hexane/ethyl acetate, 100:0 to 90:10, 43.0 g, 34%, white solid).

(128h) Ethyl-1-(4-trifluoromethoxy)-2-oxocyclohexanecarboxylate (hexane/diethyl ether, 49.5 g, 61%, colorless oil)

(128i) (±) Ethyl-1-(naphthalen-2-yl)-2-oxocyclohexanecarboxylate (hexane/ethyl acetate, 100:0 to 90:10, 79.8 g, 60%, yellow semi-solid)

2.3.4.NaBH$_4$ Reduction and Separation of Diastereomers (Synthesis of 129a-129i)

General Procedure R: To a solution of the respective ketoester 3 (e.g., 17.8 g, 56.5 mmol) in ethanol (e.g., 280 mL) at 0° C. was added sodium borohydride (e.g., 2.56 g, 67.8 mmol) portionwise. The mixture was stirred for 3 hours and was then concentrated. The residue was dissolved in diethyl ether (e.g., 200 mL) and 2 N HCl (e.g., 125 mL) was then slowly added. The phases were separated and the aqueous layer was extracted with diethyl ether (e.g., 3×100 mL). The organic layers were combined and washed with brine (e.g., 125 mL), dried over MgSO$_4$, filtered, and concentrated. The crude product was purified by silica gel flash chromatography using hexane/ethyl acetate or hexane/ethyl ether gradients to give a mixture of cis/trans diastereomers (13-100 g, 59-96% yield).

Separation of the diastereomers was accomplished using a Biotage chromatography system (Sorbent Technologies, 800 g, 40-75 μm SiO$_2$, heptane/ether, 80:20 isocratic), unless otherwise indicated. Up to 20 g of crude product were separated per injection to obtain the final products with 63-85% overall recovery. Generally, the mixture of trans-enantiomers, (±) trans 129, eluted from the column first, followed by the mixture of cis-enantiomers, (±) cis 129.

The following compounds (cis- and trans-diastereomers each) were prepared from the corresponding intermediate 128 following the procedure outlined in General Procedure R, above.

(cis 129a) (±) cis ethyl-1-(3,4-dichlorophenyl)-2-hydroxycyclohexane-carboxylate (trans 129a) (±) trans ethyl-1-(3,4-dichlorophenyl)-2-hydroxycyclohexane-carboxylate (cis 129b) (±) cis ethyl-1-(3,4-methylenedioxy)-2-hydroxycyclohexanecarboxylate (trans 129b) (±) trans ethyl-1-(3,4-methylenedioxy)-2-hydroxycyclohexanecarboxylate (cis 129c) (±) cis ethyl-1-(4-chlorophenyl)-2-hydroxycyclohexane-carboxylate (trans 129c) (±) trans ethyl-1-(4-chlorophenyl)-2-hydroxycyclohexanecarboxylate (cis 129d) (±) cis ethyl-1-(3-chlorophenyl)-2-hydroxycyclohexane-carboxylate (trans 4d) (±) trans ethyl-1-(3-chlorophenyl)-2-hydroxycyclohexane-carboxylate Separation of the diastereomers was accomplished on a Symmetry C18 Column (50×250, 7μ; MeCN/water 55:45)

(cis 129e) (±) cis ethyl-2-hydroxy-1-(4-methoxyphenyl)cyclohexane-carboxylate (trans 129e) (±) trans ethyl-2-hydroxy-1-(4-methoxyphenyl) cyclohexane-carboxylate The mixture of cis/trans isomers was separated by reverse-phase chromatography.

(cis 129f) (±) cis ethyl-1-(4-Chloro-3-fluorophenyl)-2-hydroxycyclohexane-carboxylate (trans 129f) (±) trans ethyl-1-(4-Chloro-3-fluorophenyl)-2-hydroxycyclohexane-carboxylate (cis 129g) (±) cis ethyl-1-(4-trifluoromethylphenyl)-2-hydroxycyclohexanecarboxylate (trans 129g) (±) trans ethyl-1-(4-trifluoromethylphenyl)-2-hydroxycyclohexanecarboxylate (cis 129h) (±) cis ethyl-1-(4-trifluoromethoxyphenyl)-2-hydroxycyclohexanecarboxylate (trans 129h) (±) trans ethyl-1-(4-trifluoromethoxyphenyl)-2-hydroxycyclohexanecarboxylate (cis 129i) (±) cis ethyl-2-hydroxy-1-(naphthalen-2-yl)cyclohexane-carboxylate (trans 129i) (±) trans ethyl-2-hydroxy-1-(naphthalen-2-yl)cyclohexane-carboxylate 2.3.5.Saponification (Synthesis of 130a-130i)

General Procedure S: To a solution of the respective (±) cis- or trans-hydroxy ester 129 (e.g., 3.90 g, 12.3 mmol) in water (e.g., 12.0 mL) and methanol (e.g., 22.0 mL) at 0° C. was slowly added sodium hydroxide (e.g., 1.18 g, 29.5 mmol). The mixture was stirred overnight and was then carefully acidified with 2 N HCl and extracted with ethyl acetate (3×50 mL). The organic layers were combined, washed with brine (e.g., 40 mL), dried over MgSO$_4$, and filtered. The solvent was removed in vacuo to give the respective carboxylic acid, either (±) trans 130 or (±) cis 130.Yields for this conversion were found to be between 55% and quantitative.

The following compounds were prepared from the corresponding intermediate 129 following the procedure outlined in General Procedure S, above.

(cis 130a) (±) cis-1-(3,4-Dichlorophenyl)-2-hydroxycyclohexane-carboxylic acid (trans 130a) (±) trans-1-(3,4-Dichlorophenyl)-2-hydroxycyclohexanecarboxylic acid (cis 130b) (±) cis-1-(3,4-Methylenedioxy)-2-hydroxycyclohexane-carboxylic acid (trans 130b) (±) trans-1-(3,4-Methylenedioxy)-2-hydroxycyclohexane-carboxylic acid (cis 130c) (±) cis-1-(4-Chlorophenyl)-2-hydroxycyclohexane-carboxylic acid (trans 130c) (±) trans-1-(4-Chlorophenyl)-2-hydroxycyclohexanecarboxylic acid (cis 130d) (±) cis-1-(3-Chlorophenyl)-2-hydroxycyclohexane-carboxylic acid (trans 130d) (±) trans-1-(3-Chlorophenyl)-2-hydroxycyclohexane-carboxylic acid (cis 130e) (±) cis-2-hydroxy-1-(4-methoxyphenyl)cyclohexane-carboxylic acid (trans 130e) (±) trans-2-Hydroxy-1-(4-methoxyphenyl)cyclohexane-carboxylic acid (cis 130f) (±) cis-1-(4-Chloro-3 -fluorophenyl)-2-hydroxycyclohexanecarboxylic acid (trans 130f) (±) trans-1-(4-chloro-3 -fluorophenyl)-2-hydroxycyclohexanecarboxylic acid (cis 130g) (±) cis-1-(4-Trifluoromethylphenyl)-2-hydroxycyclohexanecarboxylic acid (trans 130g) (±)trans-1-(4-Trifluoromethylphenyl)-2-hydroxycyclohexane-carboxylic Acid
(cis 130h) (±) cis-1-(4-Trifluoromethoxyphenyl)-2-hydroxycyclohexanecarboxylic acid
(trans 130h) (±)trans-1-(4-Trifluoromethoxyphenyl)-2-hydroxycyclohexane-carboxylic acid
(cis 130i) (±) cis-2-Hydroxy-1-(naphthalen-2-yl)cyclohexanecarboxylic acid
(trans 130i) (±) trans-2-Hydroxy-1-(naphthalen-2-yl)cyclohexanecarboxylic acid Preparation of 2-Phenylaminoalcohols (132a-132i)

PyBOP-mediated coupling of hydroxyacids (±) cis 130 and (±) trans 130 with methylamine (e.g., General Procedure G) gave hydroxyamides (±) cis 131 and (±) trans 131, respectively, in 39% to quantitative yield. Reduction of (±) cis 131 and (±) trans 131 with borane·dimethylsulfide complex gave aminoalcohols (±) cis 132 and (±) trans 132, respectively, in 39-95% yield. The enantiomers of (±) cis 132 and (±) trans 132 were separated using preparative chiral HPLC to give the fast moving enantiomer E1 and the slow moving enantiomer E2 (Scheme 28). The absolute configuration of the chiral centers was not determined.

Scheme 28: Preparation of Chiral 2-Hydroxy-Cycloalkylamines

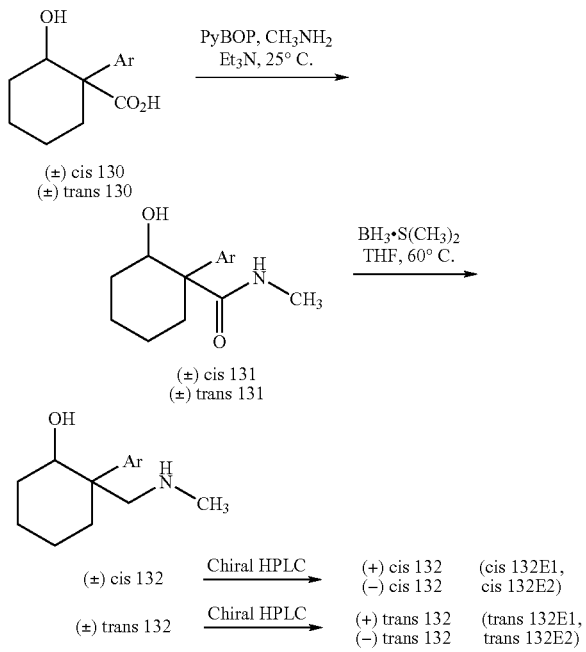

2.3.6. General Procedure G2 (Amide Bond Formation)

A mixture of the respective carboxylic acid 130 (e.g., 3.56 g, 12.3 mmol), PyBOP (e.g., 7.04 g, 13.5 mmol), methylamine (e.g., 2 M in THF, 37.0 mL, 74.0 mmol), and triethylamine (e.g., 1.24 g, 12.3 mmol) was stirred at room temperature overnight. The mixture was acidified with 2 N HCl and was then extracted with ethyl acetate (e.g., 3×60 mL). The organic layers were combined, optionally washed with NaHCO₃ solution, washed with brine (e.g., 50 mL), dried over MgSO₄, filtered, and concentrated. The residue was purified by silica gel flash chromatography using hexane/ethyl acetate or $CH_2Cl_2$/MeOH gradients and/or optionally triturated with e.g., diethyl ether to give the respective N-methyl amine 131.

2.3.7. General Procedure G3 (Amide Bond Formation)

A mixture of respective carboxylic acid 130 (e.g., 9.50 g, 37.3 mmol), PyBOP (e.g., 19.4 g, 37.3 mmol), methylamine (e.g., 2 M in THF, 20.5 mL, 41.0 mmol), N-methylmorpholine (e.g., 4.50 mL, 41.0 mmol) and DMAP (e.g., 5.00 g, 41.0 mmol) was stirred in DMF (e.g., 373 mL) at room temperature overnight. The mixture was diluted with EtOAc (e.g., 3 L). The layers were separated and the organic layer was washed with 0.5 M HCl (e.g., 3×1 L), saturated aqueous NaHCO₃ (3×600 mL), saturated aqueous LiCl (600 mL), brine (600 mL), dried, filtered and concentrated. The residue was purified by silica gel chromatography using hexane/ethyl acetate or $CH_2Cl_2$/MeOH gradients to give the respective N-methyl amine 131.

The following compounds were prepared from the corresponding intermediate 130 using the procedures outlined in General Procedure G2 or General Procedure G3, above, or slightly modified versions thereof (cis 131a) (±) cis-1-(3,4-Dichlorophenyl)-2-hydroxy-N-methylcyclohexane-carboxamide
(trans 131a) (±) trans-1-(3,4-Dichlorophenyl)-2-hydroxy-N-methylcyclohexanecarboxamide
(cis 131b) (±) cis-1-(3,4-Methylenedioxy)-2-hydroxy-N-methylcyclohexanecarboxamide
(trans 131b) (±) trans-1-(3,4-Methylenedioxy)-2-hydroxy-N-methylcyclohexanecarboxamide
(cis 131c) (±) cis- 1-(4-Chlorophenyl)-2-hydroxy-N-methylcyclohexanecarboxamide
(trans 131c) (±) trans-1-(4-Chlorophenyl)-2-hydroxy-N-methylcyclohexanecarboxamide
(cis 131d) (±) cis-1-(3-Chlorophenyl)-2-hydroxy-N-methylcyclohexanecarboxamide
(trans 131d) (±) trans-1-(3-Chlorophenyl)-2-hydroxy-N-methylcyclohexanecarboxamide
(cis 131e) (±) cis 2-Hydroxy-1-(4-methoxyphenyl)-N-methylcyclohexanecarboxamide
(trans 131e) (±) trans 2-Hydroxy-1-(4-methoxyphenyl)-N-methylcyclohexanecarboxamide
(cis 131f) (±) cis-1-(4-Chloro-3-fluorophenyl)-2-hydroxy-N-methylcyclohexane carboxamide
(trans 131f) (±) trans-1-(4-Chloro-3-fluorophenyl)-2-hydroxy-N-methylcyclohexane Carboxamide
(cis 131g) (±) cis- 1-(4-Trifluoromethylphenyl)-2-hydroxy-N-methylcyclohexane Carboxamide
(trans 131g) (±) trans-1-(4-Trifluoromethylphenyl)-2-hydroxy-N-methylcyclohexane Carboxamide
(cis 131h) (±) cis-1-(4-Trifluoromethoxyphenyl)-2-hydroxy-N-methylcyclohexane Carboxamide
(trans 131h) (±) trans-1-(4-Trifluoromethoxyphenyl)-2-hydroxy-N-methylcyclohexane Carboxamide

2.3.8. General Procedure T (Reduction of Amide 131 to Amine 132)

To a solution of the respective N-methylcarboxamide 131 (e.g., 2.70 g, 8.93 mmol) in tetrahydrofuran (90.0 mL) was slowly added borane·dimethylsulfide (2 M in THF, 13.4 mL, 26.8 mmol). The mixture was stirred 48 hours at reflux. After cooling, the mixture was acidified by careful addition of 2 N HCl. The mixture was concentrated in vacuo and the residue was washed with diethyl ether (e.g., 60 mL). The phases were separated and the aqueous layer was made basic through addition of 2 N NaOH and was then extracted with ethyl acetate (e.g., 3×150 mL). The ethyl acetate layers were combined, washed with brine (100 mL), dried over MgSO$_4$, filtered, and concentrated. The residue was purified by silica gel flash chromatography using e.g., dichloromethane/methanol gradients to give the respective amines (±) cis 132 and (±) trans 132.

The enantiomers for each of the amines (±) cis 132 and (±) trans 132 were separated using preparative chiral HPLC. Typical conditions are listed below:
1. ChiralPak AD; heptane:EtOH:DEA=95:5:0.1; μ=25 ml/min; λ=275 nm.
2. Regis O1; hexanes:IPA:DEA=90:10:0.1; μ=25 ml/min; and λ=280 nm. Absolute configurations of the chiral centers were not determined. Compounds are identified by E1 for the fast moving enantiomer and E2 for the slow moving enantiomer.

The following compounds were prepared from the corresponding intermediate 131 using the procedures outlined in General Procedure T or a slightly modified version thereof cis-2-(3,4-Dichlorophenyl)-2-((methylamino)methyl)cyclohexanol (133)

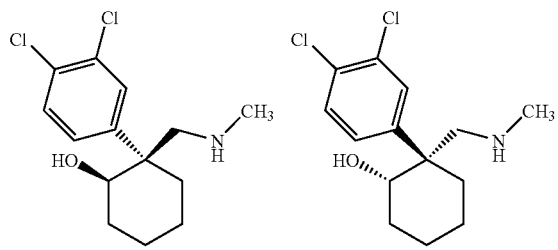

The enantiomeric mixture of (±) cis 132a was separated (ChiralPak AD column; heptane:EtOH:DEA=95:5:0.1; μ32 25 ml/min; λ=275 nm) to give 133 E1 (retention time=15.5 min) and 133 E2 (retention time=20.7 min). $^1$H NMR (CDCl$_3$) δ 0.96-1.03 (m, 1H), 1.23-1.44 (m, 3H), 1.65-1.69 (m, 1H), 1.78-1.84 (m, 2H), 2.01-2.06 (m, 1H), 2.29 (s, 3H), 2.66 (d, J=13.6 Hz, 1H), 2.91 (d, J=13.6 Hz, 1H), 3.97 (dd, J=10.0 Hz, 3.2 Hz, 1H), 7.40 (d, J=8.4 Hz, 1H), 7.71 (dd, J=12.0, 2.4 Hz, 1H), 7.96 (s, 1H). $^{13}$C NMR (CDCl$_3$) δ 2.13, 24.9, 29.9, 35.9, 36.7, 46.2, 66.9, 81.4, 118.0, 129.2, 130.4, 131.6, 132.6, 142.7.ESI MS m/z 289.

trans-2-(3,4-Dichlorophenyl)-2-((dimethylamino)methyl)cyclohexanol (134)

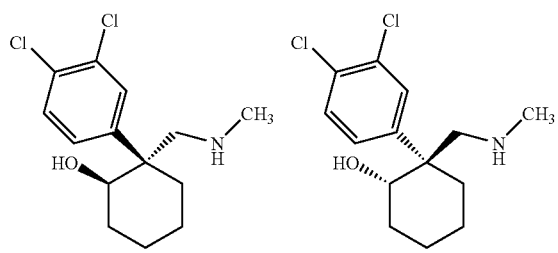

The enantiomeric mixture of (±) trans 132a was separated (ChiralPak AD column; heptane:EtOH:DEA=95:5:0.1; μ=25 ml/min; and λ=275 nm) to give 134 E1 (retention time=13.4 min) and 134 E2 (retention time=18.9 min). $^1$H NMR (CDCl$_3$) δ 1.28-1.50 (m, 4H), 1.64-1.86 (m, 3H), 1.98-2.02 (m, 1H), 2.32 (s, 3H), 2.97 (d, J=12.4 Hz, 1H), 3.30 (d, J=12.4 Hz, 1H), 4.20 (dd, J=10.0 Hz, 3.2 Hz, 1H), 7.40-7.47 (m, 2H), 7.69 (d, J=1.6 Hz, 1H). $^{13}$C NMR (CDCl$_3$) δ 21.9, 24.3, 32.4, 36.7, 37.5, 45.7, 57.1, 74.1, 126.7, 129.4, 130.4, 130.6, 132.9, 146.5.ESI MS m/z 289.

cis-2-(4-chlorophenyl)-2-((methylamino)methyl)cyclohexanol (135)

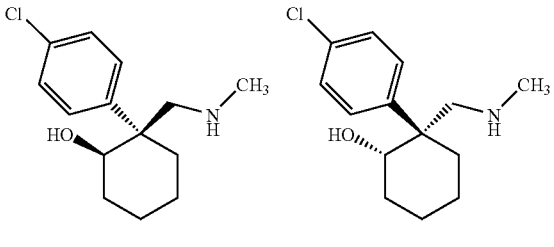 [SMILES: CNC[C@@]1(c2ccc(Cl)cc2)CCCC[C@H]1O ; CNC[C@]1(c2ccc(Cl)cc2)CCCC[C@@H]1O]

The enantiomeric mixture (±) cis 132c can be separated (e.g., Regis O1 column; hexanes:IPA:DEA=90:10:0.1; μ=25 ml/min; and λ=280 nm) to give 135 E1 and 135 E2.

trans-2-(4-chlorophenyl)-2-((methylamino)methyl)-cyclohexanol (136)

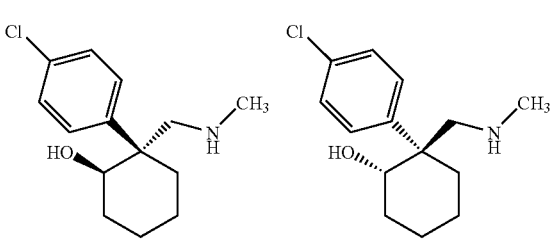 [SMILES: CNC[C@]1(c2ccc(Cl)cc2)CCCC[C@H]1O ; CNC[C@@]1(c2ccc(Cl)cc2)CCCC[C@@H]1O]

The enantiomeric mixture (±) trans 132c was separated (Regis O1 column; hexanes:IPA:DEA=90:10:0.1; μ=25 ml/min; and λ=280 nm) to give 136 E1 (retention time=6.8 min) and 136 E2 (retention time=8.9 min). $^1$H NMR (CDCl$_3$) δ 1.28-1.47 (m, 4H), 1.64-1.87 (m, 3H), 1.96-2.02 (m, 1H), 2.31 (s, 3H), 2.98 (d, J=12.4 Hz, 1H), 3.29 (d, J=12.4 Hz, 1H), 4.24 (dd, J=10.0 Hz, 3.2 Hz, 1H), 7.30 (d, J=10.8 Hz, 2H), 7.58 (d, J=10.8 Hz, 2H). $^{13}$C NMR (CDCl$_3$) δ 21.9, 24.4, 32.4, 36.7, 37.5, 45.7, 57.1, 74.3, 128.6, 128.9, 132.1, 144.6.ESI MS m/z 254.

cis-2-(3-chlorophenyl)-2-((methylamino)methyl) cyclohexanol (137)

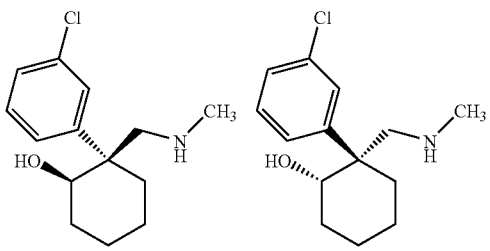

The enantiomeric mixture of (±) cis 132d can be separated (e.g., Regis O1 column; hexanes:IPA:DEA=90:10:0.1; μ=25 ml/min; and λ=280 nm) to give 137 E1 and 137 E2.

trans-2-(3-chlorophenyl)-2-((methylamino)methyl) cyclohexanol (138)

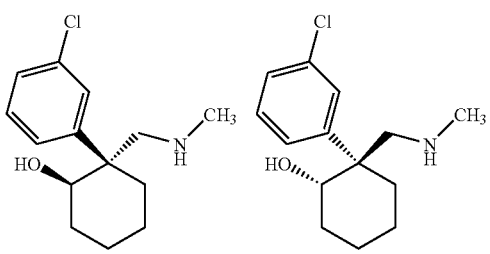

The enantiomeric mixture (±) trans 132d was separated (Regis O1 column; hexanes:IPA:DEA=90:10:0.1; μ=25 ml/min; and λ=280 nm) to give 138 E1 (retention time=5.9 min) and 138 E2 (retention time=7.6 min). $^1$H NMR (CDCl$_3$) δ 1.28-1.47 (m, 4H), 1.64-1.87 (m, 3H), 1.96-2.02 (m, 1H), 2.31 (s, 3H), 2.98 (d, J=12.4 Hz, 1H), 3.29 (d, J=12.4 Hz, 1H), 4.25 (dd, J=10.0 Hz, 3.2 Hz, 1H), 7.18-7.22 (m, 1H), 7.29-7.32 (m, 1H), 7.48-7.52 (m, 1H), 7.60 (s, 1H). $^{13}$C NMR (CDCl$_3$) δ 22.1, 24.4, 32.5, 36.7, 37.5, 45.9, 57.2, 74.1, 125.3, 126.7, 127.4, 134.8, 148.3.ESI MS m/z 254.

cis-2-((methylamino)methyl)-2-(4-methoxyphenyl) cyclohexanol (139)

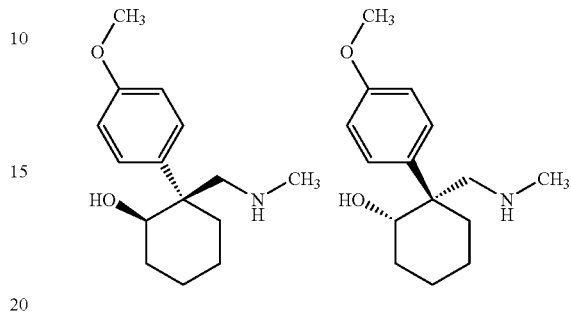

The enantiomeric mixture (±) cis 132e was separated (Regis O1 column; hexanes:IPA:DEA=90:10:0.1; μ=25 ml/min; and λ=275 nm) to give 139 E1 (retention time=5.7 min) and 139 E2 (retention time=7.1 min). $^1$H NMR (CDCl$_3$) δ 1.02-1.10 (m, 1H), 1.21-1.39 (m, 3H), 1.62-1.66 (m, 1H), 1.76-1.94 (m, 2H), 2.04-2.08 (m, 1H), 2.26 (s, 3H), 2.62 (d, J=12.4 Hz, 1H), 2.88 (d, J=12.4 Hz, 1H), 3.77 (s, 3H), 3.96 (dd, J=11.2 Hz, 4.0 Hz, 1H), 6.86 (d, J=8.8 Hz, 2H), 7.73 (d, J=8.8 Hz, 1H). $^{13}$C NMR (CDCl$_3$) δ 21.4, 25.0, 30.0, 35.8, 36.7, 46.2, 55.3, 67.1, 81.9, 113.8, 130.4, 133.7, 157.8.ESI MS m/z 250.

(±) trans-2-(4-Methoxyphenyl)-2-((methylamino) methyl)cyclohexanol (140)

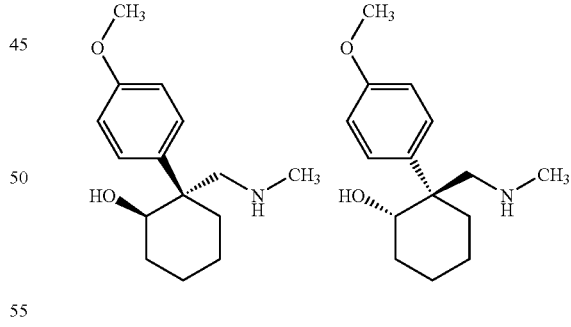

The enantiomeric mixture (±) trans 132e was separated (ChiralPak AD column; hexanes:IPA:DEA=90:10:0.1; μ=25 ml/min; and λ=275 nm) to give 140 E1 (retention time=5.3 min) and 140 E2 (retention time=7.1 min). $^1$H NMR (CDCl$_3$) δ 1.23-1.46 (m, 4H), 1.62-1.87 (m, 3H), 1.92-2.00 (m, 1H), 2.28 (s, 3H), 2.95 (d, J=12.4 Hz, 1H), 3.24 (d, J=12.4 Hz, 1H), 3.78 (s, 3H), 4.25 (dd, J=10.4 Hz, 3.2 Hz, 1H), 6.87 (d, J=8.8 Hz, 2H), 7.48 (d, J=8.8 Hz, 2H). $^{13}$C NMR (CDCl$_3$) δ 22.1, 24.4, 32.5, 36.7, 37.7, 45.1, 55.4, 57.6, 74.4, 114.1, 128.0, 137.9, 157.9.ESI MS m/z 250.

cis-2-(4-Chloro-3-fluorophenyl)-2-((methylamino)methyl)cyclohexanol (141)

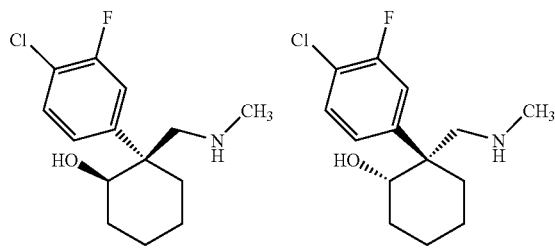 [SMILES: CNC[C@@]1(c2ccc(Cl)c(F)c2)CCCC[C@H]1O ; CNC[C@]1(c2ccc(Cl)c(F)c2)CCCC[C@@H]1O]

The enantiomeric mixture (±) cis 132f was separated (Regis O1 column; hexanes:IPA:DEA=95:5:0.1; μ=25 ml/min; λ=275 nm) to give 141 E1 (retention time=7.2 min) and 141 E2 (retention time=10.8 min). $^1$H NMR (CDCl$_3$) δ 1.28-1.50 (m, 4H), 1.64-1.86 (m, 3H), 1.98-2.02 (m, 1H), 2.32 (s, 3H), 2.97 (d, J=12.4 Hz, 1H), 3.30 (d, J=12.4 Hz, 1H), 4.19 (dd, J=10.0 Hz, 3.2 Hz, 1H), 7.32-7.38 (m, 2H), 7.42-7.52 (m, 1H). $^{13}$C NMR (CDCl$_3$) δ 22.0, 24.4, 32.5, 36.8, 37.7, 45.7, 57.1, 74.3, 115.7, 115.9, 118.6, 118.7, 123.6, 130.7, 147.5, 157.2, 159.7.ESI MS m/z 272.

trans-2-(4-chloro-3-fluorophenyl)-2-((methylamino)methyl)cyclohexanol (142)

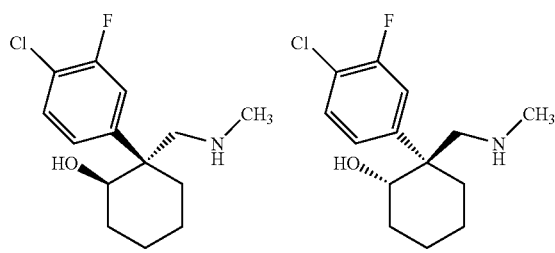 [SMILES: CNC[C@]1(c2ccc(Cl)c(F)c2)CCCC[C@H]1O ; CNC[C@@]1(c2ccc(Cl)c(F)c2)CCCC[C@@H]1O]

The enantiomeric mixture (±) trans 132f was separated (Regis O1 column; hexanes:IPA:DEA=95:5:0.1; μ=25 ml/min; λ=275 nm) to give 142 E1 (retention time=6.7 min) and 142 E2 (retention time=8.6 min). $^1$NMR (CDCl$_3$) δ 0.96-1.03 (m, 1H), 1.23-1.44 (m, 3H), 1.65-1.69 (m, 1H), 1.78-1.84 (m, 2H), 2.01-2.06 (m, 1H), 2.29 (s, 3H), 2.66 (d, J=13.6 Hz, 1H), 2.91 (d, J=13.6 Hz, 1H), 3.97 (dd, J=10.0 Hz, 3.2 Hz, 1H), 7.34 (d, J=8.4 Hz, 1H), 7.56 (dd, J=12.0, 2.4 Hz, 1H), 7.74(dd, J=12.0, 2.4 Hz, 1H). $^{13}$C NMR (CDCl$_3$) δ 21.3, 24.9, 29.9, 35.9, 36.7, 46.8, 67.0, 81.5, 118.0, 118.3, 125.9, 126.0, 130.4, 143.4, 156.9, 159.3.ESI MS m/z 272.

cis-2-((methylamino)methyl)-2-(4-(trifluoromethyl)phenyl)cyclohexanol (143)

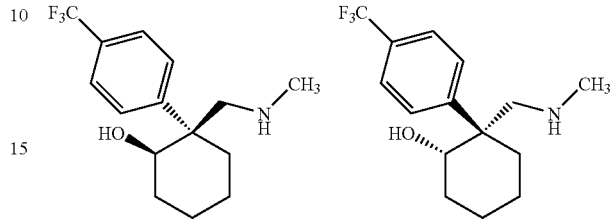

The enantiomeric mixture (±) cis 132 g was separated (Regis O1 column; hexanes:IPA:DEA=95:5:0.1; μ=25 ml/min; λ=275 nm) to give 143 E1 (retention time=8.2 min) and 143 E2 (retention time=11.8 min). $^{13}$H NMR (CDCl$_3$) δ 1.05-1.13 (m, 1H), 1.26-1.36 (m, 2H), 1.45-1.52 (m, 2H), 1.61-1.70 (m, 1H), 1.79-1.85 (m, 1H), 1.93-1.99 (m, 2H), 2.03 (s, 6H), 2.67(d, J=13.6 Hz, 1H), 3.28 (d, J=13.6 Hz, 1H), 3.95 (dd, J=10.0 Hz, 3.2 Hz, 1H), 7.58 (d, J=8.4 Hz, 2H), 7.74 (d, J=8.4 Hz, 1.2 Hz, 2H). $^{13}$C NMR (CDCl$_3$) δ 22.0, 24.4, 32.5, 36.8, 37.7, 46.0, 57.1, 74.2, 123.1, 125.6, 125.7, 125.9, 127.5, 128.5, 128.8, 150.3.ESI MS m/z 288.

trans-2-((Methylamino)methyl)-2-(4-(trifluoromethyl)phenyl)cyclohexanol (144)

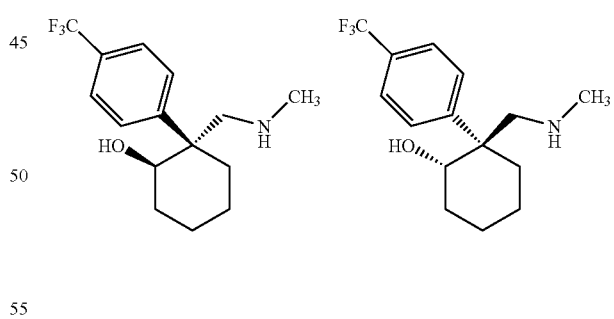

The enantiomeric mixture (±) trans 132 g was separated (Regis O1 column; hexanes:IPA:DEA=95:5:0.1; μ=25 ml/min; λ=275 nm) to give 144 E1 (retention time=7.9 min) and 144 E2 (retention time=11.2 min). $^{13}$H NMR (CDCl$_3$) δ 0.91-1.02 (m, 1H), 1.27-1.43 (m, 3H), 1.65-1.69 (m, 1H), 1.83-1.88 (m, 2H), 2.11-2.16 (m, 1H), 2.28 (s, 3H), 2.68 (d, J=13.6 Hz, 1H), 2.97 (d, J=13.6 Hz, 1H), 4.02 (dd, J=10.0 Hz, 3.2 Hz, 1H), 7.58 (d, J=8.4 Hz, 2H), 7.98 (d, J=8.4 Hz, 2H).

$^{13}$C NMR (CDCl$_3$) δ 21.4, 24.9, 30.0, 36.0, 36.7, 47.1, 67.1, 81.6, 125.3, 125.4, 125.8, 128.3, 128.6, 129.9, 146.6. ESI MS m/z 288.

cis-2-((Methylamino)methyl)-2-(4-(trifluoromethoxy)phenyl)cyclohexanol (145)

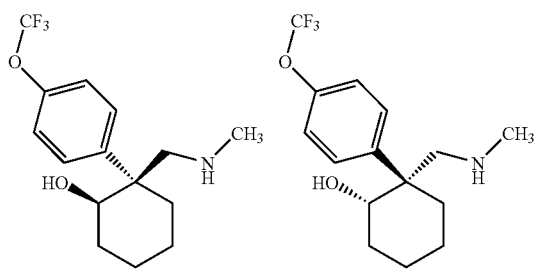 [SMILES: CNC[C@@]1(c2ccc(OC(F)(F)F)cc2)CCCC[C@H]1O ; CNC[C@]1(c2ccc(OC(F)(F)F)cc2)CCCC[C@@H]1O]

The enantiomeric mixture (±) cis 132 h was separated (Regis O1 column; hexanes:IPA:DEA=95:5:0.1; μ=25 ml/min; λ=275 nm) to give 145 E1 (retention time=5.1 min) and 145 E2 (retention time=8.2 min). $^{13}$H NMR (CDCl$_3$) δ 1.05-1.13 (m, 1H), 1.26-1.36 (m, 2H), 1.45-1.52 (m, 2H), 1.30-1.48 (m, 4H), 1.68-1.88 (m, 3H), 1.99-2.03 (m, 1H), 2.32 (s, 3H), 3.02 (d, J=12.4 Hz, 1H), 3.31 (d, J=12.4 Hz, 1H), 4.27 (dd, J=10.4 Hz, 4.0 Hz, 1H), 7.19 (d, J=8.4 Hz, 2H), 7.64 (d, J=8.4 Hz, 2H). $^{13}$C NMR (CDCl$_3$) δ 21.3, 22.0, 24.5, 32.5, 36.7, 37.9, 45.5, 57.1, 74.3, 119.4, 120.8, 121.1, 122.0, 128.5, 131.0, 144.7, 147.6. ESI MS m/z 304.

trans-2-((Methylamino)methyl)-2-(4-(trifluoromethoxy)phenyl)cyclohexanol (146)

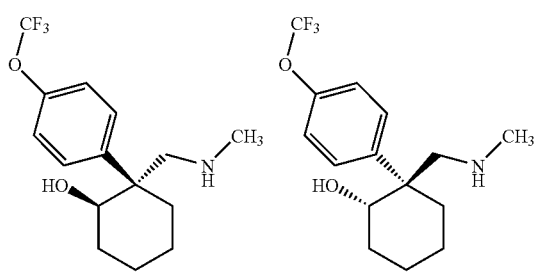 [SMILES: CNC[C@]1(c2ccc(OC(F)(F)F)cc2)CCCC[C@H]1O ; CNC[C@@]1(c2ccc(OC(F)(F)F)cc2)CCCC[C@@H]1O]

The enantiomeric mixture (±) trans 132 h was separated (Regis O1 column; hexanes:IPA:DEA=95:5:0.1; μ=25 ml/min; λ=275 nm) to give 146 E1 (retention time=4.4 min) and 146 E2 (retention time=5.8 min). $^1$H NMR (CDCl$_3$) δ 0.96-1.04 (m, 1H), 1.25-1.42 (m, 3H), 1.65-1.69 (m, 1H), 1.81-1.88 (m, 2H), 2.07-2.16 (m, 1H), 2.29 (s, 3H), 2.68 (d, J=11.6 Hz, 1H), 2.95 (d, J=11.6 Hz, 1H), 4.00 (dd, J=10.0 Hz, 3.2 Hz, 1H), 7.18 (d, J=8.4 Hz, 2H), 7.87 (d, J=8.4 Hz, 2H).

$^{13}$C NMR (CDCl$_3$) δ 21.3, 25.0, 30.0, 36.0, 36.7, 46.6 67.1, 81.6, 119.4, 120.8, 122.0, 131.0, 140.7, 147.5. ESI MS m/z 304.

cis-2-((dimethylamino)methyl)-2-(naphthalen-2-yl)cyclohexanol (147)

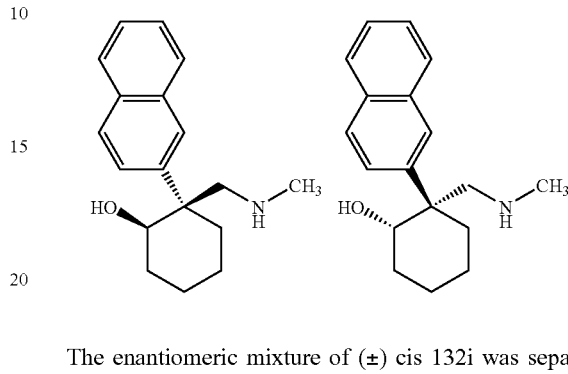

The enantiomeric mixture of (±) cis 132i was separated (ChiralPak AD column; hexanes:IPA:DEA=90:10:0.1; μ=60 ml/min; λ=280 nm) to give 147 E1 (retention time=20.7 min) and 147 E2 (retention time=28.2 min). $^1$H NMR (CDCl$_3$) δ 0.96-1.03 (m, 1H), 1.22-1.41 (m, 3H), 1.60-1.65 (m, 1H), 1.84-1.92 (m, 1H), 2.01-2.12 (m, 1H), 2.22 (s, 3H), 2.66 (d, J=13.6 Hz, 1H), 3.01 (d, J=13.6 Hz, 1H), 4.05 (dd, J=10.0 Hz, 3.2 Hz, 1H), 7.19-7.24 (m, 2H), 7.71-7.87 (m, 4H), 8.49 (s, 1H). $^{13}$C NMR (CDCl$_3$) δ 21.6, 25.1, 30.1, 35.9, 36.7, 47.1, 66.7, 81.9, 126.0, 126.1, 126.6, 127.5, 128.3, 128.5, 129.5, 132.1, 133.6, 139.3. ESI MS m/z 270.

trans-2-((dimethylamino)methyl)-2-(naphthalen-2-yl)cyclohexanol (148)

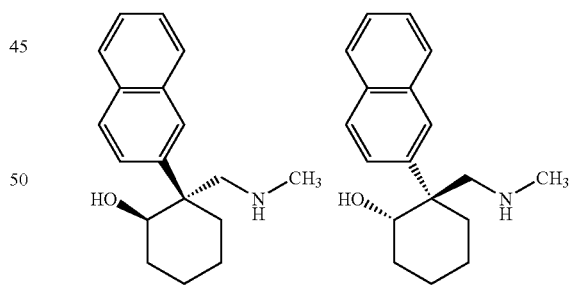

The enantiomeric mixture (±) trans 132i was separated (ChiralPak AD column; hexanes:IPA:DEA=90:10:0.1; μ=60 ml/min; λ=280 nm) to give 148 E1 (retention time=25.7 min) and 148 E2 (retention time=40.8 min). $^1$H NMR (CDCl$_3$) δ 1.28-1.50 (m, 4H), 1.71-1.86 (m, 2H), 1.95-2.06 (m, 2H), 2.25 (s, 3H), 3.06 (d, J=12.4 Hz, 1H), 3.30 (d, J=12.4 Hz, 1H), 4.45 (dd, J=10.0 Hz, 3.2 Hz, 1H), 7.39-7.44 (m, 2H), 7.60-7.63 (m, 1H), 7.76-7.85 (m, 3H), 8.14 (s, 1H). $^{13}$C NMR (CDCl$_3$) δ 22.1, 24.6, 32.7, 36.8, 37.7, 45.9, 57.1, 74.4, 124.8, 125.9, 126.2, 126.3, 127.5, 128.4, 128.5, 132.2, 133.8, 143.2. ESI MS m/z 270.

cis-2-((methylamino)methyl)-2-(naphthalen-2-yl) cyclohexanol (149)

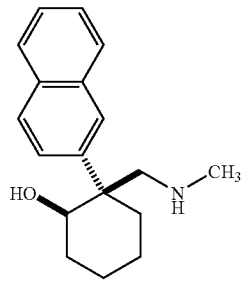

(a) cis-2-hydroxy-N-methyl-1-(naphthalen-2-yl)cyclohexanecarboxamide (300)

A mixture of (±) cis-2-hydroxy-1-(naphthalen-2-yl)cyclohexanecarboxylic acid (9.74 g, 36.1 mmol), PyBOP (18.8 g, 36.1 mmol), methylamine (2 M in THF, 19.8 mL, 39.7 mmol), N-methylmorpholine (4.36 mL, 39.7 mmol) and DMAP (4.84 g, 39.7 mmol) was stirred in DMF (361 mL) at room temperature overnight. The mixture was diluted with EtOAc (1.5 L). The layers were separated and the organic layer was washed with 0.5 M HCl (3×600 mL), saturated aqueous NaHCO$_3$ (3×500 mL), brine (300 mL), dried and concentrated. The residue was triturated with diethyl ether to give (±) cis-2-hydroxy-N-methyl-1-(naphthalen-2-yl)cyclohexanecarboxamide (7.36 g, 72%) as a light yellow solid.

(b) cis-2-((methylamino)methyl)-2-(naphthalen-2-yl) cyclohexanol

The title compound can be prepared from the above amide, for example, according to General Procedure E.

(±) trans-2-((methylamino)methyl)-2-(naphthalen-2-yl)cyclohexanol (150)

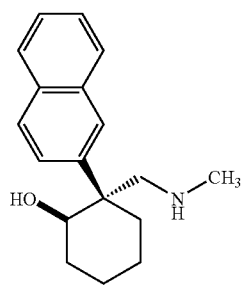

(a) (±) trans-2-hydroxy-N-methyl-1-(naphthalen-2-yl)cyclohexanecarboxamide (301)

A mixture of (±) trans-2-hydroxy-1-(naphthalen-2-yl)cyclohexanecarboxylic acid (9.72 g, 36.0 mmol), PyBOP (18.7 g, 36.0 mmol), methylamine (2 M in THF, 19.8 mL, 39.6 mmol), N-methylmorpholine (4.35 mL, 39.6 mmol) and DMAP (4.83 g, 39.6 mmol) was stirred in DMF (360 mL) at room temperature overnight. The mixture was diluted with EtOAc (1.5 L). The layers were separated and the organic layer was washed with 1 M HCl (3×600 mL), saturated aqueous NaHCO$_3$ (3×500 mL), brine (500 mL), dried and concentrated to give (±)-2-hydroxy-N-methyl-1-(naphthalen-2-yl)cyclohexanecarboxamide (8.66 g, 85%) as a light yellow solid.

(b) trans-2-((methylamino)methyl)-2-(naphthalen-2-yl)cyclohexanol

The title compound can be prepared from the above amide, for example, according to General Procedure E.

2.4. Preparation of Tertiary Amines (151a to 151i)

Treatment of the respective methylamines 132 (Scheme 29) with a methylating reagent, e.g., iodomethane and N,N'-diisopropylethylamine (DIEA) in acetone or CH$_2$Cl$_2$ (modified General Procedure F) gave the dimethylamines cis 151 E1, cis 151 E2, trans 151 E1, and trans 151 E2.

Scheme 29:

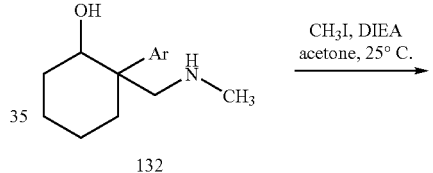

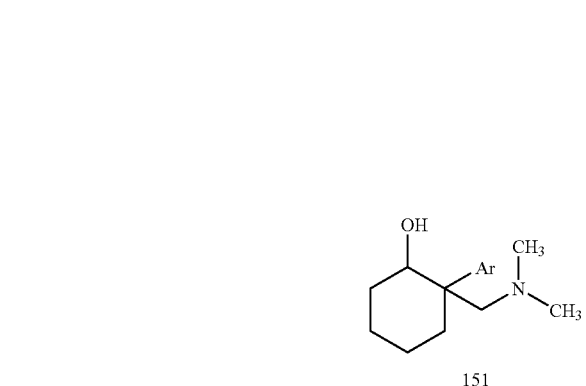

(Modified General Procedure F) To the solution of the respective N-methylamine 132 (e.g., 86 mg. 0.285 mmol) and DIEA (e.g., 0.164 ml, 0.942 mmol) in acetone (0.5 ml) was added CH$_3$I (e.g., 0.020 ml, 0.314 mmol). The mixture was stirred at room temperature overnight and the solvent was then removed in vacuo. The residue was dissolved in CH$_2$Cl$_2$ (e.g., 10 ml), washed with saturated K$_2$CO$_3$ solution (e.g., 5 ml), dried over Na$_2$SO$_4$, and evaporated in vacuo. The crude product was purified by silica gel flash chromatography using e.g., dichloromethane/methanol gradients to give the respective dimethylamine 151 in 40 to 70% yield.

The following compounds were prepared from the corresponding methylamine 133-148 using modified General Procedure F outlined above, or slightly modified versions thereof.

cis-2-(3,4-dichlorophenyl)-2-((dimethylamino)methyl)cyclohexanol (152)

trans-2-(4-chlorophenyl)-2-((dimethylamino)methyl)cyclohexanol (154)

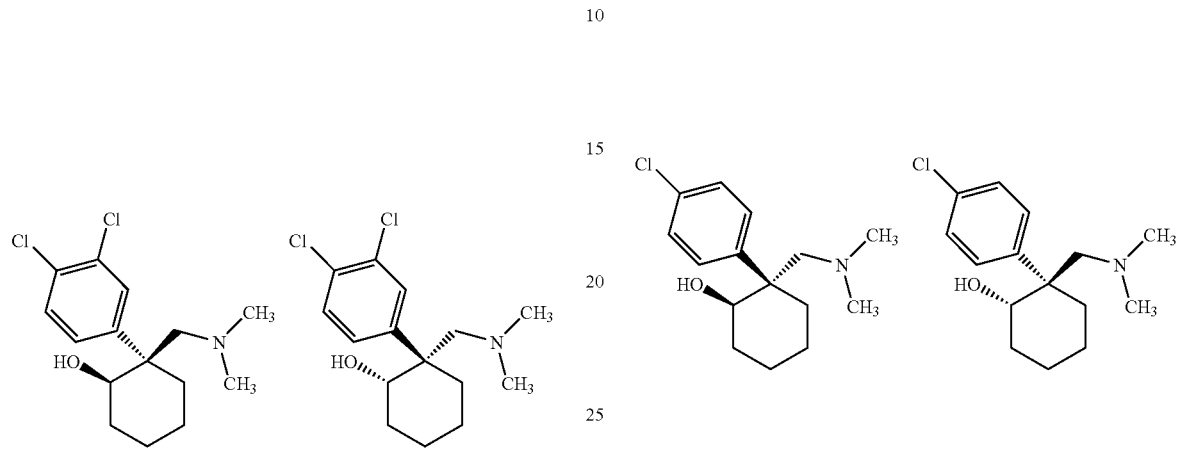

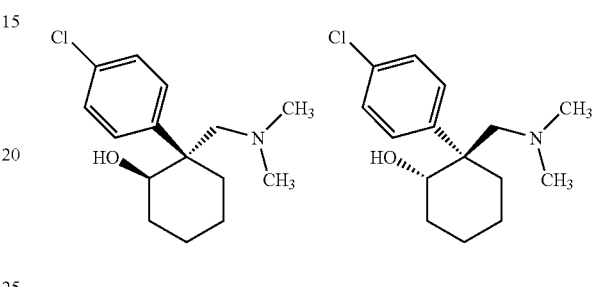

152 E1, 152 E2

The title compounds were prepared from 133 E1 and 133 E2, respectively. $^1$H NMR (CDCl$_3$) δ 0.82-0.96 (m, 1H), 1.10-1.18 (m, 1H), 1.28-1.39 (m, 2H), 1.64-1.70 (m, 1H), 1.83-1.98 (m, 9H), 2.60 (d, J=13.2 Hz, 1H), 2.70 (d, J=13.2 Hz, 1H), 3.97 (dd, J=11.2, 4.8 Hz, 1H), 7.37 (d, J=8.4 Hz, 1H), 7.73 (dd, J=8.4 Hz, 2.0 Hz, 1H). 7.98 (d, J=2 Hz, 1H). $^{13}$C NMR (CDCl$_3$) δ 21.0, 25.1, 29.9, 37.2, 46.0, 47.8, 75.9, 80.8, 129.5, 130.0, 130.2, 131.9, 132.4, 143.7. ESI MS m/z 303.

trans-2-(3,4-dichlorophenyl)-2-((dimethylamino)methyl)cyclohexanol (153)

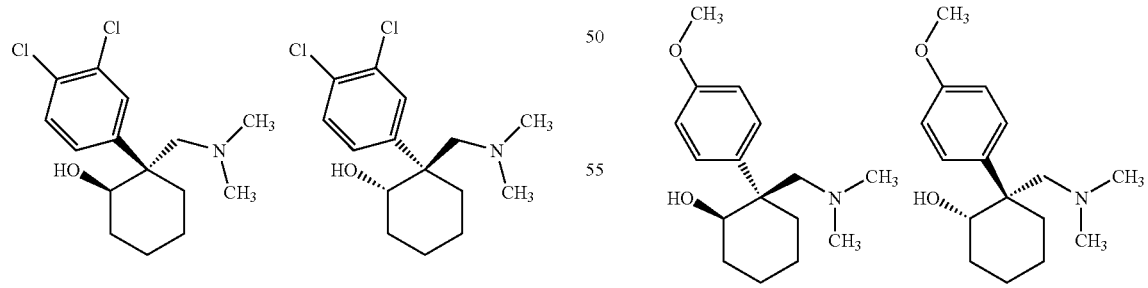

153 E1, 153 E2

The title compnds were prepared from 134 E1 and 134 E, respectively. $^1$H NMR (CDCl$_3$) δ 1.21-1.35 (m, 2H), 1.42-1.48 (m, 2H), 1.56-1.66 (m, 1H), 1.77-1.98 (m, 3H), 2.03 (s, 6H), 2.58 (d, J=14.0 Hz, 1H), 3.25 (d, J=14.0 Hz, 1H), 4.18 (dd, J=9.6 Hz, 2.8 Hz, 1H), 7.38 (d, J=8.8 Hz, 1H), 7.46 (dd, J=8.8 Hz, 2.4 Hz, 1H), 7.73 (d, J=2.4 Hz, 1H). $^{13}$C NMR (CDCl$_3$) δ 22.1, 24.1, 32.5, 36.9, 44.6, 44.7, 66.3, 74.8, 127.0, 129.6, 130.0, 130.3, 132.5, 148.2. ESI MS m/z 303.

154 E1, 154 E2

The title compounds were prepared from 136 E1 and 136 E2, respectively. $^1$H NMR (CDCl$_3$) δ 1.21-1.35 (m, 2H), 1.42-1.48 (m, 2H), 1.56-1.66 (m, 1H), 1.77-1.84 (m, 1H), 1.89-1.98 (m, 2H), 2.03 (s, 6H), 2.58 (d, J=14.0 Hz, 1H), 3.20 (d, J=14.0 Hz, 1H), 4.26 (dd, J=9.6 Hz, 2.8 Hz, 1H), 7.30 (d, J=10.8 Hz, 2H), 7.58 (d, J=10.8 Hz, 2H). $^{13}$C NMR (CDCl$_3$) δ 22.1, 24.1, 32.5, 36.7, 44.6, 47.7, 66.3, 74.8, 128.6, 128.8, 131.8, 146.0. ESI MS m/z 268.

Cis-2-((dimethylamino)methyl)-2-(4-methoxyphenyl)cyclohexanol (155)

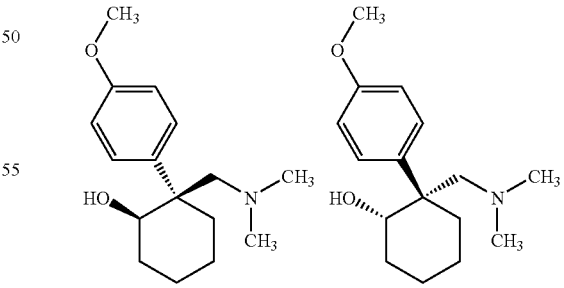

155 E1, 155 E2

The title compounds were prepared from 139 E1 and 139 E2, respectively. $^1$H NMR (CDCl$_3$) δ 0.92-1.00 (m, 1H), 1.07-1.12 (m, 1H), 1.25-1.36 (m, 2H), 1.61-1.66 (m, 1H), 1.80-2.03 (m, 9H), 2.59 (q, J=13.2 Hz, 2H), 3.95 (dd, J=11.6 Hz, 4.0 Hz, 1H), 6.82 (d, J=8.4 Hz, 2H), 7.71 (d, J=8.4 Hz, 2H).

$^{13}$C NMR (CDCl$_3$) δ 21.1, 25.3, 30.0, 37.1, 45.5, 47.7, 55.3, 76.0, 81.5, 113.6, 130.7, 134.6, 157.6. ESI MS m/z 264.

trans-2-((dimethylamino)methyl)-2-(4-methoxyphenyl)cyclohexanol (156)

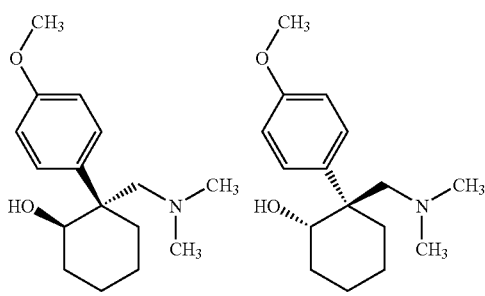 [SMILES: COc1ccc([C@@]2(CN(C)C)CCCC[C@H]2O)cc1 ; COc1ccc([C@]2(CN(C)C)CCCC[C@@H]2O)cc1]

156 E1, 156 E2

The title compounds were prepared from 140 E1 and 140 E2, respectively. $^1$H NMR (CDCl$_3$) δ 1.26-1.37 (m, 2H), 1.43-1.48 (m, 2H), 1.58-1.66 (m, 1H), 1.76-1.82 (m, 1H), 1.88-2.00 (m, 2H), 2.05 (s, 6H), 2.61 (d, J=14.0 Hz, 1H), 3.14 (d, J=14.0 Hz, 1H), 4.31 (dd, J=10.0 Hz, 3.2 Hz, 1H), 6.86 (d, J=8.8 Hz, 2H), 7.49 (d, J=8.8 Hz, 2H). $^{13}$C NMR (CDCl$_3$) δ 22.2, 13.7, 32.4, 36.1, 44.0, 47.7, 55.4, 67.4, 74.9, 113.7, 128.2, 139.1, 157.7. ESI MS m/z 263.

Cis-2-(4-chloro-3-fluorophenyl)-2-((dimethylamino)methyl)cyclohexanol (157)

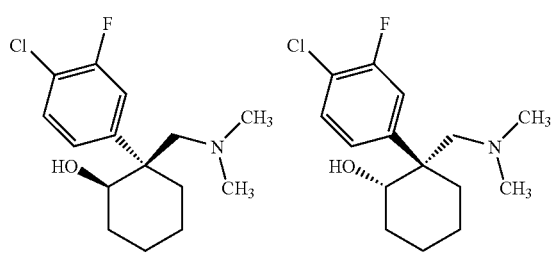 [SMILES: CN(C)C[C@@]1(c2ccc(Cl)c(F)c2)CCCC[C@H]1O ; CN(C)C[C@]1(c2ccc(Cl)c(F)c2)CCCC[C@@H]1O]

157 E1, 157 E2

The title compounds were prepared from 141 E1 and 141 E2, respectively. $^1$H NMR (CDCl$_3$) δ 1.21-1.35 (m, 2H), 1.42-1.48 (m, 2H), 1.56-1.66 (m, 1H), 1.77-1.98 (m, 3H), 2.03 (s, 6H), 2.56 (d, J=14.0 Hz, 1H), 3.25 (d, J=14.0 Hz, 1H), 4.18 (dd, J=9.6 Hz, 2.8 Hz, 1H), 7.32-7.35 (m, 1H), 7.43 (d, J=8.4 Hz, 1H). $^{13}$C NMR (CDCl$_3$) δ 22.1, 24.1, 32.5, 36.9, 44.6, 44.7, 66.4, 74.9, 115.8, 116.1, 118.2, 118.4, 123.8, 130.3, 148.9, 157.0, 159.5. ESI MS m/z 286.

Trans-2-(4-chloro-3-fluorophenyl)-2-((dimethylamino)methyl)cyclohexanol (158)

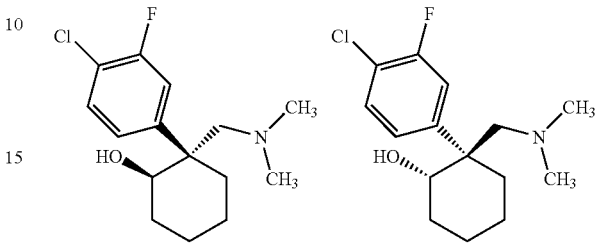

158 E, 158 E2

The title compounds were synthesized from 142 E1 and 142 E2, respectively. $^1$H NMR (CDCl$_3$) δ 0.82-0.96 (m, 1H), 1.10-1.18 (m, 1H), 1.28-1.39 (m, 2H), 1.64-1.70 (m, 1H), 1.83-1.98 (m, 9H), 2.60 (d, J=13.2 Hz, 1H), 2.70 (d, J=13.2 Hz, 1H), 3.97 (dd, J=11.2, 4.8 Hz, 1H), 7.28 (t, J=8.4 Hz, 1H), 7.55-7.58 (m, 1H). 7.75-7.79 (m, 1H). $^{13}$C NMR (CDCl$_3$) δ 21.0, 25.1, 29.9, 37.2, 46.1, 47.7, 75.9, 80.8, 118.3, 118.5, 126.3, 130.2, 144.4, 156.8, 159.3. ESI MS m/z 286.

cis-2-((dimethylamino)methyl)-2-(4-(trifluoromethyl)phenyl)cyclohexanol (159)

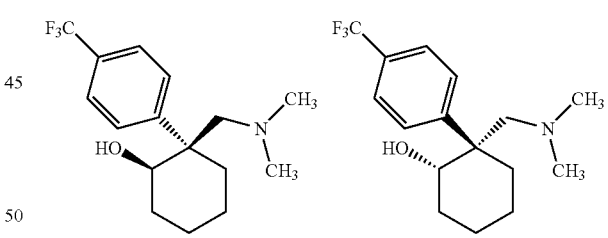

159 E1, 159 E2

The title compounds were prepared from 143 E1 and 143 E2, respectively. $^1$H NMR (CDCl$_3$) δ 1.05-1.13 (m, 1H), 1.26-1.36 (m, 2H), 1.45-1.52 (m, 2H), 1.61-1.70 (m, 1H), 1.79-1.85 (m, 1H), 1.93-1.99 (m, 2H), 2.03 (s, 6H), 2.67 (d, J=13.6 Hz, 1H), 3.28 (d, J=13.6 Hz, 1H), 3.95 (dd, J=10.0 Hz, 3.2 Hz, 1H), 7.58 (d, J=8.4 Hz, 2H), 7.74 (d, J=8.4 Hz, 2H). $^{13}$C NMR (CDCl₃) δ 22.1, 24.0, 32.4, 36.8, 44.9, 66.4, 74.8, 123.2, 125.3, 125.4, 125.9, 127.7, 128.2, 128.5, 151.7.ESI MS m/z 302.

trans-2-((dimethylamino)methyl)-2-(4-(trifluoromethyl)phenyl)cyclohexanol (160)

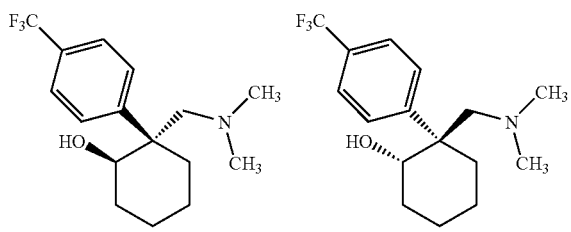 [SMILES: CN(C)C[C@]1(c2ccc(C(F)(F)F)cc2)CCCC[C@H]1O ; CN(C)C[C@@]1(c2ccc(C(F)(F)F)cc2)CCCC[C@@H]1O]

160 E1, 160 E2

The title compounds were prepared from 144 E1 and 144 E2, respectively. ¹H NMR (CDCl₃) δ 0.82-0.93 (m, 1H), 1.14-1.21 (m, 1H), 1.30-1.40 (m, 2H), 1.67-1.70 (m, 1H), 1.87-2.09 (m, 9H), 2.65-2.75 (m, 2H), 4.00-4.05 (m, 1H), 7.55 (d, J=8.4 Hz, 2H), 7.99 (d, J=8.4 Hz, 2H). ¹³C NMR (CDCl₃) δ 21.1, 25.2, 30.0, 37.4, 46.4, 47.7, 76.0, 81.0, 125.1, 125.2, 125.9, 128.0, 128.4, 130.2, 131.8, 147.6.ESI MS m/z 302.

cis-2-((dimethylamino)methyl)-2-(4-(trifluoromethoxy)phenyl)cyclohexanol (161)

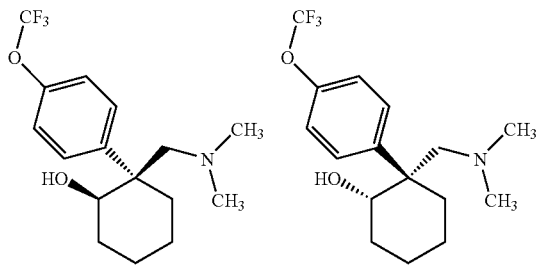 [SMILES: CN(C)C[C@@]1(c2ccc(OC(F)(F)F)cc2)CCCC[C@H]1O ; CN(C)C[C@]1(c2ccc(OC(F)(F)F)cc2)CCCC[C@@H]1O]

161 E1, 161 E2

The title compounds were prepared from 145 E1 and 145 E2, respectively. ¹H NMR (CDCl₃) δ 1.26-1.37 (m, 2H), 1.43-1.50 (m, 2H), 1.59-1.68 (m, 1H), 1.78-1.84 (m, 1H), 1.92-1.97 (m, 2H), 2.03 (s, 6H), 2.61 (d, J=14.0 Hz, 1H), 3.24 (d, J=14.0 Hz, 1H), 4.28 (dd, J=10.0 Hz, 3.2 Hz, 1H), 7.16 (d, J=8.8 Hz, 2H), 7.63 (d, J=8.8 Hz, 2H). ¹³C NMR (CDCl₃) δ 22.2, 24.0, 32.4, 36.7, 44.4, 47.7, 66.7, 74.9, 119.5, 120.8, 122.0, 128.7, 131.2, 146.1, 147.4.ESI MS m/z 302.

trans-2-((dimethylamino)methyl)-2-(4-(trifluoromethoxy)phenyl)cyclohexanol (162)

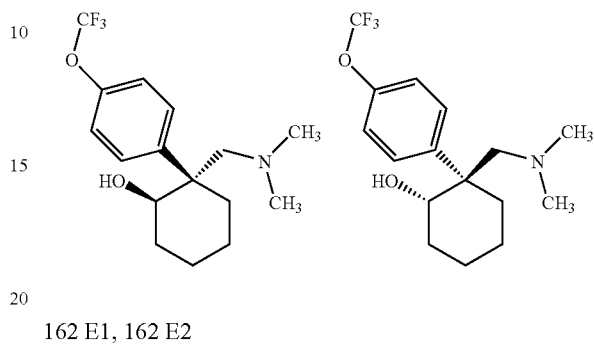

162 E1, 162 E2

The title compounds were prepared from 146 E1 and 146 E2, respectively. ¹H NMR (CDCl₃) δ 0.90-0.97 (m, 1H), 1.12-1.19 (m, 1H), 1.29-1.39 (m, 2H), 1.65-1.69 (m, 1H), 1.84-2.04 (m, 9H), 2.60 (d, J=14.0 Hz, 1H), 2.70 (d, J=14.0 Hz, 1H), 4.00 (dd, D=11.6 Hz, 4.0 Hz, 1H), 7.14 (d, J=8.4 Hz, 2H), 7.88 (d, J=8.4 Hz, 2H). ¹³C NMR (CDCl₃) δ 21.0, 25.2, 29.9, 37.3, 46.0, 47.7, 76.1, 81.1, 120.6, 122.0, 131.2, 141.7, 147.4.ESI MS m/z 318.

Cis-2-((dimethylamino)methyl)-2-(naphthalen-2-yl)cyclohexanol (163)

163 E1, 163 E2

The title compounds were synthesized from 147 E1 and 147 E2, respectively. ¹H NMR (CDCl₃) δ 0.82-0.96 (m, 1H), 1.10-1.18 (m, 1H), 1.28-1.39 (m, 2H), 1.64-1.70 (m, 1H), 1.83-1.98 (m, 9H), 2.60 (d, J=13.2 Hz, 1H), 2.70 (d, J=13.2 Hz, 1H), 4.05 (dd, J=11.2, 4.8 Hz, 1H), 7.37 (d, J=8.4 Hz, 1H), 7.73 (dd, J=8.4 Hz, 2.0 Hz, 1H). 7.98 (d, J=2 Hz, 1H). ¹³C NMR (CDCl₃) δ 21.0, 25.1, 29.9, 37.2, 46.0, 47.8, 75.9, 80.8, 126.0, 126.1, 126.6, 127.5, 128.3, 128.5, 129.5, 132.1, 133.6, 139.3.ESI MS m/z 284.

trans-2-((dimethylamino)methyl)-2-(naphthalen-2-yl)cyclohexanol (164)

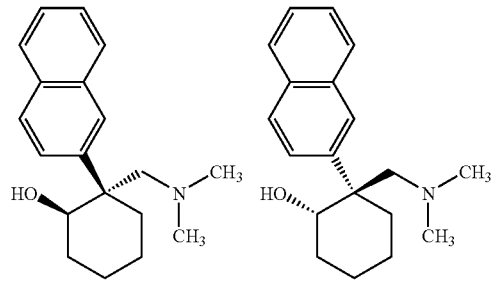 [SMILES: CN(C)C[C@]1(c2ccc3ccccc3c2)CCCC[C@H]1O ; CN(C)C[C@@]1(c2ccc3ccccc3c2)CCCC[C@@H]1O]

164 E1, 164 E2

The title compounds were prepared from 148 E1 and 148 E2, respectively. $^1$H NMR (CDCl$_3$) δ 1.29-1.42 (m, 2H), 1.47-1.54 (m, 2H), 1.65-1.74 (m, 1H), 1.80-1.86 (m, 1H), 1.97-2.10 (m, 3H), 2.03 (s, 6H), 2.72 (d, J=14.0 Hz, 1H), 3.26 (d, J=14.0 Hz, 1Hz, 1H), 4.49 (dd, J=9.6 Hz, 2.8 Hz, 1H), 7.41-7.48 (m, 2H), 7.61 d, J=8.8 Hz, 1H), 7.79-7.86 (m, 3H), 8.18 (s, 1H). $^{13}$C NMR (CDCl$_3$) δ 22.3, 24.0, 32.5, 36.4, 44.8, 47.8, 66.6, 75.1, 125.5, 125.8, 126.0, 126.2, 127.5, 127.8, 128.5, 132.1, 133.8, 144.6.ESI MS m/z 284.

2.5. Preparation of 4a-(3,4-dichlorophenyl)-3-methyloctahydro-2H-benzo[e][1,3]oxazine

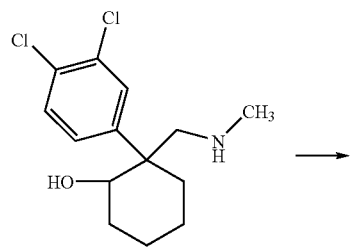

A solution of the respective methylamine 132 (e.g., 26.5 mg, 0.0919 mmol) in formaldehyde (e.g., 37%, 2 ml) and formic acid (e.g., 96%, 2 ml) was heated at 100° C. for 2 hours. After cooling to room temperature, the mixture was washed with hexanes (e.g., 3×4 ml). The aqueous solution was then made basic with 5 N KOH solution to pH 12. The mixture was extracted with t-butyl methylether (e.g., 3×5 ml) and the combined organic layers were dried over Na$_2$SO$_4$, and the solvent was evaporated. The residue was purified by reverse phase HPLC (C-18 column, CH$_3$CN/water, CH$_3$CN from 5% to 100%) to give the respective oxazine.

Cis-4a-(3,4-dichlorophenyl)-3-methyloctahydro-2H-benzo [e] [1,3] oxazine (165)

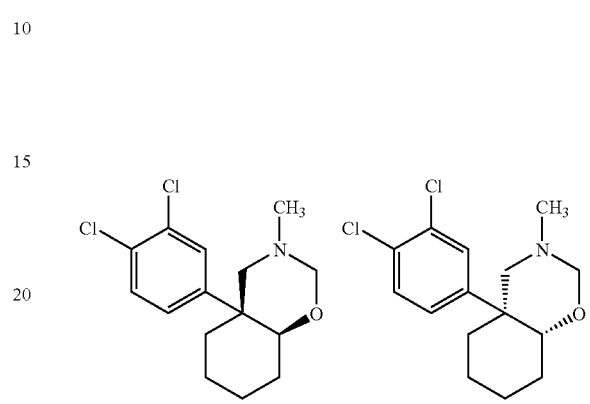

165 E1 prepared from 133 E1

165 E2 prepared from 133 E2

$^1$H NMR (CDCl$_3$) δ 0.97-1.17 (m, 1H), 1.23-1.45 (m, 3H), 1.72-1.90 (m, 3H), 2.03 (s, 3H), 2.15 (d, J=12.8 Hz, 1H), 2.81 (d, J=12.4 Hz, 1H), 3.32-3.43 (m, 1H), 3.72 (d, J=7.8 Hz, 1H), 4.57 (d, J=7.8 Hz, 1H), 4.89-4.97 (m, 1H), 7.35 (d, J=7.8 Hz, 1H), 7.60-7.68 (m, 1H), 7.81 (s, 1H). $^{13}$C NMR (CDCl3) δ 21.2, 26.0, 27.8, 35.6, 41.0, 42.8, 69.1, 85.1, 88.7, 129.5, 129.9, 130.4, 131.8, 132.0, 144.6.ESI MS m/z 300.

Trans-4a-(3,4-dichlorophenyl)-3-methyloctahydro-2H-benzo[e][1,3]oxazine (166)

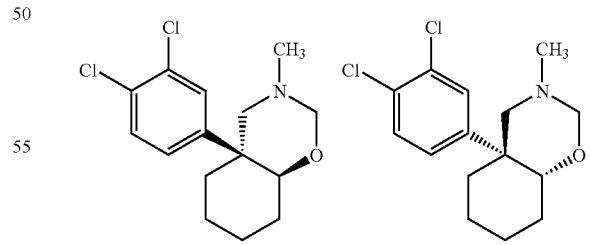

166 E1 prepared from 134 E1

166 E2 prepared from 134 E2

$^1$H NMR (CDCl$_3$) δ 1.25-1.41 (m, 2H), 1.48-1.79 (m, 4H), 1.88 (d, J=13.8 Hz, 1H), 1.98 (d, J=11.4 Hz, 1H), 2.13 (s, 3H), 2.58-2.68 (m, 2H), 3.62 (d, J=7.5 Hz, 1H), 4.00 (s, 1H), 4.55 (d, J=7.5 Hz, 1H), 7.20-7.27 (m, 1H), 7.39-7.46 (m, 2H). $^{13}$C

NMR (CDCl3) δ 20.3, 22.1, 27.0, 28.4, 40.4, 41.5, 68.5, 77.4, 87.8, 126.5, 129.3, 130.4, 130.7, 133.0, 144.7. ESI MS m/z 300.

2.6. Synthesis of cis- and trans-3-(aminomethyl)-3-(3,4-dichlorophenyl)cyclopentanol (167)

(a) Synthesis of 1-(3,4-dichlorophenyl)cyclopent-3-enecarbonitrile

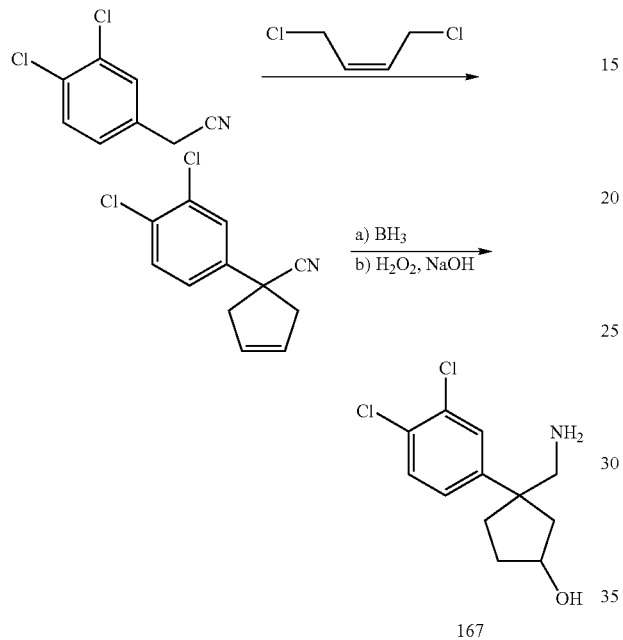

167

To ice-cold DMSO (100 mL) was added 60% NaH (1.0 g, 2.3 eq) in portions. The cooling bath was removed and the solution was stirred at ambient temperature for ten minutes. A solution of 2-(3,4-dichlorophenyl)acetonitrile (2.0 g, 10.75 mmol) in DMSO (50 mL) was added. The brown solution was stirred for 15 minutes before cis-1,4-dichlorobutene (1.0 mL, 0.9 eq) was added. The reaction mixture was stirred overnight and was then poured into water. The product was extracted with DCM. The organic layer was washed with brine, evaporated, diluted with 50% ethyl acetate in hexanes, washed with water, and evaporated. The residual oil was separated on silica to give the nitrile (966 mg, 43%) as a pale-brown oil. GCMS $R_t$=10.8 min m/z=237 (M+). $^1$H NMR (CDCl$_3$, δ): 7.51 (d, J=2.3 Hz, 1H), 7.39 (d, J=8.5 Hz, 1H), 7.28 (dd, J=2.3, 8.5 Hz, 1H), 5.79 (s, 2H), 3.27 (d, J=14.7 Hz, 2H), 2.87 (d, J=14.7 Hz, 2H). $^{13}$C NMR (CDCl$_3$, δ): 141.9, 133.2, 132.1, 131.0, 128.5, 127.6, 125.0, 124.0, 48.4.

(b) Synthesis of 3-(aminomethyl)-3-(3,4-dichlorophenyl)cyclopentanol

A mixture of 1-(3,4-dichlorophenyl)cyclopent-3-enecarbonitrile (119 mg, 0.500 mmol) and borane-THF (2 mL, 1M in THF, 2 eq) was heated at 65° C. for 2 hours. The reaction was cautiously quenched with ethanol (0.5 mL), sodium hydroxide (1mL, 5M aqueous) and stirred for two hours. It was then extracted with MTBE and evaporated. The residue was purified by HPLC to give cis 167 and trans 167.

cis 167: LCMS $R_t$=4.7 min, m/z=260 (M+1). $^1$H NMR (CDCl$_3$, δ): 7.39 (d, J=8.4 Hz, 1H), 7.37 (d, J=2.2 Hz, 1H), 7.13 (dd, J=2.2, 8.4 Hz, 1H), 4.48 (m, 1H), 3.21 (s, 1H), 2.68 (dd, J=13.0, 15.7 Hz, 2H), 2.32 (dd, J=6.4, 13.7 Hz, 1H), 2.2-1.8 (m, 4H), 1.7 (m, 1H), 1.2 (bs, 2H). $^{13}$C NMR (CDCl$_3$, δ): 147.9, 132.2, 130.1, 129.2, 126.6, 72.9, 52.6, 51.9, 45.4, 34.3, 33.0.

trans 167: LCMS $R_t$=5.7 min, m/z=260 (M+1). $^1$H NMR (CDCl$_3$, δ): 7.37 (d, J=8.4 Hz, 1H), 7.35 (d, J=2.3 Hz, 1H), 7.11 (dd, J=2.3, 8.4 Hz, 1H), 4.33 (m, 1H), 2.86 (d, J=13.0 Hz, 1H), 2.74 (d, J=13.0 Hz, 1H), 2.5 (bs, 3H), 2.25 (dd, J=6.0, 14.0 Hz, 1H), 2.2-1.7 (m, 5H). $^{13}$C NMR (CDCl$_3$, δ): 149.2, 132.2, 130.1, 129.9, 128.8, 126.1, 72.6, 52.7, 52.1, 46.7, 36.2, 32.8.

1-(1-(3,4-dichlorophenyl)cyclopent-3-enyl)-N-methylmethanamine (168)

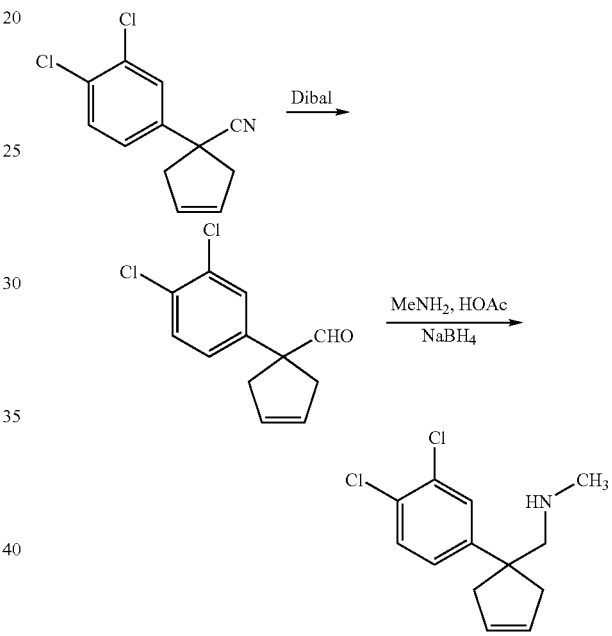

(a) Synthesis of 1-(3,4-dichlorophenyl)cyclopent-3-enecarbaldehyde

To a −78° C. solution of the nitrile (238 mg, 1 mmol) in 5 mL toluene was added dibal (2 mL, 2 eq) dropwise. After 45 minutes, the cold solution was quenched with ethyl acetate (2 mL) and stirred at ambient temperature for 30 minutes. The solution was diluted with ethyl acetate and washed with 3M HCl, water, and brine. The organic layer was dried with sodium sulfate, filtered and evaporated. The crude product was purified by silica gel column chromatography to give the aldehyde (161 mg, 67%) as a clear oil. TLC $R_f$ (25% EA/Hex) =0.13. GCMS $R_t$=7.7 min m/z=165 (M+). $^1$H NMR (CDCl$_3$, δ): 5.89 (t, J=3.1 Hz, 2H), 3.09 (t, J=2.8 Hz, 2H), 2.96 (s, 3H), 2.6 (m, 2H), 2.2 (m, 2H). $^{13}$C NMR (CDCl$_3$, δ): 180.2, 127.7, 39.1, 24.9, 23.4.

(b) Syntheis of 1-(1-(3,4-dichlorophenyl)cyclopent-3-enyl)-N-methylmethanamine (168)

To a solution of the aldehyde (100 mg, 0.4154 mmol) in methylamine (2.1mL, 2M in THF, 10 eq) was added acetic acid (104 ul, 5% of volume), and enough methanol to make a clear solution. The solution was stirred for two hours. To this was added sodium borohydride (40 mg, 3 eq) and stirring was continued for 30 minutes. The reaction was quenched with aqueous potassium carbonate and extracted with MTBE. The organic phase was separated and the solvent removed in vacuo. The residue was redissolved in MTBE and extracted with 3M HCl. The aqueous phase was separated, chilled in ice, and basicified with KOH. The aqueous phase was then extracted with MTBE and the solvent removed in vacuo. The residue was diluted in DCM, filtered through aminopropyl cartridge. The solvent was again removed to give the title compound (75.1 mg, 71%) as a clear oil. LCMS $R_t$ (SCM) =6.28 min; m/z=256 (M+1). $^1$H NMR (CDCl$_3$, δ): 7.36 (d, J=8.4 Hz, 1H), 7.35 (d, J=2.2 Hz, 1H), 7.10 (dd, J=2.2, 8.4 Hz, 1H), 5.73 (s, 2H), 5.67 (m, 6H), 2.31 (s, 3H). $^{13}$C NMR (CDCl$_3$, δ, mult): 148.6(0), 132.2(0), 130.1(1), 129.8(0), 129.2(1), 129.1(1), 126,5(1), 63.1(2), 50.6(0), 43.2(2), 37.1 (3).

2.7. Synthesis of 2-Hydroxymethyl Analogs

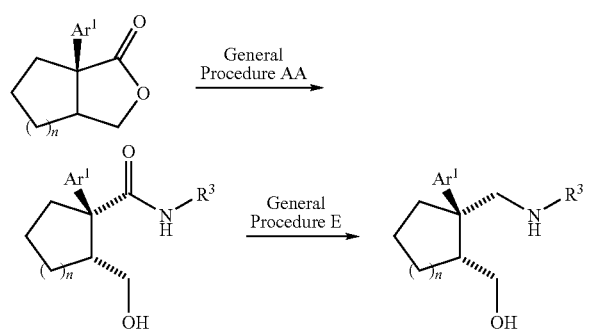

Relative Stereochemistry

Synthesis of Aryl Lactones

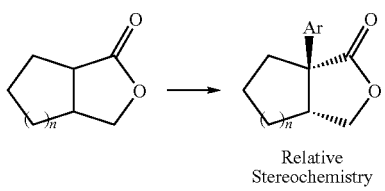

Relative Stereochemistry

General Procedure K: To a solution of lactone (5 mmol) and Pd(dba)$_2$ (5 mol %) and toluene (6 mL) which was stirring under nitrogen in a sealed vial, was added tri-t-butylphosphine (1 M in toluene, 5 mol %), LiHMDS (1M in hexanes, 1.2 eq), and the aryl bromide (1.5 eq). The solution was heated in the microwave for fifteen minutes (max temp=140° C.). After cooling, the mixture was diluted with hexane, washed with 3M HCl, and evaporated.

Alternatively, To a flame-dried 250 mL round bottom flask was added Pd(dba)$_2$ (1 mol %) and toluene. The vessel was purged with nitrogen and sealed before tri-t-butylphosphine (1M in toluene, 1.1 mol %) was added via syringe followed by the aryl bromide (51.27 mmol) as a solution in toluene (15 mL). LiHMDS (1 M in hexanes, 1.3 eq) was added and the solution was stirred at ambient temperature for 15 min. The lactone (1.3 eq) was added dropwise as a solution in toluene (20 mL). The mixture was allowed to stir at ambient temperature overnight (16 h) and then partitioned betweeen hexane and, in succession, 10% aqueous HCl, 10% aqueous K$_2$CO$_3$, and brine. The volatile components were removed in vacuo to give the crude arylated lactone.

(2-(3,4-dichlorophenyl)-2-((ethylamino)methyl)-cyclohexyl)methanol (169)

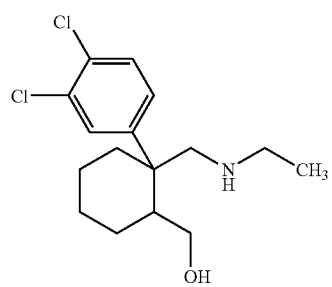 [SMILES: CCNCC1(c2ccc(Cl)c(Cl)c2)CCCCC1CO]

169 E1, 169 E2

(a) Synthesis of racemic 7a-(3,4-dichlorophenyl) hexahydroisobenzofuran-1(3H)-one The title compound was prepared in 30% yield according to General Procedure K as a pale-yellow oil. GCMS $R_t$ (SCM) =13.0 min; m/z=284 (M+). $^1$H NMR (CDCl$_3$, δ): 7.50 (d, J=2.3 Hz, 1H), 7.43 (d, J=8.5 Hz, 1H), 7.25 (dd, J=2.3, 8.5 Hz, 1H), 4.05 (dd, J=4.9, 8.9 Hz, 1H), 3.94 (dd, J=2.4, 8.9 Hz, 1H), 2.8 (m, 1H), 2.2 (m, 1H), 2.0 (m, 1H), 1.8-1.3 (m, 6H). $^{13}$C NMR (CDCl$_3$, δ, mult): 177.7(0), 140.7(0), 133.0(0), 131.7(0), 130.7(1), 128.6(1), 125.9(1), 70.1(2), 51.7(1), 40.5 (2), 34.0(2), 26.9(2), 23.0(2), 22.9(2).

(b) (2-(3,4-dichlorophenyl)-2-((ethylamino)methyl)-cyclohexyl)methanol

The title compound was prepared from racemic 7a-(3,4-dichlorophenyl)hexahydroisobenzofuran-1(3H)-one and ethylamine according to General Procedures AA, followed by General Procedure E. The racemic aminol was separated using a chiral column (Chiracel OD column; 95:5:0.1 hexanes:IPA:DEA, λ=254 nm, 1 mL/min) to give the fast moving enantiomer 169 E1 ($R_t$=7.5 min) and the slow moving enantiomer 169 E2 ($R_t$=9.7 min). LCMS $R_t$=7.88 min, m/z=316 (M+1). $^1$H NMR (CDCl$_3$, δ): 7.4 (m, 2H), 7.17 (dd, J=2.4, 8.5 Hz, 1H), 3.7 (m, 2H), 3.10 (d, J=12.3 Hz, 1H), 2.71 (d, J=12.3 Hz, 1H), 2.6 (m, 2H), 2.3 (m, 1H), 1.9-1.3 (m, 8H), 1.04 (t, J=7.2 Hz, 3H). $^{13}$C NMR (CDCl$_3$, δ, mult): 146.5(0), 133.1

(0), 130.8(1), 130.0(0), 128.5(1), 125.7(1), 63.2(2), 53.6(br, 2), 45.4(0), 43.9(2), 41.9(1), 39.8(br, 2), 26.1(2), 24.8(2), 22.0(2), 14.5(3).

cis-(2-(3,4-dichlorophenyl)-2-((methylamino)methyl)-cyclohexyl)methanol (170)

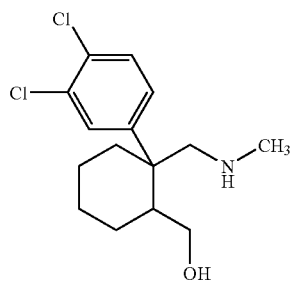 [SMILES: CNCC1(c2ccc(Cl)c(Cl)c2)CCCCC1CO]

170 E1, 170 E2

The title compound was prepared from racemic 7a-(3,4-dichlorophenyl)-hexahydroisobenzofuran-1(3H)-one and methylamine according to General Procedures AA and E. The racemic aminol was separated using a chiral column (Chiracel OD column; 95:5:0.1 hexanes:IPA:DEA, λ=254 nm, 1mL/min) to give the fast moving enantiomer 170 E1 ($R_t$=9.0 min) and the slow moving enantiomer 170 E2 ($R_t$=11.5 min). LCMS $R_t$=6.46 min, m/z=302 (M+1). $^1$H NMR (CDCl$_3$, δ): 7.42-7.40 (m, 2H), 7.18 (dd, J=2.4, 8.5 Hz, 1H), 3.7 (m, 2H), 3.05 (d, J=12.3 Hz, 1H), 2.67 (d, J=12.3 Hz, 1H), 2.35 (s, 3H), 2.0-1.2 (m, 9H). $^{13}$C NMR (CDCl$_3$, δ, mult): 146.4(0), 133.0(0), 130.8(1), 130.0(0), 128.5(1), 125.7 (1), 63.2(2), 62.5(2), 45.4(2), 42.4 (0), 41.8(1), 36.0(3), 26.1 (2), 24.8(2), 22.0(2).

cis-(2-((dimethylamino)methyl)-2-phenylcyclohexyl)methanol (171)

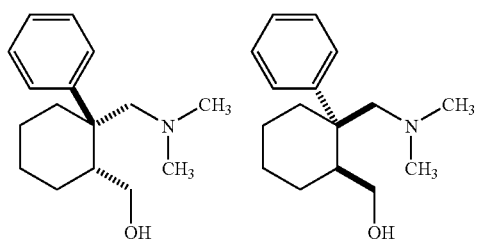

171 E1, 171 E2

(a) Synthesis of 7a-Phenyl-hexahydro-isobenzofuran-1-one

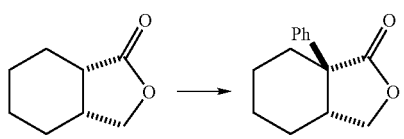

The title compound was prepared from hexahydro-isobenzofuran-1-one (10 g, 1.3 eq) and phenyl bromide (5.4 mL, 51.27 mmol) according to General Procedure K. It was obtained as a clear oil (7.40 g, 67%). HPLC $R_t$ (5-100-8)=9.8 min. $^1$H NMR (CDCl$_3$, δ): 7.4-7.2 (m, 5H), 4.05 (dd, 1H), 3.90 (dd, 1H), 2.8 (m, 1H), 2.3 (m, 1H), 2.0 (m, 1H), 1.8-1.3 (m, 6H). $^{13}$C NMR (CDCl$_3$, δ, mult): 178.6 (0), 140.5 (0), 128.8 (1), 127.3 (1), 126.3 (1), 70.3 (2), 52.5 (0), 41.0 (1), 34.2 (2), 27.5 (2), 23.4 (2), 23.2 (2).

(b) Synthesis of 2-Hydroxymethyl-1-phenyl-cyclohexanecarboxylic acid dimethylamide

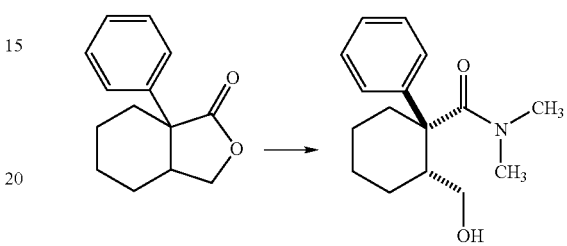

The amide was synthesized from the above lactone according to General Procedure AA. The crude product was purified by silica gel column chromatography to give a clear oil (239 mg, 100%). $^1$H NMR (CDCl$_3$, δ): 7.4-7.0 (m, 5H), 5.4 (bs, 1H), 3.5-3.2 (m, 4H), 3.0 (m, 1H), 2.6 (m, 1H), 2.4 (m, 1H), 2.2 (m, 1H), 2.1 (m, 1H), 1.9-1.7 (m, 3H), 1.6-1.3 (m, 3H), 1.17 (t, 3H), 0.90 (t, 3H). $^{13}$C NMR (CDCl$_3$, δ, mult): 175.5 (0), 142.9 (0), 128.7 (br), 126.8 (1), 63.1 (2), 57.3 (0), 53.3 (1), 43.1 (2), 41.1 (2), 35.2 (2), 26.7 (2), 26.6 (2),. 23.4 (2), 13.0 (3), 12.1 (3).

(c) Synthesis of cis-(2-((dimethylamino)methyl)-2-phenylcyclohexyl)methanol

The title compound was synthesized from the above amide according to General Procedure E. The enantiomeric amines were separated on a Chiracel OD semiprep column (95:5:0.05 Hex/IPA/DEA) to give the fast-moving enantiomer 171 E1 (6.6 mg, 5.4%) and the slow-moving enantiomer 171 E2 (6.0 mg, 4.9%). LCMS $R_t$=5.84 min, m/z=248 (M+1). $^1$H NMR (CDCl$_3$, δ): 7.42 (d, J=7.7 Hz, 2H), 7.31 (t, J=7.8 Hz, 2H), 7.18 (t, J=7.3 Hz, 1H), 3.95 (dd, J=6.6, 11.5 Hz, 1H), 3.83 (d, J=11.5 Hz, 1H), 2.96 (d, J=13.5 Hz, 1H), 2.6 (m, 1H), 2.53 (d, J=13.5 Hz, 1H), 1.99 (s, 6H), 1.9-1.1 (m, 8H). $^{13}$C NMR (CDCl$_3$, δ): 128.0, 127.0, 125.6, 64.2, 46.6, 45.3, 41.6, 26.8, 24.2, 22.1.

cis-(2-(3,4-dichlorophenyl)-2-((dimethylamino)methyl)cyclohexyl)methanol (172)

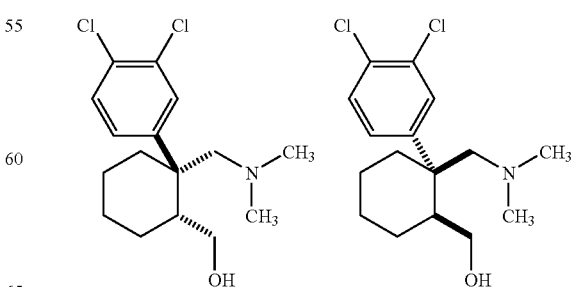

172 E, 172 E2

Powdered LAH (76 mg, 4 eq) was added to a solution of 1-(3,4-dichlorophenyl)-2-(hydroxymethyl)-N,N-dimethyl-cyclohexanecarboxamide (0.5 mmol) in THF (5 mL). After one hour at ambient temperature, the reaction was quenched with aqueous ammonium chloride, washed with MTBE, basicified with KOH, extracted with MTBE and evaporated to give the crude amine (108 mg) as a yellow-black oil. The crude oil was filterd (aminopropyl) and the enantiomers were separated on a Chiracel OD column (98:2:0.1 Hex/IPA/DEA) to give the fast-moving enantiomer 172 E1 (30.1 mg, 19%) and the slow-moving enantiomer 172 E2 (26.6 mg, 17%). LCMS $R_t$=8.33 min, m/z=316 (M+1). $^1$H NMR (CDCl$_3$, δ): 7.50 (d, J=2.4 Hz, 1H), 7.38 (d, J=8.6 Hz, 1H), 7.26 (dd, J=2.4, 8.6 Hz, 1H), 3.92 (dd, J=6.5, 11.6 Hz, 1H), 3.77 (dd, J=1.2, 11.7 Hz, 1H), 2.95 (d, J=13.7 Hz, 1H), 2.5 (m, 2H), 2.02 (s, 6H), 1.8-1.1 (m, 8H). $^{13}$C NMR (CDCl$_3$, δ, mult): 147.6, 132.2, 129.9, 129.6, 129.3, 126.6, 63.9, 46.8, 45.4, 41.8, 38.7, 29.7, 26.5, 23.9, 22.0.

cis-(2-(3,4-dichlorophenyl)-2-((methylamino)methyl)-cyclopentyl)methanol (173)

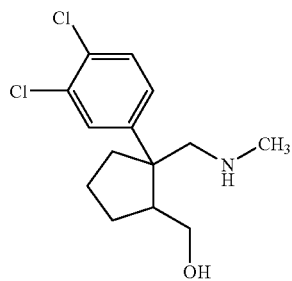 [SMILES: CNCC1(c2ccc(Cl)c(Cl)c2)CCCC1CO]

rac 173, 173 E1, 173 E2

(a) Synthesis of cis-6a-(3,4-dichlorophenyl)hexahydro-1H-cyclopentakffuran-1-one

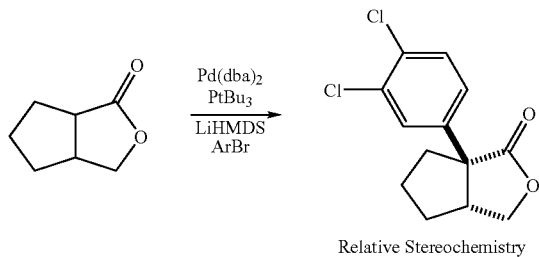

Relative Stereochemistry

The title compound was prepared from lactone (630 mg, 5 mmol) and dichlorophenylbromide (1.69 g, 1.5 eq) according to General Procedure K. The crude product was separated by silica gel column chromatography to give the lactone (578 mg, 44%) as a pale-brown oil. TLC $R_f$(25% EA/hex) =0.34. GC-MS $R_t$=12.48 min, m/z=270 (M+). $^1$H NMR (CDCl$_3$, δ): 7.49 (d, J=2.3 Hz, 1H), 7.41 (d, J=8.4 Hz, 1H), 7.24 (dd, J=2.3, 8.4 Hz, 1H), 4.50 (dd, J=7.3, 9.6 Hz, 1H), 4.14 (dd, J=2.2, 9.6 Hz, 1H), 3.1 (m, 1H), 2.60 (ddd, J=3.0, 6.4, 12.5 Hz, 1H), 2.2-1.6 (m, 5H). $^{13}$C NMR (CDCl$_3$, δ, mult): 179.7(0), 140.6(0), 132.8(0), 131.5(0), 130.6(1), 128.3(1), 125.8(1), 72.7(2), 59.4(0), 46.2(1), 40.3(2), 34.4(2), 25.8(2).

(b) Synthesis of cis-(2-(3,4-dichlorophenyl)-2-((methylamino)methyl)-cyclopentyl)methanol The title compound was prepared from the above lactone and methylamine according to General Procedures AA and E to give racemic 173, which was separated by chiral HPLC (AD column; 2:3:95:0.1 MeOH:EtOH:Hex:DEA) to give the fast moving enantiomer 173 E1 (6.5 min) and the slow moving enantiomer 173 E2 (8.5 min). LCMS (14 min) $R_t$=5.98 min, m/z=288 (M+1). $^1$H NMR (CDCl$_3$, δ): 7.6 (m, 1H), 7.4 (m, 2H), 6.8 (bs, 1H), 3.7 (m, 2H), 2.8 (m, 3H), 2.32 (s, 3H), 2.1-1.2 (m, 6H). $^{13}$C NMR (CDCl$_3$, δ, mult): 147.3(0), 132.5(0), 130.2(1), 130.1(1), 129.3(0), 126.9(1), 63.7(2), 58.3(2), 52.9(0), 47.1(1), 41.6(2), 36.0(3), 28.6(2), 22.1(2).

2.8. Synthesis of 2-Methyl-Cycloalkylamines

(±)-cis-(1-(3,4-dichlorophenyl)-2-methylcyclohexyl)methanamine hydrochloride (174)

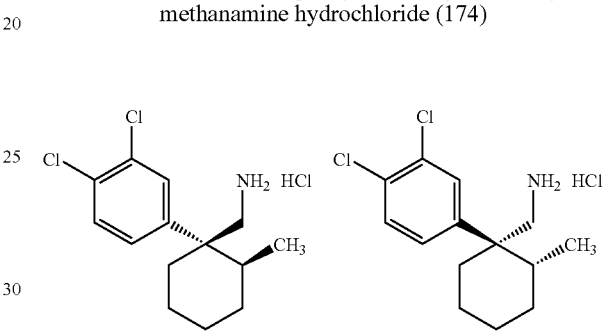

The title compound was synthesized from 1-(3,4-dichlorophenyl)-2-methylcyclohexanecarbonitrile (159 mg, 0.60 mmol) according to General Procedure E, followed by HCl salt formation. The crude HCl salt was recrystallized from CH$_3$CN (1.5 mL) to give the title compound as white crystals. HPLC $R_t$=8.86 min; $^1$H NMR (400 mHz, MeOH-d$^4$) 7.60-7.59 (m, 1H), 7.58-7.50 (m, 1H), 7.39-7.35 (m, 1H), 3.32-3.13 (m, 2H), 2.13-2.04 (m, 1H), 1.73-1.33 (m, 8H), 0.86 (d, J=6.96 Hz, 3H); LC-MS 8.8 min, (M+1)$^+$ 272 @9.0 min.

(±) cis-1-(1-(3,4-dichlorophenyl)-2-methylcyclohexyl)-N,N-dimethylmethanamine hydrochloride (175)

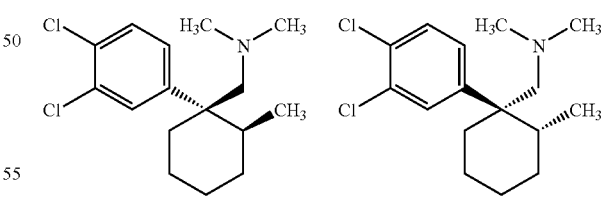

((+/−)-(cis)-1-(3,4-dichlorophenyl)-2-methylcyclohexyl)-methanamine free base (110 mg, 0.41 mmol), paraformaldehyde (ca. 100 mg), polymer bound cyanoborohydride (762 mg, 2.13 mmol/g, 1.62 mmol) and concentrated AcOH (1 mL) were suspended in 10 mL THF. The solution was shaken overnight, then filtered and diluted with EtOAc. The organic phase was washed with 3M NaOH (2×20 mL) and brine (20 mL), dried (Na$_2$SO$_4$), filtered and concentrated. The crude material was dissolved in Et$_2$O (3 mL) and HCl (ca. 1.5 mL, 2.0 M in Et$_2$O) was added. A white ppt. formed immediately.

The crude HCl salt was recrystallized from EtOAc (1.5 mL) to give pure ((+/−)-cis-1-(3,4-dichlorophenyl)-2-methylcyclohexyl)-N,N-dimethylmethanamine hydrochloride as white crystals. HPLC $R_f$=9.1 min; $^1$H NMR (400 mHz, MeOH-d$^4$) 7.73 (d, J=2.2 Hz, 1H), 7.56 (d, J=8.8 Hz, 1H), 7.51-7.48 (m, 1H), 3.58-3.54 (m, 1H), 3.42-3.39 (m, 1H), 2.64-2.52 (m, 6H), 2.20-2.18 (m, 2H), 1.83-1.76 (m, 1H), 1.63-1.42 (m, 6H), 1.01 (d, J=7.33 Hz, 3H); LC-MS 10.1 min, (M+1)$^+$ 300 @ 10.3 min.

(±) cis-1-(1-(3,4-dichlorophenyl)-2-methylcyclohexyl)-N-methylmethanamine (176)

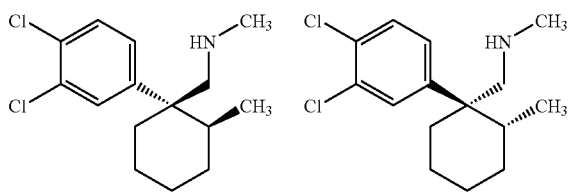 [SMILES: CNC[C@]1(c2ccc(Cl)c(Cl)c2)CCCC[C@@H]1C ; CNC[C@@]1(c2ccc(Cl)c(Cl)c2)CCCC[C@H]1C]

((+/−)-(cis)-1-(3,4-dichlorophenyl)-2-methylcyclohexyl)-methanamine free base (421 mg, 1.55 mmol) was dissolved in 3:1 THF:H$_2$O (8 mL) and K$_2$CO$_3$ (322 mg, 2.33 mmol) was added. The solution was stirred for 2 minutes, then BOC$_2$O (338 mg, 1.55 mmol) was added. After 2 h, the solution was poured into H$_2$O and the layers were separated. The organic layer was washed with H$_2$O (1×20 mL) and brine (1×20 mL), dried (Na$_2$SO$_4$), filtered and concentrated. A portion of the N-BOC amine (113 mg) was used directly in the next reaction. LAH (34 mg, 0.9 mmol) was suspended in anhydrous THF (2 mL) and the amine (113 mg, 0.30 mmol) in anhydrous THF (3 mL) was added dropwise. The solution was heated in the MW (160° C., 5 min, FHT). The crude reaction was quenched with 6M HCl (10 mL). The solution was washed with EtOAc (2×20 mL) and the EtOAc washes were discarded. After the pH of the aqueous phase was adjusted to 12 with 3M NaOH, it was washed again with EtOAc (3×20 mL). The combined "second" organic washes were dried (Na$_2$SO$_4$), filtered and concentrated. The crude amine was purified by PTLC with 10% MeOH/CH$_2$Cl$_2$ to give ((+/−)-(cis)-1-(3,4-dichlorophenyl)-2-methylcyclohexyl)-N-methylmethanamine as a clear oil. HPLC $R_f$=8.91 min; $^1$H NMR (400 mHz, CDCl$_3$) 7.48 (d, J=2.57 Hz, 1H), 7.39-7.36 (m, 1H), 7.25-7.23 (m, 1H), 2.71 (s, 2H), 2.38 (s, 3H), 2.11-2.03 (m, 1H), 1.85-1.73 (m, 2H), 1.70-1.60 (m, 1H), 1.53-1.33 (m, 5H), 0.83 (d, J=6.98 Hz, 3H); LC-MS 8.70 min, (M+1)$^−$ 286 @ 8.97 min.

(±) cis-N-((1-(3,4-dichlorophenyl)-2-methylcyclohexyl)methyl)ethanamine (177)

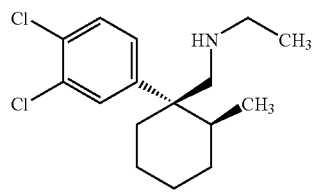

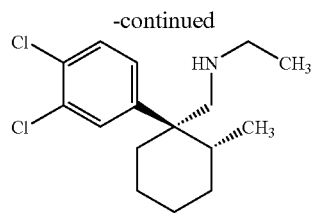

t-Butyl (1-(3,4-dichlorophenyl)-2-methylcyclohexyl)-methylcarbamate (97 mg, 0.261 mmol) was dissolved in anhydrous DMF (3 mL) and NaH (60% dispersion in mineral oil, 21 mg, 0.52 mmol) was added. The solution was heated via MW (75° C., 5 min), and cooled to RT. Ethyl iodide (62 mL, 0.78 mmol) was added and the solution was heated via MW (100° C., 20 min). The yellow mixture was poured into H$_2$O (20 mL) and washed with Et$_2$O (3×20 mL). The combined organic washes were dried (Na$_2$SO$_4$), filtered and concentrated. Purification by silica gel column chromatography with 0-10% EtOAc/hexanes gave tert-butyl (1-(3,4-dichlorophenyl)-2-methylcyclohexyl)methylethylcarbamate (32 mg, 0.08 mmol) as a clear oil. tert-butyl (1-(3,4-dichlorophenyl)-2-methylcyclohexyl)methylethylcarbamate (32 mg, 0.08 mmol) was dissolved in 1:1 CH$_2$Cl$_2$:TFA (3 mL) and stirred for 2 h then concentrated. The crude amine was dissolved in EtOAc (20 mL) and washed with 3M NaOH (2×20 mL) and brine (20 mL), then dried (Na$_2$SO$_4$), filtered and concentrated. The crude amine was purified by PTLC with 10% MeOH/CH$_2$Cl$_2$ to give the title compound as a clear oil. HPLC $R_f$=9.17 min; $^1$H NMR (400 mHz, CDCl$_3$) 7.51 (d, J=2.2 Hz, 1H), 7.37 (d, J=8.43 Hz, 1H), 7.27-7.25 (m, 1H), 2.76 (d, J=1.47 Hz, 2H), 2.59 (q, 2H), 2.08-2.05 (m, 1H), 1.78-1.77 (m, 1H), 1.67-1.64 (m, 1H), 1.52-1.36 (m, 5H), 1.05 (at, 3H), 0.81 (d, J=6.97 Hz, 3H); LC-MS 8.94 min, (M+1)$^+$ 300 @9.17 min.

Example 3

Synthesis of 3-Substituted Cyclohexylamine Analogs

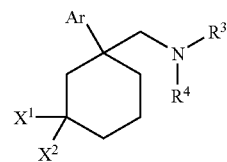

3.1. Synthesis of 3-(aminomethyl)-3-(3,4-dichlorophenyl)-cyclohexanol analogs

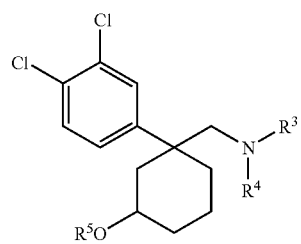

The synthesis of 3-(aminomethyl)-3-(3,4-dichlorophenyl) cyclohexanol is outlined in Scheme 30, below. Reaction of 3-ethoxy-2-cyclohexen-l-one 178 with 3,4-dichlorophenyl-magnesium bromide in THF followed by quenching the Grignard mixture with diluted $H_2SO_4$ gave 3-(3,4-dichlorophenyl)-2-cyclonexen-1-one 179. Addition of $CN^-$ to the $\alpha,\beta$-unsaturated ketone by heating 179 with KCN in the presence of $NH_4Cl$ in aqueous DMF afforded the cyano ketone 180 in 30% yield. The ketone was reduced to the alcohol 181 using $NaBH_4$ in ethanol at 0° C. The major product was the cis diastereomer and the minor product was the trans diastereomer. The amine 182 was formed through reduction of the nitrile with $BH_3$-THF at room temperature overnight in 83% yield. Protection of the amino group with Boc-anhydride afforded 183. The diastereomers were then separated using reverse phase HPLC.

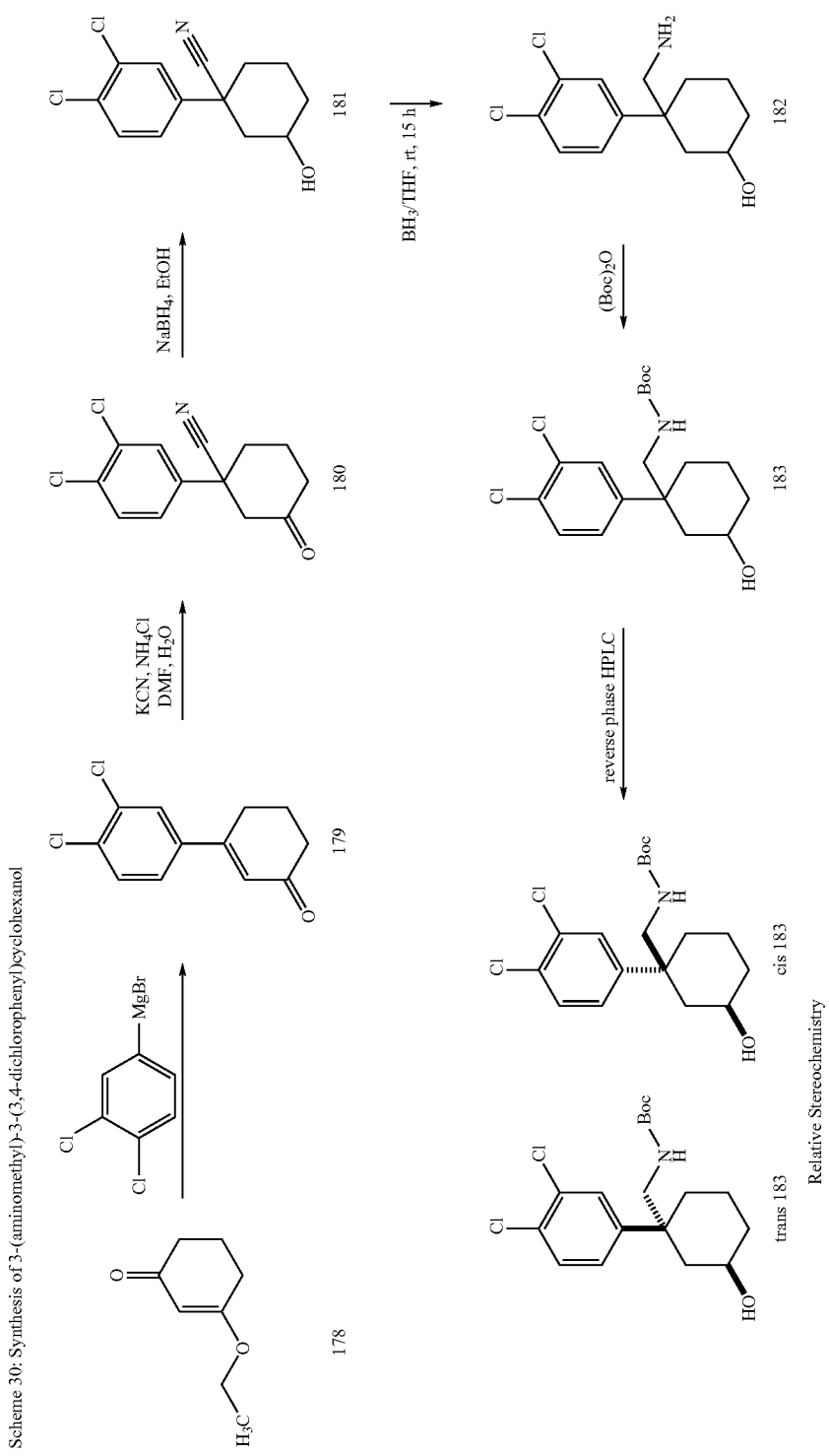
Scheme 30: Synthesis of 3-(aminomethyl)-3-(3,4-dichlorophenyl)cyclohexanol

3.1.1. Preparation of Boc Protected Primary Amines 14

The primary amine 182 (mixture of cis and trans diastereomers, 1.8 g, 6.57 mmol) was added to a 10% triethylamine solution in MeOH (40 ml). To this mixture was added di-tert-butyl dicarbonate (1.72 g, 7.88 mmol) with vigorous stirring. The mixture was stirred at room temperature for 3 hours. The solvent was then removed in vacuo. The residue was dissolved in EtOAc (70 ml), washed with saturated $K_2CO_3$ solution (3×40 ml), 5% HCl (2×40 ml), brine (40 ml), dried over $Na_2SO_4$, and evaporated. The residue was purified by silica gel column chromatography ($MeOH/CH_2Cl_2$, MeOH from 0 to 5%) to yield 183 (2.45 g, 97%) as a clear oil. The diastereomers of 183 were separated (C-18 column, 50% acetonitrile, 50% water) to give the the cis isomer cis 183 (1.83 g) and the trans isomer trans 183 (0.45 g).

cis 183: $^{13}$H NMR ($CDCl_3$) δ 1.19-1.31 (m, 4H), 1.37 (s, 9H), 1.68-1.72 (m, 1H), 1.87-1.90 (m, 1H), 2.13 (d, J=12.8 Hz, 1H), 2.41 (d, J=12.8 Hz, 1H), 2.58 (brs, 1H), 3.09-3.22 (m, 2H), 3.54-3.66 (m, 1H), 4.72 (t, J=6.0 Hz, 1H), 7.18-7.21 (m, 1H), 7.40-7.49 (m, 2H), $^{13}$C NMR (CDCl3) δ 20.2, 28.5, 32.7, 35.8, 42.0, 44.8, 53.5, 66.8, 79.7, 126.7, 129.4, 130.6, 130.8, 133.0, 143.9, 156.3. ESI MS m/z 374.

trans 183: $^1$H NMR ($CDCl_3$) δ 1.21-1.38 (m, 4H), 1.39 (s, 9H), 1.60-1.66 (m, 1H), 1.87-1.90 (m, 1H), 1.98 (d, J=10.8 Hz, 1H), 2.26 (d, J=10.8 Hz, 1H), 2.76 (brs, 1H), 1H), 3.30-3.45 (m, 2H), 398-4.08 (m, 1H), 7.06-7.18 (m, 1H), 7.39-7.43 (m, 2H). $^{13}$C NMR ($CDCl_3$) δ 20.4, 28.5, 33.0, 35.1, 42.1, 43.1, 46.6, 67.1, 79.7, 125.6, 128.4, 130.5, 130.6, 132.8, 147.6, 156.2. ESI MS m/z 374.

3.1.2. Chiral HPLC Separation of Enantiomers

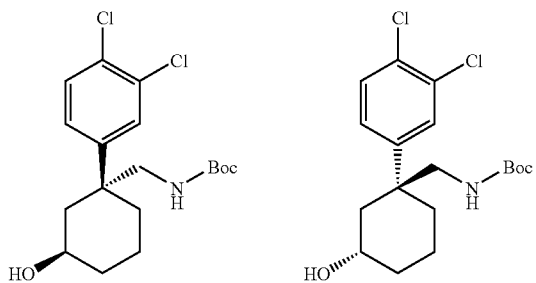 [SMILES: CC(C)(C)OC(=O)NC[C@]1(c2ccc(Cl)c(Cl)c2)CCC[C@@H](O)C1 ; CC(C)(C)OC(=O)NC[C@@]1(c2ccc(Cl)c(Cl)c2)CCC[C@H](O)C1]

The enantiomers of trans 183 were separated using a preparative HPLC procedure (ChiralPak OD column; hexanes: IPA=90:10; 8 ml/min; λ=280 nm) to give trans 183 E1 (retention time=15 min) and trans 183 E2 (retention time=21 min). The absolute configuration of the chiral centers was not determined.

3.1.3. Preparation of Primary Amines 182 (Removal of Boc-group)

General Procedure U: To the solution of the respective Boc-protected primary amine 183 (e.g., 38 mg, 0.102 mmol) in $CH_2Cl_2$ (e.g., 2 ml) was added TFA (e.g., 2 ml) at 0° C. The mixture was stirred at 0° C. for one hour and the solvent was removed in vacuo. The residue was dissolved in $CH_2Cl_2$ (10 ml), washed with saturated $K_2CO_3$ solution (2×3 ml), dried over $Na_2SO_4$, and then filtered through an aminopropyl cartridge. The solvent was removed to give the respective primary amine 182.

The following compounds were prepared following the procedure outlined in General Procedure U, above.

Cis-3-(aminomethyl)-3-(3,4-dichlorophenyl)cyclohexanol (184)

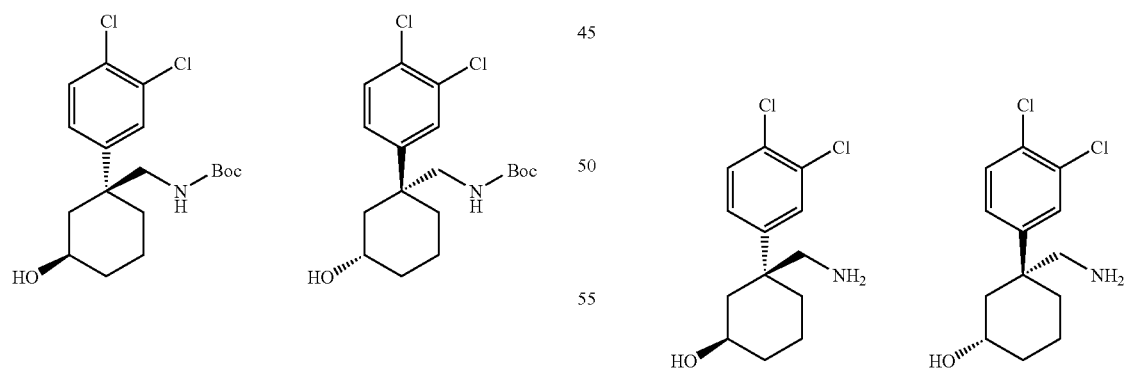

The enantiomers of cis 183 were separated using a preparative HPLC procedure (ChiralPak OD column; hexanes: IPA=90:10; 8 ml/min; λ=280 nm) to give cis 183 E1 (retention time=10 min) and cis 183 E2 (retention time=18 min). The absolute configuration of the chiral centers was not determined.

184 E1, 184 E2

$^1$H NMR ($CDCl_3$): δ1.21-1.39 (m, 4H), 1.42-1.52 (m, 2H), 1.63-1.70 (m, 1H), 1.80-1.90 (m, 1H), 2.20 (d, J=12.8 Hz, 1H), 2.43 (d, J=12.8 Hz, 1H), 2.62 (s, 2H), 3.51-3.60 (m, 1H), 7.16-7.20 (m, 1H), 7.40-7.49 (m, 2H). $^{13}$C NMR ($CDCl_3$) δ

20.5, 32.8, 36.2, 42.5, 45.5, 57.0, 67.0, 126.9, 129.5, 130.7, 130.8, 133.0, 144.3.ESI MS m/z 274.

Trans-3-(aminomethyl)-3-(3,4-dichlorophenyl)cyclohexanol (185)

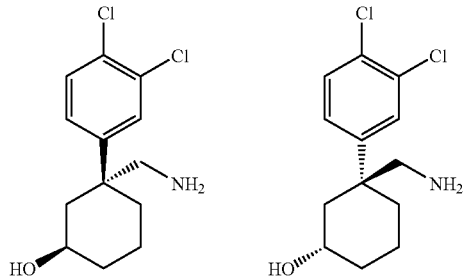 [SMILES: NC[C@]1(c2ccc(Cl)c(Cl)c2)CCC[C@@H](O)C1 ; NC[C@@]1(c2ccc(Cl)c(Cl)c2)CCC[C@H](O)C1]

185 E1, 185 E2

$^1$H NMR (CDCl$_3$): δ 1.21-1.30 (m, 4H), 1.42-1.58 (m, 3H), 1.77-1.82 (m, 1H), 2.00-2.05 (m, 2H), 2.34-2.40 (m, 1H), 2.85 (d, J=13.2 Hz, 1H), 2.90 (d, J=13.2 Hz, 1H), 3.85-3.93 (m, 1H), 7.18-7.20 (m, 1H), 7.40-7.43 (m, 2H). $^{13}$C NMR (CDCl$_3$) δ 20.3, 32.6, 35.3, 42.2, 48.6, 67.4, 125.8, 128.6, 130.4, 132.7, 133.9, 147.9.ESI MS m/z 274.

3.1.4.Preparation of Secondary Amines 15

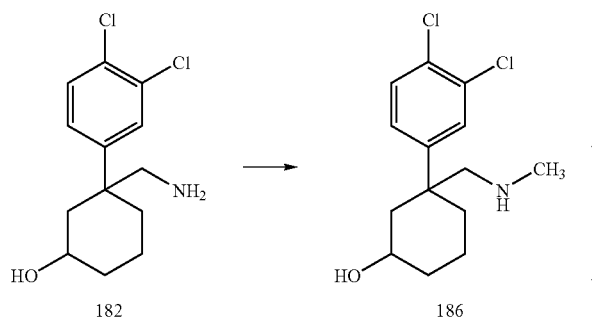

General Procedure F1: A solution of acetic anhydride (e.g., 0.118 ml, 1.254 mmol) and formic acid (e.g., 0.058 ml, 1.546 mmol) in THF (e.g., 1.5 ml) was heated in a microwave at 100° C. for 5 min. After cooling to room temperature, a solution of the respective primary amine 182 (e.g., 107 mg, 0.392 mmol) in THF (e.g., 1.5 ml) was added. The mixture was heated in the microwave at 100° C. for 5 min. The solvent was then removed in vacuo. The residue was dissolved in THF (e.g., 1.5 ml), and BH$_3$-THF (e.g., 1 ml, 1.0 mmol) was added. The mixture was heated in the microwave at 60° C. for 6 min. The reaction was then quenched by the addition of MeOH (e.g., 2 ml) and 6N HCl (e.g., 1 ml). The solvent was removed in vacuo. To the residue was added 1 N NaOH solution to pH 12. The aqueous solution was extracted with CH$_2$Cl$_2$ (e.g., 3×10 ml). The combined organic phases were dried over Na$_2$SO$_4$ and evaporated in vacuo. The residue was purified by silica gel column chromatography (MeOH/CH$_2$Cl$_2$, 0-10%) to give the respective secondary amine 186.

The following compounds were prepared according to the procedures outlined in General Procedure F1, above.

Cis-3-(3,4-dichlorophenyl)-3-amethylamino)methyb-cyclohexanol (187)

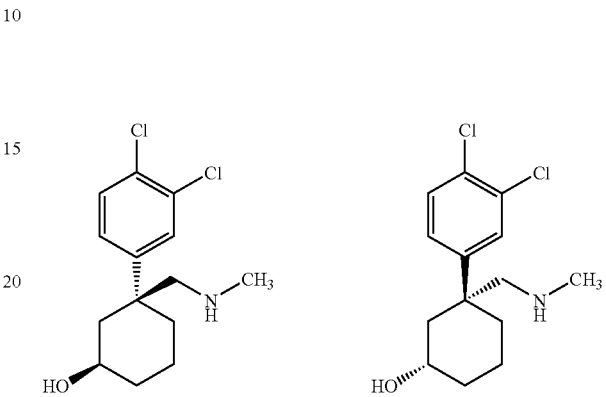

187 E1, 187 E2

$^1$H NMR (CDCl$_3$): δ 1.37-1.42 (m, 1H), 1.49-1.58 (m, 1H), 1.63-1.70 (m, 2H), 1.90-2.05 (m, 1H), 2.28 (d, J=12.8 Hz, 1H), 2.46 (s, 3H), 2.85 (d, J=12.4 Hz, 1H), 3.38 (d, J=12.4 Hz, 1H), 3.63-3.78 (m, 2H), 3.88-3.92 (m, 1H), 7.23 (d, J=7.2 Hz, 1H), 7.40-7.49 (m, 2H). $^{13}$C NMR (CDCl$_3$) δ 20.3, 30.1, 33.7, 35.1, 45.5, 61.4, 62.9, 65.9, 126.3, 129.0, 131.2, 131.4, 133.3, 144.1.ESI MS m/z 288.

Trans-3-(3,4-dichlorophenyl)-3-((methylamino)methyl)cyclohexanol (188)

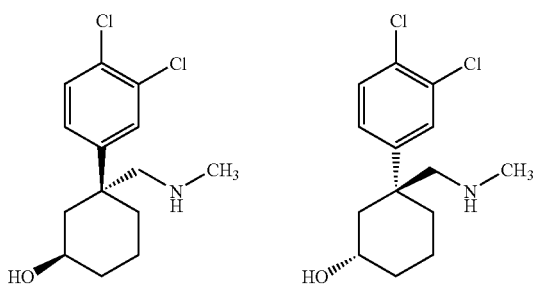 [SMILES: CNC[C@]1(c2ccc(Cl)c(Cl)c2)CCC[C@@H](O)C1 ; CNC[C@@]1(c2ccc(Cl)c(Cl)c2)CCC[C@H](O)C1]

$^1$H NMR (CDCl$_3$): δ 1.15-1.26 (m, 1H), 1.36-1.44 (m, 2H), 1.52-1.63 (m, 1H), 1.76-1.82 (m, 1H), 2.03 (t, J=13.2 Hz, 1H), 2.29 (s, 3H), 2.41-2.45 (m, 1H), 2.68 (d, J=12.0 Hz, 1H), 2.78 (d, J=12.0 Hz, 1H), 3.84-3.91 (m, 1H), 7.20 (dd, J=8.4 Hz, 1.6 Hz, 1H), 7.38-7.44 (m, 2H). $^{13}$C NMR (CDCl$_3$) δ 20.7, 33.9, 35.1, 37.4, 42.8, 42.9, 58.4, 67.0, 125.5, 128.3, 130.4, 130.5, 132.7, 148.5.ESI MS m/z 288.

188 E1, 188 E2

3.1.5. Preparation of Tertiary Amines 189

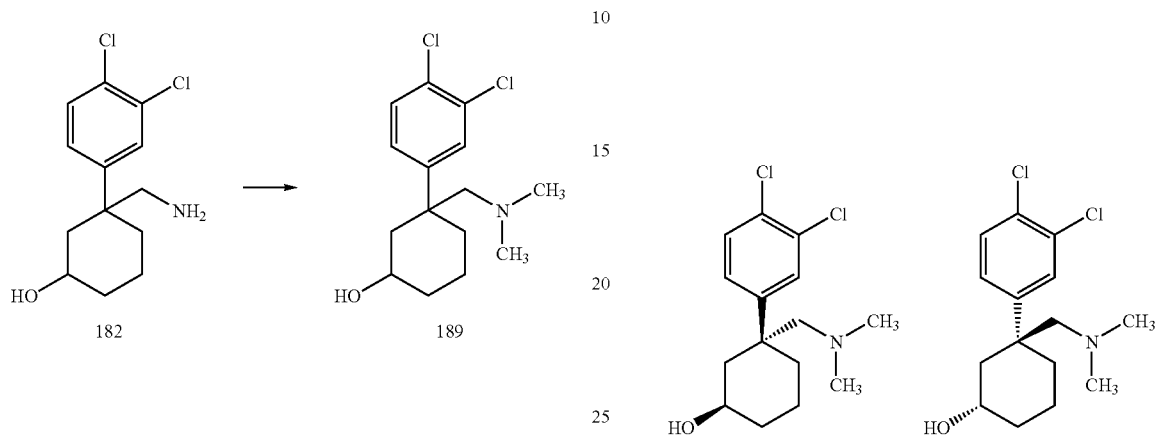

General Procedure D1: A mixture of 37% formaldehyde (e.g., 0.096 ml, 1.183 mmol) and 96% formic acid (e.g., 0.056 ml, 1.183 mmol) in water (e.g., 2 ml) was added to the respective primary amine 182 (e.g., 130 mg, 0.473 mmol) at 0° C. The mixture was heated to 100° C. overnight. The reaction mixture was then washed with hexanes (e.g., 3×10 ml), and evaporated in vacuo. The residue was purified by reverse phase HPLC (C-18 column, $CH_3CN$/water, $CH_3CN$ from 5% to 100%) to give the respective tertiary amine 189.

The following compounds were prepared according to General Procedure D1, above.

Cis-3-(3,4-dichlorophenyl)-3-((dimethylamino)methyl)cyclohexanol (190)

190 E1, 190 E2

$^1$H NMR ($CDCl_3$): δ 1.23-1.36 (m 2H), 1.46-1.53 (m, 1H), 1.59 (dd, J=12.8 Hz, 8 Hz, 1H), 1.68-1.73 (m, 1H), 1.81-1.85 (m, 1H), 2.05 (s, 6H), 2.07-2.10 (m, 1H), 2.27 (d, J=13.6 Hz, 1H), 2.37 (d, J=13.6 Hz, 1H), 2.43 (m, 1H), 2.63 (brs, 1H), 3.59-3.65 (m, 1H), 7.21 (dd, J=8.4 Hz, 2.0 Hz, 1H), 7.37 (d, J=8.4 Hz, 1H), 7.44 (d, J=2.0 Hz, 1H). $^{13}$C NMR ($CDCl_3$) δ 20.2, 33.7, 35.7, 42.2, 45.0, 48.4, 66.9, 73.5, 126.9, 129.4, 129.8, 130.3, 132.5, 146.2. ESI MS m/z 302.

Trans-3-(3,4-dichlorophenyl)-3-((dimethylamino)methyl)cyclohexanol (191)

191 E1, 191 E2

$^1$H NMR ($CDCl_3$) δ 1.16-1.26 (m, 1H), 1.34-1.45 (m, 2H), 1.50-1.61 (m, 1H), 1.75-1.81 (m, 1H), 1.95 (s, 6H), 1.99-2.03 (m, 1H), 2.14 (brs, 1H), 2.40-2.47 (m, 2H), 2.55 (d, J=13.6 Hz, 1H), 3.84-3.91 (m, 1H), 7.21 (dd, J=8.4 Hz, 2.0 Hz, 1H), 7.35 (d, J=8.4 Hz, 1H), 7.45 (d, J=2.0 Hz, 1H). 13C NMR ($CDCl_3$) δ 20.6, 33.8, 35.1, 42.6, 43.0, 48.2, 66.3, 67.7, 125.8, 128.5, 129.8, 130.0, 132.2, 150.0. ESI MS m/z 302.

3.1.6. Synthesis of cis-1-(3,4-dichlorophenyl)-3-methoxycyclohexyl)-methanamine (192)

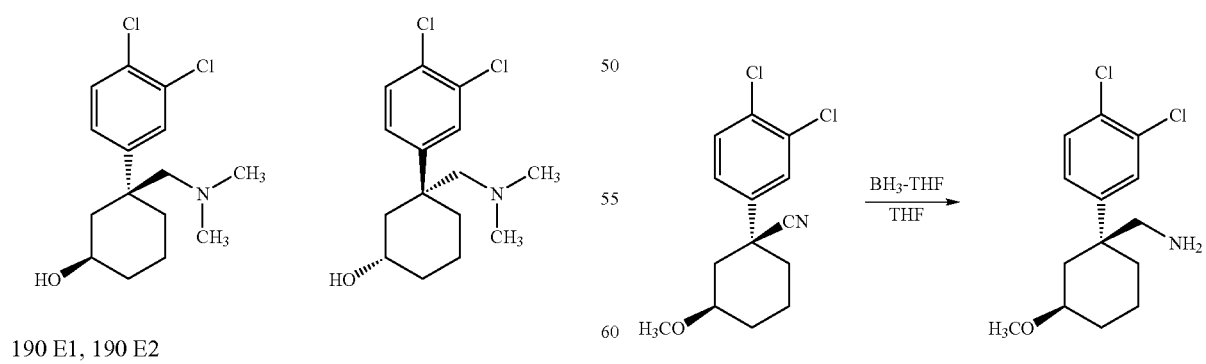

To a solution of 1-(3,4-dichloro-phenyl)-3-methoxy-cyclohexanecarbonitrile (150 mg, 0.53 mmoL) in THF (5 mL) was added $BH_3$·THF (1.0 M, 1.59 mL, 1.59 mmoL). The reaction mixture was stirred overnight before being concentrated. The residue was dissolved in MeOH (3 mL) and subjected to reverse phase column chromatography (CH$_3$CN/ H$_2$O/0.1% Formic acid=5% to 100%) to give the desired product (109 mg, 72%).

3.2. Synthesis of 3-Disubstituted Aryl-Cyclohexylamines

Synthesis of 3-Aminomethyl-3-(3,4-dichloro-phenyl)-1-methyl-cyclohexanol (193)

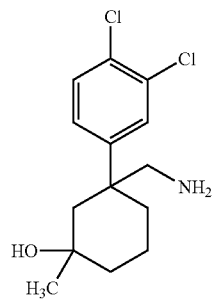 [SMILES: CC1(O)CCCC(CN)(c2ccc(Cl)c(Cl)c2)C1]

The title compound was synthesized from 1-(3,4-dichlorophenyl)-3-oxo-cyclohexanecarbonitrile (1.0 g, 3.7 mmol) according to General Procedure Y, followed by General Procedure E (Scheme 31). The crude product was dissolved in MeOH (4 ML) and subjected to reverse phase column chromatography (CH$_3$CN/H$_2$O/0.1% formic acid=5% to 100%) to give (±) 3-aminomethyl-3-(3,4-dichloro-phenyl)-1-methyl-cyclohexanol (0.57 g, 81%).

Scheme 31: Synthesis of 3-Disubstituted Cyclohexylamines

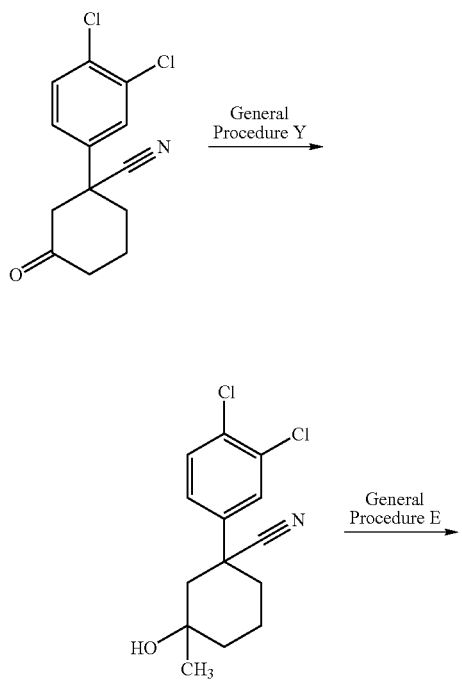

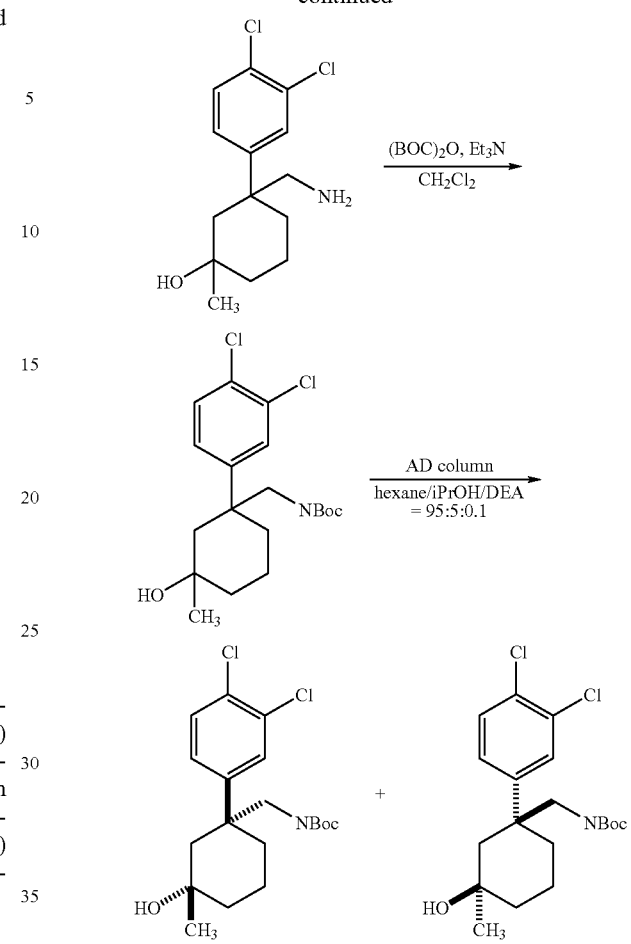

193 E1, 193 E2

To a solution of 3-aminomethyl-3-(3,4-dichloro-phenyl)-1-methyl-cyclohexanol (0.5 g, 1.74 mmoL) in CH$_2$Cl$_2$ (15 mL) was added Et$_3$N (528 mg, 727 mL, 5.22 mmol) and (BOC)$_2$O (567 mg, 2.60 mmol). The reaction mixture was stirred for 2 h at room temperature before being quenched by a saturated NH$_4$Cl solution (10.0 mL). The product was extracted with CH$_2$Cl$_2$ (2×15 mL). The combined extracts were washed with saturated brine, dried and concentrated. The residue was purified by silica gel column chromatography (ethyl acetate/hexane=1:5) to afford (±)tert-butyl (1-(3, 4-dichlorophenyl)-3-hydroxy-3-methylcyclohexyl)-methylcarbamate (0.61 g, 90%). The enantiomers were separated (chiral AD column with hexane/iso-propanol/DEA=95:5: 0.1) to afford the fast moving enantiomer E1 (0.22 g, retention time 4.085 min) and the slow moving enantiomer E2 (0.32 g, retention time 6.051 min). To a solution of the respective enantiomer E1 (200 mg, 0.52 mmol) or E2 (200 mg, 0.52 mmol) in CH$_2$Cl$_2$ (4 mL) was added TFA (2.0 mL). The reaction mixtures were stirred for 0.5 h before being concentrated. The mixtures were each purified by reverse phase column chromatography (CH$_3$CN/H$_2$O) to give the amines 193 E1 and 193 E2 in each 80% yield. $^1$H NMR (400 MHz, CDCl$_3$) δ 8.32 (broad, 1H), 7.58 (d, J=2.0 Hz, 1H), 7.53 (d, J=8.4 Hz, 1H), 7.37 (dd, J=2.0, 8.4 Hz, 1 H), 3.55 (s, 2 H), 2.15 (m, 2 H) 1.88 (m, 1H), 1.74-1.58 (m, 4 H), 1.40 (m, 1 H), 1.21 (m, 3 H); $^{13}$CNMR (100 MHz, CD$_3$OD) δ 146.42, 132.75, 131.01, 130.83, 128.41, 125.97, 69.31, 46.48, 44.85, 40.15, 37.81, 32.81, 32.54, 30.91, 18.17; ESI MS m/z=288.4.

3.3. Synthesis of Chiral 3-Methoxy-Cyclohexylamines

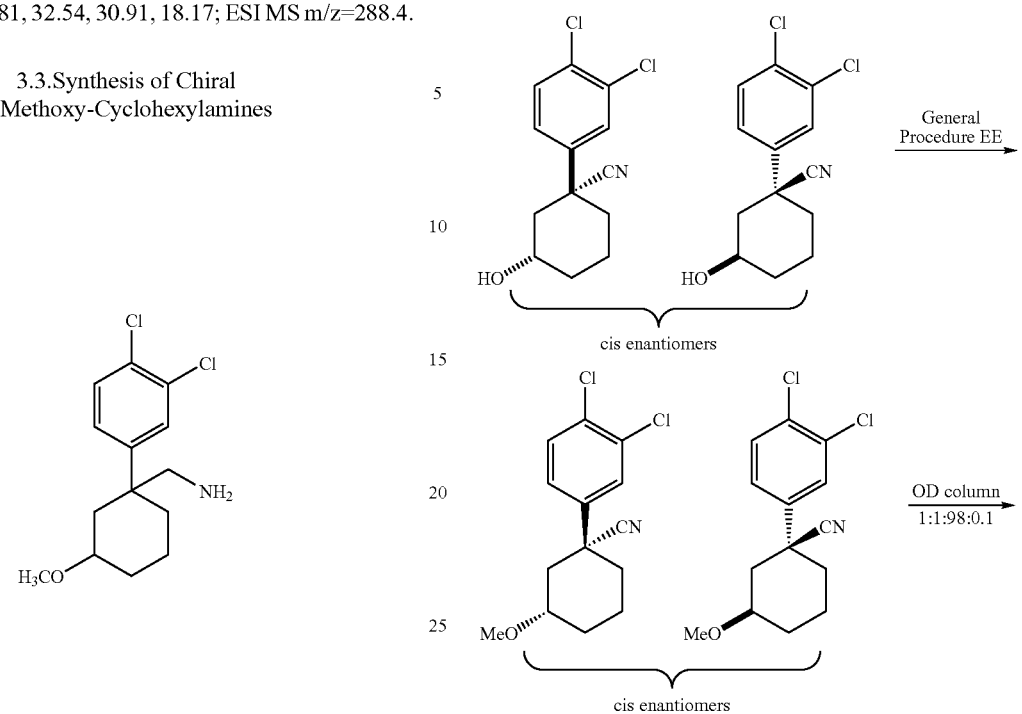

1-(3,4-dichlorophenyl)-3-methoxycyclohexanecarbonitrile was synthesized from 1-(3,4-dichloro-phenyl)-3-oxo-cyclohexanecarbonitrile (1.5 g, 5.61 mmoL) according to General Procedure W, followed by General Procedure EE (Scheme 32). The crude product was purified by silica gel column chromatography (ethyl acetate/hexane=1:7).

The cis enantiomers (170 mg) were separated (chiral OD column; ethanol/methanol/hexane/DEA=1;1:98:0.1) to give the fast moving enantiomer E1 (67 mg) and the slow moving enantiomer E2 (81 mg).

E1 was converted to 192 and E2 (120 mg, 0.42 mmoL) was converted to 194 according to General Procedure E. The crude product was dissolved in MeOH (3 mL) and subjected to reverse phase column chromatography ($CH_3CN/H_2O$/0.1% formic acid=5% to 100%) to give the desired product (90.4 mg, 75%). $^1H$ NMR (400 MHz, $CD_3Cl$) δ 7.46 (m, 2H), 7.20 (m, 1H), 3.02 (s, 3H), 3.08 (m, 1 H), 2.83 (s, 2H), 2.46 (m, 1H), 2.22 (m, 1H), 1.92 (m, 1 H), 1.76 (m, 1 H), 1.46 (m, 2 H), 1.24 (m, 2 H); $^{13}C$ NMR (100 MHz, $CD_3Cl$) δ 141.71, 133.41, 131.46, 131.27, 129.67, 126.84, 75.30, 55.99, 51.80, 42.43, 39.20, 32.66, 31.31, 19.84; ESI MS m/z 288.1.

Scheme 32:

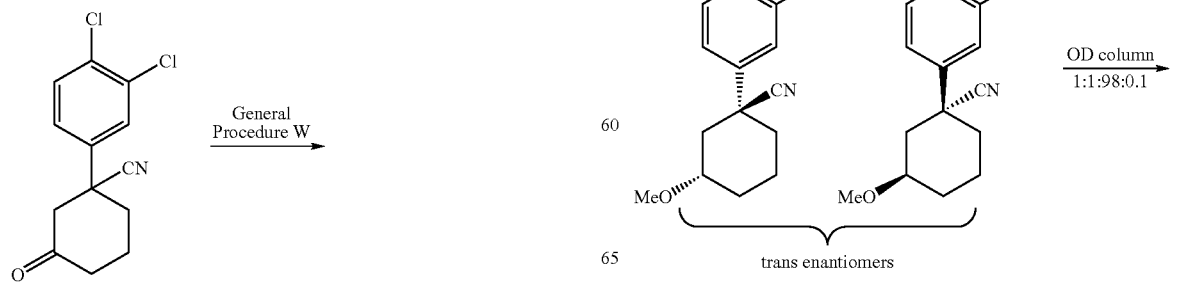

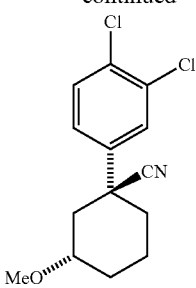

+

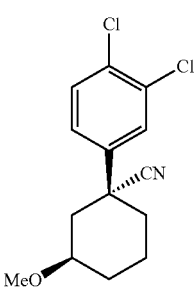

→ General Procedure E → 195 E1
195 E2

Likewise, the methylated trans-enantiomers (100 mg) were separated using a chiral OD column (ethanol/methanol/hexane/DEA=1:1:98:0.1) to give trans E1 (43 mg) and trans E2 (38 mg). Trans E2 (38 mg, 0.13 mmoL) was converted to the respective amine according to General Procedure E. The crude product was dissolved in MeOH (1 mL) and subjected to reverse phase column chromatography (CH$_3$CN/H$_2$O/0.1% formic acid=5% to 100%) to give the desired product 195 E2 (31.2 mg, 82%). $^1$H NMR (400 MHz, CD$_3$Cl) δ 7.47 (m, 2H), 7.22 (m, 1 H), 3.04 (s, 3 H), 3.10 (m, 1 H), 2.85 (s, 2 H), 2.49 (m, 1 H), 2.20 (m, 1H), 1.94 (m, 1H), 1.74 (m, 1H), 1.49 (m, 2H), 1.26 (m, 2H); $^{13}$C NMR (100 MHz, CD$_3$Cl) δ 141.69, 133.52, 131.64, 131.09, 129.78, 127.01, 76.01, 56.109, 51.68, 42.56, 39.40, 32.77, 31.42, 20.01; ESI MS m/z 288.1.

3.4. Synthesis of Secondary and Tertiary Amines

Compounds in Table 4, below were prepared from the indicated amine according to General Procedure F.

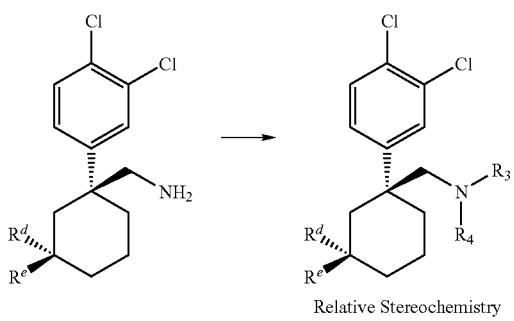

Relative Stereochemistry

TABLE 4

| R$^d$ | R$^e$ | R$^3$ | R$^4$ |
|---|---|---|---|
| colspan cis-1-(1-(3,4-dichlorophenyl)-3-methoxycyclohexyl)-N-methylmethanamine (196) | | | |
| H | OCH$_3$ | CH$_3$ | H |

The compound was prepared from 194.
The crude product was subjected to silica gel column chromatography (Ethyl acetate/hexane/DEA = 1/4/0.1%) to give 196 (26.7 mg, 32%) and 197 (37.6 mg, 37%).
$^1$H NMR (400 MHz, CD$_3$Cl) δ 7.43 (d, J = 2.0 Hz, 1 H), 7.41 (d, J = 8.8 Hz, 1 H), 7.21 (dd, J = 2.0, 8.8 Hz, 1 H), 3.12 (s, 3 H), 3.07 (m, 1 H), 2.54 (m, 1 H), 2.55 (s, 2 H), 2.28 (s, 3 H), 2.26 (m, 1 H), 2.19 (m, 1 H), 1.70 (m, 1 H), 1.40 (m, 2 H), 1.22 (m, 2 H); $^{13}$C NMR (100 MHz, CD$_3$Cl) δ 144.77, 132.98, 130.68, 130.30, 129.44, 126.80, 75.83, 66.66, 55.89, 44.22, 40.19, 37.53, 33.81, 33.37, 20.43; ESI MS m/z 308.1.

cis-1-(1-(3,4-dichlorophenyl)-3-methoxycyclohexyl)-N,N-dimethylmethanamine (197)

| H | OCH$_3$ | CH$_3$ | CH$_3$ |
|---|---|---|---|

The compound was prepared from 194.
The crude product was subjected to silica gel column chromatography (Ethyl acetate/hexane/DEA = 1/4/0.1%) to give 196 (26.7 mg, 32%) and 197 (37.6 mg, 37%).
$^1$H NMR (400 MHz, CD$_3$Cl) δ 7.45 (d, J = 2.4 Hz, 1 H), 7.38 (d, J = 8.4 Hz, 1 H), 7.22 (dd, J = 2.4, 8.4 Hz, 1 H), 3.22 (s, 3 H), 3.06 (m, 1 H), 2.56 (m, 1 H), 2.28 (s, 2 H), 2.19 (m, 1 H), 2.02 (s, 6 H), 2.04-1.96 (m, 1 H), 1.68 (m, 1 H), 1.40 (m, 1 H), 1.20 (m, 2 H); $^{13}$C NMR (100 MHz, CD$_3$Cl) δ 145.41, 132.53, 130.30, 129.84, 129.70, 127.10, 75.99, 74.35, 55.88, 48.76, 45.54, 39.82, 33.19, 32.32, 20.46; ESI MS m/z 316.1.

cis-3-(3,4-dichlorophenyl)-1-methyl-3-((methylamino)methyl)cyclohexanol (198)

| CH$_3$ | OH | CH$_3$ | H |
|---|---|---|---|

The compound was prepared from 193 E2.
$^1$HNMR (400 MHz, CD$_3$OD) δ 7.51 (d, J = 2.4 Hz, 1 H), 7.45 (d, J = 8.4 Hz, 1 H), 7.31 (dd, J = 2.4, 8.4 Hz, 1 H), 3.31 (d, J = 13.2 Hz, 1 H), 3.20 (d, J = 13.2 Hz, 1 H), 2.23 (s, 3 H), 2.00 (m, 2 H), 1.88 (m, 1 H), 1.75 (m, 1 H), 1.68 (m, 1 H), 1.60 (m, 2 H), 1.39 (m, 1 H), 1.05 (s, 3 H); $^{13}$CNMR (100 m Hz, CD$_3$OD), δ 146.32, 132.08, 130.19, 127.68, 128.37, 126.07, 69.45, 61.35, 46.74, 41.79, 38.58, 35.86, 32.74, 30.36, 18.97; ESI MS m/z 302.1.

cis-3-(3,4-dichlorophenyl)-3-((dimethylamino)methyl)-1-methylcyclohexanol (199)

| CH$_3$ | OH | CH$_3$ | CH$_3$ |
|---|---|---|---|

The compound was prepared from 193 E2.
$^1$H NMR (400 MHz, CD$_3$OD) δ 8.44 (broad, 1 H), 7.64 (d, J = 2.0 Hz, 1 H), 7.55 (d, J = 8.8 Hz, 1 H), 7.42 (dd, J = 2.0, 8.8 Hz, 1 H), 4.05 (d, J = 13.2 Hz, 1 H), 3.53 (d, J = 13.2 Hz, 1 H) 2.558 (s, 6 H), 2.30 (m, 1 H), 2.15 (m, 1 H), 1.95 (m, 1 H), 1.80 (d, J = 14 Hz, 1 H), 1.68 (m, 2 H), 1.41 (td, J = 4.0, 13.2 Hz, 2 H), 1.33 (s, 3 H); $^{13}$C NMR (100 MHz, CD$_3$OD) δ 148.30, 132.86, 130.99, 130.88, 128.21, 125.84, 69.03, 65.32, 44.56, 41.65, 39.83, 37.63, 36.48, 30.89, 18.36; ESI MS m/z 316.2.

cis-1-(1-(3,4-dichlorophenyl)-3-methoxycyclohexyl)-N-methylmethanamine (200)

| H | OCH$_3$ | CH$_3$ | H |
|---|---|---|---|

The compound was prepared from 192.
$^1$H NMR (400 MHz, CD$_3$Cl) δ 7.43 (d, J = 2.0 Hz, 1 H), 7.41 (d, J = 8.8 Hz, 1 H), 7.21 (dd, J = 2.0, 8.8 Hz, 1 H), 3.12 (s, 3 H), 3.07 (m, 1 H), 2.54 (m, 1 H), 2.55 (s, 2 H), 2.28 (s, 3 H), 2.26 (m, 1 H), 2.19 (m, 1 H), 1.70 (m, 1 H), 1.40 (m, 2 H), 1.22 (m, 2 H); $^{13}$C NMR (100 MHz, CD$_3$Cl) δ 144.77, 132.98, 130.68, 130.30, 129.44, 126.80, 75.83, 66.66, 55.89, 44.22, 40.19, 37.53, 33.81, 33.37, 20.43; ESI MS m/z 308.1.

cis-1-(1-(3,4-dichlorophenyl)-3-methoxycyclohexyl)-N,N-dimethylmethanamine (201)

| H | OCH$_3$ | CH$_3$ | CH$_3$ |
|---|---|---|---|

The compound was prepared from 192.
$^1$H NMR (400 MHz, CD$_3$Cl) δ 7.45 (d, J = 2.4 Hz, 1 H), 7.38 (d, J = 8.4 Hz, 1 H), 7.22 (dd, J = 2.4, 8.4 Hz, 1 H), 3.22 (s, 3 H), 3.06 (m, 1 H), 2.56 (m, 1 H), 2.28 (s, 2 H), 2.19 (m, 1 H), 2.02 (s, 6 H), 2.04-1.96 (m, 1 H), 1.68 (m, 1 H), 1.40 (m, 1 H), 1.20 (m, 2 H); $^{13}$C NMR (100 MHz, CD$_3$Cl) δ 145.41, 132.53, 130.30, 129.84, 129.70,

TABLE 4-continued

| $R^d$ | $R^e$ | $R^3$ | $R^4$ |
|---|---|---|---|
| 127.10, 75.99, 74.35, 55.88, 48.76, 45.54, 39.82, 33.19, 32.32, 20.46; ESI MS m/z 316.1. | | | |
| cis-3-(3,4-dichlorophenyl)-3-((methylamino)methyl)cyclohexanol (202) | | | |
| CH$_3$ | OH | CH$_3$ | H |
| The compound was prepared from 193 E1. | | | |
| $^1$HNMR (400 MHz, CD$_3$OD) δ 7.51 (d, J = 2.4 Hz, 1 H), 7.45 (d, J = 8.4 Hz, 1 H), 7.31 (dd, J = 2.4, 8.4 Hz, 1 H), 3.31 (d, J = 13.2 Hz, 1 H), 3.20 (d, J = 13.2 Hz, 1 H), 2.23 (s, 3 H), 2.00 (m, 2 H), 1.88 (m, 1 H), 1.75 (m, 1 H), 1.68 (m, 1 H), 1.60 (m, 2 H), 1.39 (m, 1 H), 1.05 (s, 3 H); $^{13}$CNMR (100 m Hz, CD$_3$OD) δ 146.32, 132.08, 130.19, 127.68, 128.37, 126.07, 69.45, 61.35, 46.74, 41.79, 38.58, 35.86, 32.74, 30.36, 18.97; ESI MS m/z 302.1. | | | |
| cis-3-(3,4-dichlorophenyl)-3-((dimethylamino)methyl)cyclohexanol (203) | | | |
| CH$_3$ | OH | CH$_3$ | CH$_3$ |
| The compound was prepared from 193 E1. | | | |
| $^1$H NMR (400 MHz, CD$_3$OD) δ 8.44 (broad, 1 H), 7.64 (d, J = 2.0 Hz, 1 H), 7.55 (d, J = 8.8 Hz, 1 H), 7.42 (dd, J = 2.0, 8.8 Hz, 1 H), 4.05 (d, J = 13.2 Hz, 1 H), 3.53 (d, J = 13.2 Hz, 1 H) 2.558 (s, 6 H), 2.30 (m, 1 H), 2.15 (m, 1 H), 1.95 (m, 1 H), 1.80 (d, J = 14 Hz, 1 H), 1.68 (m, 2 H), 1.41 (td, J = 4.0, 13.2 Hz, 2 H), 1.33 (s, 3 H); $^{13}$C NMR (100 MHz, CD$_3$OD) δ 148.30, 132.86, 130.99, 130.88, 128.21, 125.84, 69.03, 65.32, 44.56, 41.65, 39.83, 37.63, 36.48, 30.89, 18.36; ESI MS m/z 316.2. | | | |

(1-(3,4-dichlorophenyl)-3,3-difluorocyclohexyl)-methanamine (204)

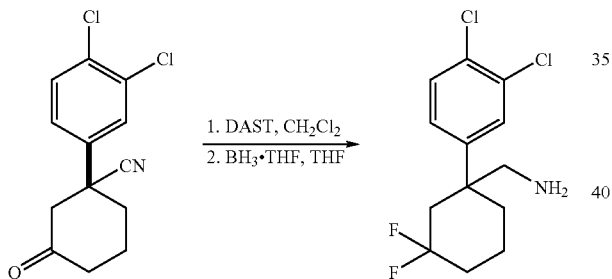

The title compound was synthesized from 1-(3,4-dichlorophenyl)-3-oxo-cyclohexanecarbonitrile (0.60 g, 2.2 mmol) according to General Procedure CC, followed by General Procedure E. The crude product was dissolved in MeOH (3 mL) and subjected to reverse phase column chromatography (CH$_3$CN/H$_2$O/0.1% Formic acid=5% to 100%) to give (86 mg, 72%). $^1$H NMR (400 MHz, CD$_3$OD) δ 7.64 (d, J=7.4 Hz, 1 H), 7.57 (d, J=8.4 Hz, 1H), 7.39 (dd, J=2.4, 8.4 Hz, 1H), 3.23 (s, 2 H), 2.4 (m, 2H), 2.52 (m, 2H), 1.95 (m, 2H), 1.80 (m, 2H); $^{13}$C NMR (100 MHz, CD$_3$OD) δ 142.17, 132.94, 131.58, 130.96, 129.06, 126.54, 123.11, 47.74, 41.65, 40.23, 32.98, 30.69, 18.21, 41.26; ESI MS m/z 294.0.

1-(1-(3,4-dichlorophenyl)-3,3-difluorocyclohexyl)-N-methylmethanamine (205)

205 E1, 205 E2

The title compound was synthesized from 204 according to General Procedure F. The crude product was subjected to silica gel column chromatography (ethyl acetate/hexane/DEA=1:4:0.1) to give the mono-methylated analog (25 mg, 30%) and the N, N-dimethylated analog (36 mg, 41%). The racemic mixture of the monomethylated analog was purified by chiral column chromatography (OJ column; Hexanepropanol/DEA=98/2/0.1) to give the fast moving enantiomer 205 E1 (5.2 mg) and the slow moving enantiomer 205 E2 (6.3 mg). $^1$H NMR (400 MHz, CD$_3$Cl) δ 7.42 (d, J=2.4 Hz, 1H), 7.41 (d, J=8.8 Hz, 1H), 7.18 (dd, J=2.4, 8.8 Hz, 1H), 2.68 (s, 2H), 2H), 2.38-2.19 (m, 2H), 2.29 (s, 3H), 2.00-1.90 (m, 2H), 1.90-1.66 (m, 4H); $^{13}$C NMR (100 MHz, CD$_3$Cl) δ 132.78, 130.69, 130.45, 128.68, 126.09, 126.03, 123.69, 61.73, 45.5, 41.26, 37.41, 34.14, 32.05, 18.84; ESI MS m/z 308.1.

1-(1-(3,4-dichlorophenyl)-3,3-difluorocyclohexyl)-N,N-dimethylmethanamine (206)

The racemic mixture of the dimethylated analog (Example above) was purified by chiral column chromatography (OJ column; hexane:propanol:DEA=98:2:0.1) to give the fast moving enantiomer 206 E1 (5.2 mg) and the slow moving enantiomer 206 E2 (6.3 mg). $^1$H NMR (400 MHz, CD$_3$OD) δ 7.41 (d, J=2.4 Hz, 1H), 7.36 (d, J=8.8 Hz, 1H), 7.18 (dd, J=2.4, 8.8 Hz, 1H), 2.36 (s, 2H), 2.36-2.24 (m, 1H), 2.07 (s, 6H), 1.94-1.80 (m, 4H), 1.74-1.64 (m, 2H); $^{13}$C NMR (100 MHz, CD$_3$OD) δ 136.17, 132.27, 130.18, 129.99, 129.03, 126.47, 70.42, 48.52, 44.5, 40.26, 34.12, 31.58, 18.881; ESI MS m/z 332.1.

Example 4

Synthesis of 4-Substituted Cyclohexylamine Analogs

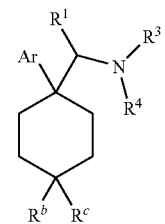

4.1. Synthesis of Aryl Acetonitriles

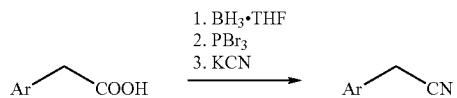

General Procedure V: To a 1.0 M solution of the carboxylic acid (1 eq) in THF was added BH$_3$/THF (3 eq). The reaction mixture was stirred overnight before being concentrated. To the residue was added diethyl ether and NaOH solution. The organic layer was separated, dried (Na$_2$SO$_4$) and concentrated. The residue was purified by silica gel column chromatography (ethyl acetate/hexane) to afford the aryl alcohol.

To a 0.4 M solution of the aryl alcohol (1 eq) in CH$_2$Cl$_2$ was added PBr$_3$ (2 eq). The reaction mixture was stirred for 3 h at room temperature before being quenched with saturated aqueous NH$_4$Cl. The organic layer was separated, dried (Na$_2$SO$_4$) and concentrated. The residue was purified by silica gel column chromatography (ethyl acetate/hexane) to afford the aryl alkyl bromide.

To a 0.2M solution of the aryl alkyl bromide (1 eq) in CH₃CN was added KCN (3 eq). The reaction mixture was heated to reflux for 6 h before being concentrated. To the residue was added diethyl ether and H₂O. The organic layer was separated, dried (Na₂SO₄) and concentrated. The residue was purified by silica gel column chromatography (ethyl acetate/hexane) to afford the desired aryl acetonitrile.

4.2. Synthesis of 1-(aryl)-4-oxocyclohexanecarbonitriles

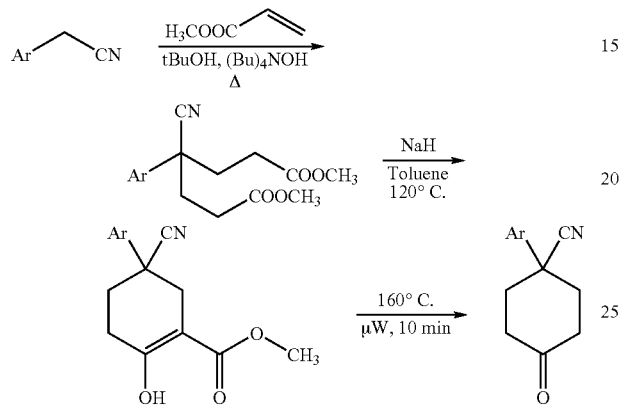

Aryl-4-oxocyclohexanecarbonitriles were prepared according to the Scheme, above, or procedures described in WO 00/25770 and WO 03/063797, the disclosures of which are incorporated herein by reference for all purposes. Minor modifications of the described procedures were used when appropriate. For example, 2.2 equivalents of acrylate may be used in step 1, NaH (60% dispersion in mineral oil) reduction was performed in refluxing toluene, and microwave irradiation was used for reactions up to a multigram scale in the final decarboxylation step. An exemplary synthesis of 1-(naphthalen-2-yl)-4-oxocyclohexanecarbonitrile is outlined below.

4.2.1. Synthesis of dimethyl 3-cyano-3-(naphthalen-2-yl)hexanedioate

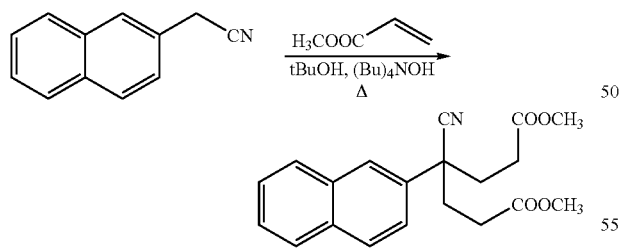

2-naphthylacetonitrile (3.45 g, 20.6 mmol) and methyl acrylate (9.7 ml, 107 mmol) were suspended in 2-methyl-2-propanol (10 ml). Heat was applied to the reaction vessel until the solution became clear. The mixture was cooled to room temperature, at which time (Bu)₄NOH (6.9 mmol, 0.33 equiv.) was added as a solution in 2-methyl-2-propanol:methanol (1:2). The combined reaction mixture was heated to reflux for 4 h under vigorous stirring at which time the reaction appeared complete by GC-MS. After allowing the reaction to cool the mixture was partitioned between H₂O (75 ml) and EtOAc (50 ml). The aqueous layer was removed and washed with EtOAc (2×50 ml). The combined organic phases were washed with NaHCO₃ (sat. aq.) and brine and dried over MgSO₄. After filtration the solvent was removed in vacuo. The crude product was purified by flash column chromatography (25% EtOAc in hexanes) to isolate the title compound as a light yellow oil (5.75 g, 82%).

4.2.2. Synthesis of methyl 5-cyano-2-hydroxy-5-(naphthalen-2-yl)cyclohex-1-enecarboxylate

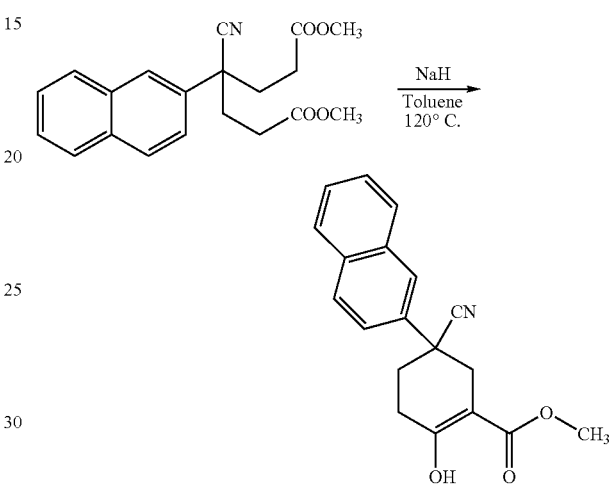

To a solution of the diester nitrile (2.3 g, 6.77 mmol) in dry toluene (46 ml) was added NaH (60% suspension in mineral oil, 820 mg, 20.33 mmol). The reaction mixture was heated to reflux for 3 h at which time no starting material remained (GC-MS). The reaction was cooled to room temperature and carefully quenched with NH₄Cl (aq., 100 ml) and extracted with EtOAc (3×50 ml). The combined organics were washed with brine, dried over MgSO₄, filtered, and the solvent removed in vacuo. The resulting oily product, suspended in mineral oil, was washed with hexanes to afford the desired product as a light yellow solid (1.4 g, 67% yield). The material was used in the following step without further purification.

4.2.3. Synthesis of 1-(naphthalen-2-yl)-4-oxocyclohexanecarbonitrile

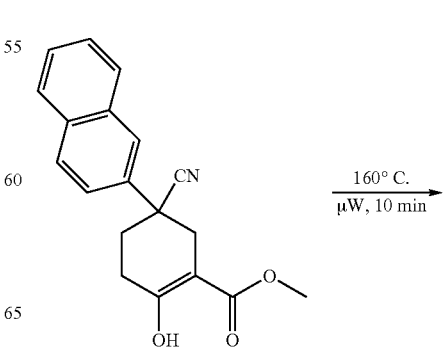

-continued

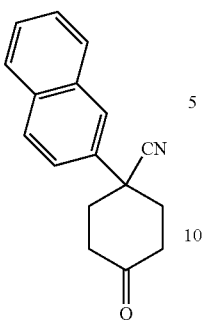

The above ketoester (0.75 g, 2.44 mmol) was dissolved in DMSO (11 ml) and H₂O (0.5 ml) and was sealed in a 20 ml microwave reaction vial equipped with a magnetic stir bar. The reaction mixture was heated to 160° C. for 10 min in a microwave reactor at which time complete conversion was observed by HPLC. The reaction was diluted with EtOAc (50 ml) and washed with 10% LiCl (aq., 2×30 ml) followed by a brine wash. The organic layer was removed, dried over MgSO₄, filtered, and the solvent was removed in vacuo. The product was further purified by flash column chromatography (25% EtOAc in hexanes) to afford the desired ketone (0.55 g, 90% yield) as a colorless oil, which solidified upon standing.

4.3. Synthesis of 4-hydroxy-1-aryl-cyclohexanecarbonitrile (NaBH₄ Reduction)

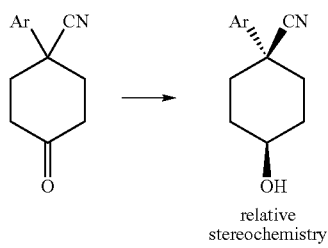
relative stereochemistry

General Procedure W: To a solution of the ketonitrile (1 eq) in dry methanol (about 0.1 M) at 0° C. was added NaBH₄ (4 eq) portionwise. The mixture was allowed to warm to 22° C. and was stirred at this temperature for about 2 h, or until complete (e.g., HPLC). It was diluted with H₂O and the aqueous layer was extracted with Et₂O. The combined organic layers were washed with brine, dried over MgSO₄ and filtered. The solvent was removed in vacuo to afford the resulting alcohol, typically as one diastereomer.

4.4. Synthesis of 4-hydroxy-1-aryl-cyclohexanecarbonitrile with Inverse Stereochemistry at C-4 (Mitsunobu Reaction)

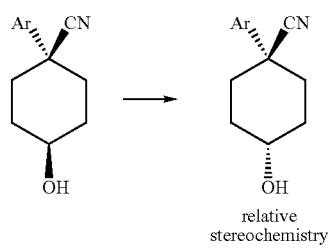
relative stereochemistry

General Procedure X: To a solution of PPh₃ (1.2 eq) in dry toluene (about 0.1 M) was added p-NO₂-benzoic acid (1.2 eq) and the resulting suspension was cooled to −30-° C. To the mixture was added a 2 M solution of the respective nitrile alcohol (1 eq) in toluene (about) in one portion and a 1.0 M solution of DEAD (1.2 eq) in toluene dropwise over 15 min. The mixture was allowed to warm to 22° C. and was stirred for 15 h, at which time the reaction was quenched with saturated aqueous NaHCO₃. The aqueous layer was extracted with EtOAc, the combined organic layers were dried over MgSO₄, filtered and the solvent was removed in vacuo to afford the benzoate intermediate, which was used without further purification (0.61 g, 74% yield).

To a solution of the crude benzoate (1 eq) in MeOH (about 0.1 M) was added a 1.0 M solution of NaOMe (95%, 1.11 eq) in THF and the mixture was allowed to stir at 22° C. for 4 h. The solvent was removed in vacuo and the resulting residue was taken up in H₂O and extracted with EtOAc. The combined organics were dried over MgSO₄, filtered and the solvent was removed in vacuo. The crude product was purified by silica gel column chromatography (EtOAc in hexanes) to afford the desired nitrile alcohol.

4.5. Synthesis of Tertiary Alcohols

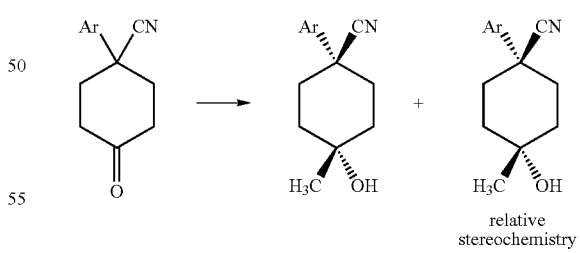
relative stereochemistry

General Procedure Y: To a solution of the ketonitrile (1 eq) in dry THF (about 0.4 M) at −78° C. was added dropwise MeLi (1.4 M in Et₂O, 2 eq) so as to maintain an internal temperature of <−60° C. The reaction mixture was stirred at −78° C. for 3 h and the reaction was then quenched with H₂O (e.g., 1 ml). The reaction mixture was allowed to warm to 22° C. and was then diluted with CH₂Cl₂. The organic layer was washed with aqueous NaHCO₃ and brine, dried over MgSO₄ and filtered and the solvent was removed in vacuo. The crude product was purified by flash column chromatography (e.g., 0-60% EtOAc in hexanes) to return starting material, fast moving diastereomer as well as the slow moving diastereomer (major product). Solvent removal afforded the desired products as white solids.

4.6. Chlorination

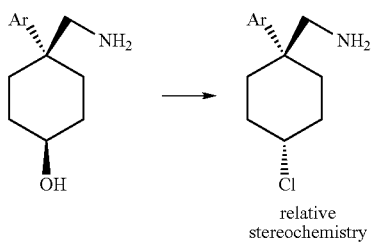

relative stereochemistry

General Procedure Z: To a solution of the amino alcohol (1 eq) in MeOH containing 10% (v/v) NEt$_3$ was added BOC$_2$O (2 eq) and the resulting mixture was stirred at 22° C. for 3 h, at which time the solvent was removed in vacuo. Silica gel column chromatography (e.g., EtOAc in hexanes) afforded the carbamate as a clear oil.

To a solution of the purified carbamate (1 eq) in DMF (about 0.1 M) and CCl$_4$ (1.5 eq) was added KF (3 eq) and PPh$_3$ (2 eq) and the resulting mixture was stirred at 22° C. for 3 h. Saturated aqueous NaHCO$_3$ was then added to quench the reaction and the aqueous layer was extracted with EtOAc. The combined organic phases were dried over Na$_2$SO$_4$, filtered and the solvent was removed in vacuo to afford the halogenated mixture e.g., as a 3:1 ratio of chlorinated to α-eliminated product (66% conversion). Silica gel column chromatography (e.g., EtOAc in hexanes) afforded the chlorinated carbamate.

The BOC group was removed and the HCl salt was prepared by the addition of 4M HCl (Et$_2$O) to the carbamate. After stirring for 1 h, the HCl salt was filtered off.

4.7. Fluorination

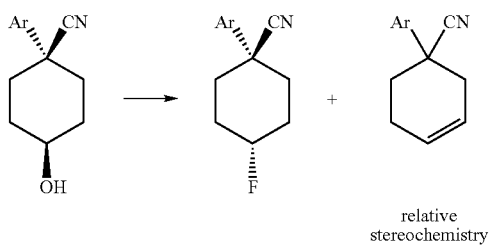

relative stereochemistry

General Procedure BB: A 0.2 M solution of the nitrile alcohol (1 eq) in CHCl$_3$ was added drop-wise to a 0.1 M solution of morpholino sulfurtrifluoride (4 eq) in CHCl$_3$ (about 0.1 M) at −15° C. over 5 min. The resulting mixture was stirred between −30 and −15° C. for 30 min, at which time MeOH (5 eq) and saturated aqueous NaHCO$_3$ were added. The aqueous layer was extracted with EtOAc, dried over Na$_2$SO$_4$, filtered and the solvent removed in vacuo. Silica gel column chromatography (e.g., EtOAc in hexanes) afforded fluorinated and α-eliminated products e.g., in a 1:1 ratio.

4.8. Difluorination

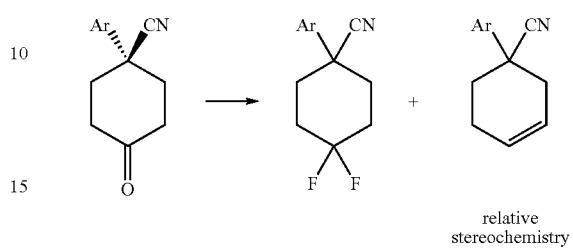

relative stereochemistry

General Procedure CC: A 0.5 M solution of the ketonitrile (1 eq) in CHCl$_3$ was added drop-wise to a 2 M solution of morpholino sulfurtrifluoride (4 eq) in CHCl$_3$ at −30° C. over 5 min. The resulting mixture was stirred between −30 and 0° C. for 2 h, at which time MeOH and saturated aqueous NaHCO$_3$ were added. The aqueous layer was extracted with EtOAc, dried over Na$_2$SO$_4$, filtered and the solvent was removed in vacuo. Silica gel column chromatography (e.g., EtOAc in hexanes) afforded difluorinated and α-eliminated products.

4.9. Synthesis of Fluoromethyl Analogs

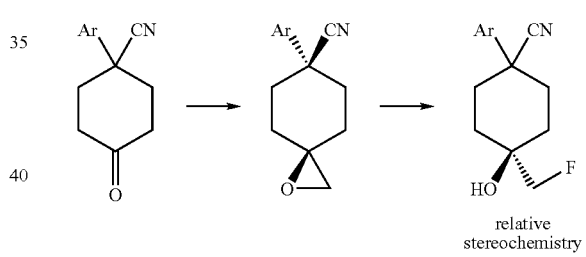

relative stereochemistry

General Procedure DD: To a solution of the ketonitrile (concentration about 0.3 M, 1 eq) and trimethylsulfonium iodide (1.5 eq) in dry DMSO was added a solution of KOtBu (1.5 eq) in dry DMSO (about 0.7 M). The mixture was stirred at 22° C. for 5 h, at which time the reaction appeared complete by GC-MS. The reaction mixture was diluted with brine, and extracted with EtOAc. The combined organic layers were dried over MgSO$_4$, filtered, and the solvent was removed in vacuo. The crude product was purified by silica gel chromatography (e.g., EtOAc in hexanes) to afford two diastereomeric epoxides, termed the faster moving diastereomer (FMD) and the slower moving diastereomer (SMD).

To a 1M solution of TBAF in THF (4 eq) in a clean glass reaction flask was added HF (48% in H$_2$O, 4 eq). The solvent was removed in vacuo and the resulting mixture was added to a mixture of the above epoxide (1 eq) and KHF$_2$ (3 eq) in a microwave reaction vial. The reagents were washed down the side of the vial with heptane (minimal volume) and the reaction mixture was heated in the microwave at 120° C., for 15 min (FHT). After the reaction mixture was cooled to 22° C., the mixture was diluted with H$_2$O and saturated aqueous NaHCO$_3$ and was extracted with EtOAc. The combined organic layers were dried over Na$_2$SO$_4$, filtered and the solvent was removed in vacuo to afford crude fluoromethylated nitrile, which was purified by silica gel chromatography (EtOAc in hexanes) to afford the pure product as a white solid (>20:1 regioselectivity).

4.10. Synthesis of Methylamine

General Procedure F2: To a 0.1 M solution of the amine (1 eq) in MeOH containing 10% (v/v) NEt$_3$ was added BOC$_2$O (1.2 eq) and the resulting mixture was stirred at 22° C. for 3 h, at which time the solvent was removed in vacuo. Silica gel column chromatography (EtOAc in hexanes) afforded the carbamate.

To a 0.1 M solution of the purified carbamate (1 eq) in THF was added LAH (1M THF, 2 eq) and the resulting mixture was heated to 65° C. for 6 h. After the reaction was complete (HPLC), 6M HCl was added followed by saturated aqueous K$_2$CO$_3$. The product was extracted with EtOAc. The combined organics were dried over MgSO$_4$, filtered and the solvent was removed in vacuo. The crude mono-methylamine was purified by either Gilson RP-HPLC or by transformation to the HCl salt and recrystallization.

4.11. Alkylation of Alcohol

General Procedure EE: To a 0.2 M solution of the alcohol (1 eq) in THF was added NaH (60% in mineral oil, 1.5 eq). The reaction mixture was stirred for 20 min before alkyl halide (2 eq) was added. It was stirred for 4 h before being quenched with saturated NH$_4$Cl solution. The product was then extracted with diethyl ether. The combined organic layers were dried (Na$_2$SO$_4$), filtered and concentrated. The residue was purified by silica gel column chromatography (ethyl acetate/hexane) to give O-alkylated product.

4.12. Preparation of Ketals

General Procedure FF: To a 0.1 M solution of the ketone (1 eq) in benzene was added ethylene glycol (3 eq) and TsOH—H$_2$O (0.4 eq). The reaction mixture was heated at reflux for 6 h before being concentrated. The residue was dissolved in EtOAc, washed with saturated aqueous NaHCO$_3$, dried (Na$_2$SO$_4$), filtered and concentrated. The residue was purified by silica gel column chromatography (Ethyl acetate/hexane/DEA) to give the ketal.

4.13. Synthesis of 4-Substituted Cycloalkylamines

Compounds in Table 5, below, were synthesized from the respective 1-(aryl)-4-oxocyclohexanecarbonitriles according to the indicated General Procedures.

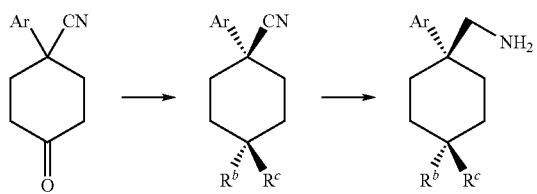

TABLE 5

Summary of 4-Substituted Cycloalkylamines

| Ar | R$^b$ | R$^c$ | General Procedure |
|---|---|---|---|
| 4-(aminomethyl)-4-(naphthalen-2-yl)cyclohexanol (207) | | | |
| [naphthalen-2-yl structure] | H | OH | W, E |

HPLC R$_t$ = 7.54 min; LC-MS (5 minute method) 2.24 min, (M + 1)$^+$ 256.0 @ 2.31 min; $^1$H-NMR (400 MHz, CDCl$_3$) 7.84-7.75(m, 4H), 7.51-7.43 (m, 3H), 3.79(m, 1H), 2.88(brs, 2H), 2.10-1.97(m, 4H), 1.75-1.56(m, 4H).

| 4-(aminomethyl)-4-(naphthalen-2-yl)cyclohexanol (208) | | | |
|---|---|---|---|
| [naphthalen-2-yl structure] | OH | H | W, X, E |

HPLC R$_t$ = 6.83 min; LC-MS (15 minute method) 4.71 min, (M + 1)$^+$ 256.0 @ 4.73 min; $^1$H-NMR (400 MHz, CD$_3$OD) 8.04-7.93(m, 4H), 7.69-7.49(m, 3H), 3.72(m, 1H), 3.13(s, 2H), 2.63(d, J = 13.5 Hz, 2H), 1.99-1.85(m, 2H), 1.80-1.68(m, 2H), 1.47-1.31(m, 2H).

| 4-(aminomethyl)-1-methyl-4-(naphthalen-2-yl)cyclohexanol (209) | | | |
|---|---|---|---|
| [naphthalen-2-yl structure] | OH | Me | Y, E |

HPLC R$_t$ = 7.06 min; LC-MS (M + 1)$^+$ 270.1; $^1$H-NMR (400 MHz, CDCl$_3$) 7.86-7.79(m, 4H), 7.58(brs, 2H), 7.43-7.35(m, 2H), 2.84(brs, 2H), 2.25(m, 2H), 1.77(m, 2H), 1.58(m, 2H), 1.49(m, 2H), 1.28(s, 3H).

| 4-(aminomethyl)-1-methyl-4-(naphthalen-2-yl)cyclohexanol (210) | | | |
|---|---|---|---|
| [naphthalen-2-yl structure] | Me | OH | Y, E |

HPLC R$_t$ = 1.39; LC-MS (15 minute method) 6.92 min, (M + 1)$^+$ 270.0 @ 6.88 min.

| (4-chloro-1-(naphthalen-2-yl)cyclohexyl)methanamine (211) | | | |
|---|---|---|---|
| [naphthalen-2-yl structure] | Cl | H | W, E, Z |

HPLC R$_t$ = 2.38 min; $^1$H-NMR (400 MHz, CD$_3$OD) 8.07-7.95(m, 4H), 7.65 (dd, J = 9.0, 1.5 Hz, 1H), 7.61-7.51(m, 2H), 4.14(m, 1H), 3.18(s, TABLE 5-continued Summary of 4-Substituted Cycloalkylamines

| Ar | $R^b$ | $R^c$ | General Procedure |
|---|---|---|---|

2H), 2.68 (d, J = 13.5 Hz, 2H), 2.20(d, J = 13.5 Hz, 2H), 1.89-1.62(m, 4H). $^{13}$C-NMR(100 MHz, CD$_3$OD) 134.0, 132.9, 129.5, 128.1, 127.4, 127.2, 126.4, 124.1, 58.6, 50.6, 40.4, 32.4, 32.1. LC-MS (15 minute method) 8.10 min, (m/z) 274.0 @ 8.18 min.
(4-fluoro-1-(naphthalen-2-yl)cyclohexyl)methanamine (212)

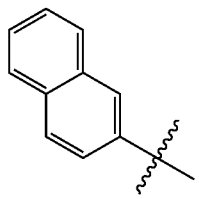 [SMILES: *c1ccc2ccccc2c1]   F   H   W, BB, E

HPLC R$_t$ = 2.14 min; $^1$H-NMR (400 MHz, CD$_3$OD) 8.00-7.87(m, 4H), 7.63-7.51(m, 3H), 4.76(m, 0.5H), 4.61(m, 0.5H), 3.19(s, 2H), 2.52(m, 2H), 2.01-1.97(m, 2H), 1.82-1.76(m, 2H), 1.64-1.59(m, 2H). LC-MS (15 minute method) 7.30 min, (M + 1)$^+$ 258.1 @ 7.36 min
(4-fluoro-1-(naphthalen-2-yl)cyclohexyl)methanamine (213)

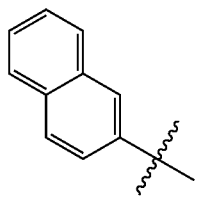 [SMILES: *c1ccc2ccccc2c1]   H   F   W, X, BB, E

HPLC R$_t$ = 1.48 min; $^1$H-NMR (400 MHz, CDCl$_3$) 7.87-7.62(m, 4H), 7.52-7.44(m, 3H), 4.75(m, 0.5H), 4.63(m, 0.5H), 2.79(s, 2H), 2.23(d, J = 13.5 Hz, 2H), 1.97-1.90(m, 4H), 1.70-1.52(m, 2H). $^{13}$C-NMR(100 MHz, CDCl$_3$) 128.6, 128.1, 127.6, 126.6, 126.3, 126.0, 125.2, 90.6, 55.4, 28.1, 27.8, 27.6. LC-MS (M + 1)+ 258.1.
4-(aminomethyl)-4-(benzo[d][1,3]dioxol-5-yl)cyclohexanol(214)

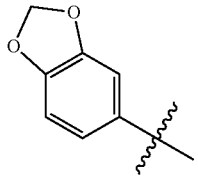 [SMILES: *c1ccc2c(c1)OCO2]   H   OH   W, E

HPLC R$_t$ = 1.18 min; LC-MS (15 minute method) 4.51 min, (M + 1)$^+$ 250.0 @ 4.4.51 min; $^1$H-NMR (400 MHz, CD$_3$OD) 8.38(brs, 1H), 6.98(d, J = 2.0 Hz, 1H), 6.85(dd, J = 8.0, 2.0 Hz, 1H), 6.82(d, J = 8.0 Hz, 1H), 5.95(s, 2H), 3.78(m, 1H), 3.03(s, 2H), 2.04-1.91(m, 4H), 1.71-1.58(m, 4H). $^{13}$C-NMR(100 MHz, CD$_3$OD) 120.3, 108.3, 107.1, 101.4, 66.2, 63.5, 40.0, 29.0.
4-(aminomethyl)-4-(benzo[d][1,3]dioxol-5-yl)-1-methylcyclohexanol (215)

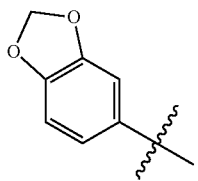 [SMILES: *c1ccc2c(c1)OCO2]   Me   OH   Y, E

HPLC R$_t$ = 1.64 min; $^1$H-NMR (400 MHz, CD$_3$OD) 8.37(brs, 1H), 6.97(s, 1H), 6.90(d, J = 8.0 Hz, 1H), 6.85(d, J = 8.0 Hz, 1H), 5.97(s, 2H), 2.92(s, 2H), 2.13(d, J = 13.5 Hz, 2H, 1.89(t, J = 13.0 Hz, 2H), 1.56(d, J = 13.5 Hz, 2H), 1.38(t, J = 13.0 Hz, 2H), 1.05(s, 3H). $^{13}$C-NMR (100 MHz, CD$_3$OD) 120.8, 108.4, 107.4, 101.5, 34.1, 29.7, 29.0, 28.8. LC-MS (M + 1)$^+$ 264.1.

4-(aminomethyl)-4-(benzo[d][1,3]dioxol-5-yl)-1-methylcyclohexanol (216)

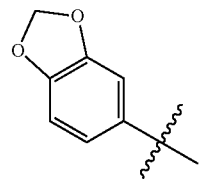 [SMILES: *c1ccc2c(c1)OCO2]   OH   Me   Y, E

HPLC R$_t$ = 2.03 min; LC-MS (15 minute method) 0.60 min, (M + 1)$^+$ 264.1 @ 0.70 min; $^1$H-NMR (400 MHz, CD$_3$OD) 8.44(brs, 1H), 6.98(d, J = 1.5 Hz, 1H), 6.91(dd, J = 8.5, 1.5 Hz, 1H), 6.86(d, J = 8.5 Hz, 1H), 5.96(s, 2H), 3.11(s, 2H), 2.20-2.01(m, 2H), 1.77-1.71(m, 2H), 1.60-1.56 (m, 4H), 1.27(s, 3H). $^{13}$C-NMR(100 MHz, CD$_3$OD) 168.1, 149.0, 147.0, 120.1, 108.3, 106.9, 101.4, 68.7, 39.7, 34.6, 30.0, 27.2.
4-aminomethyl-1-(fluoromethyl)-4-(naphthalen-2-yl)cyclohexanol (217)

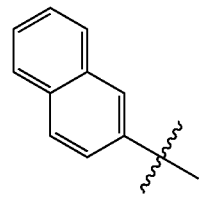 [SMILES: *c1ccc2ccccc2c1]   CH$_2$F   OH   DD, E

HPLC R$_t$ = 1.84 min; LC-MS (15 minute method) 6.65 min, (M + 1)$^+$ 288.2 @ 6.75 min; $^1$H-NMR (400 MHz, CD$_3$OD) 7.99-7.87(m, 4H), 7.63 (dd, J = 9.0, 2H), 7.54-7.50(m, 2H), 4.04(s, 1H), 3.92(s, 1H), 3.09(s, 2H), 2.46(d, J = 13.5 Hz, 2H), 2.03(t, J = 13.5 Hz, 2H), 1.63(d, J = 13.5 Hz, 2H), 1.45(t, J =13.5 Hz, 2H). $^{13}$C-NMR(100 MHz, CD$_3$OD) 136.1, 133.9, 132.8, 129.3, 128.0, 127.4, 127.3, 126.3, 124.3, 90.6, 88.9, 52.1, 41.0, 28.3, 28.2, 27.6.
4-(aminomethyl)-1-(fluoromethyl)-4-(naphthalen-2-yl)cyclohexanol (218)

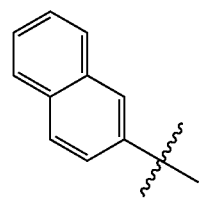 [SMILES: *c1ccc2ccccc2c1]   OH   CH$_2$F   DD, E

HPLC R$_t$ = 1.19 min; LC-MS (15 minute method) 4.91 min, (M + 1)$^+$ 288.1 @ 4.89 min; $^1$H-NMR (400 MHz, CD$_3$OD) 7.97-7.86(m, 4H), 7.63 (dd, J = 9.0, 2.0 Hz, 1H), 7.53-7.48(m, 2H), 4.38(s, 1H), 4.26(s, 1H), 3.35(s, 2H), 2.33(dt, J = 13.5, 3.5 Hz, 2H), 2.00(m, 2H), 1.81(dt, J = 13.5, 3.5 Hz, 2H), 1.65(m, 2H). $^{13}$C-NMR(100 MHz, CD$_3$OD) 133.9, 132.9, 129.1, 128.1, 127.3, 126.3, 126.2, 125.9, 123.7, 89.4, 87.7, 69.6, 45.9, 39.8, 28.5, 28.4.
4-(aminomethyl)-1-methyl-4-(4-(trifluoromethoxy)phenyl)-cyclohexanol (219)

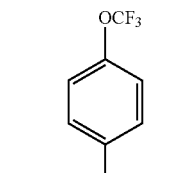   Me   OH   Y, E

HPLC R$_t$ = 1.45 min; LC-MS (15 minute method) 7.48 min, (M + 1)$^+$ 304.1 @ 7.60 min; $^1$H-NMR (400 MHz, CD$_3$OD) 8.40(brs, 2H), 7.58(dd, J = 9.0, 2.5 Hz, 2H), 7.34(d, J = 9.0 Hz, 2H), 3.00(s, 2H), 2.20(d, J = 13.5 Hz, 2H), 1.96(t, J = 13.5 Hz, 2H), 1.59(d, J = 14.0 Hz, 2H), 1.31

TABLE 5-continued

Summary of 4-Substituted Cycloalkylamines

| Ar | R$^b$ | R$^c$ | General Procedure |
|---|---|---|---|

(t, J = 13.5 Hz, 2H), 1.07(s, 3H). $^{13}$C-NMR (100 MHz, CD$_3$OD) 129.4, 121.5, 68.0, 51.9, 40.4, 34.0, 29.6, 28.5
4-(aminomethyl)-4-(4-(trifluoromethoxy)phenyl)cyclohexanol (220)

| 4-OCF$_3$-phenyl | H | OH | W, E |

HPLC R$_t$ = 1.34 min; $^1$H-NMR (400 MHz, CDCl$_3$) 8.44(brs, 1H), 7.60-7.56(m, 2H), 7.33(d, J = 9.0 Hz, 2H), 3.76(m, 1H), 3.15(s, 2H), 2.11-1.99 (m, 4H), 1.64(m, 4H). $^{13}$C-NMR(100 MHz, CDCl$_3$) 168.0, 148.4, 128.9, 121.4, 66.3, 49.0, 40.0, 29.0, 28.8. LC-MS (M + 1)$^+$ 290.2.
(4,4-difluoro-1-(naphthalen-2-yl)cyclohexyl)methanamine (221)

| naphthalen-2-yl | F | F | CC, E |

HPLC R$_t$ = 1.18 min; LC-MS (15 minute method) 7.70 min, (M + 1)$^+$ 276.2 @ 7.76 min; $^1$H-NMR (400 MHz, CD$_3$OD) 8.39(brs, 2H), 8.01-7.88(m, 4H), 7.64(d, J = 8.5 Hz, 1H), 7.54-751(m, 2H), 3.18(s, 2H), 2.60 (d, J = 13.5 Hz, 2H), 2.09-1.90(m, 4H), 1.89-1.71(m, 2H). $^{13}$C-NMR (100 MHz, CD$_3$OD) 133.8, 132.9, 129.6, 128.1, 127.4, 127.0, 126.5, 126.4, 123.8, 50.0, 30.2, 30.0, 29.7, 29.6.

Synthesis of Secondary and Tertiary Amines

Compounds in Table 6, below, were synthesized from the respective 1-(aryl)-4-oxocyclohexanecarbonitriles according to the indicated General Procedures.

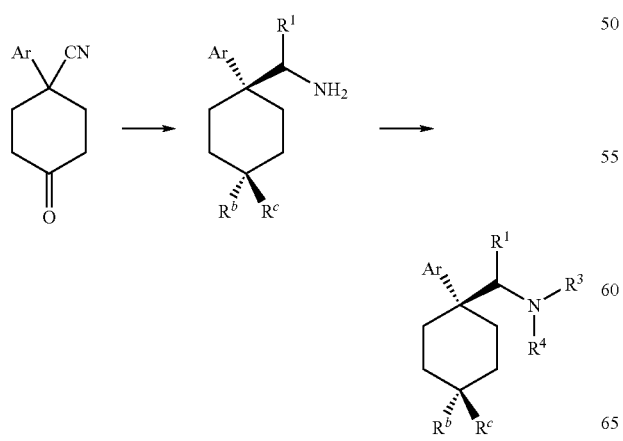

TABLE 6

Summary of Secondary and Tertiary Amines

| Ar | R$^1$ | R$^3$ | R$^4$ | R$^b$ | R$^c$ | General Procedure |
|---|---|---|---|---|---|---|

1-methyl-4-((methylamino)methyl)-4-(naphthalen-2-yl)-cyclohexanol (222)

| naphthalen-2-yl | H | H | CH$_3$ | OH | CH$_3$ | F2 |

Prepared from: 209
$^1$H-NMR(400 MHz, CDCl$_3$) 8.88(brs, 2H), 7.97-7.79(m, 4H), 7.54-7.46(m, 3H), 3.12(m, 2H), 2.24(m, 2H), 2.23(t, J = 5.0 Hz, 3H), 2.04 (m, 2H), 1.71(m, 2H), 1.60(m, 2H), 1.35(s, 3H). $^{13}$C-NMR (100 MHz, CDCl$_3$) 133.7, 132.6, 129.6, 128.6, 127.6, 127.0, 126.8, 126.7, 123.9, 70.1, 35.7, 35.1, 30.6. LC-MS (M + 1)$^+$ 284.1.
1-methyl-4-((methylamino)methyl)-4-(naphthalen-2-yl)cyclohexanol (223)

| naphthalen-2-yl | H | H | CH$_3$ | CH$_3$ | OH | E, F2 |

$^1$H-NMR(400 MHz, CDCl$_3$) 9.24(brs, 2H), 7.94-7.83(m, 4H), 7.57(d, J = 9.0 Hz, 1H), 7.53-7.48(m, 2H), 3.03(s, 2H), 2.58(s, 3H), 2.59-2.43(m, 4H), 1.68(d, J = 13.5 Hz, 2H), 1.46-1.39(m, 2H), 1.04(s, 3H). $^{13}$C-NMR(100 MHz, CDCl$_3$) 137.8, 133.7, 132.5, 129.4, 128.4, 127.7, 127.0, 126.7, 126.6, 124.5, 69.1, 62.4, 41.6, 35.1, 34.9, 30.6, 28.2. LC-MS (M + 1)$^+$ 284.1.
4-((dimethylamino)methyl)-1-methyl-4-(naphthalen-2-yl)cyclohexanol (224)

| naphthalen-2-yl | H | CH$_3$ | CH$_3$ | OH | CH$_3$ | C |

Prepared from: 209
$^1$H-NMR(400 MHz, CDCl$_3$) 7.89-7.80(m, 4H), 7.60(dd, J = 8.5, 2.0 Hz, 1H), 7.52-7.45(m, 2H), 2.54(s, 2H), 2.35-2.21(m, 2H), 2.00(s, 6H), 1.99-1.85(m, 2H), 1.73-1.53(m, 4H), 1.35(s, 3H). LC-MS (M + 1)$^+$ 298.0.
4-((dimethylamino)methyl)-1-methyl-4-(naphthalen-2-yl)cyclohexanol (225)

| naphthalen-2-yl | H | CH$_3$ | CH$_3$ | CH$_3$ | OH | C |

$^1$H-NMR(400 MHz, CDCl$_3$) 7.93(m, 4H), 7.68(dd, J = 8.8, 2.0 Hz, 1H), 7.52(m, 2H), 3.42(s, 2H), 2.50(s, 6H), 2.44(d, J = 13.2 Hz, 2H), 2.05(dt, J = 13.6, 3.2 Hz, 2H), 1.63(d, J = 13.2 Hz, 2H), 1.41(dt, J =

TABLE 6-continued

Summary of Secondary and Tertiary Amines

| Ar | R¹ | R³ | R⁴ | R$^b$ | R$^c$ | General Procedure |
|---|---|---|---|---|---|---|

13.6, 3.2 Hz, 2H), 1.05(s, 3H). $^{13}$C-NMR(100 MHz, CDCl$_3$) 138.1, 135.3, 134.3, 130.9, 129.7, 129.3, 129.0, 128.2, 126.3, 73.4, 69.5, 47.6, 42.8, 35.6, 31.4, 30.9. LC-MS (M + 1)$^+$ 298.0.
4-((methylamino)methyl)-4-(naphthalen-2-yl)cyclohexanol (226)

| | H | H | CH$_3$ | H | OH | F2 |

Prepared from : 207
$^1$H-NMR(400 MHz, CD$_3$OD) 7.99-7.87(m, 4H), 7.63(dd, J = 8.5, 2.0 Hz, 1H), 7.54-7.52(m, 2H), 3.81(m, 1H), 3.32(s, 2H), 2.57(s, 3H), 2.18(m, 4H), 1.72(m, 4H). $^{13}$C-NMR(100 MHz, CD$_3$OD) 135.1, 134.1, 130.5, 129.3, 128.6, 127.7, 127.6, 125.2, 67.5, 61.9, 35.4, 30.2, 30.1. LC-MS(M + 1)$^+$ 270.0
4-((methylamino)methyl)-4-(naphthalen-2-yl)cyclohexanol (227)

| | H | H | CH$_3$ | OH | H | F2 |

Prepared from: 208
$^1$H-NMR(400 MHz, CDCl$_3$) 7.92-7.82(m, 4H), 7.59-7.47(m, 3H), 3.77(m, 1H), 2.66(s, 2H), 2.61(d, J = 13.5 Hz, 2H), 2.29(s, 3H), 1.97-1.88(m, 2H), 1.65(t, J = 13.5 Hz, 2H), 1.42-1.20(m, 4H). LC-MS (M + 1)$^+$ 270.1.
4-((dimethylamino)methyl)-4-(naphthalen-2-yl)cyclohexanol (228)

| | H | CH$_3$ | CH$_3$ | OH | H | F |

Prepared from: 208
$^1$H-NMR(400 MHz, CD$_3$OD) 8.11-7.89(m, 4H), 7.70(d, J = 9.0 Hz, 1H), 7.60-7.51(m, 2H), 3.72(m, 1H), 3.52(brs, 2H), 2.69(d, J = 13.0 Hz, 2H), 2.57(s, 6H), 2.00-1.72(m, 4H), 1.50-1.32(m, 2H). LC-MS (M + 1)$^+$ 284.1.
4-((dimethylamino)methyl)-4-(naphthalene-2-yl)cyclohexanol (229)

| | H | CH$_3$ | CH$_3$ | H | OH | C |

Prepared from: 207
$^1$H-NMR(400 MHz, CD$_3$OD) 7.90-7.77(m, 4H), 7.63(d, J = 9.0 Hz, 1H), 7.52-7.41(m, 2H), 3.73(m, 1H), 2.72(s, 2H), 2.25-2.12(m, 2H), 2.09-1.91(m, 2H), 1.95(s, 6H), 1.82-1.60(m, 4H). LC-MS (M + 1)$^+$ 284.1.

1-(4-chloro-4-(naphthalen-2-yl)cyclohexyl)-N,N-dimethylmethanamine (230)

| | H | CH$_3$ | CH$_3$ | Cl | H | C |

Prepared from: 211
$^1$H-NMR(400 MHz, CDCl$_3$) 7.91-7.82(m, 4H), 7.55(dd, J = 9.0, 1.5 Hz, 1H), 7.52-7.47(m, 2H), 4.06(m, 1H), 2.42(s, 2H), 2.18-2.01(m, 4H), 2.04(s, 6H), 1.83-1.71(m, 4H). LC-MS (m/z) 302.3.
1-methyl-4-(1-(methylamino)ethyl)-4-(naphthalen-2-yl)cyclohexanol (231)

| | CH$_3$ | H | CH$_3$ | CH$_3$ | OH | I, F2 |

Prepared from the corresponding nitrile.
Enantiomers (E1, E2) separated by SFC w/AD column and 30% MeOH/0.1% DEA, 280 nm.
$^1$H-NMR(400 MHz, CD$_3$OD) 7.93-7.84(m, 4H), 7.63(d, J = 8.5 Hz, 1H), 7.55-7.45(m, 2H), 2.59(q, J = 7.0 Hz, 1H), 2.44-2.22(m, 1H), 2.23(s, 3H), 2.18-2.03(m, 2H), 1.66-1.23(m, 5H), 1.04(d, J = 7.0 Hz, 3H), 1.01(s, 3H). LC-MS(M + 1)$^+$ 298.1.1.
1-(4-fluoro-1-(naphthalen-2-yl)cyclohexyl)-N-methylmethanamine (232)

| | H | H | CH$_3$ | F | H | F2 |

Prepared from: 212
$^1$H-NMR(400 MHz, CDCl$_3$) 7.87-7.81(m, 4H), 7.54-7.45(m, 3H), 4.74(m, 0.5H), 4.61(m, 0.5H), 2.70(s, 2H), 2.52(m, 2H), 2.25(s, 3H), 2.01-1.94(m, 2H), 1.76-1.56(m, 4H). $^{13}$C-NMR(100 MHz, CDCl$_3$) 133.7, 132.1, 128.8, 128.3, 127.6, 126.4, 126.3, 126.1, 124.7, 92.8, 91.1, 63.7, 42.0, 37.3, 31.2, 31.1, 28.7, 28.5. LC-MS(M + 1)$^+$ 272.2.
1-(4-fluoro-1-(naphthalen-2-yl)cyclohexyl)-N,N-dimethylmethanamine (233)

| | H | CH$_3$ | CH$_3$ | F | H | C |

Prepared from: 212
$^1$H-NMR(400 MHz, CDCl$_3$) 7.82(m, 4H), 7.54(dd, J = 8.5, 2.0 Hz, 1H), 7.45(m, 2H), 4.71(m, 0.5H), 4.58(m, 0.5H), 2.45(m, 2H), 2.42(s, 2H), 2.00(s, 6H), 1.97(m, 2H), 1.77-1.57(m, 4H). $^{13}$C-NMR(100

TABLE 6-continued

Summary of Secondary and Tertiary Amines

| Ar | R¹ | R³ | R⁴ | Rᵇ | Rᶜ | General Procedure |
|---|---|---|---|---|---|---|

MHz, CDCl₃) 133.7, 132.0, 128.2, 128.1, 127.6, 126.3, 126.0, 125.7, 125.5, 93.4, 91.7, 72.2, 48.7, 30.9, 30.8, 28.8, 28.6. LC-MS(M + 1)⁺ 286.4.
4-(1-(dimethylamino)ethyl)-1-methyl-4-(naphthalen-2-yl)cyclohexanol (234)

| | CH₃ | CH₃ | CH₃ | CH₃ | OH | I, C |

Prepared from the corresponding nitrile.
Enantiomers (E1, E2) separated by Chiral HPLC, AD column, 280 nm, 90/10/0.1 hexanes/isopropanol/diethylamine.
¹H-NMR(400 MHz, CDCl₃) 7.83-7.79(m, 4H), 7.61(m, 1H), 7.49-7.43(m, 2H), 3.01(q, J = 7.5 Hz, 1H), 2.82(brd, J = 13.0 Hz, 1H), 2.62 (brs, 1H), 2.23(d, J = 13.5 Hz, 1H), 2.00(s, 6H), 2.00-1.85(m, 1H), 1.59-1.40(m, 4H), 1.30-1.21(m, 1H), 1.02(s, 3H), 0.84(d, J = 7.0 Hz, 3H). ¹³C-NMR(100 MHz, CDCl₃) 133.5, 132.0, 128.3, 127.5, 127.3, 125.9, 125.7, 69.6, 44.0, 42.5, 35.5, 35.2, 31.2, 29.7, 28.6, 11.7, 7.6. LC-MS(M + 1)⁺ 312.3.
1-(4-fluoro-1-(naphthalen-2-yl)cyclohexyl)-N,N-dimethylmethanamine (235)

| | H | CH₃ | CH₃ | H | F | C |

Prepared from: 213
¹H-NMR(400 MHz, CDCl₃) 7.81(m, 4H), 7.55(d, J = 8.0 Hz, 1H), 7.45(m, 2H), 4.72(m, 0.5H), 4.60(m, 0.5H), 2.46(s, 2H), 2.22(d, J = 13.5 Hz, 2H), 2.05-1.91(m, 4H), 1.96(s, 6H), 1.69-1.56(m, 2H). ¹³C-NMR(100 MHz, CDCl₃) 133.6, 132.0, 128.2, 127.9, 127.6, 126.3, 126.0, 125.8, 125.7, 90.8, 89.1, 73.2, 48.7, 28.7, 27.8, 27.6. LC-MS (M + 1)⁺ 286.2.
1-(4-fluoro-1-(naphthalen-2-yl)cyclohexyl)-N-methylmethanamine (236)

| | H | H | CH₃ | H | F | A |

Prepared from: 213
¹H-NMR(400 MHz, CDCl₃) 8.27(brs, 1H), 7.89-7.83(m, 4H), 7.53-7.49(m, 3H), 4.73(m, 0.5H), 4.61(m, 0.5 H), 2.84(s, 2H), 2.34(d, J = 13.5 Hz, 2H), 2.30(s, 3H), 2.08-1.96(m, 4H), 1.54(t, J = 13.0 Hz, 2H). LC-MS(M + 1)⁺ 272.2.

TABLE 6-continued

Summary of Secondary and Tertiary Amines

| Ar | R¹ | R³ | R⁴ | Rᵇ | Rᶜ | General Procedure |
|---|---|---|---|---|---|---|

4-(benzo[d][1,3]dioxol-5-yl)-4-((methylamino)methyl)cyclohexanol (237)

| | H | H | CH₃ | H | OH | F2 |

Prepared from: 214
¹H-NMR(400 MHz, CDCl₃) 6.87(d, J = 2.0 Hz, 1H), 6.81(dd, J = 8.0, 2.0 Hz, 1H), 6.76(d, J = 8.0 Hz, 1H), 5.94(s, 2H), 3.76(m, 1H), 2.65 (s, 2H), 2.29(s, 3H), 2.08-2.02(m, 2H), 1.82-1.70(m, 4H), 1.62-1.56 (m, 2H). ¹³C-NMR(100 MHz, CDCl₃) 145.8, 119.8, 108.2, 107.3, 101.1, 68.7, 62.2, 41.4, 37.5, 30.8, 30.5. LC-MS(M + 1)⁺ 264.1.
4-(benzo[d][1,3]dioxol-5-yl)-4-((dimethylamino)methyl)cyclohexanol (238)

| | H | CH₃ | CH₃ | H | OH | F |

Prepared from: 214
¹H-NMR(400 MHz, CD₃OD) 6.88(s, 1H), 6.81(d, J = 8.0 Hz, 1H), 6.75(dd, J = 8.0, 2.0 Hz, 1H), 5.92(s, 2H), 3.78(m, 1H), 2.39(s, 2H), 2.04-1.99(m, 2H), 1.99(s, 6H), 1.78-1.67(m, 4H), 1.58(m, 2H). ¹³C-NMR(100 MHz, CD₃OD) 120.1, 108.0, 107.8, 101.0, 70.7, 68.4, 48.5, 31.7, 30.3, 30.0. LC-MS(M + 1)⁺ 278.2.
4-(benzo[d][1,3]dioxol-5-yl)-1-methyl-4-((methylamino)methyl)cyclohexanol (239)

| | H | H | CH₃ | CH₃ | OH | F2 |

Prepared from: 215
¹H-NMR(400 MHz, CD₃OD) 8.45(brs, 1H), 6.98(s, 1H), 6.92(d, J = 8.0 Hz, 1H), 6.87(d, J = 8.0 Hz, 1H), 5.97(s, 2H), 3.03(s, 2H), 2.56(s, 3H), 2.14(d, J = 13.5 Hz, 2H), 1.91(t, J = 13.0 Hz, 2H), 1.55(d, J = 13.5 Hz, 2H), 1.34(t, J = 13.0 Hz, 2H), 1.07(s, 3H). ¹³C-NMR(100 MHz, CD₃OD) 168.2, 149.2, 147.2, 132.9, 120.9, 108.5, 108.4, 107.5, 101.5, 68.0, 62.4, 40.5, 34.1, 34.0, 29.8, 29.0, 28.8. LC-MS(M + 1)⁺ 278.3.
4-(benzo[d][1,3]dioxol-5-yl)-4-((dimethylamino)methyl)-1-methylcyclohexanol (240)

| | H | CH₃ | CH₃ | CH₃ | OH | C |

Prepared from: 215
¹H-NMR(400 MHz, CD₃OD) 8.54(brs, 1H), 6.99(d, J = 1.5 Hz, 1H), 6.95(dd, J = 8.5, 1.5 Hz, 1H), 6.84(d, J = 8.5 Hz, 1H), 5.96(s, 2H), 2.92(s, 2H), 2.34(s, 6H), 2.12(d, 13.0 Hz, 2H), 1.89(t, J = 13.5 Hz, 2H), 1.53(d, J = 13.0 Hz, 2H), 1.37(d, J = 13.5 Hz, 2H), 1.03(s, 3H).

TABLE 6-continued

Summary of Secondary and Tertiary Amines

| Ar | R¹ | R³ | R⁴ | Rᵇ | Rᶜ | General Procedure |
|---|---|---|---|---|---|---|

$^{13}$C-NMR(100 MHz, CD$_3$OD) 120.9, 108.2, 107.8, 101.4, 72.9, 68.2, 46.5, 34.1 29.8, 29.5. LC-MS(M + 1)$^+$ 292.2.
4-(benzo[d][1,3]dioxol-5-yl)-1-methyl-4-((methylamino)methyl)cyclohexanol (241)

| benzo[d][1,3]dioxol-5-yl | H | H | CH$_3$ | OH | CH$_3$ | F |

Prepared from: 216
$^1$H-NMR(400 MHz, CD$_3$OD) 8.39(brs, 1H), 7.00-6.86(m, 3H), 5.96 (s, 2H), 3.22(s, 2H), 2.58(s, 3H), 2.17(m, 2H), 1.78-1.74(m, 2H), 1.65-1.59(, 4H), 1.27(s, 3H). $^{13}$C-NMR(100 MHz, CD$_3$OD) 149.0, 147.2, 120.0, 108.4, 106.9, 101.5, 39.7, 34.5, 34.0, 30.3, 27.4. LC-MS (M + 1)$^+$ 278.1.
4-(benzo[d][1,3]dioxol-5-yl)-4-((dimethylamino)methyl)-1-methylcyclohexanol (242)

| benzo[d][1,3]dioxol-5-yl | H | CH$_3$ | CH$_3$ | OH | CH$_3$ | C |

Prepared from: 216
$^1$H-NMR(400 MHz, CD$_3$OD) 8.54(brs, 1H), 7.00(d, J = 2.0 Hz, 1H), 6.93(dd, J = 8.5, 2.0 Hz, 1H), 6.83(d, J = 8.5 Hz, 1H), 5.94(s, 2H), 3.03(s, 2H), 2.33(s, 6H), 2.16(m, 2H), 1.73(m, 2H), 1.57(t, J = 6.0 Hz, 4H), 1.26(s, 3H). $^{13}$C-NMR(100 MHz, CD$_3$OD) 120.1, 108.1, 107.3, 101.3, 46.4, 34.8, 30.9. LC-MS(M + 1)$^+$ 292.1.
1-(fluoromethyl)-4-((methylamino)methyl)-4-(naphthalen-2-yl)cyclohexanol (243)

| naphthalen-2-yl | H | H | CH$_3$ | CH$_2$F | OH | A |

Prepared from: 217
$^1$H-NMR(400 MHz, CD$_3$OD) 8.50(brs, 1H), 7.99-7.87(m, 4H), 7.63 (d, J = 8.0 Hz, 1H), 7.54-7.50(m, 2H), 4.03(s, 1H), 3.91(s, 1H), 3.19 (s, 2H), 2.54(s, 3H), 2.46(d, J = 13.5 Hz, 2H), 2.06(t, J = 13.5 Hz, 2H), 1.62(d, J = 13.5 Hz, 2H), 1.41(t, J = 13.5 Hz, 2H). $^{13}$C-NMR(100 MHz, CD$_3$OD) 136.0, 133.9, 132.9, 129.4, 128.0, 127.3, 127.3, 126.4, 124.2, 90.6, 88.9, 69.3, 62.4, 41.1, 34.1, 28.2, 28.1, 27.8. LC-MS (M + 1)$^+$ 302.3.
4-((dimethylamino)methyl)-1-(fluoromethyl)-4-(naphthalen-2-yl)cyclohexanole (244)

| naphthalen-2-yl | H | CH$_3$ | CH$_3$ | CH$_2$F | OH | F |

Prepared from: 217
$^1$H-NMR(400 MHz, CDCl$_3$) 7.81(m, 4H), 7.55(dd, J = 8.5, 1.5 Hz, 1H), 7.47-7.44(m, 2H), 4.08(s, 1H), 3.96(s, 1H), 2.43(s, 2H), 2.34(d, J = 13.5 Hz, 2H), 2.01(dt, J = 13.5, 3.0 Hz, 2H), 1.98(s, 6H), 1.61(d, J = 14.0 Hz, 2H), 1.38(dt, J = 13.5, 3.0 Hz, 2H). $^{13}$C-NMR(100 MHz, CDCl$_3$) 144.1, 133.7, 132.0, 128.2, 128.0, 127.6, 126.6, 126.0, 126.9, 125.7, 91.7, 90.0, 74.3, 48.8, 44.0, 29.2, 29.1, 28.4. LC-MS(M + 1)$^+$ 316.2.
1-(fluoromethyl)-4-((methylamino)methyl)-4-(naphthalen-2-yl)cyclohexanol (245)

| naphthalen-2-yl | H | H | CH$_3$ | OH | CH$_2$F | A |

Prepared from: 218
$^1$H-NMR(400 MHz, CD$_3$OD) 7.99-7.87(m, 4H), 7.64(dd, J = 8.5, 2.0 Hz, 1H), 7.53-7.51(m, 2H), 4.39(s, 1H), 4.27(s, 1H), 3.46(s, 2H), 2.58(s, 3H), 2.37-2.29(m, 2H), 2.00(m, 2H), 1.86-1.79(m, 2H), 1.65 (m, 2H). $^{13}$C-NMR(100 MHz, CD$_3$OD) 129.2, 128.1, 127.3, 126.4, 126.3, 125.8, 123.5, 34.1, 28.9, 28.4, 28.3. LC-MS(M + 1)$^+$ 302.3.
4-((dimethylamino)methyl)-1-(fluoromethyl)-4-(naphthalen-2-yl)cylcohexanol (246)

| naphthalen-2-yl | H | CH$_3$ | CH$_3$ | OH | CH$_2$F | F |

Prepared from: 218
$^1$H-NMR(400 MHz, CDCl$_3$) 7.81(m, 4H), 7.54(dd, J = 9.0, 1.5 Hz, 1H), 7.47-7.42(m, 2H), 4.45(s, 1H), 4.33(s, 1H), 2.54(s, 2H), 2.25-2.20(m, 2H), 1.96(s, 6H), 1.96-1.91(m, 2H), 1.78-1.63(m, 4H). $^{13}$C-NMR(100 MHz, CDCl$_3$) 133.7, 132.0, 128.3, 127.9, 127.5, 126.0, 125.7, 125.6, 125.3, 89.7, 88.0, 48.5, 29.8, 29.7. LC-MS(M + 1)$^+$ 316.4.
1-methyl-4-((methylamino)methyl)-4-(4-(trifluoromethoxy)phenyl)cylcohexanol (247)

| 4-(OCF$_3$)phenyl | H | H | CH$_3$ | CH$_3$ | OH | F2 |

Prepared from: 219
$^1$H-NMR(400 MHz, CD$_3$OD) 8.34(brs, 2H), 7.58(d, J = 8.5 Hz, 2H), 7.36(d, J = 8.5 Hz, 2H, 3.10(s, 2H), 2.58(s, 3H), 2.20(d, J = 13.0 Hz, 2H), 1.98(dt, J = 13.5, 3.0 Hz, 2H), 1.58(d, J = 13.5 Hz, 2H), 1.29(dt, J = 13.5, 3.0 Hz, 2H), 1.05(s, 3H). $^{13}$C-NMR(100 MHz, CD$_3$OD) 129.4, 127.3, 121.6, 67.8, 62.2, 40.5, 34.1, 33.9, 29.7, 28.7. LC-MS (M + 1)$^+$ 318.2.

TABLE 6-continued

Summary of Secondary and Tertiary Amines

| Ar | R¹ | R³ | R⁴ | Rᵇ | Rᶜ | General Procedure |
|---|---|---|---|---|---|---|

4-((dimethylamino)methyl)-1-methyl-4-(4-(trifluoromethoxy)phenyl)cylcohexanol (248)

| 4-OCF₃-C₆H₄– | H | CH₃ | CH₃ | CH₃ | OH | C |

Prepared from: 219
$^1$H-NMR(400 MHz, CDCl₃) 7.39(d, 8.5 Hz, 2H), 7.15(d, J = 8.5 Hz, 2H), 2.30(s, 2H), 2.09(d, J = 13.5 Hz, 2H), 1.97(s, 6H), 1.88(dt, J = 13.5, 3.0 Hz, 2H), 1.52(d, J = 13.0 Hz, 2H), 1.34(dt, J = 13.5, 3.5 Hz, 2H), 1.11(s, 3H). $^{13}$C-NMR(100 MHz, CDCl₃) 129.0, 120.6, 48.7, 35.2, 29.4. LC-MS(M + 1)⁺ 332.3.

4-((methylamino)methyl)-4-(4-(trifluoromethoxy)phenyl)cyclohexanol (249)

| 4-OCF₃-C₆H₄– | H | H | CH₃ | H | OH | F2 |

Prepared from: 220
LC-MS (15 minute method) 6.57 min, (M + 1)+ 304.2 @ 6.75 min; 1H-NMR(400 MHz, CD₃OD) 8.42(brs, 1H), 7.58(d, J = 8.5 Hz, 2H), 7.34 (d, J = 8.5 Hz, 2H), 3.78-3.75(m, 1H), 3.24(s, 2H), 2.59(s, 6H), 2.09-2.01(m, 4H), 1.65-1.62(m, 4H). 13C-NMR(100 MHz, CD₃OD), 167.9, 128.9, 121.5, 66.1, 59.5, 40.2, 34.1, 28.9.

4-((dimethylamino)methyl)-4-(4-(trifluoromethoxy)phenyl)cyclohexanol (250)

| 4-OCF₃-C₆H₄– | H | CH₃ | CH₃ | H | OH | C |

Prepared from: 220
$^1$H-NMR(400 MHz, CDCl₃) 7.38(d, J = 9.0 Hz, 2H), 7.14(d, J = 9.0 Hz, 2H), 3.81-3.78(m, 1H), 2.42(s, 2H), 2.10-2.03(m, 2H), 1.96(s, 6H), 1.86-1.78(m, 2H), 1.70-1.57(m, 4H). $^{13}$C-NMR(100 MHz, CDCl₃) 147.4, 128.5, 122.0, 120.6, 94.6, 70.6, 68.2, 48.5, 42.2, 30.3, 30.1, 29.6. LC-MS(M + 1)⁺ 318.3.

1-(4,4-difluoro-1-(naphthalen-2-yl)cyclohexyl)-N-methylmethanamine (251)

| naphthalen-2-yl | H | H | CH₃ | F | F | F2 |

Prepared from: 221
$^1$H-NMR(400 MHz, CDCl₃) 7.89-7.79(m, 4H), 7.53-7.48(m, 3H), 2.70(s, 2H), 2.51(d, J = 13.0 Hz, 2H), 2.26(s, 3H), 2.05-1.91(m, 4H), 1.87-1.77(m, 2H). $^{13}$C-NMR(100 MHz, CDCl₃) 139.9, 133.6, 132.2, 128.9, 128.2, 127.6, 126.5, 126.3, 126.2, 124.6, 64.1, 42.0, 37.4, 31.0, 30.9, 30.8, 30.7, 30.5. LC-MS(M + 1)⁺ 290.3.

1-(4,4-difluoro-1-(naphthalen-2-yl)cyclohexyl)-N,N-dimethylmethanamine (252)

| naphthalen-2-yl | H | CH₃ | CH₃ | F | F | F |

Prepared from: 221
$^1$H-NMR(400 MHz, CDCl₃) 7.82(m, 4H), 7.53(d, J = 8.5 Hz, 1H), 7.47(m, 2H), 2.45(apd, J = 10.0 Hz, 2H), 1.97(s, 2H), 2.05-1.89(m, 4H), 1.97(s, 6H), 1.85-1.74(m, 2H). $^{13}$C-NMR(100 MHz, CDCl₃) 128.3, 128.2, 127.6, 126.3, 126.2, 125.9, 125.3, 72.4, 48.6, 31.0, 30.7, 30.5, 30.4. LC-MS(M + 1)⁺ 304.2.

3,4-Dichlorophenyl-Cyclohexylamine Analogs

189
-continued

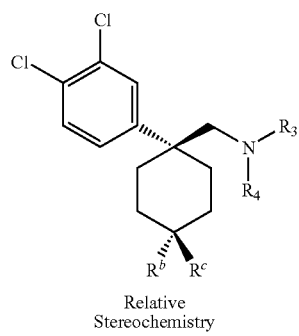

Relative Stereochemistry

TABLE 7

Summary of 3,4-Dichlorophenyl-Cyclohexylamine Analogs

| $R^b$ | $R^c$ | $R^3$ | $R^4$ | General Procedure |
|---|---|---|---|---|
| \multicolumn{5}{c}{(1-(3,4-dichlorophenyl)-4-fluorocyclohexyl)methanamine (253)} | | | | |
| F | H | H | H | W, BB, E |

$^1$H NMR (400 MHz, CDCl$_3$) δ 8.02 (broad, 1 H), 7.46 (d, J = 8.0 Hz, 1 H), 7.43 (s, 1 H), 7.19 (d, J = 8.0 Hz, 1 H), 4.62 (m, 1 H), 2.83 (s, 2 H), 2.26 (m, 2 H), 1.90 (m, 2 H), 1.58 (m, 4 H); $^{13}$C NMR (100 MHz, CDCl$_3$), δ 141.52, 133.57, 131, 80, 131.39, 129.57, 126.66, 91.08, 89.37, 49.49, 40.58, 30.02, 29.94, 27.92, 27.72; ESI MS m/z 276.
1-(1-(3,4-dichlorophenyl)-4-fluorocyclohexyl)-N,N-dimethylmethanamine (254)

| F | H | CH$_3$ | CH$_3$ | W, BB, E, D |
|---|---|---|---|---|

Prepared from 253

$^1$H NMR (400 MHz, CDCl$_3$) δ 8.31 (broad, 1 H), 7.47 (d, J = 2.4 Hz, 1 H), 7.44 (d, J = 8.4 Hz, 1 H), 7.26 (dd, J = 8.14, 2.4 Hz, 1 H), 4.62 (m, 1 H), 2.68 (s, 2 H), 2.26 (m, 2 H), 2.22 (s, 6 H), 1.95 (m, 2 H), 1.70 (t, J = 13.6 Hz, 1 H), 1.57 (m, 2 H); $^{13}$C NMR (100 MHz, CDCl$_3$) δ 166.24, 144.8, 133.23, 130.88, 129.44, 126.88, 91.90, 90.19, 70.43, 47.54, 41.98, 30.83, 30.74, 28.22, 28.02; ESI MS m/z 304.
(1-(3,4-dichlorophenyl)-4-methoxycyclohexyl)methanamine (255)

| H | OCH$_3$ | H | H | W, EE, E |
|---|---|---|---|---|

$^1$H NMR (400 MHz, CD$_3$OD) δ 7.46 (m, 2 H), 7.22 (d, J = 7.6 Hz, 1 H), 6.69 (broad, 2 H), 3.31 (s, 3 H), 2.80 (s, 2 H), 1.91 (m, 4 H), 1.72 (m, 1 H), 1.40 (m, 2 H); $^{13}$C NMR (100 MHz, CDCl$_3$) δ 142.92, 133.53, 131.78, 131.26, 129.46, 126.87, 75.16, 55.65, 50.76, 40.98, 28.54, 25.77; ESI MS m/z 288.
1-(1-(3,4-dichlorophenyl)-4-methoxycyclohexyl)-N,N-dimethylmethanamine (256)

| H | OCH$_3$ | CH$_3$ | CH$_3$ | W, EE, E, D |
|---|---|---|---|---|

Prepared from 255

$^1$H NMR (400 MHz, CD$_3$OD) 7.46 (d, J = 2.8 Hz, 1 H), 7.37 (d, J = 8.4 Hz, 1 H), 7.23 (dd, J = 2.0, 8.4 Hz, 1 H), 3.32 (s, 3 H), 3.23 (m, 1 H), 2.34 (s, 2 H), 1.87 (s, 6 H), 1.84 (m, 2 H), 1.78 (m, 2 H), 1.56 (m, 2 H), 1.48 (m, 2 H); $^{13}$C NMR (100 MHz, CD$_3$OD) 141.57, 133.26, 131.56, 131.34, 130.02, 128.66, 69.25, 50.70, 47.73, 40.57, 30.79, 30.31; ESI MS m/z 316.0.
(1-(3,4-dichlorophenyl)-4-methoxycyclohexyl)methanamine (257)

| OCH$_3$ | H | H | H | W, X, EE, E |
|---|---|---|---|---|

$^1$H NMR (400 MHz, CD$_3$OD) δ 7.44 (m, 2 H), 7.20 (d, J = 7.6 Hz, 1 H), 6.68 (broad, 2 H), 3.29 (s, 3 H), 2.82 (s, 1 H), 1.90 (m, 4 H), 1.73 (m, 1 H), 1.43 (m, 2 H); $^{13}$C NMR (100 MHz, CDCl$_3$), δ 141.92, 133.33, 131.38, 131.14, 129.75, 126.99, 75.06, 55.90, 50.95, 41.23, 28.43, 25.93; ESI MS m/z 288.
1-(1-(3,4-dichlorophenyl)-4-methoxycyclohexyl)-N,N-dimethylmethanamine (258)

| OCH$_3$ | H | CH$_3$ | CH$_3$ | W, X, EE, E, D |
|---|---|---|---|---|

Prepared from 257

$^1$H NMR (400 MHz, CD$_3$OD) 7.45 (d, J = 2.4 Hz, 1 H), 7.36 (d, J = 8.8 Hz, 1 H), 7.21 (dd, J = 2.4, 8.8 Hz, 1 H), 3.33 (s, 3 H), 3.25 (m, 1 H), 2.37 (s, 2 H), 1.96 (s, 6 H), 1.91 (m, 2 H), 1.80 (m, 2 H), 1.66 (m, 2 H), 1.54 (m, 2 H); $^{13}$C NMR (100 MHz, CD$_3$OD) 141.28, 133.16, 131.23,

TABLE 7-continued

Summary of 3,4-Dichlorophenyl-Cyclohexylamine Analogs

| $R^b$ | $R^c$ | $R^3$ | $R^4$ | General Procedure |
|---|---|---|---|---|

131.24, 129.94, 127.56, 69.15, 50.80, 47.64, 40.48, 30.89, 30.26; ESI MS m/z 316.0.
1-(1-(3,4-dichlorophenyl)-4-methoxycyclohexyl)-N-methylmethanamine (259)

| OCH$_3$ | H | CH$_3$ | H | W, X, EE, E, A |
|---|---|---|---|---|

Prepared from 257

$^1$HNMR (400 MHz, CDCl$_3$) δ 7.42 (d, J = 2.4 Hz, 1 H), 7.40 (d, J = 8.4 Hz, 1 H), 7.19 (dd, J = 2.4, 8.4 Hz, 1 H), 3.28 (s, 3 H), 3.25 (m, 1 H), 2.56 (s, 2 H), 2.32 (m, 1 H), 2.29 (s, 3 H), 1.88 (m, 2 H), 1.56 (m, 1 H), 1.24 (m, 2 H); $^{13}$C NMR (100 MHz, CDCl$_3$) δ 144.76, 132.95, 132.95, 130.64, 130.29, 129.59, 126.92, 78.96, 64.90, 55.79, 42.43, 37.48, 31.88, 29.93, 27.58; ESI MS m/z 302.1.
(1-(3,4-dichlorophenyl)-4-fluorocyclohexyl)methanamine (260)

| H | F | H | H | W, X, BB, E |
|---|---|---|---|---|

$^1$H NMR (400 MHz, CD$_3$OD) δ 8.4 (broad, 1 H), 7.65 (d, J = 2.0 Hz, 1 H), 7.59 (d, J = 8.4 Hz, 1 H), 7.42 (dd, J = 2.0, 8.4 Hz, 1 H), 4.67 (d, J = 48.4 Hz, 1 H), 3.05 (s, 2 H), 2.18 (m, 2 H), 1.90 (m, 4 H), 1.51 (m, 2 H), 1.49 (m, 2 H); $^{13}$C NMR (100 MHz, CD$_3$OD) δ 140.69, 133.19, 131.44, 131.24, 129.78, 127.43, 140.00, 88.69, 87.02, 50.75, 40.48, 27.37, 26.82, 26.61; ESI MS m/z 276.0.
1-(1-(3,4-dichlorophenyl)-4-fluorocyclohexyl)-N,N-dimethylmethanamine (261)

| H | F | CH$_3$ | CH$_3$ | W, X, BB, E, D |
|---|---|---|---|---|

Prepared from 260

$^1$H NMR (400 MHz, CD$_3$OD) 7.47 (d, J = 2.4 Hz, 1 H), 7.44 (d, J = 8.8 Hz, 1 H), 7.26 (dd, J = 2.4, 8.8 Hz, 1 H), 4.60 (m, 1 H), 2.69 (s, 2 H), 2.26 (m, 2 H), 2.22 (s, 6 H), 1.95 (m, 2 H), 1.70 (m, 2 H), 1.56 (m, 2 H); $^{13}$C NMR (100 MHz, CD$_3$OD) 141.28, 133.22, 131.24, 130.87, 129.44, 126.88, 91.90, 90.20, 70.43, 47.54, 41.98, 30.83, 30.74, 28.22, 28.03; ESI MS m/z 274.0.
4-(aminomethyl)-4-(3,4-dichlorophenyl)cyclohexanol (262)

| OH | H | H | H | W, X, E |
|---|---|---|---|---|

$^1$H NMR (400 MHz, CD$_3$OD) 7.63 (d, J = 2.4 Hz, 1 H), 7.59 (d, J = 8.8 Hz, 1 H), 7.40 (dd, J = 2.4, 8.8 Hz, 1 H), 3.66 (m, 1 H), 3.02 (s, 2 H), 2.40 (m, 2 H), 1.86 (m, 2 H), 1.62 (m, 2 H), 1.24 (m, 2 H); $^{13}$C NMR (100 MHz, CD$_3$OD) 141.28, 133.16, 131.23, 131.24, 129.94, 127.56, 69.15, 50.80, 47.64, 40.48, 30.89, 30.26; ESI MS m/z 274.0.
4-(3,4-dichlorophenyl)-4-((dimethylamino)methyl)cyclohexanol (263)

| OH | H | CH$_3$ | CH$_3$ | W, X, E, D |
|---|---|---|---|---|

Prepared from 262

$^1$H NMR (400 MHz, CD$_3$OD) 7.64 (d, J = 2.4 Hz, 1 H), 7.55 (d, J = 8.8 Hz, 1 H), 7.36 (dd, J = 2.4, 8.8 Hz, 1 H), 3.55 (m, 1 H), 3.01 (s, 2 H), 2.24 (m, 2 H), 2.23 (s, 6 H), 1.79 (m, 2 H), 1.67 (m, 2 H), 1.33 (m, 2 H); $^{13}$C NMR (100 MHz, CD$_3$OD) 141.11, 133.06, 131.33, 131.31, 129.88, 127.76, 69.35, 51.82, 47.64, 45.78, 40.32, 30.77, 29.16; ESI MS m/z 302.0.
1-(1-(3,4-dichlorophenyl)-4-fluorocyclohexyl)-N-methylmethanamine (264)

| F | H | CH$_3$ | H | W, BB, E, A |
|---|---|---|---|---|

Prepared from 253

$^1$H NMR (400 MHz, CDCl$_3$) δ 7.46 (d, J = 2.0 Hz, 1 H), 7.44 (d, J = 8.4 Hz, 1 H), 7.23 (dd, J = 2.0, 8.4 Hz, 1 H), 4.47 (d, J = 48.8 Hz, 1 H), 2.71 (s, 2 H), 2.34 (s, 3 H), 2.28 (m, 2 H), 1.94 (m, 2 H), 1.59 (m, 4 H); $^{13}$C NMR (100 MHz, CDCl$_3$), δ 144.46, 133.02, 130.69, 130.26, 129.47, 126.83, 90.63, 88.41, 64.91, 48.67, 42.24, 37.56, 29.97, 28.75, 28.92, 28.39, 27.71, 27.41; ESI MS m/z 290.0.
(1-(3,4-dichlorophenyl)-4-phenoxycyclohexyl)methanamine (265)

| OPh | H | H | H | W, X, E |
|---|---|---|---|---|

$^1$H NMR (400 MHz, CD$_3$OD) 8.40 (broad, 1 H), 7.66 (d, J = 2.0 Hz, 1 H), 7.60 (d, J = 8.8 Hz, 1 H), 7.42 (dd, J = 2.0, 8.8 Hz, 1 H), 7.22 (m, 2 H), 6.84 (m, 3 H), 4.43 (m, 1 H), 3.31 (s, 2 H), 2.40 (m, 2 H), 2.01 (m, 2 H), 1.75 (m, 2 H), 1.49 (m, 2 H); $^{13}$C NMR (100 MHz, CD$_3$OD) 157.57, 141.57, 133.23, 131.37, 131.27, 129.69, 129.32, 127.32, 120.79, 115.94, 74.26, 49.93, 48.52, 48.44, 40.45, 30.31, 27.01; ESI MS m/z 336.1.

TABLE 7-continued

Summary of 3,4-Dichlorophenyl-Cyclohexylamine Analogs

| $R^b$ | $R^c$ | $R^3$ | $R^4$ | General Procedure |
|---|---|---|---|---|

1-(1-(3,4-dichlorophenyl)-4-phenoxycyclohexyl)-N,N-dimethylmethanamine (266)

| Oph | H | $CH_3$ | $CH_3$ | W, X, E, F |

Prepared from 265
$^1$H NMR (400 MHz, $CD_3OD$) 7.46 (d, J = 2.0 Hz, 1 H), 7.40 (d, J = 8.4 Hz, 1 H), 7.24 (m, 3 H), 6.90 (m, 1 H), 6.84 (m, 2 H), 4.25 (m, 1 H), 2.36 (s, 2 H), 2.30 (m, 2 H), 2.08 (s, 6 H), 2.0 (m, 2 H), 1.70 (m, 2 H), 1.48 (m, 2 H); $^{13}$C NMR (100 MHz, $CD_3OD$) 157.57, 141.527, 133.10, 132.68, 130.45, 129.98, 129.67, 127.16, 120.92, 116.19, 75.87 72.52, 49.93, 48.56, 48.44, 40.45, 31.40, 27.82; ESI MS m/z 378.0.

(1-(3,4-dichlorophenyl)-4,4-difluorocyclohexyl)methanamine (267)

| F | F | H | H | CC, E |

$^1$H NMR (400 MHz, $CD_3OD$) δ 8.4 (broad, 1 H), 7.67 (d, J = 2.4 Hz, 1 H), 7.62 (d, J = 8.4 Hz, 1 H), 7.43 (dd, J = 8.4, 2.4 Hz, 1 H), 3.10 (s, 2 H), 2.40 (m, 2 H), 2.20 (m, 2 H), 1.90 (m, 2 H), 1.70 (m, 2 H); $^{13}$C NMR (100 MHz, $CD_3OD$) δ 133.43, 131.82, 137.41, 129.57, 127.20, 122.35, 49.58, 47.60, 40.18, 30.05, 29.76, 29.51, 29.45; ESI MS m/z 294.0.

1-(1-(3,4-dichlorophenyl)-4,4-difluorocyclohexyl)-N-methylmethanamine (268)

| F | F | $CH_3$ | H | CC, E, F |

Prepared from 267 to give 268 and 269, which were separated by silica gel column chromatography (ethyl acetate/hexane/DEA = 1:4:0.1).
$^1$H NMR (400 MHz, $CD_3OD$) δ 8.5 (broad, 1 H), 7.68 (d, J = 2.4 Hz, 1 H), 7.62 (d, J = 8.4 Hz, 1 H), 7.44 (dd, J = 8.4, 2.4 Hz, 1 H), 3.20 (s, 2 H), 2.58 (s, 3 H), 2.40 (m, 2 H), 2.05 (m, 2 H), 1.92 (m, 2 H), 1.70 (m, 2 H); $^{13}$C NMR (100 MHz, $CD_3OD$) δ 139.86, 133.53, 131.96, 131.30, 129.54, 127.16, 122.46, 59.57,48.03, 40.24, 34.09, 29.94, 29.80, 29.70, 29.45; ESI MS m/z 307.9.

1-(1-(3,4-dichlorophenyl)-4,4-difluorocyclohexyl)-N,N-dimethylmethanamine (269)

| F | F | $CH_3$ | $CH_3$ | CC, E, F |

Prepared from 267 to give 268 and 269, which were separated by silica gel column chromatography (ethyl acetate/hexane/DEA = 1:4:0.1)
$^1$H NMR (400 MHz, $CD_3OD$) δ 7.58 (d, J = 2.4 Hz, 1 H), 7.50 (d, J = 8.4 Hz, 1 H), 7.37 (dd, J = 8.4, 2.4 Hz, 1 H), 2.43 (s, 2 H), 2.30 (m, 2 H), 2.01 (s, 6 H), 1.98 (m, 2 H), 1.82 (m, 2 H), 1.65 (m, 2 H); $^{13}$C NMR (100 MHz, $CD_3OD$) δ 139.86, 133.53, 131.96, 131.30, 129.54, 127.16, 122.46, 59.57, 48.03, 40.24, 34.09, 30.41, 30.17, 29.90, 29.81; ESI MS m/z 322.0.

1-(8-(3,4-dichlorophenyl)-1,4-dioxaspiro[4.5]decan-8-yl)-N-methylmethanamine (270)

| (dioxolane) | | $CH_3$ | H | FF, E, F |

270 and 271 were separated by silica gel column chromatography (ethyl acetate/hexane/DEA = 1:4:0.1).
$^1$H NMR (400 MHz, $CD_3Cl$) δ 7.42 (d, J = 2.4 Hz, 1 H), 7.38 (d, J = 8.8 Hz, 1 H), 7.19 (dd, J = 2.4, 8.8 Hz, 1 H), 3.90 (m, 4 H), 2.59 (s, 2 H), 2.27 (s, 6 H), 2.18 (m, 2 H), 1.82 (m, 2 H), 1.62 (m, 2 H), 1.46 (m, 2 H); $^{13}$C NMR (100 MHz, $CD_3Cl$) δ 132.84, 130.54, 130.31, 129.39, 126.72, 109.02, 64.48, 64.47, 41.91, 37.57, 31.74, 31.35; ESI MS m/z 330.1.

1-(8-(3,4-dichlorophenyl)-1,4-dioxaspiro[4.5]decan-8-yl)-N,N-dimethylmethanamine (271)

| (dioxolane) | | $CH_3$ | $CH_3$ | FF, E, F |

$^1$H NMR (400 MHz, $CD_3Cl$) δ 7.44 (d, J = 2.4 Hz, 1 H), 7.36 (d, J = 8.8 Hz, 1 H), 7.21 (dd, J = 2.4, 8.8 Hz, 1 H), 3.91 (m, 4 H), 2.32 (s, 2 H), 2.13 (m, 2 H), 1.98 (s, 3 H), 1.80 (m, 2 H), 1.62 (m, 2 H), 1.42 (m, 2 H); $^{13}$C NMR (100 MHz, $CD_3Cl$) δ 145.35, 132.38, 130.14, 130.15, 129.62, 129.71, 127.11, 72.01, 64.48, 64.47, 48.58, 42.87, 31.35; ESI MS m/z 344.1.

4-(aminomethyl)-4-(3,4-dichlorophenyl)-1-methylcyclohexanol (272)

| OH | $CH_3$ | H | H | Y, E |

Stereoisomers (cis- and trans-) were separated after methylation (General Procedure S) by silica gel column chromatography (ethyl acetate/hexane = 1:15 to 1:7) and subsequent transformations were performed using one stereoisomer, respectively.
$^1$H NMR (400 MHz, $CD_3OD$) δ 8.22 (broad, 1 H), 7.33 (d, J = 2.0 Hz, 1 H), 7.32 (d, J = 8.8 Hz, 1 H), 7.10 (dd, J = 8.8, 2.0 Hz, 1 H), 2.85 (s, 2 H), 1.92 (m, 2 H), 1.51 (m, 2 H), 1.40 (m, 4 H), 1.10 (s, 3 H); $^{13}$C NMR (100 MHz, $CD_3OD$), δ 133.18, 131.29, 130.92, 129.00, 126.27, 68.63, 40.14, 34.52, 29.62, 28.171; ESI MS m/z 288.2.

4-(3,4-dichlorophenyl)-1-methyl-4-((methylamino)methyl)cyclohexanol (273)

| OH | $CH_3$ | $CH_3$ | H | Y, E, F |

Prepared from 272 to give 273 and 274, which were separated by silica gel column chromatography (ethyl acetate/hexane/DEA = 1:4:0.1).
$^1$H NMR (400 MHz, $CD_3OD$) δ 7.44 (d, J = 2.0 Hz, 1 H), 7.39 (d, J = 8.8 Hz, 1 H), 7.21 (dd, J = 2.0, 8.8 Hz, 1 H), 2.65 (s, 2H), 2.30 (s, 3 H), 2.04 (m, 2 H), 1.74 (m, 2 H), 1.62 (m, 2 H), 1.50 (m, 2 H), 1.28 (s, 3 H); $^{13}$C NMR (100 MHz, $CD_3OD$) δ 132.79, 130.48, 130.25, 129.01, 126.29, 69.90, 60.98, 41.42, 37.57, 35.66, 30.60, 29.92, 29.17; ESI MS m/z 302.2.

4-(3,4-dichlorophenyl)-4-((dimethylamino)methyl)-1-methylcyclohexanol (274)

| OH | $CH_3$ | $CH_3$ | $CH_3$ | Y, E, F |

Prepared from 272 to give 273 and 274 which were separated by silica gel column chromatography (ethyl acetate/hexane/DEA = 1:4:0.1).
$^1$H NMR (400 MHz, $CD_3OD$) δ 7.45 (d, J = 2.4 Hz, 1 H), 7.36 (d, J = 8.8 Hz, 1 H), 7.22 (dd, J = 2.4, 8.8 Hz, 1 H), 2.37 (m, 2 H), 2.20 (m, 2 H), 198 (m, 6 H), 1.76 (m, 2 H), 1.58 (m, 2 H), 1.48 (m, 2 H), 1.28 (s, 3 H); $^{13}$C NMR (100 MHz, $CD_3OD$) δ 132.32, 130.07, 129.75, 129.38, 126.74, 70.25, 48.53, 35.94, 30.546, 28.49; ESI MS m/z 316.2.

4-(aminomethyl)-4-(3,4-dichlorophenyl)-1-methylcyclohexanol (275)

| $CH_3$ | OH | H | H | Y, E |

Stereoisomers (cis- and trans-) were separated after methylation (General Procedure S) by silica gel column chromatography (ethyl acetate/hexane = 1:15 to 1:7) and subsequent transformations were performed using one stereoisomer, respectively.
$^1$H NMR (400 MHz, $CD_3OD$) δ 8.5 (broad, 1 H), 7.02 (s, 1 H), 7.57 (d, J = 8.8 Hz, 1 H), 7.40 (d, J = 8.8 Hz, 1 H), 2.98 (s, 2 H), 2.18 (m, 2 H), 1.94 (m, 2 H), 1.58 (m, 2 H), 1.28 (m, 2 H), 1.07 (s, 3 H); $^{13}$C NMR (100 MHz, $CD_3OD$) δ 140.93, 133.07, 131.19, 131.12, 129.92, 127.61, 67.90, 51.74, 40.64, 34.05, 29.66, 28.60, 28.37; ESI MS m/z 288.2.

4-(3,4-dichlorophenyl)-1-methyl-4-((methylamino)methyl)cyclohexanol (276)

| $CH_3$ | OH | $CH_3$ | H | Y, E, F |

Prepared from 275 (General Procedure F) to give 276 and 277, which were separated by silica gel column chromatography (ethyl acetate/hexane/DEA = 1:4:0.1).
$^1$H NMR (400 MHz, $CD_3OD$) δ 7.43 (d, J = 2.0 Hz, 1 H), 7.40 (d, J = 8.8 Hz, 1 H), 7.20 (dd, J = 8.8, 2.0 Hz, 1 H), 2.54 (s, 2 H), 2.27 (s, 3 H), 2.08 (m, 2 H), 1.90 (m, 2 H), 1.52 (m, 2 H), 1.30 (m, 2 H), 1.11 (s, 3 H); $^{13}$C NMR (100 MHz, $CD_3OD$) δ 132.86, 130.56, 130.23, 129.63, 127.06, 69.68, 69.94, 42.40, 37.56, 35.16, 31.05, 29.82; ESI MS m/z 302.2.

4-(3,4-dichlorophenyl)-4-((dimethylamino)methyl)-1-methylcyclohexanol (277)

| $CH_3$ | OH | $CH_3$ | $CH_3$ | Y, E, F |

Prepared from 275 (General Procedure F) to give 276 and 277, which were separated by silica gel column chromatography (ethyl acetate/hexane/DEA = 1:4:0.1).
$^1$H NMR (400 MHz, $CD_3OD$) δ 7.44 (d, J = 2.4 Hz, 1 H), 7.36 (d, J = 8.8 Hz, 1 H), 7.21 (dd, J = 2.4, 8.8 Hz, 1 H), 7.21 (dd, J = 2.4, 8.8 Hz, 1 H), 2.28 (s, 2 H), 2.04 (m, 2 H), 1.99 (s, 6 H), 1.85 (m, 2 H), 1.51 (m, 2 H), 1.30 (m, 2 H), 1.09 (s, 3 H); $^{13}$C NMR (100 MHz, $CD_3OD$) δ 132.37, 130.14, 129.92, 129.73, 127.39, 73.73, 69.65, 48.72, 43.45, 35.15, 31.16, 29.32; ESI MS m/z = 316.2.

TABLE 7-continued

Summary of 3,4-Dichlorophenyl-Cyclohexylamine Analogs

| $R^b$ | $R^c$ | $R^3$ | $R^4$ | General Procedure |
|---|---|---|---|---|

4-(aminomethyl)-4-(3,4-dichlorophenyl)-1-ethylcyclohexanol (278)

| | | | | |
|---|---|---|---|---|
| OH | ethyl | H | H | Y, E |

Stereoisomers (cis- and trans-) were separated after alkylation (General Procedure S) by silica gel column chromatography (ethyl acetate/hexane = 1:15 to 1:7) and subsequent transformations were performed using one stereoisomer, respectively.
$^1$H NMR (400 MHz, CD$_3$Cl) δ 7.40 (d, J = 2.4 Hz, 1 H), 7.39 (d, J = 8.4 Hz, 1 H), 7.17 (dd, J = 2.4, 8.4 Hz, 1 H), 2.77 (s, 2 H), 2.12-1.94 (m, 2 H), 1.90-1.74 (m, 2 H), 1.72-1.64 (m, 1 H), 1.61-1.50 (m, 3 H), 1.48-1.38 (m, 1 H), 0.89 (t, J = 8.0 Hz, 3 H); $^{13}$C NMR (100 MHz, CD$_3$Cl) δ 146.40, 132.79, 130.54, 130.35, 129.14, 126.38, 71.21, 49.55, 33.84, 32.94, 29.34, 7.51; ESI MS m/z 302.2.

4-(3,4-dichlorophenyl)-1-ethyl-4-((methylamino)methyl)cyclohexanol (279)

| | | | | |
|---|---|---|---|---|
| OH | ethyl | CH$_3$ | H | Y, E, F |

Prepared from 278 (General Procedure F) to give 279 and 280, which were separated by silica gel column chromatography (ethyl acetate/hexane/DEA = 1:4:0.1).
$^1$H NMR (400 MHz, CD$_3$Cl) δ 7.64 (d, J = 2.4 Hz, 1 H), 7.58 (d, J = 8.4 Hz, 1 H), 7.41 (dd, J = 2.4, 8.4 Hz, 1 H), 3.30 (s, 3 H), 2.58 (s, 2 H), 2.16-2.09 (m, 2 H), 1.84-1.76 (m, 2 H), 1.68-1.50 (m, 6 H), 0.94 (t, J = 7.6 Hz, 3 H); $^{13}$C NMR (100 MHz, CD$_3$Cl) δ 133.02, 131.27, 131.08, 130.96, 128.96, 126.49, 69.96, 39.96, 34.20, 31.90, 29.45, 6.33; ESI MS m/z 316.1.

4-(3,4-dichlorophenyl)-4-((dimethylamino)methyl)-1-ethylcyclohexanol (280)

| | | | | |
|---|---|---|---|---|
| OH | ethyl | CH$_3$ | CH$_3$ | Y, E, F |

Prepared from 278 (General Procedure F) to give 279 and 280, which were separated by silica gel column chromatography (ethyl acetate/hexane/DEA = 1:4:0.1).
$^1$H NMR (400 MHz, CD$_3$OD) δ 7.60 (d, J = 2.4 Hz, 1 H), 7.49 (d, J = 8.8 Hz, 1 H), 7.40 (dd, J = 2.4, 8.8 Hz, 1 H), 2.83 (s, 2 H), 2.16 (s, 6 H), 2.12-2.00 (m, 2 H), 1.86-1.74 (m, 2 H), 1.64-1.46 (m, 6 H), 0.92 (t, J = 7.2 Hz, 3 H); $^{13}$C NMR (100 MHz, CD$_3$OD) 132.20, 130.26, 130.25, 129.94, 129.17, 126.84, 70.45, 46.79, 41.18, 32.33, 29.86, 6.40; ESI MS m/z 330.0.

4-(aminomethyl)-4-(3,4-dichlorophenyl)-1-ethylcyclohexanol (281)

| | | | | |
|---|---|---|---|---|
| ethyl | OH | H | H | Y, E |

Stereoisomers (cis- and trans-) were separated after alkylation (General Procedure S) by silica gel column chromatography (ethyl acetate/hexane = 1:15 to 1:7) and subsequent transformations were performed using one stereoisomer, respectively.
$^1$H NMR (400 MHz, CD$_3$OD) δ 7.63 (d, J = 2.0 Hz, 1 H), 7.58 (d, J = 8.4 Hz, 1 H), 7.40 (dt, J = 2.0, 8.4 Hz, 1 H), 2.98 (s, 2 H), 2.18 (d, J = 13.2 Hz, 2 H), 1.90 (dt, J = 2.8, 13.6 Hz, 2 H), 1.36 (d, J = 13.2 Hz, 2 H), 1.32 (q, J = 7.6 Hz, 2 H), 1.21 (td, J = 2.8, 13.6 Hz, 2 H), 0.81 (t, J = 7.6 Hz, 3 H); $^{13}$C NMR (100 MHz, CD$_3$OD) δ 140.68, 133.11, 131.27, 131.15, 129.95, 127.63, 69.95, 51.88, 40.89, 35.68, 31.72, 28.18; ESI MS m/z 284.1.

4-(3,4-dichlorophenyl)-1-ethyl-4-((methylamino)methyl)cyclohexanol (282)

| | | | | |
|---|---|---|---|---|
| ethyl | OH | CH$_3$ | H | Y, E, F |

Prepared from 281 (General Procedure F) to give 282 and 283, which were separated by silica gel column chromatography (ethyl acetate/hexane/DEA = 1:4:0.1).
$^1$H NMR (400 MHz, CD$_3$Cl) δ 7.63 (d, J = 2.0 Hz, 1 H), 7.56 (d, J = 8.4 Hz, 1 H), 7.43 (dd, J = 2.0, 8.4 Hz, 1 H), 3.31 (s, 3 H), 2.56 (s, 2 H), 2.14-2.10 (m, 2 H), 1.82-1.78 (m, 2 H), 1.66-1.5 1 (m, 6 H), 0.93 (t, J = 7.6 Hz, 3 H); $^{13}$C NMR (100 MHz, CD$_3$Cl) δ 133.22, 131.37, 131.28, 131.02, 129.10, 126.51, 69.87, 39.93, 34.22, 32.40, 29.25; ESI MS m/z 316.1.

4-(3,4-dichlorophenyl)-4-((dimethylamino)methyl)-1-ethylcyclohexanol (283)

| | | | | |
|---|---|---|---|---|
| ethyl | OH | CH$_3$ | CH$_3$ | Y, E, F |

Prepared from 281 (General Procedure F) to give 282 and 283, which were separated by silica gel column chromatography (ethyl acetate/hexane/DEA = 1:4:0.1).
$^1$H NMR (400 MHz, CD$_3$OD) δ 7.54 (s, 1 H), 7.45 (d, J = 8.4 Hz, 1 H), 7.35 (d, J = 8.4 Hz, 1 H), 2.37 (s, 2 H), 2.09 (d, J = 13.6 Hz, 1 H), 1.98 (s, 6 H), 1.86 (t, J = 14.0 Hz, 1 H), 1.50 (d, J = 14.0 Hz, 1 H), 1.28 (q, J = 6.8 Hz, 2 H), 1.20 (t, J = 14.0 Hz, 1 H), 0.79 (t, J = 6.8 Hz, 3 H); $^{13}$C NMR (100 MHz, CD$_3$OD) δ 145.17, 131.92, 130.03, 129.99, 129.38, 127.79, 73.89, 70.62, 47.57, 43.26, 35.75, 32.09, 28.96; ESI MS m/z 332.1.

4-(aminomethyl)-4-(3,4-dichlorophenyl)-1-propylcyclohexanol (284)

| | | | | |
|---|---|---|---|---|
| n-propyl | OH | H | H | Y, E |

$^1$H NMR (400 MHz, CD$_3$OD) δ 7.63 (s, 1 H), 7.56 (d, J = 8.0 Hz, 1 H), 7.41 (d, J = 8.0 Hz, 1 H), 3.30 (s, 2 H), 2.15 (m, 2 H), 1.84 (m, 2 H), 1.64 (m, 2 H), 1.54 (m, 2 H), 1.42 (m, 2 H), 0.95 (t, J = 6.8 Hz, 3 H); $^{13}$C NMR (100 MHz, CD$_3$OD) δ 132.89, 131.13, 130.99, 129.09, 126.67, 70.03, 43.61, 39.76, 32.37, 29.48, 29.18, 16.04, 13.94; ESI MS m/z 316.4.

4-(3,4-dichlorophenyl)-4-((methylamino)methyl)-1-propylcyclohexanol (285)

| | | | | |
|---|---|---|---|---|
| n-propyl | OH | CH$_3$ | H | Y, E, F |

Prepared from 284 (General Procedure F) to give 285 and 286, which were separated by silica gel column chromatography (ethyl acetate/hexane/DEA = 1:4:0.1).
$^1$H NMR (400 MHz, CD$_3$OD) δ 8.38 (broad, 1 H), 7.64 (d, J = 2.0 Hz, 1 H), 7.62 (d, J = 8.8 Hz, 1 H), 7.41 (dd, J = 2.0, 8.8 Hz, 1 H), 3.34 (s, 2 H), 2.60 (s, 3 H), 2.16 (m, 2 H), 1.82 (m, 2 H), 1.64 (m, 2 H), 1.52 (m, 2 H), 1.42 (m, 2 H), 0.95 (t, J = 6.8 Hz, 1 H); $^{13}$C NMR (100 MHz, CD$_3$OD) δ 133.03, 131.33, 131.11, 130.99, 129.06, 126.57, 69.94, 39.87, 34.01, 32.33, 29.45, 29.14, 16.01, 15.96, 13.88; ESI MS m/z 330.2.

4-(3,4-dichlorophenyl)-4-((dimethylamino)methyl)-1-propylcyclohexanol (286)

| | | | | |
|---|---|---|---|---|
| n-propyl | OH | CH$_3$ | CH$_3$ | Y, E, F |

Prepared from 284 (General Procedure F) to give 285 and 286, which were separated by silica gel column chromatography (ethyl acetate/hexane/DEA = 1:4:0.1).
$^1$H NMR (400 MHz, CD$_3$OD) δ 7.45 (d, J = 2.0 Hz, 1 H), 7.36 (d, J = 8.8 Hz, 1 H), 7.21 (dd, J = 2.0, 8.8 Hz, 1 H), 2.40 (s, 2 H), 2.02-1.94 (m, 2 H), 1.96 (s, 6 H), 1.76 (m, 2 H), 1.60 (m, 2 H), 1.48 (m, 2 H), 1.40 (m, 2 H), 0.95 (t, J = 6.8 Hz, 1 H); $^{13}$C NMR (100 MHz, CD$_3$OD) δ 132.25, 130.03, 129.69, 129.21, 126.58, 71.52, 48.46, 43.59, 33.27, 30.08, 16.44, 14.92; ESI MS m/z 344.2.

cis-4-(3,4-dichlorophenyl)-4-((methylamino)methyl)cyclohexanol (287)

195
-continued

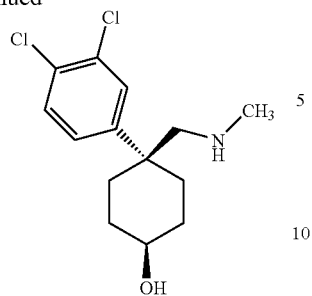

299 to 287

The title compound was prepared from (1s,4s)-4-(aminomethyl)-4-(3,4-dichlorophenyl)cyclohexanol 299 (63 mg, 0.230 mmol) according to General Procedure F2. The crude product was purified by chromatography (SiO$_2$, MeOH/CH$_2$Cl$_2$, 0:100 to 10:90) to give (1s,4s)-4-(3,4-dichlorophenyl)-4-((methylamino)methyl)cyclohexanol (40 mg, 61%) as clear oil. $^1$H NMR (400 MHz, CDCl$_3$): δ 1.57-1.72 (m 4H), 1.78-1.83 (m, 2H), 2.04-2.11 (m, 2H), 2.30 (s, 3H), 2.68 (s, 2H), 3.78-3.82 (m, 1H), 7.20 (dd, J=8.4, 2.4 Hz, 1H), 7.38 (d, J=8.4 Hz, 1H), 7.44 (s, 1H). ESI MS m/z 288.

(1s,4s)-4-(3,4-dichlorophenyl)-4-((dimethylamino)methyl)-cyclohexanol (288)

299 to 288

The title compound was prepared from (1s,4s)-4-(aminomethyl)-4-(3,4-dichlorophenyl)cyclohexanol (PharmaCore, 63 mg, 0.230 mmol) according to General Procedure F2. The crude product was purified by reverse phase HPLC (C-18 column, CH$_3$CN/water, CH$_3$CN from 5% to 100%) to give (1s,4s)-4-(3,4-dichlorophenyl)-4-((dimethylamino)methyl)cyclohexanol (50 mg, 75%). $^1$H NMR (400 MHz, CDCl$_3$): δ 1.57-1.68 (m 4H), 1.77-1.86 (m, 3H), 1.99 (s, 6H), 2.00-2.08 (m, 1H), 2.41 (s, 2H), 3.79-3.82 (m, 1H), 7.22 (dd, J=8.4, 2.4 Hz, 1H), 7.36 (d, J=8.4 Hz, 1H), 7.45 (s, 1H). $^{13}$C NMR (100 MHz, CDCl$_3$): δ 29.5, 30.2, 42.4, 48.6, 68.0, 70.4, 126.8, 129.4, 129.7, 130.1, 132.3, 147.1.
ESI MS m/z 302.

196

4-(3,4-Dichloro-phenyl)-4-methylaminomethyl-cyclohexanone (289)

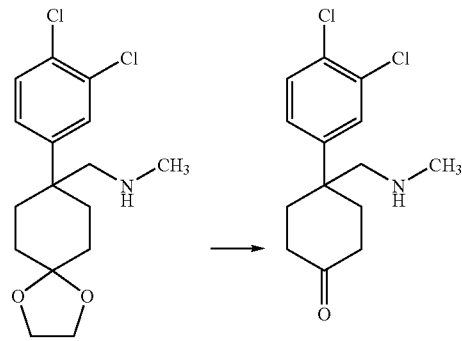 [SMILES: CNCC1(c2ccc(Cl)c(Cl)c2)CCC2(CC1)OCCO2 ; CNCC1(c2ccc(Cl)c(Cl)c2)CCC(=O)CC1]

To a solution of 270 (20 mg, 0.060 mmol) in acetone-H$_2$O (1:1, 1.5 mL) was added TsOH—H$_2$O (12 mg, 0.060 mmol). The reaction mixture was stirred overnight before being concentrated. The residue was dissolved in MeOH (1 mL) and subjected to reverse phase column chromatography (CH$_3$CN: H$_2$O 0:0.1% formic acid=5% to 100%) to give 4-(3,4-dichloro-phenyl)-4-methylaminomethyl-cyclohexanone (8.5 mg, 50%). ESI MS m/z 286.1.

trans-4-(aminomethyl)-4-(3,4-dichlorophenyl)-N-ethyl-N-methylcyclo-hexanamine (290)

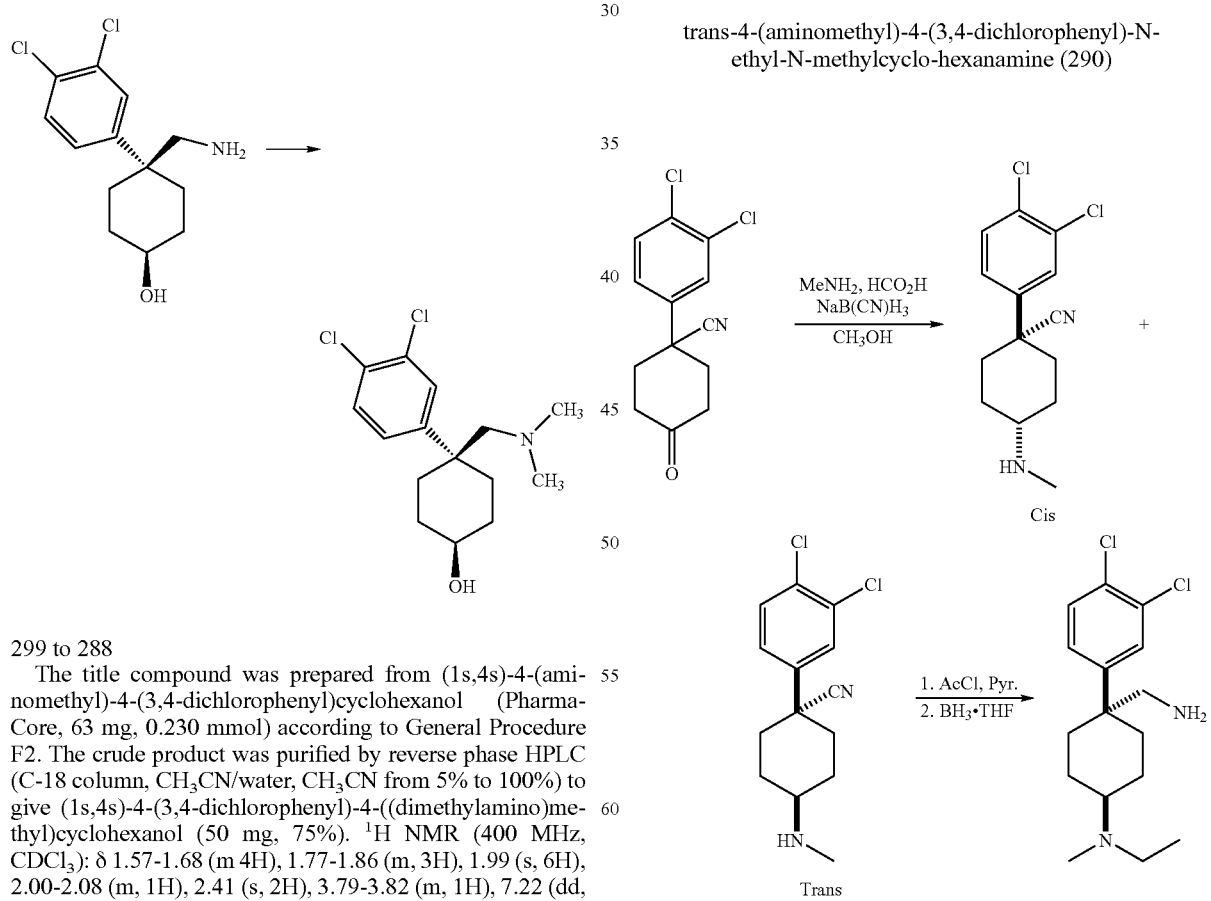

To a solution of 1-(3,4-dichlorophenyl)-4-oxocyclohexanecarbonitrile (600 mg, 2.22 mmol) in MeOH (10 mL) was added MeNH$_2$·HCl (1.0 M in THF, 4.44 mL, 4.44 mmol), HCO$_2$H (0.2 mL) and NaB(CN)H$_3$ (420 mg, 6.66 mmol). The reaction mixture was stirred overnight before being concentrated. The residue was dissolved in MeOH (2 mL) and subjected to reverse phase column chromatography (CH$_3$CN/H$_2$O/0.1% formic acid=5% to 100%) to give the mixture of cis- and trans-isomers (446 mg, 71%), which were separated (OD column, ethanol:methanol:hexane:DEA=3:2:95:0.1) to give the cis-analog (88 mg) and the trans-analog (332 mg).

To a solution of the above trans-analog (200 mg, 0.71 mmol) in CH$_2$Cl$_2$ (5 mL) was added pyridine (0.5 mL) and acetyl chloride (80.3 mg, 72.2 µL, 1.06 mmol). The reaction mixture was stirred for 2 h before being quenched with saturated NH$_4$Cl. The product was extracted with CH$_2$Cl$_2$ (20 mL×2), dried and concentrated. The residue was subjected to silica gel column chromatography (ethyl acetate/hexane=1:10 to 1:1) to give trans-1-(3,4-dichlorophenyl)-4-(ethyl(methyl)amino)cyclohexanecarbonitrile (202 mg, 88%).

The title compound was synthesized from the above nitrile (150 mg, 0.46 mmol) according to General Procedure E. The crude product was dissolved in MeOH (2 mL) and subjected to reverse phase column chromatography (CH$_3$CN:H$_2$O:0.1 formic acid=5% to 100%) (77 mg, 76%). ESI MS m/z 315.2.

(±) (1-(naphthalen-2-yl)cyclohex-3-enyl)methanamine (291)

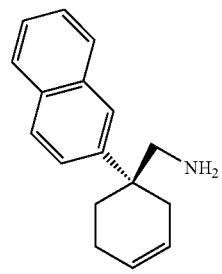

The unsaturated amine (1-(naphthalen-2-yl)cyclohex-3-enecarbonitrile) was prepared according to General Procedure BB and was formed together with the monofluorinated intermediate in a 1:1 ratio.

To a 1M solution of LAH in THF (0.2 ml, 0.184 mmol), which was diluted up to 1 ml with Et$_2$O, was added a solution of 1-(naphthalen-2-yl)cyclohex-3-enecarbonitrile (0.043 g, 0.184 mmol) in Et$_2$O (2 ml) and the resulting mixture was stirred at 35° C. for 16 h. The reaction was then quenched with K$_2$CO$_3$ (sat. aq., 5 ml). It was extracted with EtOAc (2×25 ml) and the combined organic phasese were dried over Na$_2$SO$_4$, decanted and the solvent was removed in vacuo to give the product (0.042 g, 96%), which was pure by HPLC.

The corresponding HCl salt was prepared by the addition of 2M HCl (Et$_2$O) to the free amine. After stirring for 1 h, the white precipitate was filtered off to afford pure (1-(naphthalen-2-yl)cyclohex-3-enyl)methanamine. LC-MS (m/z+) 238.1.

(±) N-methyl-1-(1-(naphthalen-2-yl)cyclohex-3-enyl)methanamine (292)

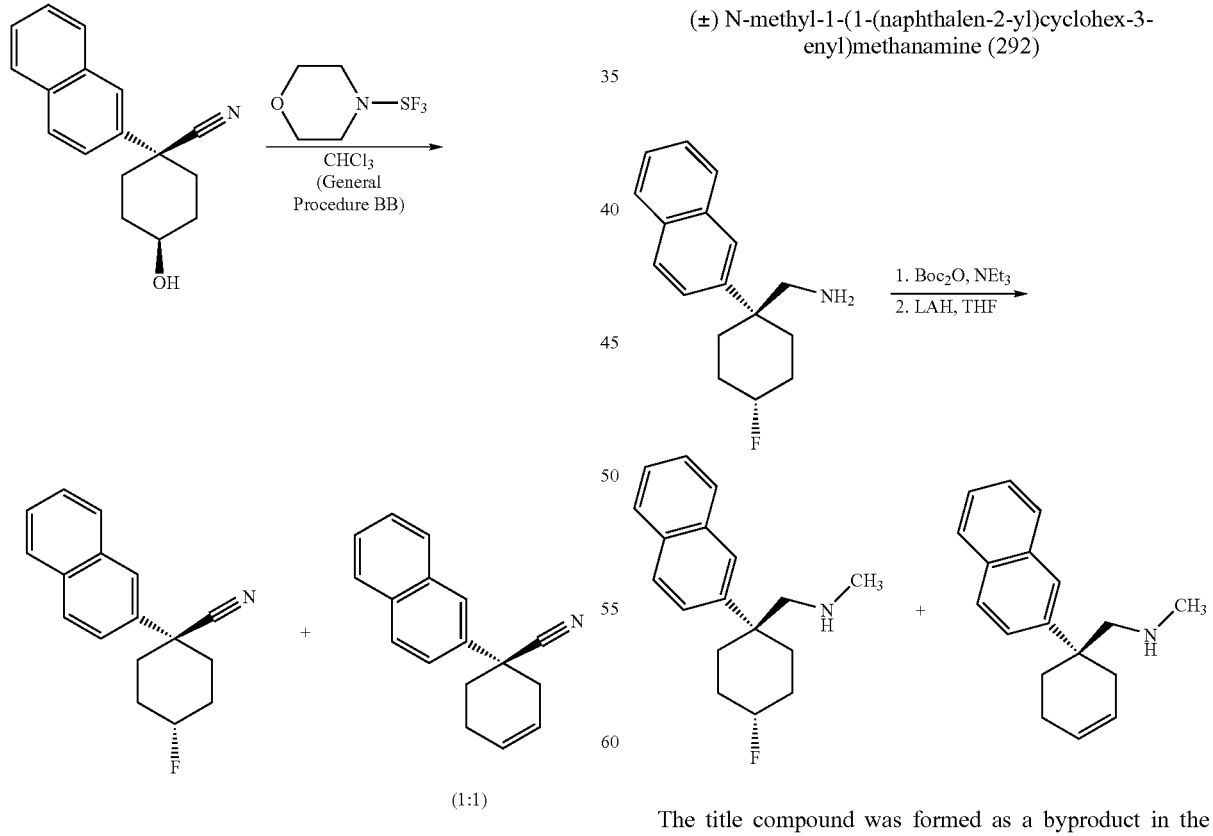

The title compound was formed as a byproduct in the reduction of the fluorinated carbamate. Preparative HPLC separation (chiralpak-AD column, 95:2.5:2.5:0.1 Hexanes:EtOH:MeOH:HNEt$_2$) afforded the crude product, which was converted to the corresponding HCl salt by the addition of 2M HCl (Et₂O) to the free amine. After stirring for 1 h, the white precipitate was filtered off to afford pure N-methyl-1-(1-(naphthalen-2-yl)cyclohex-3-enyl)methanamine hydrochloride salt (0.021 g). ¹H-NMR (400 MHz, CDCl₃) δ 9.04 (brs, 1H), 8.67 (brs, 1H), 7.79-7.67 (m, 4H), 7.45 (m, 3H), 5.80 (d, J=8.0 Hz, 1H), 5.59 (d, J=7.5 Hz, 1H), 3.21 (brs, 1H), 3.12 (brs, 1H), 2.89 (m, 1H), 2.57 (m, 1H), 2.22-1.99 (m, 2H), 2.15 (s, 6H), 1.75 (m, 2H). ¹³C-NMR (100 MHz, CDCl₃) δ 138.6, 133.5, 132.6, 129.1, 128.6, 127.7, 127.2, 126.9, 126.6, 126.5, 124.3, 59.7, 40.0, 35.6, 33.7, 31.4, 22.5. LC-MS (m/z+) 252.1.

N,N-dimethyl(1-(naphthalen-2-yl)cyclohex-3-enyl)methanamine (293)

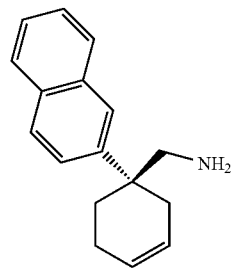
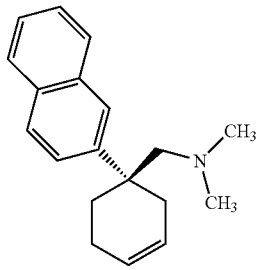

The title compound was prepared from 292 according to General Procedure C (0.023 g, 49% yield). ¹H-NMR (400 MHz, CDCl₃) δ 7.81-7.74 (m, 4H), 7.54 (dd, J=9.0, 2.0 Hz, 1H), 7.46-7.41 (m, 2H), 5.82 (m, 1H), 5.60 (apd, J=10.0 Hz, 1H), 2.70 (d, J=13.0 Hz, 1H), 2.63 (d, J=17.5 Hz, 1H), 2.53 (d, J=13.5 Hz, 1H), 2.43 (m, 1H), 2.02 (m, 2H), 1.98 (s, 6H), 1.72-1.70 (m, 2H). ¹³C-NMR (100 MHz, CDCl₃) δ 132.0, 128.3, 127.5, 127.2, 125.8, 125.8, 125.6, 125.5, 125.4, 70.8, 48.5, 34.4, 31.9, 22.9. LC-MS (m/z+) 266.1.

4',8-dimethyl-8,9-dihydro-7H-spiro[[1,3]dioxolo[4,5-h]isoquinoline-6,1'-cyclohexan]-4'-ol (diastereomer 1) (294)

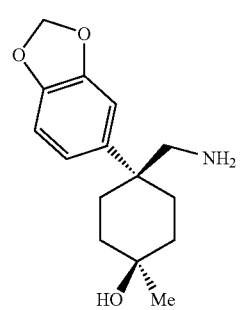

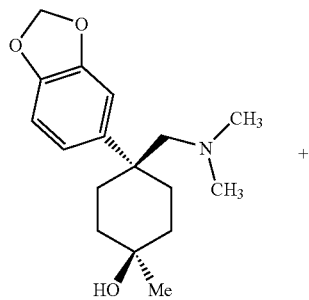

The title compound was isolated as a byproduct in the Eschweiler-Clark alkylation (General Procedure C) of the amine 215. The two products were separated by reverse phase preparative HPLC (CH₃CN:H₂O) to afford the product as the formate salt: ¹H-NMR (400 MHz, CHCl₃) δ 8.42 (brs, 1H), 6.57 (s, 1H), 5.92 (s, 1H), 3.91 (s, 2H), 3.18 (s, 2H), 2.79 (s, 3H), 1.92-1.87 (m, 2H), 1.74-1.60 (m, 6H), 1.39 (s, 3H). LC-MS (m/z+) 290.3.

4',8-dimethyl-8,9-dihydro-7H-spiro[[1,3]dioxolo[4,5-h]isoquinoline-6,1'-cyclohexan]-4'-ol (diastereomer 2) (295)

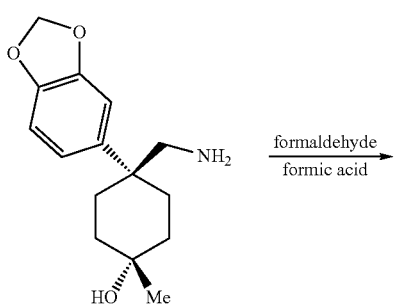

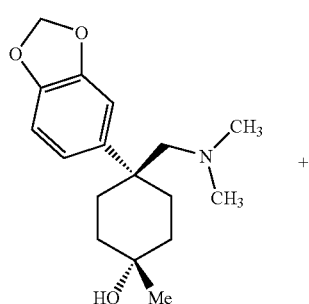

-continued

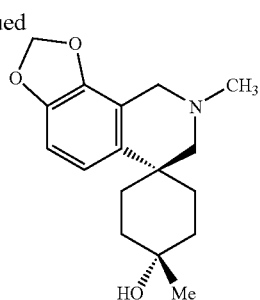

The title compound was isolated as a byproduct in the Eschweiler-Clark alkylation (General Procedure C) of the amine 216. The two products were separated by reverse phase preparative HPLC (CH$_3$CN:H$_2$O). $^1$H-NMR (400 MHz, CD$_3$OD) δ 8.38 (brs, 1H), 7.02 (s, 1H), 6.59 (s, 1H), 5.93 (s, 2H), 4.07 (s, 2H), 3.34 (s, 2H), 2.91 (s, 3H), 2.23-2.19 (m, 2H), 1.65-1.53 (m, 6H), 1.26 (s, 3H). $^{13}$C-NMR (100 MHz, CD$_3$OD) δ 106.2, 101.6, 58.1, 56.5, 43.6, 33.7, 32.4, 30.1. LC-MS (M+1) 290.2.

2-(1-(3,4-dichlorophenyl)cyclohexyl)pyrrolidine (296)

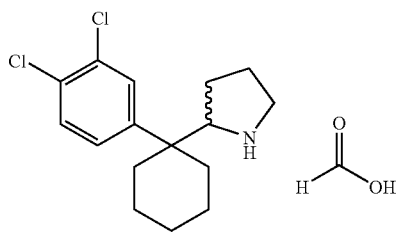 [SMILES: Clc1ccc(C2(C3CCCN3)CCCCC2)cc1Cl ; O=CO]

(a) (R)—N-(1-(1-(3,4-dichlorophenyl)cyclohexyl)-3-(1,3-dioxan-2-yl)propyl)-2-methylpropane-2-sulfinamide

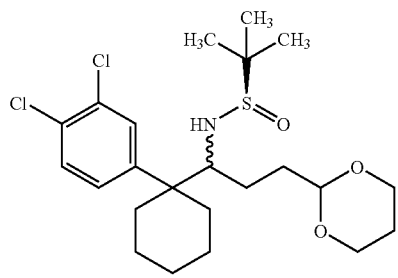 [SMILES: CC(C)(C)[S@@](=O)NC(CCC1OCCCO1)C1(c2ccc(Cl)c(Cl)c2)CCCCC1]

A flame dried flask under N$_2$ was charged with anhydrous Et$_2$O (5 mL) and (1,3-Dioxan-2-ylethyl)-magnesium bromide (0.5M in THF, 5.6 mL, 2.8 mmol) and cooled to −78° C. (R,E)-N-((1-(3,4-dichlorophenyl)cyclohexyl)methylene)-2-methylpropane-2-sulfinamide (460 mg, 1.28 mmol) in anhydrous Et$_2$O (3 mL) was added dropwise and the solution was stirred at −78° C. for 1 h, then allowed to warm to RT overnight. After 20 h sat'd aqueous Na$_2$SO$_4$ solution (4 mL) was added and the suspension was filtered, dried (Na$_2$SO$_4$), filtered and concentrated. Purification on the Biotage with a 25M column and an ethyl acetate/hexane (0.1% DEA) gradient (0→100% EtOAc over 3 CV, hold at 100% EtOAc for 5 CV) gave the pure title compound (300 mg, 49%) as a clear oil. HPLC R$_t$=2.62 min; $^1$H NMR (400 MHz, CDCl$_3$) 7.45-7.43 (m, 2H), 7.24-7.22 (d, J=8.43 Hz, 1H), 4.44-4.42 (m, 1H), 4.11-4.04 (m, 2H), 3.75-3.67 (m, 2H), 3.11-3.01 (m, 2H), 2.64 (d, J=12.8 Hz, 1H), 2.27 (d, J=13.9 Hz, 1H), 2.04-1.99 (m, 1H), 1.88-1.44 (m, 8H), 1.33-1.19 (m, 12H), 0.93-0.80 (m, 1H); $^{13}$C NMR (100 MHz, CDCl$_3$) 141.8, 132.7, 130.8, 130.4, 130.2, 128.4, 101.7, 66.8, 66.3, 57.1, 46.2, 34.3, 32.5, 26.1, 25.7 (d), 23.1, 22.2, 21.8; LC-MS 10.5 min, (M+1)$^+$476 @10.6 min.

(b) 2-(1-(3,4-dichlorophenyl)cyclohexyl)pyrrolidine formate

The above sulfinamide (58 mg, 0.13 mmol) was dissolved in wet acetone (3 mL) and 6 M HCl (1 mL) was added. The clear reaction was stirred for 16 h, poured into 6 M HCl and washed with Et$_2$O (2×10 mL). The Et$_2$O washes were discarded. The aqueous phase was made basic (pH =10-11) with sat'd aqueous K$_2$CO$_3$, at which point a white precipitate appeared. The basic aqueous phase was washed with EtOAc (4×20 mL) and the EtOAc washes were combined, dried (Na$_2$SO$_4$), filtered and concentrated. The crude imine was dissolved in anhydrous THF (4 mL) in a product vial and polymer bound cyanoborohydride (Argonaut, 2.43 mmol/g, 327 mg, 0.796 mmol) and glacial acetic acid (35 mL, 0.597 mmol) were added. The slightly yellow clear solution was shaken at RT for 16 h and filtered. The resin was washed with CH$_2$Cl$_2$ and the combined washes were concentrated. The crude amine was dissolved in MeOH (3 mL) and purified on the Gilson with the standard method. Fractions containing the major peak (Rt~3.4 min) were concentrated on the Genevac and combined to give the title compound as a formate salt (37 mg, 31%). HPLC R$_t$=1.5 min; $^1$H NMR (400 MHz, CDCl$_3$) 8.45 (s, 1H), 7.48 (d, J=1.83 Hz, 1H), 7.45 (d, J=8.43 Hz, 1H), 7.28-7.26 (m, 1H), 3.48-3.43 (m, 1H), 3.17-3.11 (m, 1H), 3.04-2.98 (m, 1H), 2.31 (d, J=12.8 Hz, 2H), 1.84-1.51 (m, 10H), 1.26-1.16 (m, 2H); $^{13}$C NMR (100 MHz, CDCl$_3$) 168.1, 141.2, 133.3, 131.2, 131.0, 130.5, 127.8, 69.4, 45.3, 43.7, 33.1, 31.0, 25.9 (d), 23.6, 21.8 (d); LC-MS 8.35 min, (M+1)$^+$298 @8.51 min.

2-(1-(naphthalen-2-yl)cyclohexyl)pyrrolidine (297)

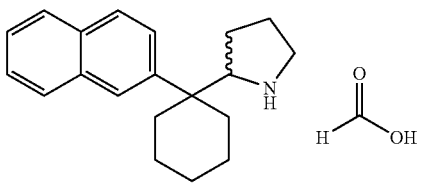 [SMILES: c1ccc2cc(C3(C4CCCN4)CCCCC3)ccc2c1 ; O=CO]

(a) Synthesis of (R)—N-(3-(1,3-dioxan-2-yl)-1-(1-(naphthalen-2-yl)cyclohexyl)propyl)-2-methylpropane-2-sulfinamide

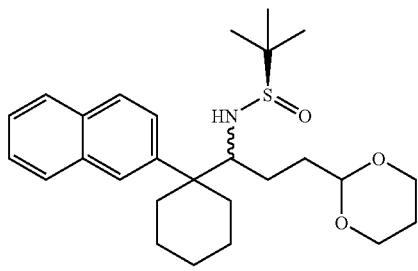 [SMILES: CC(C)(C)[S@@](=O)NC(CCC1OCCCO1)C1(c2ccc3ccccc3c2)CCCCC1]

A flame dried flask under N$_2$ was charged with anhydrous Et$_2$O (3 mL) and (1,3-Dioxan-2-ylethyl)-magnesium bromide (0.5M in THF, 6.78 mL, 3.39 mmol) and cooled to −78° C. (R,E)-2-methyl-N-((1-(naphthalen-2-yl)cyclohexyl)methylene)propane-2-sulfinamide (524 mg, 1.54 mmol) in anhydrous Et$_2$O (3 mL) was added dropwise and the solution was stirred at −78° C. for 1 h, then allowed to warm to RT overnight. After 20 h sat'd aqueous Na$_2$SO$_4$ solution (4 mL) was added and the suspension was filtered, dried (Na$_2$SO$_4$), filtered and concentrated. Purification on the Biotage with a 25M column and an ethyl acetate/hexane (0.1% DEA) gradient (0→100% EtOAc over 3 CV, hold at 100% EtOAc for 5 CV) gave the title compound (581 mg, 83%) as a clear oil. HPLC (JPK method) R$_f$=2.61 min; $^1$H NMR (400 MHz, CDCl$_3$) 7.85-7.80 (m, 4H), 7.53 (d, J=8.8 Hz, 1H), 7.48-7.45 (m, 2H), 4.38 (t, J=5.13 Hz, 1H), 4.10-3.99 (m, 2H), 3.77-3.62 (m, 2H), 3.25 (d, J=8.8 Hz, 1H), 3.15-3.10 (m, 1H), 2.88 (d, J=12.1 Hz, 1H), 2.51 (d, J=11.7 Hz, 1H), 2.03-1.90 (m, 2H), 1.64-1.59 (m, 4H), 1.49-1.42 (m, 2H), 1.31-1.23 (m, 4H), 1.12 (s, 9H), 0.87-0.83 (m, 1H); $^{13}$C NMR (100 MHz, CDCl$_3$) 138.5, 133.6, 132.0, 128.2, 128.1, 127.5, 126.9, 126.2, 126.0, 102.1, 67.0, 66.7, 57.0, 46.4, 35.0, 34.8, 32.8, 26.2 (d), 25.9, 23.3, 22.6, 22.2; LC-MS 10.4 min, (M+1)$^+$458 @10.6 min.

(b) Synthesis of 2-(1-(naphthalen-2-yl)cyclohexyl)pyrrolidine formate

The above sulfinamide (317 mg, 0.694 mmol) was dissolved in wet acetone (12 mL) and 6 M HCl (4 mL) was added. The clear reaction was stirred for 16 h, poured into 6 M HCl and washed with Et$_2$O (2×20 mL). The Et$_2$O washes were discarded. The aqueous phase was made basic (pH=10-11) with sat'd aqueous K$_2$CO$_3$, at which point a white precipitate appeared. The basic aqueous phase was washed with EtOAc (4×30 mL) and the EtOAc washes were combined, dried (Na$_2$SO$_4$), filtered and concentrated. The crude imine was dissolved in anhydrous THF (7 mL) in a product vial and polymer bound cyanoborohydride (Argonaut, 2.43 mmol/g, 697 mg, 1.69 mmol) and glacial acetic acid (73 mL, 1.27 mmol) were added. The slightly yellow clear solution was shaken at RT for 16 h and filtered. The resin was washed with CH$_2$Cl$_2$ and the combined washes were concentrated. The crude amine was dissolved in MeOH (3 mL) and purified on the Gilson with the standard method. Fractions containing the major peak (Rt~3.4 min) were concentrated on the Genevac and combined to give the title compound as the formate salt (96 mg, 49%). HPLC R$_f$=1.58 min; $^1$H NMR (400 MHz, CDCl$_3$) 8.51 (s, 1H), 7.88-7.78 (m, 4H), 7.55-7.52 (dd, J=1.47, 8.80 Hz, 1H), 7.48-7.42 (m, 2H), 3.61-3.57 (m, 1H), 3.04-2.99 (m, 1H), 2.86-2.82 (m, 1H), 2.56-2.53 (m, 2H), 1.84-1.53 (m, 9H), 1.39-1.25 (m, 3H); $^{13}$C NMR (100 MHz, CDCl$_3$) 168.3, 137.7, 133.6, 132.2, 128.7, 128.3, 127.8, 127.4, 126.3, 126.2, 125.5, 69.5, 45.2, 43.8, 33.4, 31.1, 26.0 (d), 23.6, 22.0 (d); LC-MS 8.14 min, (M+1)$^+$280 @ 8.23 min.

Example 5

Scaled-up Syntheses of 225, 93, 48 E1 and 277

5.1. Scaled-up Synthesis of (1s,4s)-4-((dimethylamino)methyl)-1-methyl-4-(naphthalen-2-yl)cyclohexanol (225)

5.1.1. General

Reagents and solvents were used as received from commercial suppliers. Proton and carbon nuclear magnetic resonance spectra were obtained on a Bruker AC 300 spectrometer at 300 and 75 MHz, respectively. High-pressure liquid chromatography was performed on an Agilent 1100 series instrument. Gas chromatography-mass spectroscopy was performed on a Hewlett-Packard G1800A GCD System.

Compound 225 was prepared following the procedures outlined in Scheme 33, below.

Scheme 33: Preparation of 225 hydrochloride

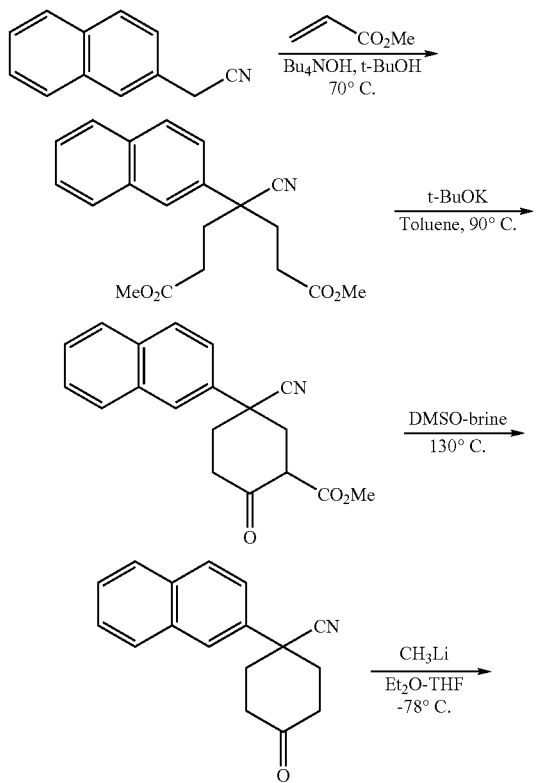

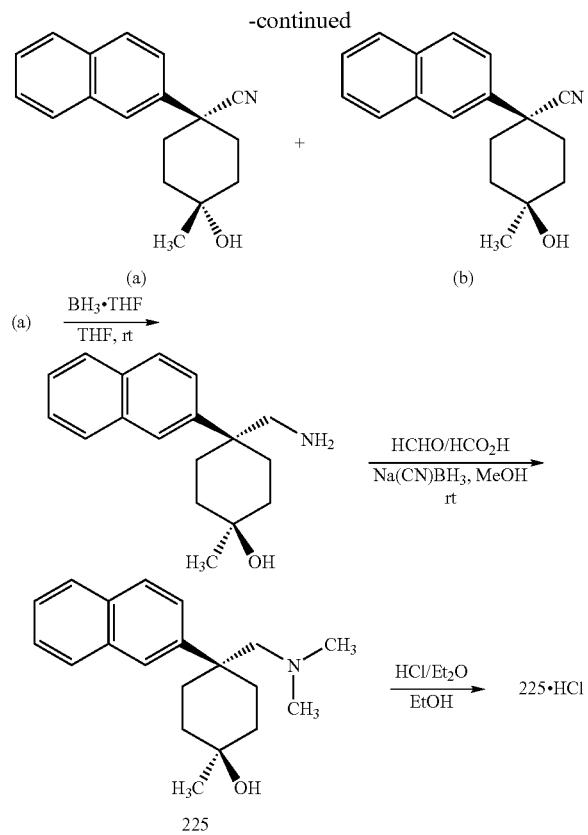

5.1.2. Preparation of dimethyl 4-cyano-4-(naphthalen-2-yl)heptanedioate

A 3-L, three-necked flask equipped with a temperature probe, reflux condenser, addition funnel and overhead stirrer was charged with 2-naphthylacetonitrile (300 g, 1.79 mol), methylacrylate (600 mL, 6.65 mol) and tent-butanol (900 mL). A solution of tetrabutylammonium hydroxide (1 M; 75 mL, 75 mmol) in methanol was added slowly through an addition funnel over a period of 30 min (Note: Highly exothermic). The resulting clear solution was stirred at 70° C. for 2 h and assayed by TLC (3:7 EtOAc/Heptane; stained using Hanessian solution) and GC. The reaction mixture was cooled to room temperature before being concentrated under reduced pressure. The residue was partitioned between 2 M HCl (1 L) and MTBE (4 L). The phases were separated and the aqueous phase was extracted with MTBE (500 mL). The combined organic phases were washed with brine (1 L), dried over $MgSO_4$, filtered and concentrated under reduced pressure at 40-45° C. to give a residue which was passed through a bed of silica (1:4 EtOAc/Heptane) to yield the title compound [569 g, 93%, 100% (AUC) by GC] as an off-white solid. $^1$H NMR ($CDCl_3$, 300 MHz): δ 7.75 (2 d merged, 2H), 7.45 (dd, 1H), 3.5 (s, 6H), 2.4-2.2 (m, 6H), 2.15-1.98 (m, 2H).

5.1.3. Preparation of methyl 5-cyano-5-(naphthalen-2-yl)-2-oxocyclohexanecarboxylate A 12-L, three-neck flask equipped with a temperature probe, reflux condenser, addition funnel and overhead stirrer was charged with potassium tert-butoxide (365 g, 3.2 mol) and toluene (2.4 L). A solution of dimethyl 4-cyano-4-(naphthalen-2-yl)heptanedioate (500 g, 1.4 mol) in toluene (4 L) was added through an addition funnel. The reaction mixture was heated to 90° C. and stirred for 1.5 h. The progress of the reaction was monitored by TLC (3:7 EtOAc:Heptane). The reaction mixture was cooled to 20° C. and quenched slowly with 2 M HCl (2 L) and extracted with EtOAc (4 L). The phases were separated and the organic phase was washed with brine (2×1 L), dried over $MgSO_4$, filtered and concentrated under reduced pressure at 40-45° C. to yield compound 9 (546 g, 120%) as a yellow solid. It was taken into the next step without further purification. $^1$H NMR ($DMSO-d_6$, 300 MHz): δ 8.1 (s, 1H), 8.0-7.9 (m, 4H), 7.7 (dd, 1H), 7.5 (m, 2H), 7.3 (dd, 1H), 7.2 (m, 1H), 3.7 (s, 3H), 3.4 (s, 1H), 3 (d, 1H), 2.9-2.6 (m, 2H), 2.5 (d, 1H), 2.8-2.5 (m, 2H), 2.48-2.3 (m, 6H).

5.1.4. Preparation of 1-(naphthalen-2-yl)-4-oxocyclohexanecarbonitrile

A 12-L, four-neck flask equipped with a temperature probe, reflux condenser and overhead stirrer was charged with methyl 5-cyano-5-(naphthalen-2-yl)-2-oxocyclohexanecarboxylate (600 g, 1.9 mol), brine (1 L) and DMSO (6 L). The mixture was heated to 135° C. and stirred for 12 h. The progress of the reaction was monitored by TLC (2:3 EtOAc/Heptane). After 12 h, the reaction mixture was cooled to room temperature, diluted with water (6 L) and extracted twice with MTBE (5 L, 3 L). The combined organic phases were washed with brine (4×3 L), dried over $MgSO_4$ and filtered. The filtrate was concentrated under reduced pressure at 40-45° C. to give a residue which was triturated with heptane/MTBE (1:1, 2 L). The resulting slurry was stirred for 2 h, filtered and dried under high vacuum for 12 h to yield the title compound (301 g, 62%) as an off-white solid. $^1$H NMR ($DMSO-d_6$, 300 MHz): 6 8.1 (s, 1H), 8.0-7.9 (m, 4H), 7.8 (dd, 1H), 7.6 (m, 2H), 7.3 (dd, 1H), 7.2 (m, 1H), 3.1 (s, 1H), 2.8 (m, 2H), 2.2-2.6 (m, 8H), 1.2(s, 2H).

5.1.5. Preparation of cis-4-hydroxy-4-methyl-1-(naphthalen-2-yl)cyclohexanecarbonitrile A dried 5-L, three-neck flask equipped with a temperature probe, addition funnel, nitrogen line and overhead stirrer was charged with 1 M solution of MeLi in ether (800 mL, 1.23 mol) using canula under anhydrous atmosphere. (Note: MeLi is highly flammable; strictly anhydrous conditions are required.) The solution was cooled to −70° C. and added to a solution of 1-(naphthalen-2-yl)-4-oxocyclohexanecarbonitrile (160 g, 0.642 mol) in anhydrous THF (1,600 mL) slowly over a period of 40 min maintaining the temperature below −50° C. The mixture was stirred at −70° C. for 1 h. Progress of the reaction was monitored by TLC (2:3 EtOAc/Heptane) and GC. The reaction was cautiously quenched with saturated ammonium chloride solution (700 mL) when the starting material was <15% by GC. The typical ratio of starting material:(a):(b) by GC was 1:7:2. The desired cis-nitrile (a) was a major and more polar compound by TLC. The reaction mixture was gradually warmed to room temperature and diluted with EtOAc (500 mL), DI water (200 mL), and the mixture was stirred for 5 min. The phases were separated and the aqueous phase was extracted with EtOAc (500 mL). The combined organic phases were washed with brine (1 L), dried over $MgSO_4$, filtered and concentrated under reduced pressure at 40-45° C. to afford a residue which was purified by chromatography (10-40% EtOAc in heptane). The pure fractions of most polar compound by TLC were pooled and concentrated to yield the cis-nitrile (a) [88.5 g, 52%, 99% (AUC) by GC] as an off-white solid. $^1$H NMR ($DMSO-d_6$, 300 MHz): δ 8.1 (s, 1H), 8.0-7.8 (m, 3H), 7.75 (dd, 1H), 7.58 (2H, dd), 4.65 (s, 1H), 2.3-2.0 (m, 4H), 1.8 (dt, 2H), 1.68 (dd, 2H), 1.2 (s, 3H).

5.1.6. Preparation of cis-4-(aminomethyl)-1-methyl-4-(naphthalen-2-yl)cyclohexanol A dried 5-L, three-neck flask equipped with a temperature probe, addition funnel, nitrogen line and overhead stirrer was charged with 1.0 M solution of BH$_3$.THF (1.29 L, 1.29 mol) using canula under anhydrous atmosphere. (Note: BH$_3$.THF is highly flammable; strictly anhydrous conditions are required.) The solution was cooled to 10° C. and added to a solution of nitrile (a) (114 g, 0.429 mol) in anhydrous THF (1.2 L) slowly over period of 30 min maintaining the temperature below 25° C. The mixture was stirred at room temperature for 16 h. The reaction was cautiously quenched with 6 M HCl (250 mL) until pH 1-2. (Note: Evolution of hydrogen gas; proper vent was needed). The reaction mixture was concentrated under reduced pressure to give a residue which was diluted with MTBE (600 mL) and water (300 mL). The precipitated boron salts were filtered and the phases of filtrate were separated. The aqueous phase was adjusted to pH 9-10 using 6 M NaOH solution and extracted with dichloromethane (3×400 mL). The combined organic phases were washed with brine (300 mL), dried over MgSO$_4$, filtered and concentrated under reduced pressure at 40-45° C. to yield the primary amine (92.1 g, 80%) as a foamy solid which was taken into next step without further purification. $^1$H NMR (CD$_3$OD, 300 MHz): δ 7.95-7.8 (m, 4H), 7.6 (d, 1H), 7.5-7.4 (m, 2H), 2.7 (s, 2H), 2.3 (dd, 2H), 1.9 (dt, 2H), 1.6 (dd, 2H), 1.4 (dt, 2H), 1.05 (s, 3H).

5.1.7. Preparation of 225

A 3-L, three-neck flask equipped with a temperature probe, nitrogen line, condenser, heating mantle and overhead stirrer was charged with cis-4-(aminomethyl)-1-methyl-4-(naphthalen-2-yl)cyclohexanol (92 g, 0.341mol), 37% aqueous formaldehyde (300 mL), formic acid (46 mL) and water (300 mL). The mixture was heated to 85° C. and stirred overnight. (Note: Gas evolution (CO$_2$) was observed at 60° C.) The reaction was monitored by TLC (9:1 DCM/MeOH). After 16 h, the reaction mixture was cooled to room temperature, diluted with water (400 mL) and washed with heptane (2×300 mL). The aqueous phase was adjusted to pH 2.0 using 6 M HCl and washed with dichloromethane (2×100 mL). The aqueous phase was adjusted to pH 9-10 using 6 M NaOH and extracted with dichloromethane (3×400 mL). The combined organic phases were washed with brine (500 mL), dried over MgSO$_4$, filtered and concentrated under reduced pressure at 40-45° C. to yield 225 (71.1 g, 70.3%) as a off-white solid, which was taken into salt formation step without further purification. $^1$H NMR (CDCl$_3$, 300 MHz): δ 7.92-7.8 (m, 4H), 7.65 (d, 1H), 7.5-7.4 (m, 2H), 2.45 (s, 2H), 2.3 (dd, 2H), 1.99 (s and dd merged, 8H), 1.6 (dd, 2H), 1.5 (dt, 2H), 1.1 (s, 3H).

5.1.8. Preparation of 225 Hydrochloride

A 2-L, three-neck flask equipped with a temperature probe, heating mantle, nitrogen line and overhead stirrer was charged with 225 (83 g, 0.28 mol), ethanol (300 mL) and heated to 50° C. until a clear solution was obtained. The solution was cooled to room temperature and added to a solution of 2 M HCl in ether (150 mL) slowly over period of 10 min. The precipitated solids were stirred for 1 h at room temperature and filtered. The cake was washed with mixture of MTBE/EtOH (2:1, 100 mL), dried overnight under high vacuum to provide 225 hydrochloride [60.4 g, 66%, 97.7% (AUC) by HPLC]. $^1$H NMR (CD$_3$OD, 300 MHz): δ 8.1 (m, 4H), 7.7 (d, 1H), 7.6 (dd, 2H), 3.5 (s, 2H), 2.55 (s, 6H), 2.45 (dd, 2H), 2.1 (dt, 2H), 1.75 (dd, 2H), 1.5 (dt, 2H), 1.1 (s, 3H). $^{13}$C NMR (CD$_3$OD, 300 MHz): δ 138.1, 135.3, 134.3, 130.8, 129.7, 129.2, 128.9, 128.1, 126.2, 73.3, 69.5, 47.5, 42.8, 35.6, 31.3, 30.89.

5.2. Scaled-up Synthesis of N-methyl-1-(1-(naphthalen-2-yl)cyclohexyl)methanamine (93)

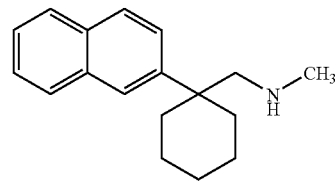 [SMILES: CNCC1(c2ccc3ccccc3c2)CCCCC1]

The title compound was synthesized according to Scheme 34, below.

Scheme 34:

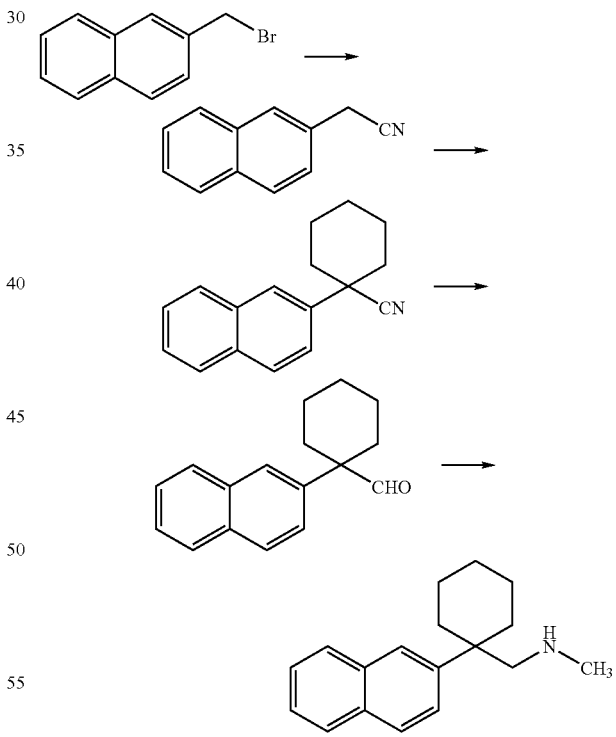

5.2.1. Synthesis of 2-Naphthylacetonitrile

To a stirred solution of sodium cyanide (10.5 g, 0.214 mol) in H$_2$O (20 mL) was added a solution of 2-(bromomethyl)naphthalene (40.0 g, 0.181 mol) in EtOH (170 mL). The resulting mixture was heated at reflux for 3 h, then spin-evaporated in vacuo. The residue was partitioned between H$_2$O (175 mL) and CH$_2$Cl$_2$ (200 mL). The aqueous layer was further extracted with $CH_2Cl_2$ (3×200 mL). The combined organic layers were dried over $MgSO_4$ (5 g) and spin-evaporated in vacuo to a solid. The solid was dissolved in refluxing EtOH (100 mL). The clarified solution was stored at 3° C. for 16 h. Solids were collected by filtration and dried to constant weight in vacuo to give 24.8 g (81.9%) of product suitable for further transformation. A total of 257.2 g of material was prepared in this fashion.

5.2.2. Synthesis of 1-(2-Naphthyl)cyclohexanecarbonitrile

To a stirred suspension of NaH (12.0 g, 0.3 mol) (60 wt % oil dispersion) in DMSO (480 mL) was added a solution of 1 (20.0 g, 0.120 mol) in DMSO (120 mL) dropwise, in a thin stream. The resulting mixture was stirred at 25° C. for 1 h. The mixture was cooled to 15° C. and 1,5-dibromopentane (41.2 g, 0.179 mol) was added dropwise, while maintaining the temperature at ≤22° C. The resulting mixture was stirred at 25° C. for 18 h. The mixture was cooled to 15° C. and quenched with sat. aq. $NH_4Cl$ (100 mL). The resulting mixture was partitioned between $H_2O$ (1.2 L) and t-butyl methyl ether (MTBE) (300 mL). The aqueous layer was further extracted with MTBE (200 mL). The combined organic layers were washed with brine (200 mL), dried over $MgSO_4$ (5 g) and spin-evaporated in vacuo to an oil. The oil was chromatographed on a silica gel column (1.0 kg) packed in, and eluted with hexanes-EtOAc (4:1) (8.0 L). Appropriate fractions as determined by TLC were combined and spin-evaporated in vacuo to an oil, which solidified when pumped down, giving 27.4 g (97.0%) of purified product. A total of 240.2 g of product suitable for further transformation was prepared in this fashion.

5.2.3. Synthesis of 1-(2-Naphthyl)cyclohexanecarboxaldehyde)

To a cold (−78° C.), stirred mixture of 2 (140.9 g, 0.5988 mol) in toluene (1.85 L) was added diisobutylaluminum hydride (DIBAL-H) (1.0 M in toluene) (1.273 L) dropwise, at such a rate as to maintain the temperature at ≤−65°. The resulting mixture was stirred at −78° C. for 3 h. EtOAc (1.5 L) was added, followed by the dropwise addition of aq. 1 M HCl (1.5 L). The resulting mixture was filtered to remove gelatinous solids. The filter cake was washed with EtOAc (3×500 mL). The combined organic layer was washed with brine (500 mL), dried over $MgSO_4$ (20 g) and spin-evaporated in vacuo to give 127.0 g (89.0%) of product suitable for further transformation. A total of 197.7 g of product was prepared in a similar fashion.

5.2.4. Synthesis of N-methyl(1-(naphthalen-2-yl)cyclohexyl)-methanamine

To a stirred solution of 3 (127.0 g, 0.5329 mol) in 2.0 M methylamine (in THF) (1.8 L, 3.6 mol) was added 20 drops of acetic acid. The resulting mixture was stirred at 25° C. for 3 h. Potassium borohydride (64.2 g, 1.19 mol) was added, and stirring at 25° C. was continued for 18 h. The mixture was quenched by the careful addition of aq. 1 M HCl to pH∼2. The resulting biphasic mixture was separated. The organic layer was extracted with aq. 1 M HCL (2×500 mL). The combined aqueous layers were basified with 6 M NaOH to pH∼10, and extracted with EtOAc (3×1.0 L). The combined organic layers were washed with brine (750 mL), dried over $MgSO_4$ (20 g) and spin-evaporated in vacuo to give 88.4 g (65.5%) of crude free-base as an oil. This material was combined with 61.3 g of similar material and chromatographed on a silica gel pad (1.5 kg) packed in and eluted with $CH_2Cl_2$—MeOH (6:1) (12.2 L). Appropriate fractions as determined by TLC were combined and spin-evaporated in vacuo to give 141.0 g (94.2% recovery) of an oil. The oil was dissolved in $CH_2Cl_2$ (500 mL). A solution of 1.0 M HCl (in $Et_2O$) (600 mL) was slowly added with stirring. The resulting suspension was filtered. The solids were suspended in warm (38° C.) $CH_2Cl_2$ (500 mL), then re-collected by filtration and dried to constant weight in vacuo at 25° C. to give 91.1 g of 93 HCl salt, mp; 228-230° C. (dec., uncorrected).

5.3. Scaled-up Asymmetric Synthesis of 48 E1

The title compound was prepared via asymmetric synthesis according to the synthetic route outlined in Scheme 35, below. The absolute configuration of the chiral center a to the amine was not determined. Rather, the final material was correlated via chiral HPLC to an authentic sample of 48 E1 and 48 E2 and the intermediates were assigned by analogy.

Scheme 35: Asymmetric Synthesis of 48 E1

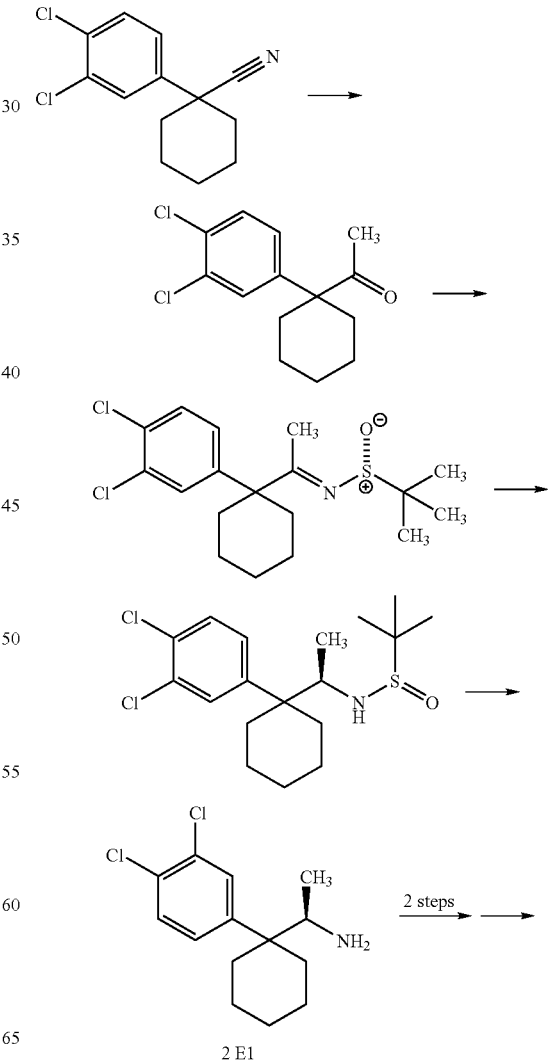

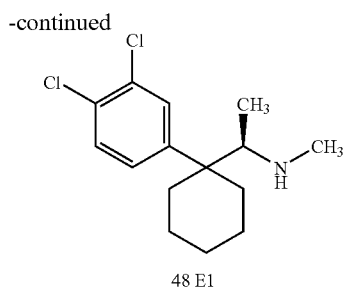

48 E1

5.3.1. Synthesis of 1-(1-(3,4-dichlorophenyl)cyclohexyl)ethanone

A 2 L round bottom flask was charged with a magnetic stir bar and 100.8 g (396.6 mmol) of 1-(3,4-dichloro-phenyl)-cyclohexanecarbonitrile and was flushed with $N_2$. The solid was then dissolved with 960 mL of dry toluene and the mixture was cooled to –78° C. The chilled homogeneous solution was then treated with 300 mL of a 1.6 M solution of MeLi (in $Et_2O$). The resulting pale yellow solution was allowed to slowly warm to r.t. and left to stir for 12 h. The mixture was then chilled to –20° C. and quenched with 2 N HCl. The biphasic mixture was extracted with MTBE (2×). The combined organic layers were washed sequentially with a saturated solution of $K_2HCO_3$ and brine before drying over $Na_2SO_4$. The dried mixture was filtered and all volatiles were removed under reduced pressure to give 107.5 g (396.6 mmol) of the title compound as a pale yellow oil in >90% purity (as determined by reverse phase LCMS). This material was used in subsequent steps without further purification: $^1$H NMR (400 MHz, $CDCl_3$) δ 7.41-7.39 (m, 2 H), 7.14 (d, 1 H, J=8.4 Hz), 2.31-2.28 (m, 2 H), 1.91 (s, 3 H), 1.79-1.74 (m, 2 H), 1.69-1.54 (m, 3 H), 1.51-1.41 (m, 2 H), 1.35-1.26 (m, 1 H).

5.3.2. Synthesis of N-(1-(1-(3,4-dichlorophenyl)cyclohexyl)ethylidene)-2-methylpropane-2-sulfinamide A mixture of 10.53 g (38.8 mmol) of 1-(1-(3,4-dichlorophenyl)cyclohexyl)-ethanone (7.02 g, 57.9 mmol) of (R)-TBSA, 16.1 mL of $Ti(OEt)_4$ and 80 mL of anhydrous toluene was heated to 110° C. under an atmosphere of $N_2$ for 2 days. The mixture was cooled to rt and poured into a vigorously stirred solution of brine and the resulting biphasic mixture was extracted with EtOAc. The combined organic layers were dried ($Na_2SO_4$), filtered and concentrated under reduced pressure. The resulting residue was chromatographed on $SiO_2$ using Hexanes/EtOAc (9:1) to afford 9.5 g (65%) of the title compound: $^1$H NMR (300 MHz, $CDCl_3$) δ 7.43-7.39 (m, 2 H), 7.17 (dd, 1 H, J=8.7, 2.4 Hz), 2.25-2.15 (m, 2 H), 2.06 (s, 3 H), 1.95-1.88 (m, 2 H), 1.61-1.50 (m, 6 H), 1.31 (s, 9H); $^{13}$C NMR (75 MHz, $CDCl_3$) δ 187.1, 144.2, 133.1, 131.2, 130.8, 129.3, 126.7, 57.1, 53.9, 34.5, 34.3, 26.0, 22.92, 22.89, 22.7, 19.7.

5.3.3. Synthesis of N-(1-(1-(3,4-dichlorophenyl)cyclohexyl)ethyl)-2-methylpropane-2-sulfinamide 2-Methyl-propane-2-sulfinic acid {1-[1-(3,4-dichloro-phenyl)-cyclohexyl]-ethyl}-amide: 56 g (149.6 mmol) of 2-Methyl-propane-2-sulfinic acid {1-[1-(3,4-dichloro-phenyl)-cyclohexyl]-ethylidene}-amide was dissolved in 1 L of THF. The solution was chilled to –20° C. and treated with 49 g (190 mmol) of $Cp_2ZrHCl$. The mixture was allowed to warm to rt and left to stir overnight before cooling back to –20° C. and quenching with a saturated solution of $NH_4Cl$. The mixture was warmed to rt extracted with EtOAc (3×). The combined organic layers were washed with $H_2O$, brine and then dried over $Na_2SO_4$. All volatiles were then removed under reduced pressure. The resulting mixture was suspended in MTBE and filtered. All volatiles were again removed under reduced pressure to give 54 g (96%) of the title compound as a white solid in >90% chemical purity and was used without further purification. The diastereomeric ratio was determined to be >98% (reverse phase HPLC: Symmetry C18 column; solvent gradiant using $H_2O$:ACN with 0.05% TFA): $^1$H NMR (300 MHz, $CDCl_3$) δ 7.45-7.41 (m, 2 H), 7.20 (dd, 1 H, J=8.6, 2.3 Hz), 3.34-3.25 (m, 1 H), 3.01 (d, 1 H, J=6.9 Hz), 2.50-2.44 (m, 1 H), 2.23-2.17 (m, 1 H), 1.65-1.48 (m, 5 H), 1.34-1.17 (m, 3 H), 1.13 (s, 9 H), 0.98 (d, 3 H, J=6.6 Hz); $^{13}$C NMR (75 MHz, $CDCl_3$) δ 141.9, 132.8, 131.1, 130.6, 130.4, 128.5, 60.6, 56.1, 46.5, 33.7, 33.0, 26.6, 22.8, 22.3, 22.1, 16.8.

5.3.4. Synthesis of 1-(1-(3,4-dichlorophenyl)cyclohexyl)ethanamine 54 g (143.5 mmol) of 2-Methyl-propane-2-sulfinic acid {1-[1-(3,4-dichloro-phenyl)-cyclohexyl]-ethyl}-amide was dissolved in 300 mL of MeOH, cooled to 0° C. and 300 mL of a 4N HCl solution (in dioxane) was added. After 3 h, the solution was concentrated under reduced pressure. The resulting slurry was suspended in 1.2 L of $Et_2O$ and left to stir over night at rt before collecting the solid by filtration. The resulting pale yellow solid was washed with $Et_2O$ and dried. The solid was dissolved in $CH_2Cl_2$ and washed with a 20% $K_2HCO_3$. The organic layer was isolated, washed with brine and concentrated under reduced pressure to yield 38 g (97%) of 2 E1 in >99% ee (Chiralpak AD, using heptane/EtOH/DEA 95:5:0.1 as the eluent).

5.3.5. Synthesis of N-(1-(1-(3,4-dichlorophenyl)cyclohexyl)-ethyl)formamide

N-{1-[1-(3,4-Dichloro-phenyl)-cyclohexyl]-ethyl}-formamide: 50 g (184.4 mmol) of 1-[1-(3,4-Dichloro-phenyl)-cyclohexyl]-ethylamine was dissolved in 1 L of ethylformate and left to stir under an $N_2$ atmosphere for 24 h before removing all volatiles under reduced pressure. The resulting solid was filtered through a plug of $SiO_2$ (using $CH_2Cl_2$/MeOH (20:1) as the eluent) to afford 51.32 g (93%) of the title compound after the removal of all volatiles. This material was used in the subsequent step without further purification.

5.3.6. Synthesis of 1-(1-(3,4-dichlorophenyl)cyclohexyl)-N-methylethanamine hydrochloride (48 E1)

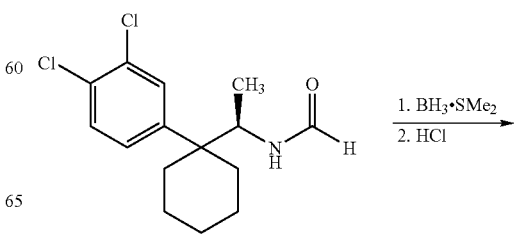

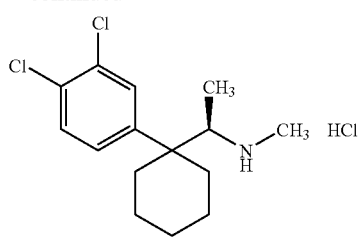

To the refluxing solution of N-{1-[1-(3,4-dichloro-phenyl)-cyclohexyl]-ethyl}-formamide (5.2 g, 17.32 mmol) in anhydrous THF (75 mL) was added slowly $BH_3.SMe_2$ (2N solution in THF, 26 mL, 51.96 mmol). The solution was stirred at 70° C. for 20 mins then a distillation head was installed. The solution was refluxed for 2 h, during which $SMe_2$ was distilled, and the solution was cooled to R.T. and concentrated using a rotary evaporator. The pale yellow residue was cooled to 0° C. and added slowly to methanol (20 mL) to destroy the excess borane. The resulting clear solution was added to 6N aqueous HCl (50 mL) and heated to reflux for 40 minutes, then cooled to room temperature. The solid that formed was filtered and washed with water (2×50 mL), followed by slurrying in ethyl ether (200 mL) and filtration to give 48 E1 as a white solid. (4.04g, 72.5%). Note: Same reaction was run on a 50 g scale with 70% yield.

5.4. Scaled-up Synthesis of 277

5.4.1. General Experimental Details

Reagents and solvents were used as received from commercial suppliers. Proton and carbon nuclear magnetic resonance spectra were obtained on a Bruker AC 300 spectrometer at 300 and 75 MHz, respectively. High-pressure liquid chromatography was performed on an Agilent 1100 series instrument. Gas chromatography-mass spectroscopy was performed on a Hewlett-Packard G1800A GCD System.

Scheme 36: Preparation of 277 Hydrochloride

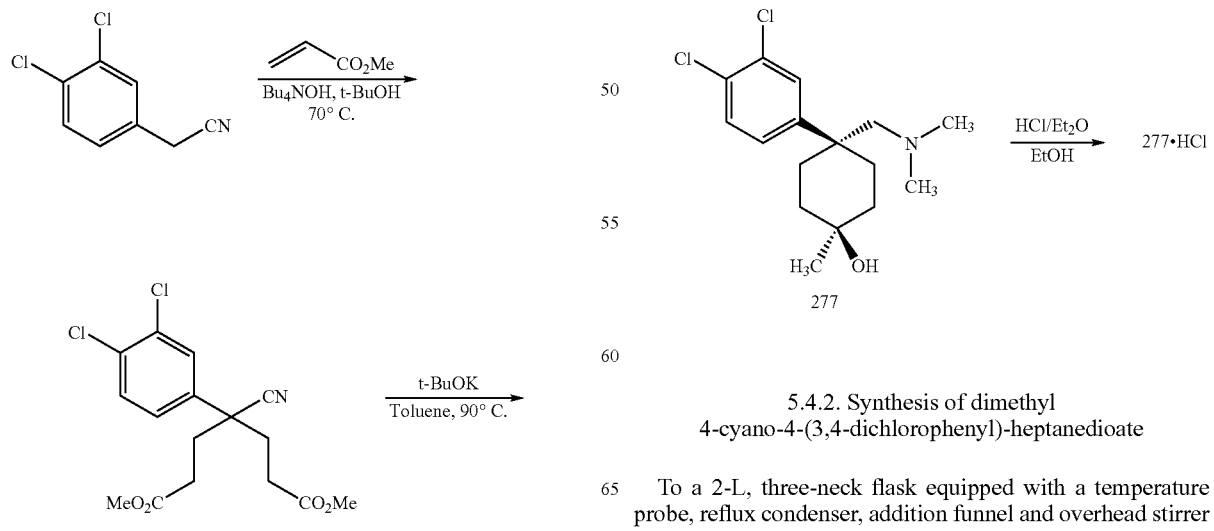

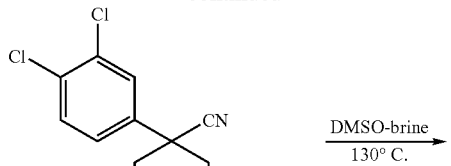

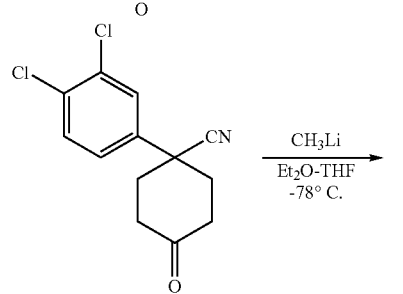

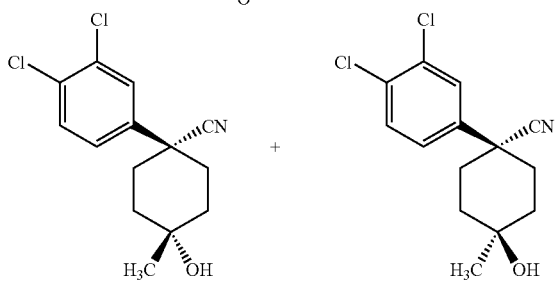

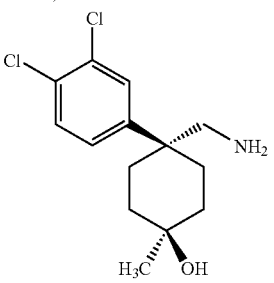

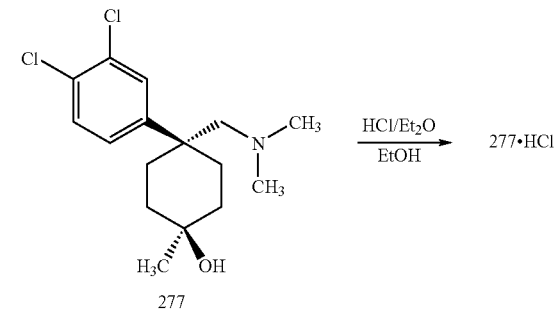

5.4.2. Synthesis of dimethyl 4-cyano-4-(3,4-dichlorophenyl)-heptanedioate

To a 2-L, three-neck flask equipped with a temperature probe, reflux condenser, addition funnel and overhead stirrer was charged with 3,4-dichlorophenylacetonitrile (100 g, 0.54 mol), methylacrylate (139.56 g, 1.62 mol) and tent-butanol (475 mL). To the mixture was added very slowly (highly exothermic) 1.0 M solution of tetrabutylammonium hydroxide (11 mL, 0.011 mol) in methanol. After the addition was complete, the temperature rose from 21.1° C. to 68.4° C. The resulting clear solution was stirred at 70° C. for 2 h and assayed by TLC (3:7 EtOAc/Heptane; stained using Hanessian solution) and GC. The reaction mixture was cooled to room temperature before being concentrated under reduced pressure. The residue was partitioned between 2 M HCl (500 mL), brine (200 mL) and MTBE (1.5 L). The phases were separated and the aqueous phase was extracted with MTBE (250 mL). The combined organic phases were washed with brine (500 mL), dried over $MgSO_4$ and filtered. The filtrate was concentrated under reduced pressure at 40-45° C. to yield the title compound [192.1 g, 99%, 100% (AUC) by GC] as an off-white solid. $^1H$ NMR (DMSO-$d_6$, 300 MHz): δ 7.75 (m, 2H), 7.45 (dd, 1H), 3.5 (s, 6H), 2.4-2.2 (m, 6H), 2.15-1.98 (m, 2H).

5.4.3. Synthesis of methyl 5-cyano-5-(3,4-dichlorophenyl)-2-oxocyclohexanecarboxylate To a 12-L, three-neck flask equipped with a temperature probe, reflux condenser, addition funnel and overhead stirrer was charged with potassium tert-butoxide (266 g, 2.3 mol) and toluene (1 L). A solution of dimethyl 4-cyano-4-(3,4-dichlorophenyl)-heptanedioate (402 g, crude, 386 g theoretical, 1.07 mol) in toluene (3 L) was added through an addition funnel. The reaction mixture was heated to 90° C. and stirred for 1 h. The progress of the reaction was monitored by TLC (4:6 EtOAc/Heptane; stained using Hanessian solution). After 1 h, the reaction mixture was cooled to 15° C. and quenched slowly with 2 M HCl (2.3 L). The phases were separated and the aqueous phase was extracted with MTBE (1 L). The combined organic phases were washed with brine (2×1 L), dried over $MgSO_4$, filtered and concentrated under reduced pressure at 40-45° C. to yield the title compound (424 g, >100%) as a yellow solid. The crude was taken into next step without further purification.

$^1H$ NMR (CDCl$_3$, 300 MHz): δ 7.8 (d, 1H), 7.7 (d, 1H), 7.6 (dd, 1H), 3.7 (s, 3H), 2.9 (d, 1H), 2.8-2.5 (m, 3H), 2.4-2.3 (m, 3H).

5.4.4. Synthesis of 1-(3,4-dichlorophenyl)-4-oxocyclohexanecarbonitrile

To 12-L, four-neck flask equipped with a temperature probe, reflux condenser and overhead stirrer was charged with methyl 5-cyano-5-(3,4-dichlorophenyl)-2-oxocyclohexanecarboxylate (424 g, crude, 350 g theoretical, 1.07 mol), brine (500 mL) and DMSO (3.4 L). The mixture was heated to 135° C. and stirred for 12 h. The progress of the reaction was monitored by TLC (4:6 EtOAc/Heptane; stained using Hanessian solution). The reaction mixture was cooled to room temperature and combined with the crude mixture from a previous 145 g batch reaction, diluted with water (6 L), extracted with MTBE (6 L), and then EtOAc/MTBE (3:5, 8 L). The organics were combined and washed with brine (4×2.5 L), dried over $MgSO_4$, filtered and concentrated under reduced pressure at 40-45° C. to afford a residue which was triturated with heptane/MTBE (1:1, 1.2 L). The resulting slurry was stirred for 0.5 h, filtered and dried under high vacuum for 2 h to afford the title compound [313 g, 77% over 2 steps, 100% (AUC) by GC] as an off-white solid. $^1H$ NMR (DMSO-$d_6$, 300 MHz): δ 7.9 (d, 1H), 7.75 (dd, 1H), 7.6 (dd, 1H), 2.8-2.5 (m, 2H), 2.48-2.3 (m, 6H).

5.4.5. Synthesis of 1-(3,4-dichlorophenyl)-4-hydroxy-4-methylcyclohexanecarbonitrile To a dry 5-L, three-neck flask equipped with a temperature probe, addition funnel, nitrogen line and overhead stirrer was charged with 1.0 M solution of MeLi in ether (680 mL, 1.04 mol) using canula under anhydrous atmosphere (Note: MeLi is highly flammable; strictly anhydrous conditions are required). The solution was cooled to −70° C. and added a solution of 1-(3,4-dichlorophenyl)-4-oxocyclohexanecarbonitrile (198 g, 0.738 mol) in anhydrous THF (1,600 mL) slowly over a period of 45 min while maintaining the temperature below −50° C. The mixture was stirred at −70° C. for 1 h. The progress of the reaction was monitored by TLC (2:3 EtOAc/heptane; stained using Hanessian solution) and GC. The reaction was cautiously quenched with saturated ammonium chloride solution (700 mL) when starting material was <15% by GC. The typical ratio of starting material: (a): (b) by GC was 3.1:70.5:26.4. The desired cis-nitrile (a) was a major and more polar compound by TLC. The reaction mixture was diluted with EtOAc (600 mL), DI water (300 mL), and stirred for 5 min. The phases were separated and the aqueous phase was extracted with EtOAc (600 mL). The combined organic phases were washed with brine (1 L), dried over $MgSO_4$ and filtered. The filtrate was concentrated under reduced pressure at 40-45° C. to yield a residue which was purified by chromatography (10-40% EtOAc in heptane). The pure fractions of most polar compounds by TLC were pooled and concentrated to yield the cis nitrile (a) [114 g, 54.5%, 100% (AUC) by GC] as an off-white solid. $^1H$ NMR (DMSO-$d_6$, 300 MHz): δ 7.85 (s, 1H), 7.7 (d, 1H), 7.55 (dd, 1H), 4.6 (s, 1H), 2.15-1.85 (m, 4H), 1.8 (dt, 2H), 1.6 (dd, 2H), 1.15 (s, 3H).

5.4.6. Synthesis of cis-4-(aminomethyl)-4-(3,4-dichlorophenyl)-1-methylcyclohexanol To a dry 5-L, three-neck flask equipped with a temperature probe, addition funnel, nitrogen line and overhead stirrer was charged with 1.0 M solution of $BH_3$.THF (980 mL, 0.984 mol) using canula under anhydrous atmosphere (Note: $BH_3$.THF is highly flammable; strictly anhydrous conditions are required). The solution was cooled to 10-15° C. and added to a solution of the cis-nitrile (a) (114 g, 0.401 mol) in anhydrous THF (1,400 mL) slowly over a period of 30 min while maintaining the temperature below 25° C. The mixture was stirred at room temperature overnight. The reaction was cautiously quenched with 6 M HCl (300 mL) until pH 2-2.0. The reaction mixture was concentrated under reduced pressure and the residue was taken into a 5-L flask equipped with overhead stirrer and addition funnel. DI water (500 mL) was added into the flask and adjusted pH to 9-10 using 6 M NaOH solution. The aqueous phase was extracted with dichloromethane (3×500 mL). The combined organic phases were taken into another 5-L flask and charged slowly with 6 M HCl (400 ml). The precipitated HCl salt was filtered and the filtrate was taken into a separating funnel. The aqueous phase was taken into a 5-L flask and charged with water (2 L) and the HCl salt. The pH of the mixture was adjusted to 9-10 using 6 M NaOH solution and extracted with dichloromethane (2 L). The combined organic phases were washed with brine (1 L), dried over $MgSO_4$ and filtered. The filtrate was concentrated under reduced pressure at 40-45° C. to yield the title compound (104 g, 90%) as a foamy solid which was taken into next step without further purification. $^1H$ NMR (CD$_3$OD, 300

MHz): δ 7.45 (d and s merged, 2H), 7.25 (dd, 1H), 2.5 (s, 2H), 1.95 (dt, 2H), 1.7 (ddd, 2H), 1.45 (dt, 2H), 1.15 (ddd, 2H), 0.9 (s, 3H).

5.4.7. Synthesis of 4-(3,4-dichlorophenyl)-4-((dimethylamino)methyl)-1-methylcyclohexanol (277)

To a 3-L, three-neck flask equipped with a temperature probe, nitrogen line and overhead stirrer was charged with cis-4-(aminomethyl)-4-(3,4-dichlorophenyl)-1-methylcyclohexanol (99 g, 0.343 mol), 37% aqueous formaldehyde (80 mL), formic acid (80 mL) and cooled to 5-10° C. Sodium cyanoborohydride (72 g, 1.14 mol) was added in portions and stirred for 1 h at room temperature. The progress of the reaction was monitored by TLC (9:1:0.1 DCM/MeOH/TEA). After 2 h, the reaction was not complete. Additional 37% aqueous formaldehyde (3.2 mL), formic acid (3.2 mL), and sodium cyanoborohydride (2.88 g, 4.58 mmol) was added. The reaction was quenched with 6 M NaOH solution (100 mL) and concentrated under reduced pressure to give a residue which was diluted with dichloromethane (2 L), 6 M NaOH solution (500 mL), and brine (500 mL). The phases were separated and the aqueous phase was extracted with dichloromethane (1 L). The combined organic phases were dried over $MgSO_4$ and filtered. The filtrate was concentrated under reduced pressure at 40-45° C. to yield 277 (104 g, 96%) as an off-white solid which was taken into salt formation step without further purification. $^1$H NMR ($CDCl_3$, 300 MHz): δ 7.45 (s, 1H), 7.4 (d, 1H), 7.2 (dd, 1H), 2.3 (s, 2H), 2.05 (dd, 1H), 2.0 (s, 6H), 1.9 (ddd, 2H), 1.55 (dd, 2H), 1.3 (m, 3H), 1.1 (s, 3H).

5.4.8. Preparation of 4-(3,4-dichlorophenyl)-4-((dimethylamino)methyl)-1-methylcyclohexanol 277 hydrochloride To a 3-L, three-neck flask equipped with a temperature probe, nitrogen line and overhead stirrer was charged with free base of 277 (crude from previous reaction, 0.328 mol) and ethanol (500 mL). The mixture was heated to 50° C. until a clear solution was obtained. The solution was cooled to room temperature and added to a solution of 2 M HCl in ether (200 mL) slowly. After 5 min, precipitation of HCl salt was observed. The slurry was stirred for 1 h at room temperature and filtered. The cake was washed with a mixture of MTBE/EtOH (2:1, 200 mL) and dried over night under high vacuum to yield 277 hydrochloride [80.8 g, 70%, 98.0% (AUC) by HPLC]. $^1$H NMR ($D_2O$, 300 MHz): δ 7.65 (d, 1H), 7.55 (d, 1H), 7.5 (dd, 1H), 3.5 (s, 2H), 2.5 (s, 6H), 2.15 (dd, 2H), 1.85 (dt, 2H), 1.5 (dd, 2H), 1.3 (dt, 2H), 0.05 (s, 3H).

Example 6

In Vitro Analyses (Monoamine Uptake Assays)

The compounds of the invention were tested for their inhibition of functional uptake of serotonin (5-HT), norepinephrine (NE), and dopamine (DA), in synaptosomes prepared from rat whole brain, hypothalamus, or corpus striatum, respectively, and/or using recombinant human transporters, as described herein, below. Compounds were initially tested at 10 μM in duplicate. Compounds showing ≥50% inhibition of uptake were further tested at 10 different concentrations in duplicate in order to obtain full inhibition curves. $IC_{50}$ values (concentration inhibiting control activity by 50%) were then determined by nonlinear regression analysis of the inhibition curves. Results are summarized in Table 8, below.

6.1. Serotonin Functional Uptake Assay for Rat Reuptake Transporter

Quantification of 5-HT uptake was performed using synaptosomes isolated in a 0.32M sucrose buffer from a male Wistar rat cortex. The uptake of radiolabelled 5-HT by synaptosomes (100 μg of proteins/point) was allowed by incubating them in a well for 15 min at 37° C. in presence of test compounds and [$^3$H]5-hydroxytryptamine (serotonin; 0.1 μCi/point).

Synaptosomes and [$^3$H]serotonin were prepared in a Krebs buffer pH 7.4 containing 25 mM $NaHCO_3$, 11 mM glucose and 50 μM ascorbic acid. This incubation buffer was oxygenated during 5 minutes before incubation. Basal control was incubated for 15 minutes at 4° C. in order to avoid any uptake. Following this incubation the uptake was stopped by filtration through a unifilter 96-wells GFB Packard plate washed with Krebs buffer containing 25 mM $NaHCO_3$ in order to eliminate the free [$^3$H]serotonin. The radioactivity associated to the synaptosomes retained on the unifilter corresponding to the uptake was then measured with a microplate scintillation counter (Topcount, Packard) using a scintillation fluid. Non-specific binding was measured in the presence of an excess of cold, unlabeled ligand. Specific binding was obtained by subtracting nonspecific binding from total binding.

The reference compound was imipramine tested at 10 concentrations ranging from $10^{-11}$ M to $10^{-5}$ M in order to obtain an $IC_{50}$ value. See, Perovics and Muller, Arzeim. Forsch./Drug Res., 45:1145-1148 (1995).

6.2. Serotonin Functional Uptake Assay for Human Reuptake Transporter

Inhibition of human serotonin reuptake transporter was assayed using the recombinant human serotonin transporter expressed in HEK-293 cells using a published method (Gu H et al., J. Biol. Chem. 1994, 269 (10): 7124-7130). HEK-293 cells expressing human serotonin transporter were plated before the assay. Test compound and/or vehicle was preincubated with cells in modified HEPES buffer pH 7.1 or pH 7.4 for 20 minutes at 18 to 25° C. and 65 nM [$^3$H]serotonin was then added for an additional timed incubation period (ten to thirty minutes). Cells with internalized [$^3$H]serotonin were washed and the amount of tritium taken into cells is counted using a liquid scintillation counter to determine [$^3$H]serotonin uptake. Non-specific binding of tritium was measured in a control reaction containing 10 μM fluoxetine, and was subtracted from the counts for assays to correct for non-specific binding of tritium. Reduction of [$^3$H]serotonin uptake by 50 percent or more (≥50%) relative to an uninhibited control reaction indicates significant inhibitory activity. Compounds were screened at 10, 1, 0.1, 0.01 and 0.001 μM. The reference compound for the assay was fluoxetine, for which the $IC_{50}$ value of 7.1 nM was obtained in a typical experiment.

6.3. Dopamine Functional Uptake Assay for Rat Reuptake Transporter

Quantification of dopamine uptake was performed using synaptosomes isolated in a 0.32 M sucrose buffer from a male Wistar rat striatum. The uptake of radiolabelled dopamine by synaptosomes (20 μg of proteins/point) was allowed by incubating them for 15 minutes at 37° C. in the presence of test compounds and [$^3$H]-dopamine (0.1 µCi/point). The experiment was performed in a deep well.

Synaptosomes and [$^3$H]-dopamine were prepared in a Krebs buffer pH 7.4 containing 25 mM NaHCO$_3$, 11 mM glucose and 50 µM ascorbic acid. This incubation buffer was oxygenated for 5 minutes before incubation. Basal control was incubated for 15 minutes at 4° C. in order to avoid any uptake. Following this incubation, the uptake was stopped by filtration through a unifilter 96-wells GFB Packard plate washed with Krebs buffer containing 25 mM NaHCO$_3$ in order to eliminate free [$^3$H]-dopamine. The radioactivity associated to the synaptosomes retained onto the unifilter corresponding to the uptake was then measured with a microplate scintillation counter (Topcount, Packard) using a scintillation fluid.

The reference compound was GRB 12909 tested at 8 concentrations ranging from $10^{-11}$ M to $10^{-6}$ M in order to obtain an IC$_{50}$ value. See, Jankowsky et al., *J. Neurochem.* 1986, 46:1272-1276).

6.4. Dopamine Functional Uptake Assay for Human Reuptake Transporter

Inhibition of human dopamine reuptake transporter was assayed using the recombinant human dopamine transporter expressed in either CHO-K1 or HEK293 cells using a published method (Pristupa, Z. B. et al., *Mol. Pharmacol.* 45: 125-135, 1994). Either CHO-K1 or HEK293 cells expressing human recombinant dopamine transporter were plated before the assay. Test compound and/or vehicle was preincubated with cells in modified HEPES buffer pH 7.1 or pH 7.4 for 20 minutes at 18 to 25° C. and 50 nM [$^3$H]dopamine was then added for an additional timed incubation period (10 to 30 minutes). After washing the cells to remove [$^3$H]dopamine not internalized, the cells were lysed, and the amount of tritium in the lysate was measured using a liquid scintillation counter to determine [$^3$H]dopamine uptake. Non-specific binding of tritium was measured in a control reaction containing 10 µM nomifensine, and was subtracted from the counts for assays to correct for non-specific binding of tritium. Reduction of [$^3$H]dopamine uptake by 50 percent or more (≥50%) relative to an uninhibited control reaction indicates significant inhibitory activity. Compounds were screened at 10, 1, 0.1, 0.01 and 0.001 µM. The reference compound for the assay was nomifensine, for which the IC$_{50}$ value of 11 nM was obtained in a typical experiment.

6.5. Norepinephrine Functional Uptake Assay For Rat Reuptake Transporter

Quantification of norepinephrine uptake was performed using synaptosomes isolated in a 0.32 M sucrose buffer from a male Wistar rat hypothalamus. The uptake of radiolabelled norepinephrine by synaptosomes (100 µg of proteins/point) was allowed by incubating them for 20 minutes at 37° C. in presence of test compounds and [$^3$H]-norepinephrine (0.1 µCi/point). The experiment was performed in a deep well.

Synaptosomes and [$^3$H]-norepinephrine were prepared in a Krebs buffer pH 7.4 containing 25 mM NaHCO$_3$, 11 mM glucose and 50 µM ascorbic acid. This incubation buffer was oxygenated for 5 minutes before incubation. Basal control was incubated for 20 minutes at 4° C. in order to avoid any uptake. Following this incubation, the uptake was stopped by filtration through a unifilter 96-wells GFB Packard plate washed with Krebs buffer containing 25 mM NaHCO$_3$ in order to eliminate the free [$^3$H]-norepinephrine. The radioactivity associated to the synaptosomes retained onto the unifilter corresponding to the uptake was then measured with a microplate scintillation counter (Topcount, Packard) using a scintillation fluid.

The reference compound was protriptyline tested at 13 concentrations ranging from $10^{-11}$ M to $10^{-5}$ M in order to obtain an IC$_{50}$ value. See, Perovics and Müller, *Arzeim. Forsch./Drug Res.*, 45:1145-1148 (1995).

6.6. Norepinephrine Functional Uptake Assay for Human Reuptake Transporter

Inhibition of human norepinephrine reuptake transporter was assayed using the recombinant human norepinephrine transporter expressed in either HEK293 or MDCK cells using a published method (Galli A et al., *J. Exp. Biol.* 198: 2197-2212, 1995). The cells were plated before the assay. Test compound and/or vehicle was preincubated with cells in modified HEPES buffer pH 7.1 or pH 7.4 for 20 minutes at 18 to 25° C. Following the preincubation, 25 nM [$^3$H]norepinephrine was added for an additional timed incubation period (10 to 20 minutes). After the cells were washed to remove [$^3$H]norepinephrine not internalized, the cells were lysed, and the amount of tritium in the cell lysate was measured using a liquid scintillation counter to determine [$^3$H]norepinephrine uptake. Non-specific binding of tritium was measured in a control reaction containing 10 µM imipramine (or 10 µM nisoxetine), and was subtracted from the counts for assays to correct for non-specific binding of tritium. Reduction of [$^3$H] norepinephrine uptake by 50 percent or more (≥50%) relative to an uninhibited control reaction indicates significant inhibitory activity. Compounds were screened at 10, 1, 0.1, 0.01 and 0.001 µM. The reference compounds for the assay were desipramine and nisoxetine, for which 1050 values of 1.9 nM and 5.3 nM respectively were obtained in typical experiments.

6.7. Results for Monoamine Uptake Assays

The results of the monoamine uptake assays are provided in Table 8, below.

TABLE 8

Summary of Results - In vitro Monoamine Uptake Assays

| Cmpd. No. | Human IC$_{50}$ (nM) | | | Rat IC$_{50}$ (nM) | | |
|---|---|---|---|---|---|---|
| | hSERT | hNET | hDAT | rSERT | rNET | rDAT |
| 73 | 2240 | 6 | 1 | 710 | 15 | 6 |
| 74 | 19 | 4 | 1 | 30 | 6 | 10 |
| 27 | 201 | 273 | 150 | 500 | 150 | 95 |
| 75 | 169 | 85 | 21 | 110 | 20 | 58 |
| 76 | 156 | 9 | 1 | | | |
| 77 | 158 | 19 | 4 | | | |
| 170 E1 | 1030 | 189 | 1190 | | | |
| 170 E2 | 673 | 26 | 427 | | | |
| 78 | 651 | 36 | 2 | | | |
| 172 E1 | 51 | 4 | 66 | | | |
| 172 E2 | 89 | 127 | 762 | | | |
| 174 | 246 | 2495 | 2781 | | | |
| 175 | 55 | 15 | 125 | | | |
| 176 | 533 | 612 | 775 | | | |
| 177 | 3220 | 84 | 322 | | | |
| 28 | 4560 | 1840 | 707 | | | |
| 29 | 5240 | 1480 | 195 | | | |
| 30 | 4520 | >10,000 | 5870 | | | |
| 31 | >10,000 | >10,000 | >10,000 | | | |
| 80 | 9170 | >10,000 | >10,000 | | | |
| 79 | 768 | 270 | 884 | | | |
| 101 | 96 | 529 | 268 | | | |

TABLE 8-continued

Summary of Results - In vitro Monoamine Uptake Assays

| Cmpd. No. | Human IC$_{50}$ (nM) hSERT | hNET | hDAT | Rat IC$_{50}$ (nM) rSERT | rNET | rDAT |
|---|---|---|---|---|---|---|
| 102 | 195 | 586 | 420 | | | |
| 100 | 1500 | 6630 | 3410 | | | |
| 103 | 3540 | 5090 | 7740 | | | |
| 81 | 2720 | 2190 | 3640 | | | |
| 88 | 829 | 171 | 93 | | | |
| 89 | 278 | 63 | 9 | | | |
| 32 | 949 | 902 | 424 | | | |
| 87 | 1470 | 334 | 139 | | | |
| 82 | 55 | 9990 | 42 | | | |
| 83 | 57 | 61 | 57 | | | |
| 33 | 305 | 232 | 83 | | | |
| 98 | >10,000 | 782 | 419 | | | |
| 105 | 1530 | 28 | 625 | | | |
| 107 | 224 | 146 | 546 | | | |
| 104 | 9490 | 516 | 5160 | | | |
| 106 | 8330 | 816 | 1770 | | | |
| 34 | >10,000 | 6690 | 5320 | | | |
| 35 | >10,000 | 2970 | 4710 | | | |
| 36 | 6550 | 1630 | >10,000 | | | |
| 37 | >10,000 | 5760 | >10,000 | | | |
| 84 | 1870 | 326 | 395 | | | |
| 85 | 102 | 51 | 26 | | | |
| 96 | 688 | 137 | 170 | | | |
| 97 | 31 | 10 | 11 | | | |
| 95 | 480 | 160 | 324 | | | |
| 91 | >10,000 | 8550 | 1830 | | | |
| 90 | 839 | 1850 | 3360 | | | |
| 92 | 33 | 206 | 125 | | | |
| 93 | 34 | 295 | 90 | | | |
| 94 | 3 | 7 | 3 | | | |
| 99 | 145 | 26 | 17 | | | |
| 86 | 249 | 346 | 384 | | | |
| 133 E1 | 969 | 217 | 355 | | | |
| 133 E2 | 342 | 374 | 886 | | | |
| 134 E1 | 260 | 179 | 598 | | | |
| 134 E2 | 1260 | 132 | 149 | | | |
| 173 | 1550 | 277 | 412 | | | |
| 1 | 1290 | 175 | 103 | | | |
| 41 | 898 | 22 | 82 | | | |
| 165 E1 | 1580 | 183 | 66 | | | |
| 165 E2 | 661 | 620 | 978 | | | |
| 166 E1 | 176 | 310 | 245 | | | |
| 166 E2 | 90 | 32 | 99 | | | |
| 173 E1 | 1660 | 1350 | 388 | | | |
| 173 E2 | 406 | 174 | 280 | | | |
| 2 | 543 | 316 | 69 | | | |
| 169 E2 | 332 | 22 | 87 | | | |
| 169 E1 | 1100 | 242 | 778 | | | |
| 152 E1 | 405 | 32 | 18 | | | |
| 152 E2 | 77 | 157 | 585 | | | |
| 153 E1 | 17 | 19 | 85 | | | |
| 153 E2 | 64 | 135 | 25 | | | |
| 42 | 935 | 280 | 761 | | | |
| cis 121 E1 | >10,000 | 2060 | 3390 | | | |
| cis 121 E2 | 3160 | 6580 | >10,000 | | | |
| trans 121 E1 | 247 | 303 | 687 | | | |
| trans 121 E2 | 8150 | 392 | 665 | | | |
| 2 E1 | 406 | 167 | 180 | | | |
| 2 E2 | 821 | 1040 | 770 | | | |
| 108 | 65 | 36 | 85 | | | |
| 43 | 15 | 7 | 64 | | | |
| 3 | 331 | 888 | <1 | | | |
| 109 | 9674 | 114 | 12 | | | |
| 4 | 637 | 2783 | 75 | | | |
| 110 | 7932 | 790 | 2 | | | |
| 111 | 8571 | 232 | 1.7 | | | |
| 112 | 299 | 39 | <1 | | | |
| 298 | >10,000 | 6730 | 76 | | | |
| 184 E1 | >10,000 | 2977 | 213 | | | |
| 184 E2 | >10,000 | 3385 | 789 | | | |
| 187 E1 | 1896 | 1095 | 209 | | | |
| 187 E2 | 376 | 928 | 17 | | | |
| 116 | 2060 | 633 | 3 | | | |
| 117 | 7903 | 405 | 33 | | | |
| 115 | >10,000 | 41 | <1 | | | |
| 114 | >10,000 | 1813 | 16 | | | |
| 113 | 2574 | 2217 | 285 | | | |
| 185 E1 | >10,000 | >10,000 | 421 | | | |
| 185 E2 | >10,000 | >10,000 | 121 | | | |
| 190 E1 | 2962 | 442 | 24 | | | |
| 190 E2 | 44 | 17 | 3 | 120 | 340 | 45 |
| 191 E1 | 2532 | 747 | 42 | | | |
| 191 E2 | 426 | 74 | 2 | | | |
| 45 | 5936 | 964 | 9 | | | |
| 46 | >10,000 | >10,000 | 349 | | | |
| 188 E1 | 4479 | 10000 | 426 | | | |
| 188 E2 | >10,000 | 5287 | 66 | | | |
| 44 E1 | 12 | 10 | 36 | 14 | 2.2 | 150 |
| cis 167 | >10,000 | >10,000 | 2217 | | | |
| trans 167 | 4912 | 1092 | 145 | | | |
| 168 | 1465 | 732 | 108 | | | |
| 253 | 906 | 949 | 37 | | | |
| 254 | 294 | 19 | <1 | 190 | 2.4 | 100 |
| 71 | 1298 | 1342 | 123 | | | |
| 72 | 136 | 63 | 1.7 | | | |
| 299 | 3873 | 2377 | 720 | | | |
| 44 E2 | 239 | 570 | 219 | 210 | 44 | 1800 |
| 5 | 7115 | 5004 | 1522 | | | |
| 287 | 1037 | 335 | 192 | | | |
| 255 | 1421 | 2472 | 170 | | | |
| 256 | 69 | 39 | 157 | 280 | 130 | 990 |
| 288 | 84 | 18 | 22 | 67 | 11 | 370 |
| 47 | 364 | 2894 | 5171 | | | |
| 48 E2 | 149 | 441 | 297 | 230 | 74 | 550 |
| 48 E1 | 81 | 57 | 30 | 54 | 5.1 | 170 |
| 257 | 2075 | 6546 | 1999 | | | |
| 259 | 5892 | 1179 | 665 | | | |
| 6 | >10,000 | >10,000 | 1000 | | | |
| 7 | 255 | 3987 | 527 | | | |
| 260 | 2146 | 1772 | 306 | | | |
| 261 | 30 | 62 | 7 | | | |
| 262 | >10,000 | >10,000 | 4283 | | | |
| 263 | 674 | 187 | 498 | | | |
| 8 | 855 | 8733 | 996 | | | |
| 9 | >10,000 | 9987 | >10,000 | | | |
| 49 | 286 | 9217 | 739 | | | |
| 10 | 1905 | 7446 | 2928 | | | |
| 264 | 1052 | 194 | 17 | | | |
| 11 | 7549 | 2811 | 532 | | | |
| 265 | 109 | 3464 | 1454 | | | |
| 266 | 168 | 2811 | 859 | | | |
| 12 | 1517 | 5761 | 6043 | 1100 | 480 | 1900 |
| 57 | 1079 | 3177 | 1777 | 2200 | 740 | 2300 |
| 51 | 2948 | >10,000 | >10,000 | | | |
| 50 | 1069 | 950 | 499 | | | |
| cis 124 | 6857 | 5934 | 5313 | | | |
| trans 124 E1 | 2489 | 842 | 1475 | | | |
| 124 E2 | 227 | 288 | 187 | | | |
| 14 | 2953 | 257 | 46 | | | |
| 267 | 1290 | 3256 | 147 | | | |
| 268 | 704 | 241 | 27 | | | |
| 269 | 787 | 36 | <1 | | | |
| 300 | >10,000 | 7625 | 1733 | | | |
| 301 | >10,000 | >10,000 | 8785 | | | |
| cis 125 | 684 | 399 | 871 | | | |
| trans 125 E1 | 6 | 158 | 1408 | | | |
| trans 125 E2 | 32 | 783 | 1113 | | | |

TABLE 8-continued

Summary of Results - In vitro Monoamine Uptake Assays

| Cmpd. No. | Human IC$_{50}$ (nM) hSERT | hNET | hDAT | Rat IC$_{50}$ (nM) rSERT | rNET | rDAT |
|---|---|---|---|---|---|---|
| 52 | 44 | 1063 | 176 | | | |
| 13 | 377 | 324 | 122 | | | |
| 194 | 330 | 1832 | 2369 | | | |
| 196 | 1445 | 732 | 911 | | | |
| 197 | 227 | 67 | 450 | | | |
| 192 | >10,000 | >10,000 | 1957 | | | |
| 200 | 2051 | 3742 | 1100 | | | |
| 201 | 261 | 518 | 88 | | | |
| 204 | 2253 | 3457 | 296 | | | |
| 205 E1 | 4208 | 999 | 800 | | | |
| 205 E2 | 1714 | 326 | 12 | | | |
| cis 132i | 708 | 5555 | 153 | | | |
| trans 132i | 28 | 353 | 140 | | | |
| 15 | 1398 | >10,000 | >10,000 | | | |
| 206 E1 | 72 | 121 | 59 | | | |
| 206 E2 | 306 | 7 | <1 | | | |
| 147 E1 | 94 | 5764 | 1391 | 18 | 370 | 1200 |
| 147 E2 | 2500 | 9706 | 1344 | 1700 | 1200 | 1500 |
| 148 E1 | 97 | 538 | 464 | 36 | 81 | 250 |
| 148 E2 | 229 | 1136 | 289 | 330 | 4900 | 680 |
| 53 | <1 | 20 | 1 | 6.5 | 2.9 | 6.1 |
| 54 | 2387 | 857 | 85 | | | |
| 55 | <1 | 61 | 72 | | | |
| 163 E1 | 43 | 2793 | 413 | 260 | 4200 | 1100 |
| 163 E2 | 139 | 2650 | 309 | 1900 | 3200 | 1500 |
| 164 E1 | 2 | 152 | 36 | 9.6 | 500 | 230 |
| 164 E2 | 13 | 194 | 40 | 45 | 720 | 140 |
| 195 E2 | 45 | >10,000 | 5320 | | | |
| 270 | 469 | 515 | 376 | | | |
| 271 | 79 | 42 | 197 | | | |
| 289 | 469 | 1467 | 282 | | | |
| 290 | 992 | >10,000 | 1388 | | | |
| 17 | 657 | 119 | 29 | | | |
| 16 | 1764 | 4034 | 4085 | | | |
| 13 E1 | 187 | 528 | 66 | | | |
| 18 | 3892 | 794 | 184 | | | |
| 19 | 107 | 3177 | 2316 | | | |
| 13 E2 | 60 | 779 | 108 | | | |
| 56 E1 | <1 | 21 | 28 | 2.9 | 2.3 | 24 |
| 56 E2 | 63 | 468 | 145 | 120 | 79 | 100 |
| 272 | >10,000 | 9572 | 2601 | | | |
| 273 | 830 | 474 | 528 | | | |
| 274 | 809 | 321 | 251 | | | |
| 275 | 1187 | 943 | 518 | | | |
| 276 | 210 | 55 | 71 | 360 | 17 | 190 |
| 277 | 34 | 13 | 41 | 42 | 2.7 | 43 |
| 58 E1 | 6 | 23 | 63 | 9.5 | 3.6 | 22 |
| 58 E2 | 118 | 341 | 176 | 100 | 33 | 160 |
| 140 E1 | 2688 | >10,000 | 8819 | | | |
| 140 E2 | >10,000 | >10,000 | 5667 | | | |
| 139 E1 | >10,000 | >10,000 | >10,000 | | | |
| 139 E2 | >10,000 | >10,000 | >10,000 | | | |
| 20 | 24 | 5847 | 275 | | | |
| 20 E1 | 40 | 6439 | 369 | | | |
| 20 E2 | 60 | >10,000 | 437 | | | |
| 21 | 2095 | 7192 | 43 | | | |
| 207 | 142 | 3602 | 1025 | | | |
| 209 | 1158 | >10,000 | 4758 | | | |
| 222 | 609 | 5347 | 2090 | | | |
| 225 | 7 | 23 | 167 | | | |
| 223 | 73 | 145 | 874 | | | |
| 22 | 296 | 3727 | 141 | | | |
| 155 E1 | 2986 | >10,000 | >10,000 | | | |
| 155 E2 | 6281 | >10,000 | >10,000 | | | |
| 136 E1 | >10,000 | 6497 | 2871 | | | |
| 136 E2 | >10,000 | >10,000 | 3375 | | | |
| 138 E1 | >10,000 | 1341 | 918 | | | |
| 138 E2 | 6996 | 3946 | 2539 | | | |
| 21 E1 | 9661 | 7606 | 234 | | | |
| 21 E2 | 1235 | 6041 | 64 | | | |
| 193 E2 | 957 | >10,000 | 3163 | | | |
| 193 E1 | 416 | 897 | 266 | | | |
| 198 | 2324 | >10,000 | 1940 | | | |
| 202 | 868 | 1625 | 58 | | | |
| 199 | 2188 | 2585 | 462 | | | |
| 203 | 56 | 166 | 1.4 | | | |
| 156 E1 | 76 | >10,000 | 1310 | | | |
| 156 E2 | 653 | >10,000 | 3996 | | | |
| 226 | 44 | 737 | 278 | | | |
| 23 | 62 | 7678 | 682 | | | |
| 22 E1 | 63 | 2624 | 136 | | | |
| 22 E2 | 101 | 5566 | 112 | | | |
| 208 | 1987 | >10,000 | 7667 | | | |
| 227 | 742 | 4103 | 5778 | | | |
| 228 | 96 | 387 | 1565 | | | |
| 229 | 11 | 33 | 40 | | | |
| 224 | 69 | 665 | 993 | | | |
| 154 E1 | 2170 | 3679 | 795 | | | |
| 154 E2 | 439 | 981 | 888 | | | |
| 16 E1 | 1755 | 1291 | 1286 | | | |
| 16 E2 | 7296 | 1910 | 9248 | | | |
| 211 | 55 | 1274 | 195 | | | |
| 230 | 30 | 104 | 11 | | | |
| 231 E1 | 1276 | 136 | 460 | | | |
| 231 E2 | 63 | 19 | 83 | | | |
| 291 | 185 | 784 | 72 | | | |
| 212 | 91 | 948 | 75 | | | |
| 213 | 283 | 2031 | 337 | | | |
| 17 E1 | 355 | 66 | 71 | | | |
| 17 E2 | 709 | 93 | 5 | | | |
| 60 E1 | 184 | 86 | 748 | | | |
| 60 E2 | 4632 | 3304 | 6740 | | | |
| 61 E1 | 5947 | 1504 | 959 | | | |
| 59 E2 | 4396 | 2197 | 3875 | | | |
| 59 E1 | 1589 | 486 | 1754 | | | |
| 61 E2 | 9442 | 1555 | 116 | | | |
| 293 | 42 | 33 | 4 | | | |
| 232 | 744 | 904 | 25 | | | |
| 233 | 37 | 64 | 3 | | | |
| 62 E1 | 3176 | 414 | 39 | | | |
| 62 E2 | 4241 | 121 | 4 | | | |
| 19 E1 | 1514 | 1901 | 696 | | | |
| 19 E2 | 398 | 4027 | 735 | | | |
| 234 E1 | 3382 | 820 | 346 | | | |
| 234 E2 | 18 | 33 | 21 | | | |
| 63 E2 | 2 | 1110 | 1818 | | | |
| 64 E1 | 58 | 2797 | >10,000 | | | |
| 64 E2 | 32 | 2647 | 3640 | | | |
| 63 E1 | 194 | 5946 | 6537 | | | |
| 235 | 9 | 256 | 92 | | | |
| 292 | 360 | 903 | 89 | | | |
| 236 | 38 | 718 | 444 | | | |
| 38 | 472 | >10,000 | 9647 | | | |
| 65 | 1618 | 3644 | 1936 | | | |
| 66 | 221 | 587 | 355 | | | |
| 278 | 5143 | >10,000 | 3193 | | | |
| 279 | 383 | 2477 | 1449 | | | |
| 280 | 7 | 371 | 242 | | | |
| 25 | 78 | 1029 | 90 | | | |
| 26 | 740 | 2102 | 238 | | | |
| 214 | >10,000 | 10000 | >10,000 | | | |
| 237 | 7296 | >10000 | 9129 | | | |
| 238 | 1178 | 3533 | 5715 | | | |
| 215 | 4192 | >10,000 | 6243 | | | |
| 239 | 8661 | 7372 | 9451 | | | |
| 240 | 1812 | 3694 | 9029 | | | |
| 39 | 295 | 6644 | 2237 | | | |
| 67 | 230 | 3149 | 1761 | | | |
| 68 | 19 | 603 | 343 | | | |
| 294 | >10,000 | >10,000 | >10,000 | | | |
| 281 | 256 | 788 | 384 | | | |
| 282 | 296 | 289 | 186 | | | |
| 283 | 20 | 41 | 37 | | | |
| 216 | >10,000 | >10,000 | >10,000 | | | |
| 241 | >10,000 | >10,000 | >10,000 | | | |

TABLE 8-continued

Summary of Results - In vitro Monoamine Uptake Assays

| Cmpd. No. | Human IC$_{50}$ (nM) | | | Rat IC$_{50}$ (nM) | | |
|---|---|---|---|---|---|---|
| | hSERT | hNET | hDAT | rSERT | rNET | rDAT |
| 242 | 7656 | >10,000 | >10,000 | | | |
| 295 | >10,000 | >10,000 | >10,000 | | | |
| 217 | 47 | 1838 | 1975 | | | |
| 243 | 26 | 293 | 851 | | | |
| 244 | 14 | 59 | 334 | | | |
| 24 | 364 | 6380 | 1370 | | | |
| 141 E1 | 3687 | 2229 | 1252 | | | |
| 141 E2 | 2771 | 10000 | 3665 | | | |
| 142 E1 | 1898 | >10,000 | 5247 | | | |
| 142 E2 | 2315 | >10,000 | 7852 | | | |
| 218 | 480 | >10,000 | 5587 | | | |
| 245 | 538 | 10000 | 2274 | | | |
| 246 | 43 | 984 | 282 | | | |
| 40 | 753 | 7668 | 2324 | | | |
| 69 | 930 | 2290 | 605 | | | |
| 70 | 29 | 261 | 214 | | | |
| 157 E1 | 1303 | 3725 | 575 | | | |
| 157 E2 | 290 | 3446 | 849 | | | |
| 158 E1 | 8439 | 7497 | 945 | | | |
| 158 E2 | 2991 | >10,000 | 5023 | | | |
| 145 E1 | 75 | 10000 | 4726 | | | |
| 145 E2 | 220 | >10,000 | 6520 | | | |
| 146 E1 | 4545 | >10,000 | >10,000 | | | |
| 146 E2 | 2284 | >10,000 | >10,000 | | | |
| 219 | 269 | >10,000 | >10,000 | | | |
| 247 | 707 | 9690 | 10000 | | | |
| 248 | 159 | 5689 | 7252 | | | |
| 220 | 6150 | 10000 | >10,000 | | | |
| 249 | 405 | >10,000 | >10,000 | | | |
| 250 | 47 | 1669 | 10000 | | | |
| 284 | 7896 | 6662 | 2462 | | | |
| 285 | 1139 | 4038 | 1897 | | | |
| 286 | 46 | 182 | 198 | | | |
| 162 E2 | 247 | >10,000 | >10,000 | | | |
| 162 E1 | 495 | >10,000 | >10,000 | | | |
| 161 E2 | 1.1 | 4395 | 4609 | | | |
| 161 E1 | 9 | 8626 | 9950 | | | |
| 221 | 61 | 5825 | 182 | | | |
| 251 | 199 | 2131 | 107 | | | |
| 252 | 11 | 108 | 6 | | | |
| 252 | 12 | 134 | 5 | | | |
| 143 E1 | 8611 | >10,000 | 8787 | | | |
| 143 E2 | 7172 | >10,000 | 8630 | | | |
| 144 E1 | 5626 | >10,000 | 10000 | | | |
| 144 E2 | 8748 | >10,000 | 9858 | | | |
| 159 E1 | 1255 | >10,000 | 3801 | | | |
| 159 E2 | 42 | 10000 | 2310 | | | |
| 160 E1 | 7193 | >10,000 | 9725 | | | |
| 160 E2 | 5091 | >10,000 | >10,000 | | | |
| 296 | 73 | 87 | 27 | | | |
| 297 | 40 | 57 | 13 | | | |

In Table 8, compound numbers correspond to those used in the Examples above. In addition, the following abbreviations have been used in Table I: SERT (serotonin transporter), NET (norepinephrine transporter) and DAT (dopamine transporter).

The above results indicate that compounds of the invention exhibit potent inhibition of neuronal uptake of NE, DA, and/or 5-HT, and compare favorably with potencies seen for various existing therapeutic agents. For example, reported potencies (IC$_{50}$ or K$_i$ values) of approved and launched drugs include: fluoxetine (PROZAC®), 7 nM for inhibition of human 5-HT reuptake transporter; methylphenidate (RITALIN®), 193 nM and 38 nM for inhibition of human dopamine and norepinephrine reuptake transporters, respectively (Eshleman et al., *J. Pharmacol. Exp. Ther.* 1999, 289: 877-885); amitriptyline (ELAVIL®), 63 nM and 67 nM for inhibition of the human norepinephrine and serotonin reuptake transporters, respectively and venlafaxine (EFFEXOR®), a so-called serotonin norepinephrine reuptake inhibitor (SNRI) 145 and 1420 nM, for inhibition of the human serotonin, and norepinephrine reuptake transporters respectively (Vaishnavi et al., *Biol. Psychiatry.* 2004, 55: 320-322). The multiple inhibition of the neuronal uptake of NE, DA and/or 5-HT displayed by the compounds of the invention provides the clinician with the ability to more effectively treat CNS disorders, including without limitation affective disorders, cerebral function disorders, anxiety disorders, neuropathic pain, and migraine or migraine headache, by elevating various monoamine levels in the brain simultaneously and over the same dose-range without the need to titrate separate drugs.

Example 7

Ex Vivo Binding Assays

Receptor occupancy of central noradrenaline (NA), 5-HT and dopamine (DA) transporter sites following peripheral administration of compounds was determined using [$^3$H] nisoxetine, [$^3$H] citalopram and [$^3$H] WIN 35428 binding, respectively. Liquid scintillation counting was used to quantify the radioactivity.

7.1. Methods

C57BL/6 mice (25-30 g) were dosed orally with either vehicle or compound at 4 dose levels. Mice were sacrificed 60 minutes after treatment. Whole brains were removed and cortex and striata dissected out before being frozen on dry ice. The brain tissue was stored at −20° C. until the day of the assay. The cortex from each hemisphere was frozen separately. One was used to determine occupancy of NA transporter sites and the other occupancy of 5-HT transporter sites. Striatum was used to determine occupancy of DA transporter sites.

7.2. Membrane Preparation

Frontal cortex from each hemisphere or striata was homogenised individually in ice-cold assay buffer using a tight fitting glass/Teflon homogeniser and used immediately in the binding assay.

[$^3$H] Citalopram Binding to 5-HT Transporter (SERT) Sites in Mouse Brain

Cortical membranes (400 µl; equivalent to 1.25 mg wet weight of tissue/tube) were incubated with 50 µl of [$^3$H] citalopram at a single concentration of 1.3 nM and either 50 µl of buffer (total binding) or 50 µl of paroxetine (0.5 µM; non-specific binding) for 1 h at 27° C. For each animal, three tubes were used for the determination of total binding and three tubes were used for the determination of non-specific binding.

[$^3$H] Nisoxetine Binding to Norepinephrine Transporter (NET) Sites in Mouse Brain Cortical membranes (400 µl; equivalent to 6.0 mg wet weight of tissue/tube) were incubated with 50 µl of [$^3$H] nisoxetine at a single concentration of 0.6 nM and either 50 µl of buffer (total binding) or 50 µl of mazindol (1 µM; non-specific binding) for 4 h at 4° C. For each animal, three tubes were used for the determination of total binding and three tubes were used for the determination of non-specific binding.

[$^3$H] WIN 35428 Binding to DA Transporter (DAT) Sites in Mouse Brain

Striatal membranes (200 µl; equivalent to 2 mg wet weight of tissue/tube) were incubated with 25 µl of [$^3$H] WIN 35428 at a single concentration of 24 nM and either 25 µl of buffer (total binding) or 25 µl of GBR12935 (1 µM; non-specific binding) for 2 h at 4° C. For each animal, two tubes were used for the determination of total binding and two tubes for the determination of non-specific binding.

Membrane bound radioactivity was recovered by filtration under vacuum through Skatron 11731 filters, presoaked in 0.5% PEI, using a Skatron cell harvester. Filters were rapidly washed with ice-cold phosphate buffer and radioactivity (dpm) was determined by liquid scintillation counting (1 ml Packard MV Gold scintillator).

7.3. Data Analysis

A value for specific binding (dpm) was generated by the subtraction of mean non-specific binding (dpm) from mean total binding (dpm) for each animal. Data are presented as mean specific binding (dpm) and as a percentage of the vehicle-treated control taken as 100%.

7.4. Results Summary

Ex vivo SERT, NET and DAT binding/receptor occupancy data were generated for selected compounds of the invention. Results are summarized in Table 9, below. Results showed that the compounds exhibited varying SERT, NET and DAT inhibition ratios.

TABLE 9

Ex Vivo Binding Profile in Mice.

| Treatment | Dose (mg/kg, PO) | Mean Specific Binding (dpm) ± S.E.M. (Values in Brackets Denote % Transporter Occupancy) | | |
|---|---|---|---|---|
| | | NET | SERT | DAT |
| 225 | 0 | 1570 ± 31 | 4639 ± 294 | 20453 ± 2500 |
| | 1 | 1170 ± 68 (25)* | 3842 ± 152 (17)* | 19787 ± 3338 (3) |
| | 3 | 813 ± 64 (48)* | 2118 ± 139 (54)* | 21666 ± 3698 (–6) |
| | 10 | 393 ± 21 (75)* | 904 ± 35 (81)* | 18872 ± 2775 (8) |
| | 30 | 230 ± 33 (85)* | 414 ± 37 (91)* | 14618 ± 1209 (29) |
| 48 E1 | 0 | 2405 ± 150 | 4345 ± 123 | 20378 ± 1315 |
| | 1 | 2111 ± 119 (12) | 4398 ± 39 (–1) | 20656 ± 1531 (–1) |
| | 3 | 1911 ± 144 (21)* | 3957 ± 224 (9) | 18039 ± 1265 (11) |
| | 10 | 954 ± 115 (60)* | 2796 ± 100 (36)* | 9792 ± 977 (52)* |
| | 30 | 346 ± 55 (86)* | 1003 ± 104 (77)* | 3173 ± 541 (84)* |
| 276 | 0 | 1541 ± 87 | 4269 ± 299 | 15011 ± 2450 |
| | 1 | 1602 ± 51 (–4) | 3743 ± 199 (12) | 18155 ± 2275 (–21) |
| | 3 | 1631 ± 92 (–6) | 3685 ± 292 (14) | 16312 ± 2396 (–9) |
| | 10 | 1553 ± 27 (–1) | 3092 ± 207 (28)* | 15879 ± 2265 (–6) |
| | 30 | 1138 ± 59 (26)* | 1558 ± 169 (64)* | 10397 ± 931 (31) |
| 58 E1 | 0 | 1763 ± 45 | 3410 ± 200 | 16873 ± 1162 |
| | 1 | 1705 ± 71 (3) | 3245 ± 107 (5) | 15732 ± 1360 (7) |
| | 3 | 1748 ± 56 (1) | 3021 ± 182 (11) | 14938 ± 2613 (11) |
| | 10 | 1262 ± 79 (28)* | 1799 ± 115 (47)* | 17215 ± 2151 (–2) |
| | 30 | 502 ± 36 (71)* | 469 ± 43 (86)* | 12876 ± 2152 (24) |
| 153 E2 | 0 | 1915 ± 57 | 3223 ± 109 | 20775 ± 1607 |
| | 1 | 1804 ± 79 (6) | 3271 ± 199 (–1) | 22774 ± 916 (–10) |
| | 3 | 1726 ± 44 (10) | 2968 ± 100 (8) | 24159 ± 1313 (–16) |
| | 10 | 1734 ± 62 (9) | 2327 ± 150 (28)* | 22015 ± 1912 (–6) |
| | 30 | 1140 ± 53 (40)* | 1359 ± 89 (58)* | 16194 ± 1293 (22) |
| 164 E1 | 0 | 1040 ± 76 | 3504 ± 223 | 21321 ± 1994 |
| | 1 | 1122 ± 58 (–8) | 2796 ± 133 (20)* | 23574 ± 1313 (–11) |
| | 3 | 1046 ± 23 (–1) | 2273 ± 74 (35)* | 18002 ± 1516 (16) |
| | 10 | 903 ± 48 (13) | 783 ± 61 (78)* | 17727 ± 2871 (17) |
| | 30 | 610 ± 59 (41) | 271 ± 50 (92)* | 15630 ± 1085 (27) |
| 56 E1 | 0 | 767 ± 34 | 3326 ± 78 | 43705 ± 2192 |
| | 1 | 616 ± 50 (20)* | 2625 ± 138 (19)* | 41561 ± 1611 (5) |

TABLE 9-continued

Ex Vivo Binding Profile in Mice.

| Treatment | Dose (mg/kg, PO) | Mean Specific Binding (dpm) ± S.E.M. (Values in Brackets Denote % Transporter Occupancy) | | |
|---|---|---|---|---|
| | | NET | SERT | DAT |
| | 3 | 368 ± 17 (52)* | 1346 ± 109 (58)* | 42127 ± 2130 (4) |
| | 10 | 106 ± 20 (86)* | 278 ± 42 (91)* | 33478 ± 1779 (23)* |
| | 30 | 19 ± 2 (98)* | 151 ± 60 (95)* | 14637 ± 1567 (67)* |
| 277 | 0 | 1007 ± 16 | 1423 ± 120 | 43023 ± 2628 |
| | 1 | 950 ± 46 (6) | 1508 ± 86 (–6) | 35827 ± 2302 (17) |
| | 3 | 824 ± 30 (18)* | 1491 ± 75 (–5) | 34136 ± 4104 (21) |
| | 10 | 533 ± 25 (47)* | 1416 ± 43 (0) | 33230 ± 2807 (23) |
| | 30 | 294 ± 42 (71)* | 1384 ± 101 (3) | 31743 ± 4406 (26) |

*p < 0.05, vs. vehicle (0); One Way ANOVA

Example 8

In Vivo Analyses

8.1. Rat Forced Swim Test

The method, which detects antidepressant activity, followed that described by Porsolt et al (*Eur. J. Pharmacol.*, 47, 379-391, 1978) and modified by Lucki et al. (*Psychopharm.*, 121, 66-72, 1995). Rats forced to swim in a situation from which they cannot escape rapidly become immobile. Antidepressants decrease the duration of immobility. In addition, distinct patterns of active behaviors are produced by antidepressants that selectively inhibit norepinephrine (NE) and serotonin (5-HT) uptake in this test. Selective NE reuptake inhibitors decrease immobility by increasing climbing behaviors whereas selective 5-HT reuptake inhibitors decrease immobility by increasing swimming behaviors.

Rats were individually placed in a cylinder (Height=40 cm; Diameter=20 cm) containing 22 cm water (25° C.) for 15 minutes on the first day of the experiment (Session 1) and were then put back in the water 24 hours later for a 5 minute test (Session 2). The sessions were videotaped and duration of immobility as well as swimming and climbing behaviors during the 5 minute test were measured. Twelve rats were tested in each group. The test was performed blind. Compounds were typically evaluated at 3 doses (1-30 mg/kg), administered orally 2 times: 24 hours and 30-60 minutes before the test (Session 2), and compared with a vehicle control group. Desipramine (20 mg/kg i.p.), administered under the same experimental conditions, was used as the positive reference substance.

Data were analyzed by one way analysis of variance (ANOVA) followed by post-hoc comparisons where appropriate. An effect will be considered significant if p<0.05. Data are represented as the mean and standard error to the mean (s.e.m).

8.2. Mouse Tail Suspension Test

The method, which detects antidepressant activity, follows that described by Stéru et al (*Psychopharmacology*, 85, 367-370, 1985). Rodents, suspended by the tail, rapidly become immobile. Antidepressants decrease the duration of immobility.

The behavior of the animal was recorded automatically for 5 minutes using a computerized device (Med-Associates Inc.) similar to that developed by Stéru et al (*Prog. Neuropsychopharmacol. Exp. Psychiatry*, 11, 659-671, 1987). Ten to twelve mice were tested in each group. The test was performed blind. Compounds were typically evaluated at 3 doses (1-30 mg/kg), administered orally one time: 30-60 minutes before the test, and compared with a vehicle control group. Desipramine (100 mg/kg), administered under the same experimental conditions, was used as the positive reference substance.

Data were analyzed by one way analysis of variance (ANOVA) followed by post-hoc comparisons where appropriate. An effect was considered significant if $p<0.05$. Data are represented as the mean and standard error to the mean (s.e.m).

8.3. Locomotor Activity

In order to ensure effects of the compounds on immobility time were not related to a general stimulant effect on baseline motor activity, locomotor activity was assessed using photocell monitored cages (Med-Associates Inc.). Each test chamber was equipped with infrared photocell beams to measure movement of the animals. Horizontal and vertical activity were measured Rats or mice were pretreated with vehicle or test compounds and placed back in home cage, following which they will be individually placed in locomotor cages and activity was monitored in 5 minute intervals for up to 60 min.

Data were analyzed by one way analysis of variance (ANOVA) followed by post-hoc comparisons where appropriate. An effect was considered significant if $p<0.05$. Data are represented as the mean and standard error to the mean (s.e.m).

8.4. Result Summary

Selected compounds of the invention were evaluated in the mouse tail suspension and locomotor activity test (Table 10). Results showed that all tested compounds exhibited an antidepressant-like profile (i.e., significantly decreased immobility time) with MED's in the range of 3-30 mg/kg, PO. At doses active in the tail suspension test, no change or a decrease in baseline motor activity was observed indicating that antidepressant-like activity was not due to a general stimulant effect.

Selected compounds of the invention were also evaluated in the rat forced swim and locomotor activity tests (Table 11). All tested compounds exhibited antidepressant-like effects with MED's in the range of 10-30 mg/kg, PO. The decrease in immobility produced by these compounds appeared to be due to increases in swimming and climbing behaviors indicative of mixed transporter activity (i.e., SNRI profiles). In conclusion, the tested compounds of the invention exibited an antidepressant profile in at least three animal models, the mouse tail suspension test and rat locomotor activity test as well as the rat forced swim test.

TABLE 10

Mouse Tail Suspension and Locomotor Activity Results

| Treatment Dose (mg/kg, PO) | | Mouse Tail Suspension Mean Immobility Time ± S.E.M. | Mouse Locomotor Activity Total Distance Traveled ± S.E.M. |
|---|---|---|---|
| 153 E2 | 0 | 200.1 ± 5.8 | 537.2 ± 67.2 |
| | 3 | 195.4 ± 7.7 | 625.5 ± 88.8 |
| | 10 | 170.2 ± 6.3 * | 519.5 ± 88.4 |
| | 30 | 154.5 ± 8.4 * | 573.7 ± 63.6 |
| 44 E1 | 0 | 198.3 ± 7.6 | 660.0 ± 51.6 |
| | 3 | 188.9 ± 7.3 | 576.5 ± 66.9 |
| | 10 | 174.5 ± 8.1 | 721.1 ± 36.5 |
| | 30 | 120.4 ± 9.0 * | 402.3 ± 71.0 * |
| 93 | 0 | 204.6 ± 5.6 | 494.0 ± 64.1 |
| | 3 | 203.5 ± 8.0 | 644.0 ± 55.7 |
| | 10 | 185.4 ± 7.9 | 606.9 ± 72.4 |
| | 30 | 162.0 ± 8.1 * | 737.6 ± 89.5 |
| 48 E1 | 0 | 199.9 ± 6.7 | 647.7 ± 42.6 |
| | 3 | 189.8 ± 7.2 | 622.5 ± 101.6 |
| | 10 | 174.1 ± 5.8 * | 620.0 ± 79.4 |
| | 30 | 134.5 ± 9.6 * | 468.6 ± 114.2 |
| 134 E2 | 0 | 200.0 ± 6.7 | 782.8 ± 94.2 |
| | 3 | 191.4 ± 6.2 | 862.7 ± 100.4 |
| | 10 | 170.8 ± 6.0 * | 671.6 ± 63.3 |
| | 30 | 137.2 ± 7.2 * | 728.2 ± 107.7 |
| 75 | 0 | 194.2 ± 6.0 | 659.4 ± 63.1 |
| | 3 | 187.8 ± 9.6 | 653.5 ± 48.4 |
| | 10 | 177.7 ± 5.8 | 608.8 ± 83.4 |
| | 30 | 143.5 ± 5.8 * | 655.3 ± 117.7 |
| 148 E1 | 0 | 207.6 ± 7.8 | 445.7 ± 71.5 |
| | 3 | 193.7 ± 6.0 | 584.8 ± 65.7 |
| | 10 | 189.3 ± 5.9 | 486.3 ± 74.3 |
| | 30 | 174.5 ± 5.0 * | 559.6 ± 88.2 |
| 225 | 0 | 195.1 ± 4.1 | 735.2 ± 54.5 |
| | 0.3 | 188.1 ± 8.0 | 519.5 ± 56.4 * |
| | 1 | 186.5 ± 5.2 | 423.4 ± 62.3 * |
| | 3 | 158.5 ± 4.9 * | 415.9 ± 61.6 * |
| 225 | 0 | 192.5 ± 6.3 | 336.6 ± 77.5 |
| | 3 | 155.2 ± 6.0 * | 341.8 ± 78.3 |
| | 10 | 137.8 ± 5.2 * | 234.2 ± 49.4 |
| | 30 | 136.3 ± 2.5 * | 177.4 ± 47.8 |
| 164 E1 | 0 | 197.3 ± 7.0 | 509.4 ± 92.7 |
| | 3 | 183.8 ± 6.5 | 377.8 ± 67.6 |
| | 10 | 162.1 ± 4.6 * | 210.3 ± 40.4 * |
| | 30 | 155.3 ± 7.8 * | 494.0 ± 84.9 |
| 56 E1 | 0 | 203.6 ± 4.5 | 439.6 ± 63.5 |
| | 3 | 184.0 ± 4.8 | 410.2 ± 89.3 |
| | 10 | 174.8 ± 6.1 * | 440.2 ± 62.6 |
| | 30 | 141.9 ± 7.4 * | 252.2 ± 55.8 |
| 277 | 0 | 199.8 ± 6.1 | 378.9 ± 45.2 |
| | 3 | 182.3 ± 8.1 | 418.8 ± 80.6 |
| | 10 | 164.4 ± 6.8 * | 411.8 ± 87.8 |
| | 30 | 147.1 ± 3.1 * | 327.7 ± 67.1 |
| 276 | 0 | 202.7 ± 6.3 | 565.9 ± 104.3 |
| | 3 | 182.0 ± 4.2 | 625.9 ± 47.5 |
| | 10 | 164.1 ± 5.7 * | 382.4 ± 63.4 |
| | 30 | 160.2 ± 7.2 * | 607.8 ± 57.8 |
| 164 E2 | 0 | 184.6 ± 10.1 | 520.4 ± 103.8 |
| | 3 | 181.8 ± 6.3 | 518.2 ± 106.1 |
| | 10 | 179.1 ± 4.5 | 464.5 ± 86.2 |
| | 30 | 141.8 ± 6.0 * | 669.9 ± 75.6 |
| 17 E1 | 0 | 197.3 ± 5.6 | 463.0 ± 73.4 |
| | 3 | 184.7 ± 9.0 | 649.3 ± 78.4 |
| | 10 | 182.6 ± 4.1 | 478.3 ± 88.5 |
| | 30 | 150.9 ± 7.8 * | 428.3 ± 120.6 |

* $p < 0.05$, vs. vehicle (0); One Way ANOVA

TABLE 11

Rat Forced Swim and Locomoter Activity Results

| Treatment Dose (mg/kg, PO) | | Rat Forced Swim (Means ± S.E.M.) | | | Rat Locomotor Activity Total Distance Traveled ± S.E.M. |
|---|---|---|---|---|---|
| | | Immobility | Swimming | Climbing | |
| 48 E1 | 0 | 48.0 ± 2.1 | 4.8 ± 1.2 | 7.0 ± 1.5 | 1480.0 ± 67.4 |
| | 3 | 49.6 ± 1.5 | 3.7 ± 1.0 | 7.1 ± 0.6 | 1869.9 ± 188.4 |
| | 10 | 35.6 ± 3.5* | 6.5 ± 1.6 | 17.9 ± 2.5* | 1825.3 ± 109.3 |
| | 30 | 26.9 ± 4.4* | 9.7 ± 1.7* | 20.6 ± 2.9* | 1840.6 ± 56.6 |
| 153 E2 | 0 | 50.8 ± 1.8 | 1.0 ± 0.3 | 8.2 ± 1.8 | 1685.1 ± 106.8 |
| | 3 | 49.9 ± 1.7 | 1.9 ± 0.8 | 8.8 ± 1.5 | 1577.8 ± 80.1 |
| | 10 | 44.0 ± 2.1 | 4.3 ± 1.1* | 11.7 ± 1.8 | 1994.2 ± 263.9 |
| | 30 | 31.3 ± 6.7* | 4.6 ± 1.3* | 22.2 ± 5.2* | 2033.7 ± 215.4 |
| 93 | 0 | 48.5 ± 1.4 | 3.7 ± 0.7 | 7.8 ± 1.1 | 1682.2 ± 66.8 |
| | 3 | 44.5 ± 2.5 | 6.5 ± 1.6 | 9.0 ± 1.3 | 1802.6 ± 150.6 |
| | 10 | 41.4 ± 2.8 | 6.9 ± 1.3 | 12.8 ± 2.2 | 1641.0 ± 144.5 |
| | 30 | 25.8 ± 5.4* | 12.0 ± 2.1* | 22.2 ± 3.5* | 2095.6 ± 147.2 |
| 277 | 0 | 46.5 ± 2.9 | 1.2 ± 0.6 | 12.1 ± 2.7 | 1586.0 ± 191.3 |
| | 3 | 50.4 ± 1.1 | 0.8 ± 0.3 | 9.0 ± 1.2 | 1406.2 ± 84.9 |
| | 10 | 42.5 ± 2.6 | 3.7 ± 0.9* | 13.8 ± 2.3 | 1861.4 ± 187.8 |
| | 30 | 14.6 ± 3.5* | 6.1 ± 1.4* | 35.6 ± 5.2* | 2612.4 ± 210.8* |
| 225 | 0 | 52.4 ± 1.8 | 0.8 ± 0.4 | 6.8 ± 1.8 | 1610.3 ± 101.1 |
| | 3 | 50.8 ± 1.8 | 0.8 ± 0.3 | 8.4 ± 1.7 | 1783.4 ± 182.7 |
| | 10 | 47.6 ± 3.0 | 1.2 ± 0.6 | 11.1 ± 2.7 | 1628.5 ± 159.2 |
| | 30 | 33.4 ± 4.8* | 1.1 ± 0.5 | 25.0 ± 4.6* | 2182.8 ± 151.2* |
| 56 E1 | 0 | 53.8 ± 0.6 | 0.4 ± 0.2 | 5.8 ± 0.7 | 1272.6 ± 113.2 |
| | 3 | 52.2 ± 1.6 | 0.3 ± 0.2 | 7.1 ± 1.6 | 1227.9 ± 84.4 |
| | 10 | 50.7 ± 1.0 | 0.8 ± 0.3 | 8.6 ± 0.9 | 1230.8 ± 64.8 |
| | 30 | 40.4 ± 2.7* | 1.0 ± 0.4 | 17.9 ± 2.4* | 1359.8 ± 132.7 |

*p < 0.05, vs. vehicle (0); One Way ANOVA

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A compound having a structure according to Formula (II):

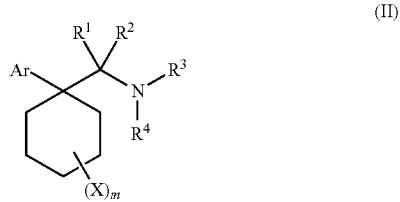

(II)

wherein
m is 0, 1, 2, 3, 4, 5, 6, 7, 8, 9, or 10;
Ar is

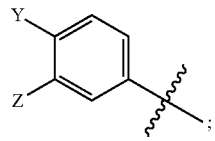

wherein

Y and Z are (i) both halogen; or (ii) one of Y and Z is $CF_3$ or $OCF_3$, and the other is hydrogen;

each X is independently H, halogen, $CF_3$, $OR^5$, acyl, $C(O)OR^5$, $NR^6R^7$, substituted or unsubstituted alkyl, or substituted or unsubstituted heteroalkyl;

wherein each $R^5$ is independently H, acyl, substituted or unsubstituted alkyl, substituted or unsubstituted heteroalkyl, or substituted or unsubstituted aryl;

each $R^6$ and $R^7$ is independently H, or substituted or unsubstituted alkyl;

each $R^1$ and $R^2$ is independently H, or substituted or unsubstituted alkyl; and $R^3$ and $R^4$ are each independently H, substituted or unsubstituted alkyl, or substituted or unsubstituted heteroalkyl;

or a pharmaceutically acceptable salt, enantiomer, diastereomer, racemic mixture, enantiomerically enriched mixture, or enantiomerically pure form thereof;

wherein substituents for alkyl or heteroalkyl radicals are selected from unsubstituted alkyl, unsubstituted heteroalkyl, unsubstituted aryl, unsubstituted heteroaryl, unsubstituted heterocycloalkyl, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O) NR"R'", —NR"CO₂R', —NR—C(NR'R"R'") =NR'''', —NR—C(NR'R")=NR'", —S(O)R', —S(O)₂R', —S(O)₂NR'R", —NRSO₂R', —CN and —NO₂ in a number ranging from zero to (2m'+1), where m' is the total number of carbon atoms in such a radical; R', R", R'" and R'''' are each independently selected from hydrogen, unsubstituted heteroalkyl, unsubstituted aryl, unsubstituted alkyl, alkoxy or thioalkoxy groups, or arylalkyl groups; and substituents for aryl radicals are selected from unsubstituted alkyl, unsubstituted heteroalkyl, unsubstituted aryl, unsubstituted heteroaryl, unsubstituted heterocycloalkyl, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O) R', —NR'—C(O)NR"R'", —NR"CO₂R', —NR—C (NR'R"R'")=NR'''', —NR—C(NR'R")=NR'", —S(O) R', —S(O)₂R', —S(O)₂NR'R", —NRSO₂R', —CN, —NO₂, —R', —N₃, —CH(Ph)₂, fluoro(C₁-C₄)alkoxy, and fluoro(C₁-C₄)alkyl, in a number ranging from zero to the total number of open valences on the aromatic ring system; and where R', R", R'" and R'''' are each independently selected from hydrogen, unsubstituted alkyl, unsubstituted heteroalkyl, unsubstituted aryl and unsubstituted heteroaryl.

2. The compound according to claim 1 or a pharmaceutically acceptable salt, enantiomer, diastereomer, racemic mixture, enantiomerically enriched mixture, or enantiomerically pure form thereof, wherein said compound is chiral.

3. The compound according to claim 1 or a pharmaceutically acceptable salt, enantiomer, diastereomer, racemic mixture, enantiomerically enriched mixture, or enantiomerically pure form thereof, wherein said compound has the structure:

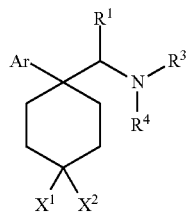

wherein
  $X^1$ and $X^2$ are each independently H, halogen, $CF_3$, $OR^5$, $NR^6R^7$, substituted or unsubstituted $C_1$-$C_4$ alkyl, or substituted or unsubstituted $C_1$-$C_4$ heteroalkyl.

4. The compound according to claim 3 or a pharmaceutically acceptable salt, enantiomer, diastereomer, racemic mixture, enantiomerically enriched mixture, or enantiomerically pure form thereof, wherein $X^1$ and $X^2$ are each independently H, methyl, ethyl, propyl, OH, OMe, OEt, F, Cl, $CH_2OH$, $CH_2OMe$, or $CF_3$.

5. The compound according to claim 3 or a pharmaceutically acceptable salt, enantiomer, diastereomer, racemic mixture, enantiomerically enriched mixture, or enantiomerically pure form thereof, wherein $R^1$ is H or substituted or unsubstituted $C_1$-$C_4$ alkyl.

6. The compound according to claim 3 or a pharmaceutically acceptable salt, enantiomer, diastereomer, racemic mixture, enantiomerically enriched mixture, or enantiomerically pure form thereof, wherein $R^3$ and $R^4$ are each independently substituted or unsubstituted alkyl, or substituted or unsubstituted heteroalkyl.

7. The compound of claim 1 or a pharmaceutically acceptable salt, enantiomer, diastereomer, racemic mixture, enantiomerically enriched mixture, or enantiomerically pure form thereof, wherein Y and Z are each independently a halogen.

8. A composition comprising a first stereoisomer of a compound according to claim 1 or a pharmaceutically acceptable salt, enantiomer, diastereomer, racemic mixture, enantiomerically enriched mixture, or enantiomerically pure form thereof, and at least one additional stereoisomer of a compound according to claim 1, wherein said first stereoisomer is present in a diastereomeric excess of at least 80% relative to said at least one additional stereoisomer, and said first stereoisomer and said at least one additional stereoisomer are stereoisomers of one another.

9. A pharmaceutical composition comprising a compound of claim 1 or a pharmaceutically acceptable salt, enantiomer, diastereomer, racemic mixture, enantiomerically enriched mixture, or enantiomerically pure form thereof, and a pharmaceutically acceptable carrier.

10. A method of inhibiting binding of a monoamine transporter ligand to a monoamine transporter, said method comprising contacting said monoamine transporter and a compound of claim 1 or a pharmaceutically acceptable salt, enantiomer, diastereomer, racemic mixture, enantiomerically enriched mixture, or enantiomerically pure form thereof, in the presence of said monoamine transporter ligand, wherein said monoamine transporter is serotonin transporter, dopamine transporter, or norepinephrine transporter, or a combination thereof.

11. A method of inhibiting the activity of at least one monoamine transporter, said method comprising contacting said monoamine transporter and a compound of claim 1 or a pharmaceutically acceptable salt, enantiomer, diastereomer, racemic mixture, enantiomerically enriched mixture, or enantiomerically pure form thereof, wherein said monoamine transporter is serotonin transporter, dopamine transporter, or norepinephrine transporter, or a combination thereof.

12. A method of treating a central nervous system disorder, said method comprising administering to a subject in need thereof a therapeutically effective amount of a compound of claim 1 or a pharmaceutically acceptable salt, enantiomer, diastereomer, racemic mixture, enantiomerically enriched mixture, or enantiomerically pure form thereof, wherein said central nervous system disorder is depression.

13. The compound according to claim 1, or a pharmaceutically acceptable salt, enantiomer, diastereomer, racemic mixture, enantiomerically enriched mixture, or enantiomerically pure form thereof, wherein the compound is:
  (±) 1-(1-(3,4-dichlorophenyl)cyclohexyl)ethanamine;
  (R)-1-(1-(3,4-dichlorophenyl)cyclohexyl)ethanamine;
  (S)-1-(1-(3,4-dichlorophenyl)cyclohexyl)ethanamine;
  1-(1-(3,4-dichlorophenyl)cyclohexyl)-N-methylethanamine;
  1-(1-(3,4-dichlorophenyl)cyclohexyl)propan-1-amine;
  1-(1-(3,4-dichlorophenyl)cyclohexyl)-N,N-dimethylmethanamine;
  1-(1-(3,4-dichlorophenyl)cyclohexyl)-N-methylmethanamine;
  (1-(4-chloro-3-fluorophenyl)cyclohexyl)-N-methylmethanamine;
  (1-(3-chloro-4-fluorophenyl)cyclohexyl)-N,N-dimethylmethanamine; or
  cis-3-(3,4-dichlorophenyl)-3-((dimethylamino)methyl)cyclohexanol.

14. The compound according to claim 13, or a pharmaceutically acceptable salt, enantiomer, diastereomer, racemic mixture, enantiomerically enriched mixture, or enantiomerically pure form thereof, wherein the compound is:
  (±) 1-(1-(3,4-dichlorophenyl)cyclohexyl)ethanamine;
  (R)-1-(1-(3,4-dichlorophenyl)cyclohexyl)ethanamine;
  (S)-1-(1-(3,4-dichlorophenyl)cyclohexyl)ethanamine; or
  1-(1-(3,4-dichlorophenyl)cyclohexyl)-N-methylethanamine.

15. The compound according to claim 1, or a pharmaceutically acceptable salt, enantiomer, diastereomer, racemic mixture, enantiomerically enriched mixture, or enantiomerically pure form thereof, wherein the compound is:
  4-(aminomethyl)-4-(3,4-dichlorophenyl)-1-methylcyclohexanol;
  4-(3,4-dichlorophenyl)-1-methyl-4-((methylamino)methyl)cyclohexanol;
  4-(3,4-dichlorophenyl)-4-((dimethylamino)methyl)-1-methylcyclohexanol;
  trans-2-(3,4-dichlorophenyl)-2-((dimethylamino)methyl)cyclohexanol;
  (1s,4s)-4-(3,4-dichlorophenyl)-4-((dimethylamino)methyl)-cyclohexanol;
  4-(3,4-dichlorophenyl)-4-((dimethylamino)methyl)-1-ethylcyclohexanol;
  1-(1-(3,4-dichlorophenyl)-4-methoxycyclohexyl)-N,N-dimethylmethanamine; or
  1-(1-(3,4-dichlorophenyl)-4-fluorocyclohexyl)-N,N-dimethylmethanamine.

16. The compound according to claim 15, or a pharmaceutically acceptable salt, enantiomer, diastereomer, racemic mixture, enantiomerically enriched mixture, or enantiomerically pure form thereof, wherein the compound is:
  4-(aminomethyl)-4-(3,4-dichlorophenyl)-1-methylcyclohexanol;
  4-(3,4-dichlorophenyl)-1-methyl-4-((methylamino)methyl)cyclohexanol; or 4-(3,4-dichlorophenyl)-4-((dimethylamino)methyl)-1-methylcyclohexanol.

17. The compound according to claim 1 or a pharmaceutically acceptable salt, enantiomer, diastereomer, racemic mixture, enantiomerically enriched mixture, or enantiomerically pure form thereof, wherein the compound is:

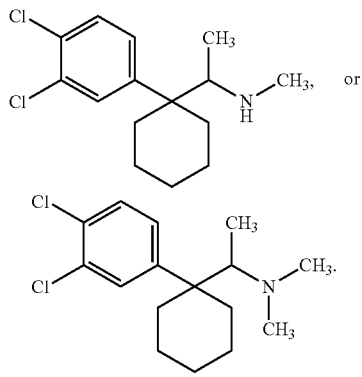

18. The compound according to claim 1 or a pharmaceutically acceptable salt, enantiomer, diastereomer, racemic mixture, enantiomerically enriched mixture, or enantiomerically pure form thereof, wherein the compound is:

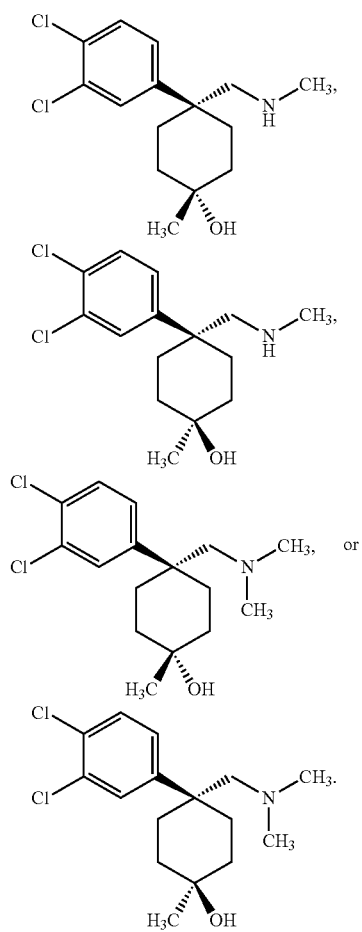

19. The compound according to claim 1 or a pharmaceutically acceptable salt, enantiomer, diastereomer, racemic mixture, enantiomerically enriched mixture, or enantiomerically pure form thereof, wherein the compound is:

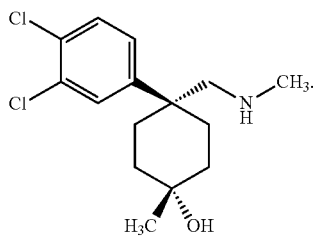 [SMILES: CNC[C@]1(c2ccc(Cl)c(Cl)c2)CC[C@](C)(O)CC1]

20. The compound according to claim 1, or a pharmaceutically acceptable salt, enantiomer, diastereomer, racemic mixture, enantiomerically enriched mixture, or enantiomerically pure form thereof, wherein the compound is:

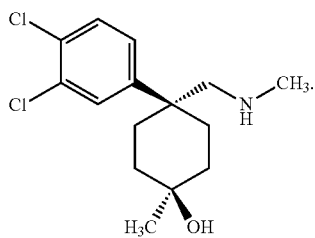 [SMILES: CNC[C@]1(c2ccc(Cl)c(Cl)c2)CC[C@@](C)(O)CC1]

21. The compound according to claim 1, or a pharmaceutically acceptable salt, enantiomer, diastereomer, racemic mixture, enantiomerically enriched mixture, or enantiomerically pure form thereof, wherein the compound is:

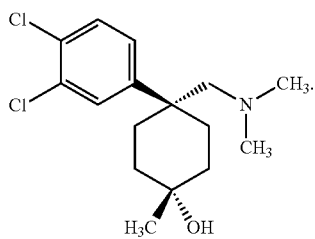 [SMILES: CN(C)C[C@]1(c2ccc(Cl)c(Cl)c2)CC[C@](C)(O)CC1]

22. The compound according to claim 1, or a pharmaceutically acceptable salt, enantiomer, diastereomer, racemic mixture, enantiomerically enriched mixture, or enantiomerically pure form thereof, wherein the compound is:

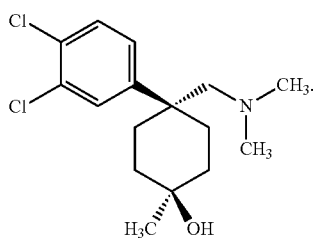 [SMILES: CN(C)C[C@]1(c2ccc(Cl)c(Cl)c2)CC[C@@](C)(O)CC1]

23. The compound according to claim 7 or a pharmaceutically acceptable salt, enantiomer, diastereomer, racemic mixture, enantiomerically enriched mixture, or enantiomerically pure form thereof, wherein both Y and Z are Cl.

* * * * *